US009062294B2

United States Patent
Franklin et al.

(10) Patent No.: US 9,062,294 B2
(45) Date of Patent: *Jun. 23, 2015

(54) RENEWABLE FUELS PRODUCED FROM OLEAGINOUS MICROORGANISMS

(75) Inventors: Scott Franklin, La Jolla, CA (US); Aravind Somanchi, Redwood City, CA (US); Karen Espina, San Francisco, CA (US); George Rudenko, Mountain View, CA (US); Penelope Chua, San Francisco, CA (US)

(73) Assignee: Solazyme, Inc., South San Francisco, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 13/555,009

(22) Filed: Jul. 20, 2012

(65) Prior Publication Data

US 2014/0249342 A1    Sep. 4, 2014

Related U.S. Application Data

(63) Continuation of application No. 13/550,412, filed on Jul. 16, 2012, now Pat. No. 8,435,767, which is a (Continued)

(51) Int. Cl.
*C12N 9/20* (2006.01)
*C12N 9/24* (2006.01)

(Continued)

(52) U.S. Cl.
CPC ............... *C12N 9/2402* (2013.01); *C12P 7/64* (2013.01); *C07K 2319/01* (2013.01); *C10L 1/02* (2013.01); *C12N 9/00* (2013.01); *C12N 9/16* (2013.01); *C12P 7/20* (2013.01); *C12P 7/6418* (2013.01); *C12P 7/6463* (2013.01); *C12P 7/649* (2013.01);

(Continued)

(58) Field of Classification Search
USPC ............... 435/134, 196, 193, 189, 233, 69.1; 208/46

See application file for complete search history.

(56) References Cited

U.S. PATENT DOCUMENTS 3,280,502 A    10/1966    Farrow et al.
3,320,693 A    5/1967    Shirota et al.

(Continued)

FOREIGN PATENT DOCUMENTS

CN    1940021 A    4/2007
CN    101130513 A    2/2008

(Continued)

OTHER PUBLICATIONS

Aguirre et al., "Engineering challenges in biodiesel production from microalgae," Critical Reviews in Biotechnology, 33(3): 293-308, (2013).

(Continued)

*Primary Examiner* — Rosanne Kosson
(74) *Attorney, Agent, or Firm* — Alston & Bird LLP

(57) ABSTRACT

Disclosed herein are methods of manufacturing renewable chemicals through the manufacture of novel triglyceride oils followed by chemical modification of the oils. Methods such as transesterification, hydrogenation, hydrocracking, deoxygenation, isomerization, interesterification, hydroxylation, hydrolysis and saponification are disclosed. Novel oils containing fatty acid chain lengths of C8, C10, C12 or C14 are also disclosed and are useful as feedstocks in the methods of the invention.

30 Claims, 12 Drawing Sheets

Related U.S. Application Data continuation of application No. 12/981,409, filed on Dec. 29, 2010, now Pat. No. 8,222,010, which is a continuation of application No. 12/628,149, filed on Nov. 30, 2009, now Pat. No. 7,883,882.

(60) Provisional application No. 61/118,590, filed on Nov. 28, 2008, provisional application No. 61/118,994, filed on Dec. 1, 2008, provisional application No. 61/174,357, filed on Apr. 30, 2009, provisional application No. 61/219,525, filed on Jun. 23, 2009.

(51) Int. Cl.
| | |
|---|---|
| *C12P 7/64* | (2006.01) |
| *C10L 1/02* | (2006.01) |
| *C12N 9/00* | (2006.01) |
| *C12N 9/16* | (2006.01) |
| *C12P 7/20* | (2006.01) |
| *C12N 15/79* | (2006.01) |
| *C07C 1/207* | (2006.01) |

(52) U.S. Cl.
CPC .............. *Y02E 50/13* (2013.01); *Y02T 50/678* (2013.01); *C12N 15/79* (2013.01); *C12P 7/6409* (2013.01); *C07C 1/2078* (2013.01)

(56) References Cited

U.S. PATENT DOCUMENTS

| | | | |
|---|---|---|---|
| 3,957,578 A | 5/1976 | Narita et al. | |
| 3,962,466 A | 6/1976 | Nakabayashi | |
| 4,103,039 A | 7/1978 | Mandai et al. | |
| 4,140,805 A | 2/1979 | Edwards et al. | |
| 4,673,490 A | 6/1987 | Subramanian et al. | |
| 4,755,467 A | 7/1988 | Scopes et al. | |
| 4,992,605 A | 2/1991 | Craig et al. | |
| 5,001,059 A | 3/1991 | Skatrud et al. | |
| 5,130,242 A | 7/1992 | Barclay | |
| 5,212,087 A | 5/1993 | Fournier et al. | |
| 5,252,198 A | 10/1993 | Harrison et al. | |
| 5,270,175 A | 12/1993 | Moll et al. | |
| 5,270,177 A | 12/1993 | Ramos Lazcano et al. | |
| 5,304,481 A | 4/1994 | Davies et al. | |
| 5,354,878 A | 10/1994 | Connemann et al. | |
| 5,391,724 A | 2/1995 | Kindl et al. | |
| 5,436,394 A | 7/1995 | Willmitzer et al. | |
| 5,455,167 A | 10/1995 | Voelker et al. | |
| 5,492,938 A | 2/1996 | Kyle et al. | |
| 5,518,918 A | 5/1996 | Barclay et al. | |
| 5,693,507 A | 12/1997 | Daniell et al. | |
| 5,711,983 A | 1/1998 | Kyle et al. | |
| 5,723,761 A | 3/1998 | Voelker et al. | |
| 5,792,631 A | 8/1998 | Running | |
| 5,888,947 A | 3/1999 | Lambert et al. | |
| 5,900,370 A | 5/1999 | Running | |
| 5,945,585 A * | 8/1999 | Hitz et al. | 800/312 |
| 6,372,460 B1 | 4/2002 | Gladue et al. | |
| 6,680,426 B2 | 1/2004 | Daniell et al. | |
| 6,762,345 B1 | 7/2004 | Cahoon et al. | |
| 7,053,267 B2 | 5/2006 | Knauf et al. | |
| 7,063,957 B2 | 6/2006 | Chen | |
| 7,081,567 B2 | 7/2006 | Xue et al. | |
| 7,135,620 B2 | 11/2006 | Daniell et al. | |
| 7,268,276 B2 | 9/2007 | Ruezinsky et al. | |
| 7,468,267 B2 | 12/2008 | Monod et al. | |
| 7,504,259 B2 | 3/2009 | Yadav et al. | |
| 7,588,931 B2 | 9/2009 | Damude et al. | |
| 7,622,570 B2 | 11/2009 | Oswald et al. | |
| 7,883,882 B2 | 2/2011 | Franklin et al. | |
| 7,935,515 B2 | 5/2011 | Franklin et al. | |
| 7,939,710 B1 | 5/2011 | Apt et al. | |
| 8,029,579 B2 | 10/2011 | Knuth et al. | |
| 8,119,583 B2 | 2/2012 | Day et al. | |
| 8,187,860 B2 | 5/2012 | Franklin et al. | |
| 8,222,010 B2 | 7/2012 | Franklin et al. | |
| 8,268,610 B2 | 9/2012 | Franklin et al. | |
| 8,278,261 B2 | 10/2012 | Day et al. | |
| 8,283,483 B2 | 10/2012 | Williams et al. | |
| 8,435,767 B2 | 5/2013 | Franklin et al. | |
| 8,450,083 B2 | 5/2013 | Day et al. | |
| 8,647,397 B2 | 2/2014 | Trimbur et al. | |
| 8,674,180 B2 | 3/2014 | Franklin et al. | |
| 8,697,427 B2 | 4/2014 | Franklin et al. | |
| 2002/0178467 A1 | 11/2002 | Dehesh | |
| 2003/0082595 A1 | 5/2003 | Jiang et al. | |
| 2003/0097686 A1 | 5/2003 | Knauf et al. | |
| 2003/0145350 A1 | 7/2003 | Spener et al. | |
| 2003/0229237 A1 | 12/2003 | Haas et al. | |
| 2004/0074760 A1 | 4/2004 | Portnoff et al. | |
| 2004/0230085 A1 | 11/2004 | Jakkula et al. | |
| 2005/0005333 A1 | 1/2005 | Ruezinsky et al. | |
| 2005/0084941 A1 | 4/2005 | Abe et al. | |
| 2005/0102716 A1 | 5/2005 | Venkatramesh et al. | |
| 2005/0112735 A1 | 5/2005 | Zappi et al. | |
| 2005/0262588 A1 | 11/2005 | Dehesh et al. | |
| 2005/0266537 A1 | 12/2005 | Chen | |
| 2006/0048240 A1 | 3/2006 | Alexandrov et al. | |
| 2006/0075522 A1 | 4/2006 | Cleveland et al. | |
| 2006/0094088 A1 | 5/2006 | Picataggio et al. | |
| 2006/0094089 A1 | 5/2006 | Barclay | |
| 2006/0130182 A1 | 6/2006 | Heim et al. | |
| 2006/0153826 A1 | 7/2006 | Arnould et al. | |
| 2006/0156436 A1 | 7/2006 | Nakamura et al. | |
| 2006/0162006 A9 | 7/2006 | Sherman et al. | |
| 2006/0199984 A1 | 9/2006 | Kuechler et al. | |
| 2006/0225341 A1 | 10/2006 | Rohr et al. | |
| 2007/0009988 A1 | 1/2007 | Monod et al. | |
| 2007/0048848 A1 | 3/2007 | Sears | |
| 2007/0099280 A1 | 5/2007 | Barclay | |
| 2007/0118916 A1 | 5/2007 | Puzio et al. | |
| 2007/0166266 A1 | 7/2007 | Dillon et al. | |
| 2007/0167396 A1 | 7/2007 | Dillon et al. | |
| 2007/0254354 A1 | 11/2007 | Millis et al. | |
| 2007/0261138 A1 | 11/2007 | Graham et al. | |
| 2008/0014620 A1 | 1/2008 | Op Den Camp et al. | |
| 2008/0038804 A1 | 2/2008 | Du et al. | |
| 2008/0160593 A1 | 7/2008 | Oyler | |
| 2008/0229451 A1 | 9/2008 | Cao et al. | |
| 2008/0256666 A1 | 10/2008 | Zhu et al. | |
| 2009/0004715 A1 | 1/2009 | Trimbur et al. | |
| 2009/0011480 A1 | 1/2009 | Trimbur et al. | |
| 2009/0018300 A1 | 1/2009 | Bloom et al. | |
| 2009/0035842 A1 | 2/2009 | Trimbur et al. | |
| 2009/0047721 A1 | 2/2009 | Trimbur et al. | |
| 2009/0061493 A1 | 3/2009 | Trimbur et al. | |
| 2009/0064567 A1 | 3/2009 | Lippmeier et al. | |
| 2009/0142322 A1 | 6/2009 | Ye | |
| 2009/0145392 A1 | 6/2009 | Clark et al. | |
| 2009/0148918 A1 | 6/2009 | Trimbur et al. | |
| 2009/0176272 A1 | 7/2009 | Champagne et al. | |
| 2009/0211150 A1 | 8/2009 | Wu et al. | |
| 2009/0234146 A1 | 9/2009 | Cooney et al. | |
| 2009/0274736 A1 | 11/2009 | Dillon et al. | |
| 2009/0298159 A1 | 12/2009 | Wu et al. | |
| 2009/0317878 A1 | 12/2009 | Champagne et al. | |
| 2010/0021912 A1 | 1/2010 | Farese et al. | |
| 2010/0035320 A1 | 2/2010 | Blanchard et al. | |
| 2010/0058651 A1 | 3/2010 | Knuth et al. | |
| 2010/0093031 A1 | 4/2010 | Kobayashi et al. | |
| 2010/0105955 A1 | 4/2010 | Alibhai et al. | |
| 2010/0120643 A1 | 5/2010 | Brown et al. | |
| 2010/0151112 A1 | 6/2010 | Franklin et al. | |
| 2010/0151538 A1 | 6/2010 | Franklin et al. | |
| 2010/0154293 A1 | 6/2010 | Hom et al. | |
| 2010/0170144 A1 | 7/2010 | Day et al. | |
| 2010/0228068 A1 | 9/2010 | O'Connor et al. | |
| 2010/0239712 A1 | 9/2010 | Brooks et al. | |
| 2010/0297292 A1 | 11/2010 | Brooks et al. | |
| 2010/0297295 A1 | 11/2010 | Brooks et al. | |
| 2010/0297296 A1 | 11/2010 | Brooks et al. | |
| 2010/0297323 A1 | 11/2010 | Brooks et al. | |
| 2010/0297325 A1 | 11/2010 | Brooks et al. | |
| 2010/0297331 A1 | 11/2010 | Brooks et al. | |

(56) References Cited

U.S. PATENT DOCUMENTS

| | | |
|---|---|---|
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323413 A1 | 12/2010 | Trimbur et al. |
| 2010/0323414 A1 | 12/2010 | Trimbur et al. |
| 2011/0014665 A1 | 1/2011 | Trimbur et al. |
| 2011/0015417 A1 | 1/2011 | Trimbur et al. |
| 2011/0047863 A1 | 3/2011 | Trimbur et al. |
| 2011/0065821 A1 | 3/2011 | Abraham et al. |
| 2011/0072714 A1 | 3/2011 | Gaertner et al. |
| 2011/0190522 A1 | 8/2011 | Trimbur et al. |
| 2011/0203168 A1 | 8/2011 | Franklin et al. |
| 2012/0009636 A1 | 1/2012 | Berry et al. |
| 2012/0028319 A1 | 2/2012 | Trimbur et al. |
| 2012/0122192 A1 | 5/2012 | Trimbur et al. |
| 2012/0128851 A1 | 5/2012 | Brooks et al. |
| 2012/0164701 A1 | 6/2012 | Trimbur et al. |
| 2013/0006006 A1 | 1/2013 | Day et al. |
| 2013/0031678 A1 | 1/2013 | Zheng et al. |
| 2013/0089916 A1 | 4/2013 | Franklin et al. |
| 2013/0122180 A1 | 5/2013 | Brooks et al. |
| 2013/0165677 A1 | 6/2013 | Franklin et al. |
| 2013/0273621 A1 | 10/2013 | Franklin et al. |
| 2013/0295268 A1 | 11/2013 | Day et al. |
| 2013/0296591 A1 | 11/2013 | Day et al. |
| 2013/0330790 A1 | 12/2013 | Trimbur et al. |

FOREIGN PATENT DOCUMENTS

| | | |
|---|---|---|
| EP | 0562504 B1 | 11/1995 |
| EP | 1681337 A1 | 7/2006 |
| EP | 1741767 A1 | 1/2007 |
| FR | 2924126 A1 | 5/2009 |
| GB | 824151 A | 11/1959 |
| JP | 07-075557 | 3/1995 |
| JP | 2000-136199 | 5/2000 |
| JP | 2008-148663 | 7/2008 |
| WO | WO 92/11373 A1 | 7/1992 |
| WO | WO 94/10288 A2 | 5/1994 |
| WO | WO 95/13390 A2 | 5/1995 |
| WO | WO 95/31553 A1 | 11/1995 |
| WO | WO 00/61740 A1 | 10/2000 |
| WO | WO 02/08403 A2 | 1/2002 |
| WO | WO 2005/003310 A2 | 1/2005 |
| WO | WO 2005/035693 A2 | 4/2005 |
| WO | WO 2006/055322 A2 | 5/2006 |
| WO | WO 2007/027669 A1 | 3/2007 |
| WO | WO 2007/038566 A2 | 4/2007 |
| WO | WO 2007/106903 A2 | 9/2007 |
| WO | WO 2008/002643 A2 | 1/2008 |
| WO | WO 2008/011811 A1 | 1/2008 |
| WO | WO 2008/060571 A2 | 5/2008 |
| WO | WO 2008/083352 A1 | 7/2008 |
| WO | WO 2008/130372 A2 | 10/2008 |
| WO | WO 2008/134836 A2 | 11/2008 |
| WO | WO 2008/151149 A2 | 12/2008 |
| WO | WO 2009/126843 A2 | 10/2009 |
| WO | WO 2010/019813 A2 | 1/2010 |
| WO | WO 2010/019813 A2 | 2/2010 |
| WO | WO 2010/045368 A2 | 4/2010 |
| WO | WO 2010/063031 A2 | 6/2010 |
| WO | WO 2010/063032 A2 | 6/2010 |
| WO | WO 2010/120923 A1 | 10/2010 |
| WO | WO 2010/120939 A2 | 10/2010 |
| WO | WO 2011/090730 A1 | 7/2011 |

OTHER PUBLICATIONS

Altschul et al., "Basic local alignment search tool," J Mol Biol, 215(3):403-410, (1990).

Andersen, "Biology and Systematics of Heterokont and Haptophyte Algae," American Journal of Botany, 91(10):1508-1522, (2004).

Appel et al., "A multicopy vector system for genetic studies in *Mucor circinelloides* and other zygomycetes," Molecular Genetics and Genomics, 271(5):595-602, (2004).

Apt et al., "Stable nuclear transformation of the diatom *Phaeodactylum tricornutum*," Mol Gen Genet, 252(5):572-579, (1996).

Barnes et al., "Contribution of 5'- and 3'-untranslated regions of plastid mRNAs to the expression of *Chlamydomonas reinhardtii* chloroplast genes," Mol Genet Genomics, 274(6):625-636, (2005).

Bhunia et al., "Algal Biodiesel Production: Challenges and Opportunities," Bioenergy and Biofuel from Biowastes and Biomass, American Society of Civil Engineers, pp. 313-345, (2010).

Blowers et al., "Studies on *Chlamydomonas* chloroplast transformation: foreign DNA can be stably maintained in the chromosome," Plant Cell, 1(1):123-132, (1989).

Bordes et al., "A new recombinant protein expression system for high-throughput screening in the yeast *Yarrowia lipolytica*," Journal of Microbiological Methods, 70(3):493-502, (2007).

Boutry et al., "Targeting of bacterial chloramphenicol acetyltransferase to mitochondria in transgenic plants," Nature, 328(6128):340-2, (1987).

Boynton et al., "Chloroplast Transformation in *Chlamydomonas* with High Velocity Microprojectiles," Science, 240(4858):1534-1538, (1988).

Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].

Cahoon et al., "A Determinant of Substrate Specificity Predicted from the Acyl-Acyl Carrier Protein Desaturase of Developing Cat's Claw Seed," Plant Physiol., 117:593-598, (1998).

Chang et al., "Deletion of the Δ12-oleic acid desaturase gene of a nonaflatoxigenic *Aspergillus parasiticus* field isolate affects conidiation and sclerotial development," Journal of Applied Microbiology, 97:1178-1184, (2004).

Chattopadhyay et al., "Effect of single amino acid mutations in the conserved GDNQ motif of L protein of *Rinderpest virus* on RNA synthesis in vitro and in vivo," Virus Research, 99:139-145, (2004).

Chen et al., "Recognition of prokaryotic transcription terminators by spinach chloroplast RNA polymerase," Nucleic Acids Research, 16(17):8411-8431, (1988).

Chen et al., "Heterotrophic Growth of *Chlamydomonas reinhardtii* on Acetate in Chemostat Culture," Process Biochemistry, 31(6):601-604, (1996).

Chen et al., "Highly Effective Expression of Rabbit Neutrophil Peptide-1 Gene in *Chlorella Ellipsoidea* Cells," Current Genetics, 39:365-370, (2001).

Chica et al., "Semi-rational approaches to engineering enzyme activity: combining the benefits of directed evolution and rational design ," Current Opinion in Biotechnology, 16:378-384, (2005).

Chow et al., "Electrotranformation of *Chlorella vulgaris*," Plant Cell Reports, 18:778-780, (1999).

Ciferri, "Thiamine-deficiency of *Prototheca*, a Yeast-like Achloric Alga," Nature, 178:1475-1476, (1956).

Cobley et al., "CpeR is an activator required for expression of the phycoerythrin operon (cpeBA) in the cyanobacterium *Fremyella diplosiphon* and is encoded in the phycoerythrin linker-polypeptide operon (cpeCDESTR)," Molecular Microbiology, 44(6):1517-1531, (2002).

Cobley et al., Construction of Shuttle Plasmids Which Can Be Efficiently Mobilized From *Escherichia coli* Into the Chromatically Adapting Cyanobacterium, Plasmid, 30:90-105, (1993).

Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemistry, 263(29):15104-15109 (1988).

Davies et al.,"Expression of the Arylsulfatase Gene from the Beta 2-Tubulin Promoter in *Chlamydomonas reinhardtii*," Nucleic Acids Research, 20(12):2959-2965, (1992).

Dawson et al., "Stable Transformation of *Chlorella*: Rescure of Nitrate Reductase-Deficient Mutants with the Nitrate Reductase Gene," Current Microbiology, 35:356-362, (1997).

(56) References Cited

OTHER PUBLICATIONS

Day, AL. et al., "Safety evaluation of a high-lipid algal biomass from *Chlorella protorhecoides*," Regol. Toxicol. Pharmacol., doi:10.1016/j.yrtph.2009.06.014, 15 pages, (2009).
Debuchy et al., "The argininosuccinate lyase gene of *Chlamydomonas reinhardtii*: an important tool for nuclear transformation and for correlating the genetic and molecular maps of the ARG7 locus," EMBO J., 8(10):2803-2809, (1989).
Deshnium et al., "Transformation of *Synechococcus* with a gene for choline oxidase enhances tolerance to salt stress," Plant Mol Biol, 29(5):897-907, (1995).
Devos et al., "Practical Limits of Function Prediction," PROTEINS: Structure, Function, and Genetics, 41:98-107, (2000).
El-Sheekh et al., "Variation of Some Nutritional Constituents and Fatty Acid Profiles of *Chlorella vulgaris* Beijerinck Grown under Auto and Heterotrophic Conditions," International Journal of Botany, 5(2):153-159, (2009).
El-Sheekh, MM., "Stable Transformation of the Intact Cells of *Chlorella kessleri* With High Velocity Microprojectiles," Biologia Plantarium 42(2): 209-216, (1999).
EPO Supplementary European Search Report and European Search Opinion for application EP 09829850.8 mailed May 16, 2014.
EPO Supplementary European Search Report and European Search Opinion for application EP09729658 mailed Jan. 3, 2013.
Falciatore et al., "Transformation of Nonselectable Reporter Genes in Marine Diatoms," Marine Biotechnology; 1:239-251, (1999).
Franklin et al., "Prospects for molecular farming in the green alga *Chlamydomonas reinhardtii*," Current Opinion in Plant Biology, 7:159-165, (2004).
Franzen et al., "Chloroplast transit peptides from the green alga *Chlamydomonas reinhardtii* share features with both mitochondrial and higher plant chloroplast presequences," FEBS Letters, 260(2):165-168, (1990).
Frenz et al., "Hydrocarbon recovery by extraction with a biocompatible solvent from free and immobilized cultures of *Botryococcus braunii*," Enzyme Microb Technol, 11(11):717-724, (1989).
Frohns et al., "Potassium ion channels of *Chlorella* viruses cause rapid depolarization of host cells during infection," J Virol, 80(5):2437-2444, (2006).
Fromm et al., "Expression of Genes Transferred into Monocot and Dicot Plant Cells by Electroporation," Proc Natl Acad Sci, 82:5824-5828, (1985).
Funes et al., "The typically mitochondrial DNA-encoded ATP6 subunit of the F1F0-ATPase is encoded by a nuclear gene in *Chlamydomonas reinhardtii*," J Biol Chem, 277(8):6051-6058, (2002).
Gonzalez et al., "Optimization of Fatty Add Extraction from *Phaeodactylum tricornutum* UTEX 640 Biomass," JAOCS, 75(12):1735-1740, (1998).
Graves et al., "Hyaluronan synthesis in virus PBCV-1-infected *Chlorella*-like green algae," Virology, 257(1):15-23, (1999).
Gruber et al., "*Escherichia coli*-Anacystis nidulans plasmid shuttle vectors containing the PL promoter from bacteriophage lambda," Current Microbiology, 22(1):15-19, (1991).
Gunstone, "Enzymes as biocatalysts in the modification of natural lipids," Journal of the Science of Food and Agriculture, 79:1535-1549, (1999).
Guo-Zhong et al., "The Actin Gene Promoter-driven Bar as a Dominant Selectable Marker for Nuclear Transformation of *Dunaliella salina*," Acta Genetica Sinica, 32(4): 424-433, (2005).
Hall et al., "Expression of a foreign gene in *Chlamydomonas reinhardtii*," Gene, 124(1):75-81, (1993).
Hallman et al., "Reporter Genes and Highly Regulated Promoters as Tools for Transformation Experienents in *Volvox carteri*," Proc Natl Acad Sci U S A., 91(24):11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, *Chlorella*," Current Microbiology, 38:335-341, (1999).
Heifetz, "Genetic Engineering of the Chloroplast," Biochimie, 82:655-666, (2000).
Henikoff et al., "Amino Acid Substitution Matrices from Protein Blocks," Proc Natl Acad of Sci, 89(22):10915-10919, (1992).
Hillen et al., "Hydrocracking of the Oils of *Botryococcus braunii* to Transport Fuels," Biotechnology and Bioengineering, 24(1):193-205, (1982).
Hiramatsu et al., "Expression of a chitinase gene and lysis of the host cell wall during *Chlorella* virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Huang et al., "Expression of Mercuric Reductase From *Bacillus megaterium* MB1 in Eukaryotic Microalga *Chlorella* sp. DT: An Approach for Mercury Phytoremediation," Appl. Microbiol. Biotechnol., 72:197-205, (2006).
Inoue et al., "Analysis of oil derived from liquefaction of *Botryococcus braunii*," Biomass and Bioenergy, 6(4):269-274, (1994).
Iturriaga et al. "Heterologous transformation of *Mucor circinelloides* with the *Phycomyces blakesleeanus* leu1 gene," Current Genetics, 21(3):215-223, (1992).
Jakobiak et al., "The Bacterial Paromomycin Resistance Gene, aphH, as a Dominant Selectable Marker in *Volvox carteri*," Protist, 55: 381-393, (2004).
Jarvis et al. "Transient Expression of Firefly Luciferase in Protoplasts of the Green Alga *Chlorella ellipsoidea*," Current Genet., 19: 317-322, (1991).
Jiang et al., "The actin gene promoter-driven bar as a dominant selectable marker for nuclear transformation of *Dunaliella sauna*,"Yi Chuan Xue Bao, 32(4):424-433, (2005).
Kalscheuer et al., "Establishment of a Gene Transfer System for *Rhodococcus opacus* PD630 Based on Electroporation and its Application for Recombinant Biosynthesis of Poly(3-hyroxyalkanoic acids)," Applied Microbiology and Biotechnology, 52(4):508-515, (1999).
Kamiya, "Effects of Blue Light and Ammonia on Nitrogen Metabolism in a Colorless Mutant of *Chlorella*," Plant Celll Physiol., 30(4):513-521, (1989).
Kang et al., "Genetic diversity in *Chlorella* viruses flanking key, a gene that encodes a potassium ion channel protein," Virology, 326(1):150-159, (2004).
Kang et al., "The regulation activity of *Chlorella* virus gene 5'upstream sequence in *Escherichia coli* and eucaryotic algae," Institute of Microbiology, Chinese Academy of Sciences, Beijing, 16(4):443-6, (2000). Abstract only.
Karabuluta et al., "Determination of changes in some physical and chemical properties of soybean oil during hydrogenation," Food Chemistry, 81:453-456, (2003).
Karlin et al., "Applications and statistics for multiple high-scoring segments in molecular sequences," Proc Natl Acad Sci, 90(12):5873-5877, (1993).
Kawasaki et al., "Characterization of Immediate Early Genes Expressed in *Chlorovirus* Infections," Nucleic Acids Symp Ser, 44:161-162, (2000).
Kawasaki et al., "Immediate Early Genes Expressed in *Chlorovirus* Infections," Virology, 318(1):214-223, (2004).
Kim et al. "Stable Integraion and Functional Expression of Flounder Growth Hormone Gene in Tranformed Microalga, *Chlorella ellipsoidea*," Mar. Biotechnol. 4:63-73 (2002).
Kimchi-Sarfaty et al., "A 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of *Chlamydomonas reinhardtii*," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).

(56) References Cited

OTHER PUBLICATIONS

Knauf, "The application of genetic engineering to oilseed crops," Trends in Biotechnology, 5(2):40-47, (1987).
Knothe, "'Designer' Biodiesel: Optimizing Fatty Ester Composition to Improve Fuel Properties," Energy & Fuels, 22:1358-1364, (2008).
Knothe, "Analyzing Biodiesel: Standards and Other Methods," JAOCS, 83(10):823-833, (2006).
Kohler et al., "The green fluorescent protein as a marker to visualize plant mitochondria in vivo," Plant J 11(3):613-621, (1997).
Koksharova, "Genetic Tools for Cyanobacteria," Appl Microbiol Biotechnol, 58(2):123-37, (2002).
Krebbers et al., "The maize chloroplast genes for the beta and epsilon subunits of the photosynthetic coupling factor CF1 are fused," Nucleic Acids Res, 10(16): 4985-5002, (1982).
Kuo et al., "Diversity of Oleic Acid, Ricinoleic Acid and Linoleic Acid Conversions Among *Pseudomonas aeruginosa* Strains," Current Microbiology, 49:261-266, (2004).
La Scala et al., "The effect of fatty acid composition on the acrylation kinetics of epoxidized triacylglycerols," Journal of the American Oil Chemists' Society, 79(1):59-63, (2002).
Lapidot et al., "Stable Chloroplast Transformation of the Unicellular Red Alga *Porphyridium* Species," Plant Physiol, 129:7-12, (2002).
Lawford et al., "Performance Testing of *Zymomonas mobilis* Metabolically Engeineered for Confermation of Glucose, Xylose, and Arabinose," Appl Biochem Biotechnol., 98-100:429-48, (2002).
Levitan et al., "Dual targeting of the protein disulfide isomerase RB60 to the chloroplast and the endoplasmic reticulum," Proc Natl Acad Sci, 102(17):6225-6230, (2005).
Li et al., "Isolation and Purification of Lutein from the Microalga *Chlorella vulgaris* by Extraction after Saponification," J. Agric. Food Chem., 50(5):1070-1072, (2002).
Li et al., "Perspectives of microbial oils for biodiesel production," Appl Microbial Biotechnol., 80(5):749-756, (2008). Abstract only.
Lindley, "The impact of food processing antioxidants in vegetable oils, fruits, and vegetables," Trends in Food Science & Technology. 9:336-340, (1998).
Lu et al., "Molecular cloning and stress-dependent expression of a gene encoding Al2-fatty acid desaturase in the Antarctic microalga *Chlorella vulgaris* NJ-7," Extremophiles, 13:875-884, (2009).
Lu, "Biosynthesis and Gene Engineering of Plant Fatty Acids," Chinese Bulletin of Botany, 17(6):481-491, (2000). Abstract only.
Lumbreras et al., "Efficient Foreign Gene Expression in *Chlamydomonas reinhardtii* Mediated by an Endogenous Intron," Plant Journal, 14(4):441-447, (1998).
Manuell et al., "Robust expression of a bioactive mammalian protein in *Chlamydomonas* chloroplast," Plant Biotech J, 5(3):402-412, (2007).
Maruyama et al., "Introduction of Foreign DNA Into *Chlorella saccharophila* by Electroporation," Biotechnology Techniques, 8:821-826, (2004).
Mayfield et al., "Expression and Assembly of a Fully Active Antibody in Algae," Proc Natl Acad Sci, 100(2):438-442, (2003).
Mayfield et al., "Stable nuclear transformation of *Chlamydomonas reinhardtii* by using a *C. reinhardtii* gene as the selectable marker," Proc. Natl. Acad. Sci. USA, Cell Biology, 87:2087-2091, (1990).
Mendes et al., "Supercritical Carbon Dioxide Extraction of Compounds With Pharmaceutical Importance from Microalgae," Inorganica Chimica Acta, 356:328-334, (2003).
Metzger et al., "*Botryococcus braunii*: A Rich Source for Hydrocarbons and Related Ether Lipids," Applied Microbiology and Biotechnology, 66(5):486-496, (2005).
Minowa et al., "Oil Production from Algal Cells of *Dunaliella tertiolecta* by Direct Thermochemical Liquefaction," Fuel, 74(12):1735-1738, (1995).
Mitra et al., "A *Chlorella* Virus Gene Promoter Functions as a Strong Promoter Both in Plants and Bacteria," Biochemical and Biophysical Research Communications, 204(1):189-194, (1994).
Mitra et al., "The *Chlorella* Virus Adenine Methyltransferase Gene Promoter is a Strong Promoter in Plants," Plant Molecular Biology, 26(1):85-93, (1994).

Mullet et al., "Multiple transcripts for higher plantrbcL andatpB genes and localization of the transcription initiation site of therbcL gene," Plant Molecular Biology, 4(1):39-54, (1985).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1, 2007: <URL: http://www.sciencemag.org>].
Needleman et al., "A general method applicable to the search for similarities in the amino acid sequence of two proteins," Journal of Molecular Biology, 48(3):443-453, (1970).
Onai et al., "Natural Tranformation of the Termophillic Cyanbacterium *Thermosynechococcus elongatus* BP-1: A Simple and Efficicent Method for Gene Transfer," Mol Genet Genomics, 271(1):50-9, (2004).
Park et al., "Isolation and Characterization of *Chlorella* Virus From Fresh Water in Korea and Application in *Chlorella* Transformation System," Plant Pathol. J., 21(1):13-20, (2005).
PCT International Preliminary Report on Patentability for application PCT/US2011/059224 mailed May 16, 2013.
PCT International Search Report and Written Opinion of the International Searching Authority for application PCT/US2013/037261 mailed Aug. 23, 2013.
PCT International Search Report for application PCT/US2011/059224 mailed Jun. 27, 2012.
Pearson et al., "Improved tools for biological sequence comparison," Proc Natl Acad Sci, 85(8):2444-2448, (1988).
Pratoomyot et al., "Fatty acids composition of 10 microalgal species," Songklanakarin J. Sci. Technol., 27(6):1179-1187, (2005).
Proschold et al., "Portrait of a Species: *Chlamydomonas reinhardtii*," Genetics, 170(4):1601-1610, (2005).
Qingyu et al., "Fine Cell Structure and Biochemical Compositions of *Chlorella* Protothecoides after Transferring from Autotrophic to Heterotrophic Metabolism," Journal of Nanjing University, Natural Sciences Edition, 29(4):622-630, (1993). Abstract.
Randolph-Anderson et al., "Further characterization of the respiratory deficient dum-1 mutation of *Chlamydomonas reinhardtii* and its use as a recipient for mitochondrial transformation," Mol Gen Genet, 236(2-3):235-244, (1993).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Running et al., "Extracellular production of L-ascorbic acid by *Chlorella* protothecoides, *Prototheca* species, and mutants of *P. moriformis* during aerobic culturing at low pH," Journal of Industrial Microbiology & Biotechnology, 29:93-98, (2002).
Saha et al., "Transformation in *Aspergillus ochraceus*," Current Microbiology, 30(2):83-86, (1995).
Sakuradani, "Studies of Metabolic Engineering of Useful Lipid-producing Microorganisms," NISR Research Grant, (2004).
Sanford, "The biolistic process," Trends in Biotechnology, 6(12):299-302, (1988).
Sansawa et al., "Production of Intracellular Phytochemicals in *Chlorella* under Heterotrophic Conditions," Journal of Bioscience and Bioengineering, 98(6):437-444, (2004).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and CO2 mitigation by thermochemical liquefaction of microalgae," Biomass and Bioenergy, 17(1):33-39, (1999).
Schechter et al., "Relations between Structure and Function in Cytoplasmic Membrane Vesicles Isolated from an *Escherichia coli* Fatty-Acid Auxotroph," Eur. J. Biochem, 49 61-76, (1974).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Seffernick et al., "Melamine Deaminase and Atrazine Chlorohydrolase: 98 Percent Identical but Functionally Different," Journal of Bacteriology, 183(8):2405-2410, (2001).

(56) References Cited

OTHER PUBLICATIONS

Sen et al., "Developments in Directed Evolution for Improving Enzyme Functions," Appl Biochem Biotechnol, 143:212-223, (2007).
Shao et al., "Cloning and expression of metallothionein mutant α-KKS-α in *Anabaena* sp. PCC 7120," Marine Pollution Bulletin, 45(1012):163-167, (2002).
Shi et al., "High-Yield Production of Lutein by the Green Microalga *Chlorella protothecoides* in Heterotrophic Fed-Batch Culture," Biotechnol. Prog., 18(4):723-727 (2002).
Shi, et al., "Production of biomass and lutein by *Chlorella protothecoides* at various glucose concentrations in heterotrophic cultures ," Process Biochemistry, 34:341-347, (1999).
Skolnick et al., "From genes to protein structure and function: novel applications of computational approaches in the genomic era," TIBTECH, 18: 34-39, (2000).
Smallwood et al., "Different Substitutions at Conserved Amino Acids in Domains II and III in the Sendai L RNA Polymerase Protein Inactivate Viral RNA Synthesis," Virology, 304:135-145, (2002).
Smith et al., "Comparison of Biosequences," Adv Appl Math, 2(4):482-489, (1981).
Stemmer et al., "Single-Step Assembly of a Gene and Entire Plasmid from Large Numbers of Oligodeoxyribonucleotides," Gene, 164:49-53, (1995).
Suda, et al., "Evidence for a novel *Chlorella* virus-encoded alginate lyase," FEMS Microbiology Letters, 180(1):45-53, (1999).
Sun et al., "Characterization of two chitinase genes and one chitosanase gene encoded by *Chlorella* virus PBCV-1," Virology, 263(2):376-387, (1999).
Sung et al., "The research on the lipid content and composition of microalgae and their impact factors," Marine Science, 12(33)122-128, (2009). (English translation of first two pages).
Takeno et al., "Establishment of an overall transformation system for an oil-producing filamentous fungus, *Mortierella alpina* 1S-4," Appl Microbiol Biotechnol, 65:419-425, (2004).
Tan et al., "Establishment of a Micro-Particle Bombardment Transformation System for *Dunaliella salina*," J Microbiol.;43(4):361-365, (2005).
Tang et al., "Insertion mutagenesis of *Chlamydomonas reinhardtii* by electroporation and heterologous DNA," Biochem Mol Biol Int, 36(5):1025-1035, (1995).
Tasaki et al., "Digestibility of Yellow *Chlorella* in Suckling Goat Kids,"The Japanese Journal of Zootechnical Science, 48(11):661-663, (1977).
Tomasinsig et al., "The Cathelicidins—Structure, Function and Evolution," Current Protein and Peptide Science, 6: 23-34, (2005).
U.S. Appl. No. 12/131,773, Advisory Action mailed Jan. 27, 2014.
U.S. Appl. No. 12/131,773, Final Office Action mailed Oct. 15, 2013.
U.S. Appl. No. 12/131,773, Non-Final Office Action mailed Jun. 5, 2013.
U.S. Appl. No. 12/131,773, Notice of Allowance and Examiner Initiated Interview Summary mailed Apr. 1, 2014.
U.S. Appl. No. 12/131,793, Non-Final Office Action mailed Apr. 3, 2013.
U.S. Appl. No. 12/131,793, Notice of Allowance mailed Apr. 3, 2013.
U.S. Appl. No. 12/194,389, Notice of Allowance mailed Jan. 15, 2014.
U.S. Appl. No. 12/628,140, Final Office Action mailed Mar. 15, 2013.
U.S. Appl. No. 12/628,144, Non-Final Office Action mailed May 16, 2014.
U.S. Appl. No. 12/642,487, Final Office Action mailed Jan. 30, 2014.
U.S. Appl. No. 12/642,487, Non-Final Office Action mailed Jan. 4, 2013.
U.S. Appl. No. 12/772,163, Non-Final Office Action mailed Dec. 12, 2012.
U.S. Appl. No. 12/772,163, Notice of Allowance mailed May 28, 2013.
U.S. Appl. No. 12/772,170, Non-Final Office Action mailed Dec. 17, 2013.
U.S. Appl. No. 12/772,173 Notice of Allowance mailed Mar. 29, 2013.
U.S. Appl. No. 12/960,388, Notice of Allowance mailed May 28, 2013.
U.S. Appl. No. 12/960,388, Requirement for Restriction/Election mailed Apr. 1, 2013.
U.S. Appl. No. 13/045,500, Non-Final Office Action mailed Jun. 5, 2014.
U.S. Appl. No. 13/087,311, Final Office Action mailed Dec. 16, 2013.
U.S. Appl. No. 13/087,311, Non-Final Office Action mailed Apr. 23, 2013.
U.S. Appl. No. 13/087,311, Non-Final Office Action mailed Jun. 24, 2014.
U.S. Appl. No. 13/118,365, Final Office Action mailed Jul. 22, 2013.
U.S. Appl. No. 13/118,365, Non-Final Office Action mailed Feb. 11, 2013.
U.S. Appl. No. 13/273,179, Non-Final Office Action mailed Jan. 28, 2014.
U.S. Appl. No. 13/273,179, Requirement for Restriction/Election mailed Nov. 14, 2013.
U.S. Appl. No. 13/288,815, Non-Final Office Action mailed Jun. 18, 2014.
U.S. Appl. No. 13/288,815, Requirement for Restriction/Election mailed Jan. 30, 2014.
U.S. Appl. No. 13/464,948, Final Office Action mailed Feb. 13, 2014.
U.S. Appl. No. 13/464,948, Non-Final Office Action mailed Oct. 9, 2013.
U.S. Appl. No. 13/464,948, Requirement for Restriction/Election mailed Aug. 21, 2013.
U.S. Appl. No. 13/479,194, Non-Final Office Action mailed Mar. 26, 2014.
U.S. Appl. No. 13/479,200, Non-Final Office Action mailed Apr. 10, 2013.
U.S. Appl. No. 13/479,200, Non-Final Office Action mailed Sep. 9, 2013.
U.S. Appl. No. 13/479,200, Notice of Allowance mailed Nov. 25, 2013.
U.S. Appl. No. 13/479,200,Requirement for Restriction/Election mailed Jan. 15, 2013.
U.S. Appl. No. 13/527,480, Final Office Action mailed Jan. 16, 2014.
U.S. Appl. No. 13/527,480, Non-Final Office Action mailed Jun. 26, 2013.
U.S. Appl. No. 13/527,480, Requirement for Restriction/Election mailed May 3, 2013.
U.S. Appl. No. 13/543,666, Non-Final Office Action mailed Sep. 5, 2013.
U.S. Appl. No. 13/543,666, Notice of Allowance mailed Feb. 10, 2014.
U.S. Appl. No. 13/543,666, Requirement for Restriction/Election mailed Jan. 3, 2013.
U.S. Appl. No. 13/547,457, Non-Final Office Action mailed Mar. 20, 2014.
U.S. Appl. No. 13/547,457, Non-Final Office Action mailed Jul. 8, 2013.
U.S. Appl. No. 13/558,252, Notice of Allowance mailed Oct. 23, 2013.
U.S. Appl. No. 13/550,412, Notice of Allowance mailed Feb. 21, 2013.
U.S. Appl. No. 13/558,252, Final Office Action mailed Jul. 9, 2013.
U.S. Appl. No. 13/558,252, Non-Final Office Action mailed Jan. 18, 2013.
U.S. Appl. No. 13/601,937, Non-Final Office Action mailed Jun. 10, 2013.
U.S. Appl. No. 13/601,937, Requirement for Restriction/Election mailed Feb. 27, 2013.
U.S. Appl. No. 13/621,722, Requirement for Restriction/Election mailed Jan. 31, 2013.
U.S. Appl. No. 13/621,722, Final Office Action mailed Oct. 25, 2013.
U.S. Appl. No. 13/621,722, Non-Final Office Action mailed May 9, 2013.
U.S. Appl. No. 13/621,722, Notice of Allowance and Examiner Initiated Interview Summary mailed Jan. 10, 2014.

(56) References Cited

OTHER PUBLICATIONS

U.S. Appl. No. 13/628,039, Non-Final Office Action mailed Jun. 4, 2013.
U.S. Appl. No. 13/628,039, Notice of Allowance and Examiner-Initiated Interview Summary mailed Feb. 20, 2014.
U.S. Appl. No. 13/628,039, Requirement for Restriction/Election mailed Mar. 7, 2013.
U.S. Appl. No. 13/630,757, Requirement for Restriction/Election mailed Jun. 12, 2014.
U.S. Appl. No. 13/650,018, Non-Final Office Action mailed Dec. 23, 2013.
U.S. Appl. No. 13/650,018, Requirement for Restriction/Election mailed Aug. 22, 2013.
U.S. Appl. No. 13/650,024, Non-Final Office Action mailed Jul. 2, 2013.
U.S. Appl. No. 13/650,024, Notice of Allowance mailed Oct. 17, 2013.
U.S. Appl. No. 13/852,116, Non-Final Office Action mailed Mar. 26, 2014.
U.S. Appl. No. 13/865,974, Non-Final Office Action mailed May 2, 2014.
U.S. Appl. No. 13/865,974, Requirement for Restriction/Election mailed Jan. 29, 2014.
U.S. Appl. No. 13/889,214, Non-Final Office Action mailed Sep. 18, 2013.
U.S. Appl. No. 13/889,214, Notice of Allowance mailed Apr. 28, 2014.
U.S. Appl. No. 13/889,221, Non-Final Office Action mailed Sep. 6, 2013.
U.S. Appl. No. 13/889,221, Notice of Allowance mailed Apr. 24, 2014.
U.S. Appl. No. 13/941,346, Non-Final Office Action mailed Jan. 21, 2014.
U.S. Appl. No. 13/941,346, Non-Final Office Action mailed Jun. 26, 2014.
U.S. Appl. No. 13/941,353, Requirement for Restriction/Election mailed Jan. 16, 2014.
U.S. Appl. No. 13/941,357, Non-Final Office Action mailed Jun. 3, 2014.
U.S. Appl. No. 13/941,357, Requirement for Restriction/Election mailed Jan. 7, 2014.
U.S. Appl. No. 12/772,173, Notice of Allowance mailed Jul. 10, 2013.
Urano, et al., "Effect of Osmotic Stabilizers on Protoplast Generation of *Chlorella ellipsoidea* Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2):155-159, (2003).
Vazquez-Bermudez et al., "Uptake of 2-Oxoglutarate in *Synechococcus* Strains Transformed with the *Escherichia coli* kgtP Gene," Journal of Bacteriology, 182(1):211-215, (2000).
Walker et al., "Characterization of the *Dunaliella tertiolecta* RbcS Genes and Their Promoter Activity in *Chlamydomonas reinhardtii*," Plant Cell Rep, 23(10-11):727-735, (2005).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).
Whisstock et al., "Prediction of protein function from protein sequence and structure," Quarterly Reviews of Biophysics, 36(3):307-340, (2003).
Whittle et al., "Engineering Δ9-16:0-Acyl Carrier Protein (ACP) Desaturase Specificity Based on Combinatorial Saturation Mutagenesis and Logical Redesign of the Castor Δ9-18:0-ACP Desaturase," The Journal of Biological Chemistry, 276(24):21500-21505, (2001).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45):26782-26785, (1995).
Witkowski et al., "Conversion of a β-Ketoacyl Synthase to a Malonyl Decarboxylase by Replacement of the Active-Site Cysteine with Glutamine," Biochemistry, 38:11643-11650, (1999).
Wolk et al., "Construction of Shuttle Vectors Capable of Conjugative Transfer From *Escherichia coli* to Nitrogen-Fixing Filamentous Cyanobacteria," Proc Natl Acad Sci U S A., 81(5):1561-1565, (1984).
Wong et al., "*Arabidopsis thaliana* small subunit leader and transit peptide enhance the expression of *Bacillus thuringiensis* proteins in transgenic plants," Plant Mol Biol, 20(1):81-93, (1992).
Wu et al., "Comparative study on Liposoluble Compounds in Autotrophic and Heterotrophic *Chlorella protothecoides*," Acta Botanica Sinica, 35(11);849-858, (1992).
Xiong et al., "High-density fermentation of microalga *Chlorella protothecoides* in bioreactor for microbio-diesel production," Appl. Microbiol. Biotechnol., 78:29-36, (2008).
Yamada et al., "Alternative expression of a chitosanase gene produces two different proteins in cells infected with *Chlorella* virus CVK2," Virology, 230(2):361-368, (1997).
Yamada et al., "*Chlorella* viruses," Adv Virus Res, 66:293-336, (2006).
Yuan et al., "Modification of the substrate specificity of an acyl-acyl carrier protein thioesterase by protein engineering," Proc. NatL Acad. Sci. USA, Biochemistry, 92:10639-10643, (1995).
Zhang et al., "Mello enzyme: the controlling activity for lipid production? Overexpression of malic enzyme in *Mucor circinelloides* leads to a 2.5-fold increase in lipid accumulation," Microbiology, 153(7):2013-2025, (2007).
Zurawski et al., "Nucleotide sequence of the gene for the Mr 32,000 thylakoid membrane protein from *Spinacia oleracea* and *Nicotiana debneyi* predicts a totally conserved primary translation product of Mr 38,950," Proc Natl Acad Sci, 79(24):7699-7703, (1982).
"Enzymatic Assay of INVERTASE (EC 3.2.1.26)," Sigma-Aldrich Co. LLC., (1999). Retrieved from the Internet Aug. 21, 2012: < http://www.sigmaaldrich.com/etc/medialib/docs/Sigma/General_Information/invertase_temp_25.Par.0001.File.tmp/invertase_temp_25.pdf.
A Look Back at the U.S. Department of Energy's Aquatic Species Program: Biodiesel from Algae, NREL/TP-580-24190, John Sheehan, Terri Dunahay, John Benemann and Paul Roessler, (1998).
Alberto et al., "Crystal structure of inactivated *Thermotoga maritima* invertase in complex with the trisaccharide substrate raffinose," Biochem. J., 395:457-462 (2006).
Angerbauer et al., "Conversion of sewage sludge into lipids by *Lipomyces starkeyi* for biodiesel production," Bioresource Technology, 99:3051-3056, (2008).
Bergh et al., "Expression of the *Saccharomyces cerevisiae* glycoprotein invertase in mouse fibroblasts: Glycosylation, secretion, and enzymatic activity," Proc. Natl. Acad. Sci. USA, 84:3570-3574, (1987).
Bonaventure et al., "Disruption of the FATB Gene in *Arabidopsis* Dethonstrates an Essential Role of Saturated Fatty Acids in Plant Growth," The Plant Cell 15:1020-1033, (2003).
Broun et al., "A bifunctional oleate 12-hydroxylase: desaturase from *Lesquerella fendleri*," The Plant Journal, 13(2):201-210, (1998).
Canakci et al., "Biodiesel production from oils and fats with high free fatty acids," Transactions of the ASAE, 44(6):1429-1436, (2001).
Canam, "An Investigation of the Physiological Roles and Enzymatic Properties of Invertases in Tobacco and Hybrid Poplar," Thomas Benjamin Canam, 165 pages, (2008).
Carlson et al., "The Secreted Form of Invertase in *Saccharomyces cerevisiae* Is Synthesized from mRNA Encoding a Signal Sequence," Molecular and Cellular Biology,3(3):439-447, (1983).
Cartens et al,. "Eicosapentaenoic Acid (20:5n-3) from the Marine Microalga *Phaeodactylum tricornutum*," Journal of the American Oil Chemists' Society, 73(8):1025-1031, (1996).

(56) References Cited

OTHER PUBLICATIONS

Chen et al., "High cell density culture of microalgae in heterotrophic growth," Trends in Biotechnology, 14:421-426, (1996).
Cheng et al., "Sugars modulate an unusual mode of control of the cell-wall invertase gene (Incw1) through its 3'untranslated region in a cell suspension culture of maize," Proc. Natl. Acad. Sci. USA, 96:10512-10517, (1999).
Chisti et al., "Biodiesel from microalgae," Biotechnology Advances, 25:294-306, (2007).
Cho et al., "Molecular cloning and expression analysis of the cell-wall invertase gene family in rice (*Oryza sativa* L.)," Plant Cell Rep, 24:225-236, (2005).
Courchesne et al., "Enhancement of Lipid Production Using Biochemical, Genetic and Transcription Factor Engineering Approaches," J Biotechnol. Epub, 141(1-2):31-41, (2009).
Covello et al., "Functional Expression of the Extraplastidial *Arabidopsis thaliana* Oleate Desaturase Gene (FAD2) in *Saccharomyces cerevisiae*," Plant Physiol., 111:223-226, (1996).
Dai et al., "Biodiesel generation from oleaginous yeast *Rhodotorula glutinis* with xylose assimilating capacity," African Journal of Biotechnology, 6(18):2130-2134, (2007).
De Coninck et al., "*Arabidopsis* AtcwINV3 and 6 are not invertases but are fructan exohydrolases (FEHs) with different substrate specificities," Plant, Cell and Environment, 28,:432-443, (2005).
Dehesh et al., "Production of high levels of 8:0 and 10:0 fatty acids in transgenic canola by overexpression of Ch FatB2, a thioesterase cDNA from *Cuphea hookeriana*," The Plant Journal, 9(2):167-172, (1996).
Demirbas, "Fuel Conversional Aspects of Palm Oil and Sunflower Oil," Energy Sources, 25:457-466, (2003).
Deng et al., "Ionic Liquid as a Green Catalytic Reaction Medium for Esterifications," J. Mol. Catalysis A: Chemical, 165:33-36, (2001).
Dimou et al., "Genes coding for a putative cell-wall invertase and two putative monosaccharide/H+ transporters are expressed in roots of etiolated *Glycine max* seedlings," Plant Science, 169:798-804, (2005).
Dormann et al., "Cloning and Expression in *Escherichia coli* of a Novel Thioesterase from *Arabidopsis thaliana* Specific for Long-Chain Acyl-Acyl Carrier Proteins," Archives of Biochemistry and Biophysics, 316(1):612-618, 1995.
Dunahay et al., "Genetic Engineering of Macroalgae for Fuel Production," Applied Biochemistry and Biotechnology, 34/35:331-339 (1992).
Eccleston et al., "Medium-chain Fatty Acid Biosynthesis and Utilization in *Brassica mapus* Plants Expressing Lauroyl-Acyl Carrier Protein Thioesterase," Planta 198:46-53, (1996).
Ehneβ et al., "Co-ordinated induction of mRNAs for extracellular invertase and a glucose transporter in *Chenopodium rubrum* by cytokinins," The Plant Journal, 11(3):539-548, (1997).
European Search Report and European Search Opinion for application EP08769988 mailed Jul. 1, 2011.
European Search Report and European Search Opinion for application EP11158642 mailed Jul. 1, 2011.
Ferrentino, "Microalgal oil extraction and in situ transesterification," University of New Hampshire, Pub. No. MT 1447885, 93 pages, (2007).
Ferrentino, et al., "Microalgal Oil Extraction and In-situ Transesterification," AIChE Annual Mtg, San Francisco, CA, Nov. 11-13, 2006. Abstract.
Forster et al., "Citric acid production from sucrose using a recombinant strain of the yeast *Yarrowia lipolyticae*," Appl Microbiol Biotechnol, 75:1409-1417, (2007).
Foyer et al., "Sucrose and Invertase, an Uneasy Alliance," Iger Innovations, pp. 18-21, (1997).
Fukuda et al., "Biodiesel Fuel Production by Transesterification of Oils," J. Biosci. Bioeng., 92(5):405-416, (2001).
Gallagher et al., "Isolation and characterization of a cDNA clone from *Lolium temulentum* L. encoding for a sucrose hydrolytic enzyme which shows alkaline/neutral invertase activity," Journal of Experimental Bota, 49(322.):789-795, (1998).

Gascon et al., "Comparative Study of the Properties of the Purified Internal and External Invertases from Yeast," The Journal of Biological Chemistry, 243(7):1573-1577, (1968).
Godt et al., "Regulation and Tissue-Specific Distribution of mRNAs for Three Extracellular Invertase Isoenzymes of Tomato Suggests an Important Function in Establishing and Maintaining Sink Metabolism," Plant Physiol, 115:273-282, (1997).
Goetz et al., "The different pH optima and substrate specificities of extracellular and vacuolar invertases from plants are determined by a single amino-acid substitution," The Plant Journal, 20(6):707-711, (1999).
Grinna et al., "Size Distribution and General Structual Features of N-Linked Oligosaccharides from the Methylotrophic Yeast, *Pichia pastoris*," Yeast, 5:107-115, (1989).
Haas et al., "The General Applicability of in Situ Transesterification for the Production of Fatty Acid Esters from a Variety of Feedstocks," J Am Oil Chem Soc, 84:963-970, (2007).
Hajirezaeil et al., "Impact of elevated cytosolic and apoplastic invertase activity on carbon metabolism during potato tuber development," Journal of Experimental Botany, GMP Special Issue, 51:439-445, (2000).
Henderson et al., "Lipid Composition and Biosynthesis in the Marine Dinoflagellate *Crypthecodznzum cohnii*," Phytochem. 27(6)1679-1683 (1988).
Hodge, "Chemistry and Emissions of NExBTL," Neste Oil, (2006). [Retrieved from the Internet Jan. 10, 2012: <http://bioenergy.ucdavis.edu/downloads/Neste_NExBTL_Enviro_Benefits_ofparaffins.pdf>]; p. 4.
Hu et al., "Microalgal Triacylglycerols as Feedstocks for Biofuel Production: Perspectives and Advances," The Plant Journal 54:621-639, (2008).
Huber et al., "Production of Liquid Alkanes by Aqueous-Phase Processing of Biomass-Derived Carbohydrates," Science, 308:1446-1450, (2005).
Huber et al., "Synthesis of Transportation Fuels from Biomass: Chemistry, Catalysts, and Engineering," Chem. Rev., 106: 4044-4098, (2006).
Jaworski et al., "Industrial oils from transgenic plants," Current Opinion in Plant Biology, 6:178-184, (2003).
Ji et al., "The rice genome encodes two vacuolar invertases with fructan exohydrolase activity but lacks the related fructan biosynthesis genes of the Pooideae," New Phytologist, 173:50-62, (2007).
Kern et al., "Stability, quaternary structure, and folding of internal, external, and core-glycosylated invertase from yeast," Protein Sci., 1:120-131, (1992).
Kessler et al., "Physiological and Biochemical Contributions to the Taxonomy of the Genus *Prototheca* III. Utilization of Organic Carbon and Nitrogen Compounds," Arch Microbiol, 132:103-106, (1982).
Krinsky et al., "The Appearance of Neoxanthin during the Regreening of Dark-grown *Euglena*," Plant Physiol. 39(3):441-445 (1964).
Lalonde et al., "The Dual Function of Sugar Carriers: Transport and Sugar Sensing," The Plant Cell 11:707-726, (1999).
Lammens et al., "*Arabidopsis thaliana* cell wall invertase in complex with ligands," HASYLAB, Annual Report 2006, Part II, Scientific User Contributions Part II, Protein Crystallography at EMBL Beamlines, pp. 61-62, (2006). [Retrieved from the Internet Aug.
Lara et al., "Extracellular Invertase Is an Essential Component of Cytokinin-Mediated Delay of Senescence," The Plant Cell, 16:1276-1287, (2004).
Le Roy et al., "Unraveling the Difference between Invertases and Fructan Exohydrolases: A Single Amino Acid (Asp-239) Substitution Transforms *Arabidopsis* Cell Wall Invertase1 into a Fructan 1-Exohydrolase," Plant Physiology, 145:616-625, (2007).
Leon-Banares et al., "Transgenic microalgae as green cell-factories," Trends in Biotechnology, 22(1):45-52, (2004).
Li et al., "Large-scale biodiesel production from microalga *Chlorella protothecoides* through heterotrophic cultivation in bioreactors," Biotechnology and Bioengineering, 98(04):764-771, (2007).
Li et al., "Articles: Biocatalysts and Bioreactor Design, Biofuels From Microalgae," Biotechnol. Prog., 24:815-820, (2008).

(56) References Cited

OTHER PUBLICATIONS

Li et al., "DNA variation at the invertase locus invGE/GF is associated with tuber quality traits in populations of potato breeding clones," Genetics, 40 pages, (2005). Published on Mar. 31, 2005 as 10.1534/genetics.104.040006.
Li et al., "Enzymatic transesterification of yeast oil for biodiesel fuel production," The Chinese Journal of Process Engineering, 07(01):137-140 (2007), and machine translation.
Liras et al., "Biosynthesis and Secretion of Yeast Invertase Effect of Cycloheximide and 2-Deoxy-D-glucose," Eur. J. Biochem., 23:160-165, (1971).
Liu et al., "Biodiesel production by direct methanolysis of oleaginous microbial biomass," Journal of Chemical Technology and Biotechnology, 82:775-780, (2007).
Mayer et al., A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Resid.
Meng et al., "Biodiesel production from oleaginous microorganisms," Renewable Energy, 34:1-5, (2009).
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of *Chlorella protothecoides*," J. Biotech., 110:85-93, (2004).
Mitsljhashi et al., "Differential Expression of Acid Invertase Genes during Seed Germination in *Arabidopsis thaliana*," Biosci. Biotechnol. Biochem, 68(3):602-608, (2004).
Neigeborn et al., "Genes Affecting the Regulation of Suc2 Gene Expression by Glucose Repression in *Saccharomyces cerevisiae*," Genetics, 108:845-858, (1984).
Neigeborn et al., "Mutations Causing Constitutive Invertase Synthesis in Yeast: Genetic Interactions with snf Mutations," Genetics, 115:247-253, (1987).
Nguyen-Quoc et al., "A role for 'futile cycles' involving invertase and sucrose synthase in sucrose metabolism of tomato fruit," Journal of Experimental Botany, 52(358):881-889, (2001).
O'Mullan et al., "Purification and some properties of extracellular invertase B from *Zymomonas rrtobiris*," Appl Microbiol Biotechnol, 38:341-346, (1992).
Otles et al., "Fatty Acid Composition of *Chlorella* and *Spirulina* Microalgae Species," Journal of AOAC International, 84(6)1708-1714, (2001).
Pagny et al., "Fusion with HDEL Protects Cell Wall Invertase from Early Degradation when N-glycosylation is Inhibited," Plant Cell Physiol., 44(2):173-182 , (2003).
PCT International Preliminary Report on Patentability (Chapter I) of May 31, 2011 for application PCT/US09/066142.
PCT International Preliminary Report on Patentability (Chapter I) of Aug. 13, 2012 for application PCT/US11/38463.
PCT International Preliminary Report on Patentability (Chapter I) of Dec. 7, 2009 for application PCT/US08/65563.
PCT International Search Report for application PCT/US2011/032582 mailed Aug. 9, 2011.
PCT International Search Report for application PCT/US2011/038463 mailed Jan. 18, 2012.
PCT International Search Report for application PCT/US2012/023696 mailed May 23, 2012.
PCT International Search Report for application PCT/US2012/036690 mailed Aug. 30, 2012.
PCT International Search Report of Aug. 20, 2010 for application PCT/US2009/066142.
PCT International Search Report of Nov. 5, 2010 for application PCT/US2009/066141.
PCT International Search Report of Nov. 6, 2008 for application PCT/US08/65563.
PCT Written Opinion of the International Search Authority of Aug. 20, 2010 for application PCT/US2009/066142.
PCT Written Opinion of the International Searching Authority for application PCT/US2011/032582 mailed Aug. 9, 2011.
PCT Written Opinion of the International Searching Authority for application PCT/US2011/038463 mailed Jan. 18, 2012.
PCT Written Opinion of the International Searching Authority for application PCT/US2012/023696 mailed May 23, 2012.
PCT Written Opinion of the International Searching Authority for application PCT/US2012/036690 mailed Aug. 30, 2012.
PCT Written Opinion of the International Searching Authority of Nov. 5, 2010 for application PCT/US2009/066141.
PCT Written Opinion of the International Searching Authority of Nov. 6, 2008 for application PCT/US08/65563.
Perlman et al., "Mutations affecting the signal sequence alter synthesis and secretion of yeast invertase," Proc. Natl. Acad. Sci. USA, 83:5033-5037, (1986).
Petkov et al., "Which are fatty acids of the green alga *Chlorella*?," Biochemical Systematics and Ecology, 35:281-285, (2007).
Pons et al., "Three Acidic Residues Are at the Active Site of a β-Propeller Architecture in Glycoside Hydrolase Families 32, 43, 62, and 68," PROTEINS: Structure, Function, and Bioinformatics , 54:424-432, (2004).
Proels et al., "Novel mode of hormone induction of tandem tomato invertase genes in floral tissues," Plant Molecular Bioingy , 52:191-201, (2003).
Reddy et al., "Characterization of the Glycosylation Sites in Yeast External inver," The Journal of Biological Chemistry, 263(15):6978-6955, (1988).
Riesmeier et al., "Potato Sucrose Transporter Expression in Minor Veins Indicates a Role in Phloem Loading," The Plant Cell, 5:1591-1598, (1993).
Ritsema et al., "Engineering fructan metabolism in plants," J. Plant Physiol., 160:811-820, (2003).
Roig et al., "*Candida albicans* UBI3 and 11814 promoter regions confer differential regulation of invertase production to *Saccharomyces cerevisiae* cells in response to stress," Int Microbiol, 5:33-36, (2002).
Roitsch et al., "Expression of yeast invertase in oocytes from *Xenopus laevis*," Eur. J. Biochem, 181:733-739, (1989).
Roitsch et al., "Extracellular invertase: key metabolic enzyme and PR protein," Journal of Experimental Botany, Regulation of Carbon Metabolism Special Issue, 54(382):513-524, (2003).
Roitsch et al., "Function and regulation of plant invertases: sweet sensations," TRENDS in Plant Science, .9(12):606-613 , (2004).
Roitsch et al., "Induction of Apoplastic Invertase of *Chenopodium rubrum* by ID-Glucose and a Glucose Analog and Tissue-Specific Expression Suggest a Role in Sink-Source Regulation," Plant Physiol., 108:285-294, (1995).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Sergeeva et al., "Vacuolar invertase regulates elongationof *Arabidopsis thaliana* roots as revealed by QTL and mutant analysis," PNAS, 103(8):2994-2999, (2006).
Sherson et al., "Roles of cell-wall invertases and monosaccharide transporters in the growth and development of *Arabidopsis*," Journal of Experimental Botany, 54(382):525-531, (2003).
Simpson et al., "Requirements for mini-exon inclusion in potato invertase mRNAs provides evidence for exon-scanning interactions in plants," RNA, 6:422-433, (2000).
Sinha et al., "Metabolizable and Non-Metabolizable Sugars Activate Different Signal Transduction Pathways in Tomato," Plant Physiology, 128:1480-1489, (2002).
Sitthiwong et al., "Changes in Carbohydrate Content and the Activites of Acid Invertase, Sucrose Synthase and Sucrose Phosphate Synthase in Vegetable Soybean During Fruit Development," Asian Journal of Plant Sciences, 4(6):684-690, (2005).
Sonnewald et al., "Transgenic tobacco plants expressing yeast-derived invertase in either the cytosol, vacuole or apoplast: a powerful tool for studying sucrose metabolism and sink/source interactions," The Plant Journal, 1(1):95-106, (1991).
Spolaore et al., "Commercial Applications of Microalgae," J. Biosci. Bioeng. 101(2):87-96 (2006).
Suh et al., "What limits production of unusual monoenoic fatty acids in transgenic plants?," Planta, 215:584-595, (2002).

(56) References Cited

OTHER PUBLICATIONS

Trimble et al., "Structure of Oligosaccharides on *Saccharomyces* SUC2 Invertase Secreted by the Methylotrophic Yeast *Pichia pastoris*," J. Biol. Chem., 266(34):22807-22817, (1991).
Trimble et al., "Structure of oligosaccharides on *Saccharomyces* SUC2 Invertase Secreted by the Methylotrophic Yeast *Pichia pastoris*," The Journal of Biological Chemistry, 266(34):22807-22817, (1991).
Tymowska-Lalanne et al., "Expression of the *Arabidopsis thaliana* invertase gene family," Planta, 207: 259-265, (1998).
U.S. Appl. No. 12/131,766, Advisory Action mailed Oct. 13, 2011.
U.S. Appl. No. 12/131,766, Non-Final Office Action mailed Aug. 1, 2011.
U.S. Appl. No. 12/131,766, Non-Final Office Action mailed Nov. 23, 2010.
U.S. Appl. No. 12/131,766, Non-Final Office Action mailed Dec. 10, 2009.
U.S. Appl. No. 12/131,766, Requirement for Restriction/Election mailed Aug. 5, 2009.
U.S. Appl. No. 12/131,766, Requirement for Restriction/Election mailed Aug. 17, 2010.
U.S. Appl. No. 12/131,773, Final Office Action mailed Mar. 21, 2011.
U.S. Appl. No. 12/131,773, Non-Final Office Action mailed Jun. 25, 2010.
U.S. Appl. No. 12/131,773, Non-Final Office Action mailed Dec. 15, 2009.
U.S. Appl. No. 12/131,773, Requirement for Restriction/Election mailed Aug. 6, 2009.
U.S. Appl. No. 12/131,793, Final Office Action mailed Mar. 30, 2010.
U.S. Appl. No. 12/131,793, Non-Final Office Action mailed Jun. 21, 2012.
U.S. Appl. No. 12/131,793, Non-Final Office Action mailed Sep. 16, 2009.
U.S. Appl. No. 12/131,793, Non-Final Office Action mailed Nov. 13, 2012.
U.S. Appl. No. 12/131,793, Requirement for Restriction/Election mailed Aug. 6, 2009.
U.S. Appl. No. 12/131,804, Final Office Action mailed Feb. 2, 2011.
U.S. Appl. No. 12/131,804, Non-Final Office Action mailed Oct. 26, 2012.
U.S. Appl. No. 12/131,804, Non-Final Office Action mailed Mar. 3, 2010.
U.S. Appl. No. 12/131,804, Non-Final Office Action mailed Jun. 7, 2012.
U.S. Appl. No. 12/131,804, Requirement for Restriction/Election mailed Sep. 17, 2009.
U.S. Appl. No. 12/131,804, Requirement for Restriction/Election mailed Nov. 18, 2009.
U.S. Appl. No. 12/194,389, Final Office Action mailed Jan. 5, 2011.
U.S. Appl. No. 12/194,389, Non-Final Office Action mailed Feb. 4, 2010.
U.S. Appl. No. 12/194,389, Requirement for Restriction/Election mailed Oct. 5, 2010.
U.S. Appl. No. 12/194,389, Requirement for Restriction/Election mailed Nov. 2, 2009.
U.S. Appl. No. 12/628,140, Non-Final Office Action mailed Oct. 30, 2012.
U.S. Appl. No. 12/628,144, Final Office Action mailed Nov. 16, 2010.
U.S. Appl. No. 12/628,144, Final Office Action mailed Dec. 5, 2011.
U.S. Appl. No. 12/628,144, Non-Final Office Action mailed Jun. 7, 2011.
U.S. Appl. No. 12/628,144, Non-Final Office Action mailed Jul. 8, 2010.
U.S. Appl. No. 12/628,147, Examiner Interview Summary Record mailed Mar. 3, 2011.
U.S. Appl. No. 12/628,147, Final Office Action mailed Jul. 12, 2012.
U.S. Appl. No. 12/628,147, Final Office Action mailed Oct. 1, 2010.
U.S. Appl. No. 12/628,147, Non-Final Office Action mailed May 25, 2010.
U.S. Appl. No. 12/628,147, Non-Final Office Action mailed Oct. 25, 2011.
U.S. Appl. No. 12/628,149, Non-Final Office Action mailed Jun. 25, 2010.
U.S. Appl. No. 12/628,149, Non-Final Office Action mailed Sep. 16, 2010.
U.S. Appl. No. 12/628,149, Notice of Allowance mailed Dec. 15, 2010.
U.S. Appl. No. 12/628,150, Non-Final Office Action mailed Apr. 29, 2010.
U.S. Appl. No. 12/628,150, Non-Final Office Action mailed Oct. 13, 2010.
U.S. Appl. No. 12/628,150, Notice of Allowance mailed Mar. 21, 2011.
U.S. Appl. No. 12/642,487, Requirement for Restriction/Election mailed Jun. 18, 2012.
U.S. Appl. No. 12/642,487, Requirement for Restriction/Election mailed Nov. 8, 2012.
U.S. Appl. No. 12/772,163, Non-Final Office Action mailed May 25, 2012.
U.S. Appl. No. 12/772,163, Requirement for Restriction/Election mailed Jun. 24, 2011.
U.S. Appl. No. 12/772,164, Final Office Action mailed May 24, 2012.
U.S. Appl. No. 12/772,164, Non-Final Office Action mailed Oct. 12, 2011.
U.S. Appl. No. 12/772,164, Requirement for Restriction/Election mailed Jul. 20, 2011.
U.S. Appl. No. 12/772,170, Final Office Action mailed Feb. 21, 2012.
U.S. Appl. No. 12/772,170, Non-Final Office Action mailed Sep. 13, 2011.
U.S. Appl. No. 12/772,170, Requirement for Restriction/Election mailed Jul. 13, 2011.
U.S. Appl. No. 12/772,173, Final Office Action mailed May 7, 2012.
U.S. Appl. No. 12/772,173, Non-Final Office Action mailed Dec. 16, 2011.
U.S. Appl. No. 12/772,173, Requirement for Restriction/Election mailed Oct. 26, 2011.
U.S. Appl. No. 12/772,174, Non-Final Office Action mailed Nov. 29, 2011.
U.S. Appl. No. 12/772,174, Requirement for Restriction/Election mailed Aug. 10, 2011.
U.S. Appl. No. 12/981,409, Non-Final Office Action mailed Jan. 6, 2012.
U.S. Appl. No. 12/981,409, Notice of Allowance mailed May 29, 2012.
U.S. Appl. No. 12/981,409, Requirement for Restriction/Election mailed Apr. 19, 2012.
U.S. Appl. No. 12/981,409, Requirement for Restriction/Election mailed Oct. 28, 2011.
U.S. Appl. No. 13/029,061, Requirement for Restriction/Election mailed Nov. 29, 2011.
U.S. Appl. No. 13/045,500, Non-Final Office Action mailed Mar. 9, 2012.
U.S. Appl. No. 13/045,500, Final Office Action mailed Sep. 26, 2012.
U.S. Appl. No. 13/073,757, Non-Final Office Action mailed Aug. 15, 2011.
U.S. Appl. No. 13/073,757, Non-Final Office Action mailed Dec. 29, 2011.
U.S. Appl. No. 13/073,757, Notice of Allowance mailed Apr. 17, 2012.
U.S. Appl. No. 13/118,365, Requirement for Restriction/Election mailed Oct. 11, 2012.
U.S. Appl. No. 13/406,417, Non-Final Office Action mailed Nov. 5, 2012.
U.S. Appl. No. 13/406,417, Requirement for Restriction/Election mailed Apr. 30, 2012.
U.S. Appl. No. 13/550,412, Non-Final Office Action mailed Oct. 29, 2012.
U.S. Appl. No. 12/628,147, Notice of Allowance and Examiner Initiated Interview Summary mailed Aug. 7, 2012.
Van De Loo et al., "An oleate 12-hydroxylase from *Ricinus communis* L. is a fatty acyl desaturase homolog," Proc. Natl. Acad. Sci. USA, 92:6743-6747, (1995).

(56) References Cited

OTHER PUBLICATIONS

Van Gerpen, "Commercial Biodiesel Production," Oilseed and Biodiesel Workshop, Billings, Montana, Jan. 9, 2008, downloaded from http://www.deq.state.mt.us/Energy/bioenergy/Biodiesel_Production_Educ_Presentations/10Montana_Production_Jan_2008_JVP.pdf on.
Van Gerpen, Fuel Processing Technology, 86:1097-1107 (2005).
Voetz et al., "Three Different cDNAs Encoding Acyl Carrier Proteins from *Cuphea lanceolata*," Plant Physiol., 106:785-786, (1994).
Weber et al., "Invertases and life beyond sucrose cleavage," Trends in Plant Science, 5(2):47-48, (2000).
Wu et al., "A Comparative Study of Gases Generated from Simulant Thermal Degradation of Autotrophic and Heterotrophic *Chlorella*," Progress in Natural Science, 2(4):311-318, (1992).
Wu et al., "New Discoveries in Study on Hydrocarbons From Thermal Degradation of Heterotrophically Yellowing Algae," Science in China, 37(3):326-35, (1994).
Xu et al., "High quality biodiesel production from a microalga *Chlorella protothecoides* by heterotrophic growth in fermenters," Journal of Biotechnology, 126:499-507, (2006).
Yanase et al., "Expression of the Extracellular Levansucrase and Invertase Genes from *Zymomonas mobilis* in *Escherichia coli* Cells," Biosci, Biotechnol. Biochem., 62(9):1802-1805, (1998).
Zárate et al., "Characterization of the heterologous invertase produced by *Schizosaccharomyces pombe* from the SUC2 gene of *Saccharomyces cerevisiae*," Journal of Applied Bacteriology, 80:45-52, (1996).
Zarowska et al., "Production of Citric Acid on Sugar Beet Molasses by Single and Mixed Cultures of *Yarrowia lipolytica*," Electronic Journal of Polish Agricultural Universities, 4(2):1-7, (2001). [Retrieved from the Internet Oct. 3, 2011: <URL: http://.
Zhang et al., "Cloning and Characterization of an Invertase Gene From the Garden Pea (*Pisum sativum* L)," Jiesheng Zhang, M.S. Plant Biology Thesis, 82 pages, (2003).
Zhao et al., "Toward cheaper microbial oil for biodiesel oil," China Biotechnology, 25(02):8-11 (2005).
GenBank Accession No. AAC49001.1, May 1995. [Retrieved from the Internet Oct. 14, 2014: <URL: http://www.ncbi.nlrrtnih.gov/protein/595955?sat=13&satkey=6522409>].
Jones et al., "Palmitoyl-Acyl Carrier Protein (ACP) Thioesterase and the Evolutionary Origin of Plant Acyl-ACP Thioesterases," Plant Cell, 7:359-371, (1995).
Bonaventure et al., "Disruption of the FATB Gene in Arabidopsis Dethonstrates an Essential Role of Saturated Fatty Acids in Plants Growth," The Plant Cell 15:1020-1033, (2003).
Chasan, "Engineering Fatty Acids—The Long and Short of it," Plant Cell, 7:235-237, (1995).
Dehesh et al., "KAS IV: a 3-ketoacyl-ACP synthase from *Cuphea* sp. is a medium chain specific condensing enzyme," The Plant Journal, 15:383-390, (1998).

Dehesh et al., "Production of high levels of 8:0 and 10:0 fatty acids in transgenic canola by overexpression of Ch FatB2, a thioesterase cDNA from *Cuphea hookeriana*," The Plant Journal, 9(2): 167-172, (1996).
Dormann et al., "Cloning and Expression in *Escherichia coli* of a Novel Thioesterase from Arabidopsis thaliana Specific for Long-Chain Acyl-Acyl Carrier Protiens," Archives of Biochemistry and Biophysics, 316(1):612-618, (1995).
Eccleston et al., "Medium-chain Fatty Acid Biosynthesis ad Utilization in *Brassica* Mapus Plants Expressing Lauroyl-Acyl Carrier Protein Thioesterase," Planta 198:46-53, (1996).
Facciotti et al., "Improved stearate phenotype in transgenic canola expressing a modified acyl-acyl carrier protein thioesterase," Nat Biotechnol., 17(6):593-597, (1999).
Heise et al., "Factors Controlling Medium-Chain Fatty Acid Synthesis In Plastids From *Cuphea* Embryos," Prog. Lipid Res., 33(1/2):87-95, (1994).
Jha et al., "Cloning and functional expression of an acyl-ACP thioesterase FatB type from *Diploknema (Madhuca) butyracea* seeds in *Escherichia coli*," Plant Physiology and Biochemistry, 44:645-655, (2006).
Mayer et al., Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Caytatic Resid.
Mayer et al., "Identification of amino acid residues involved in substrate specificity of plant acyl-ACP thioesterases using a bioinformatics-guided approach," BMC Plant Biology, 7(1):1-11, (2007).
Mekhedov et al., "Toward a Functional Catalog of the Plant Genome. A Survey of Genes for Lipid Biosynthesis," Plant Physiology, 122:389-401, (2000).
Rehm et al., "Heterologous expression of the acyl-acyl carrier protein thioesterase gene from the plant Umbellularia californica mediates polyhydroxyalkanoate biosynthesis in recombinant *Escherichia coli*," Appl Microbiol Biotechnol, 55:205-209, (2001).
Schütt et al., "The role of acyl carrier protein isoforms from *Cuphea lanceolata* seeds in the de-novo biosynthesis of medium-chain fatty acids," Publication, Planta, 205:263-268, (1998).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from *Cuphea lanceolate*'," Plant Physiol., 106:785-786, (1994).
Wiberg et al., "The distribution of caprylate, caprate and laurate in lipids from developing and mature seeds of transgenic *Brassica napus* L.," Planta, 212:33-40, (2000).
Yuan et al., "Modification of the substrate specificity of an acyl-acyl carrier protein thioesterase by protein engineering," Proc. Natl. Acad. Sci. USA, Biochemistry, 92:10639-10643, (1995).

\* cited by examiner

SEQUENCE LISTING

```
<160> NUMBER OF SEQ ID NOS: 143

<210> SEQ ID NO 1
<211> LENGTH: 1187
<212> TYPE: DNA
<213> ORGANISM: Chlorella sp.

<400> SEQUENCE: 1
gatcagacgg gcctgacctg cgagataatc aagtgctcgt aggcaaccaa ctcagcagct      60
gcttggtgtt gggtctgcag gatagtgttg cagggcccca aggacagcag gggaacttac     120
accttgtccc cgacccagtt ttatggagtg cattgcctca agagcctagc cggagcgcta     180
ggctacatac ttgccgcacc ggtatgaggg gatatagtac tcgcactgcg ctgtctagtg     240
agatgggcag tgctgcccat aaacaactgg ctgctcagcc atttgttggc ggaccattct     300
gggggggcca gcaatgcctg actttcgggt agggtgaaaa ctgaacaaag actaccaaaa     360
cagaatttct tcctccttgg aggtaagcgc aggccggccc gcctgcgccc acatggcgct     420
ccgaacacct ccatagctgt aagggcgcaa acatggccgg actgttgtca gcactctttc     480
atggccatac aaggtcatgt cgagattagt gctgagtaag acactatcac cccatgttcg     540
attgaagccg tgacttcatg ccaacctgcc cctgggcgta gcagacgtat gccatcatga     600
ccactagccg acatgcgctg tcttttgcca ccaaaacaac tggtacaccg ctcgaagtcg     660
tgccgcacac ctccgggagt gagtccggcg actcctcccc ggcgggccgc ggccctacct     720
gggtagggtc gccatacgcc cacgaccaaa cgacgcagga ggggattggg gtagggaatc     780
ccaaccagcc taaccaagac ggcacctata ataataggtg ggggactaa cagccctata      840 tcgcaagctt tgggtgccta tcttgagaag cacgagttgg agtggctgtg tacggtcgac     900
cctaaggtgg gtgtgccgca gcctgaaaca aagcgtctag cagctgcttc tataatgtgt     960
cagccgttgt gtttcagtta tattgtatgc tattgtttgt tcgtgctagg gtggcgcagg    1020
cccacctact gtggcgggcc attggttggt gcttgaattg cctcaccatc taaggtctga    1080
acgctcactc aaacgccttt gtacaactgc agaactttcc ttggcgctgc aactacagtg    1140
tgcaaaccag cacatagcac tcccttacat cacccagcag tacaaca                  1187

<210> SEQ ID NO 2
<211> LENGTH: 1414
<212> TYPE: DNA
<213> ORGANISM: Chlorella ellipsoidea

<400> SEQUENCE: 2
cgctgcgcac cagggccgcc agctcgctga tgtcgctcca aatgcggtcc cccgattttt      60
tgttcttcat cttctccacc ttggtggcct tcttggccag ggccttcagc tgcatgcgca     120
cagaccgttg agctcctgat cagcatcctc aggaggccct tgacaagca agcccctgtg      180
```

```
caagcccatt cacggggtac cagtggtgct gaggtagatg ggtttgaaaa ggattgctcg    240
gtcgattgct gctcatggaa ttggcatgtg catgcatgtt cacaatatgc caccaggctt    300
tggagcaaga gagcatgaat gccttcaggc aggttgaaag ttcctggggg tgaagaggca    360
gggccgagga ttgaggagg aaagcatcaa gtcgtcgctc atgctcatgt tttcagtcag     420
agtttgccaa gctcacagga gcagagacaa gactggctgc tcaggtgttg catcgtgtgt    480
gtggtggggg gggggggtt aatacggtac gaaatgcact tggaattccc acctcatgcc     540
agcggaccca catgcttgaa ttcgaggcct gtggggtgag aaatgctcac tctgccctcg    600
ttgctgaggt acttcaggcc gctgagctca aagtcgatgc cctgctcgtc tatcagggcc    660
tgcacctctg ggctgaccgg ctcagcctcc ttcgcgggca tggagtaggc gccggcagcg    720
ttcatgtccg ggcccaggc agcggtggtg ccataaatgt cggtgatggt ggggaggggg     780
gccgtcgcca caccattgcc gttgctggct gacgcatgca catgtggcct ggctggcacc    840
ggcagcactg gtctccagcc agccagcaag tggctgttca ggaaagcggc catgttgttg    900
gtccctgcgc atgtaattcc ccagatcaaa ggagggaaca gcttggattt gatgtagtgc    960
ccaaccggac tgaatgtgcg atggcaggtc cctttgagtc tcccgaatta ctagcagggc    1020
actgtgacct aacgcagcat gccaaccgca aaaaatgat tgcagaaaa tgaagcggtg      1080 tgtcaatatt tgctgtattt attcgtttta atcagcaacc aagttcgaaa cgcaactatc    1140
gtggtgatca agtgaacctc atcagactta cctcgttcgg caaggaaacg gaggcaccaa    1200
attccaattt gatattatcg cttgccaagc tagagctgat ctttgggaaa ccaactgcca    1260
gacagtggac tgtgatggag tgccccgagt ggtggagcct cttcgattcg gttagtcatt    1320
actaacgtga accctcagtg aagggaccat cagaccagaa agaccagatc tcctcctcga    1380
caccgagaga gtgttgcggc agtaggacga caag                                1414
```

<210> SEQ ID NO 3
<211> LENGTH: 512
<212> TYPE: PRT
<213> ORGANISM: Unknown
<220> FEATURE:
<223> OTHER INFORMATION: Description of Unknown: Yeast sequence

<400> SEQUENCE: 3

```
Met Thr Asn Glu Thr Ser Asp Arg Pro Leu Val His Phe Thr Pro Asn
1               5                   10                  15

Lys Gly Trp Met Asn Asp Pro Asn Gly Leu Trp Tyr Asp Glu Lys Asp
            20                  25                  30

Ala Lys Trp His Leu Tyr Phe Gln Tyr Asn Pro Asn Asp Thr Val Trp
        35                  40                  45

Gly Thr Pro Leu Phe Trp Gly His Ala Thr Ser Asp Asp Leu Thr Asn
    50                  55                  60

Trp Glu Asp Gln Pro Ile Ala Ile Ala Pro Lys Arg Asn Asp Ser Gly
65                  70                  75                  80

Ala Phe Ser Gly Ser Met Val Val Asp Tyr Asn Asn Thr Ser Gly Phe
                85                  90                  95

Phe Asn Asp Thr Ile Asp Pro Arg Gln Arg Cys Val Ala Ile Trp Thr
            100                 105                 110

Tyr Asn Thr Pro Glu Ser Glu Glu Gln Tyr Ile Ser Tyr Ser Leu Asp
        115                 120                 125

Gly Gly Tyr Thr Phe Thr Glu Tyr Gln Lys Asn Pro Val Leu Ala Ala
    130                 135                 140
```

```
Asn Ser Thr Gln Phe Arg Asp Pro Lys Val Phe Trp Tyr Glu Pro Ser
145                 150                 155                 160

Gln Lys Trp Ile Met Thr Ala Ala Lys Ser Gln Asp Tyr Lys Ile Glu
            165                 170                 175

Ile Tyr Ser Ser Asp Leu Lys Ser Trp Lys Leu Glu Ser Ala Phe
        180                 185                 190

Ala Asn Glu Gly Phe Leu Gly Tyr Gln Tyr Glu Cys Pro Gly Leu Ile
    195                 200                 205

Glu Val Pro Thr Glu Gln Asp Pro Ser Lys Ser Tyr Trp Val Met Phe
        210                 215                 220

Ile Ser Ile Asn Pro Gly Ala Pro Ala Gly Gly Ser Phe Asn Gln Tyr
225                 230                 235                 240

Phe Val Gly Ser Phe Asn Gly Thr His Phe Glu Ala Phe Asp Asn Gln
                245                 250                 255

Ser Arg Val Val Asp Phe Gly Lys Asp Tyr Tyr Ala Leu Gln Thr Phe
                260                 265                 270

Phe Asn Thr Asp Pro Thr Tyr Gly Ser Ala Leu Gly Ile Ala Trp Ala
            275                 280                 285

Ser Asn Trp Glu Tyr Ser Ala Phe Val Pro Thr Asn Pro Trp Arg Ser
290                 295                 300

Ser Met Ser Leu Val Arg Lys Phe Ser Leu Asn Thr Glu Tyr Gln Ala
305                 310                 315                 320

Asn Pro Glu Thr Glu Leu Ile Asn Leu Lys Ala Glu Pro Ile Leu Asn
                325                 330                 335

Ile Ser Asn Ala Gly Pro Trp Ser Arg Phe Ala Thr Asn Thr Thr Leu
            340                 345                 350

Thr Lys Ala Asn Ser Tyr Asn Val Asp Leu Ser Asn Ser Thr Gly Thr
            355                 360                 365

Leu Glu Phe Glu Leu Val Tyr Ala Val Asn Thr Thr Gln Thr Ile Ser
    370                 375                 380

Lys Ser Val Phe Ala Asp Leu Ser Leu Trp Phe Lys Gly Leu Glu Asp
385                 390                 395                 400

Pro Glu Glu Tyr Leu Arg Met Gly Phe Glu Val Ser Ala Ser Ser Phe
                405                 410                 415

Phe Leu Asp Arg Gly Asn Ser Lys Val Lys Phe Val Lys Glu Asn Pro
            420                 425                 430

Tyr Phe Thr Asn Arg Met Ser Val Asn Asn Gln Pro Phe Lys Ser Glu
                435                 440                 445

Asn Asp Leu Ser Tyr Tyr Lys Val Tyr Gly Leu Leu Asp Gln Asn Ile
    450                 455                 460

Leu Glu Leu Tyr Phe Asn Asp Gly Asp Val Val Ser Thr Asn Thr Tyr
465                 470                 475                 480

Phe Met Thr Thr Gly Asn Ala Leu Gly Ser Val Asn Met Thr Thr Gly
                485                 490                 495

Val Asp Asn Leu Phe Tyr Ile Asp Lys Phe Gln Val Arg Glu Val Lys
                500                 505                 510

<210> SEQ ID NO 4
<211> LENGTH: 20
<212> TYPE: PRT
<213> ORGANISM: Unknown
<220> FEATURE:
<223> OTHER INFORMATION: Description of Unknown: Yeast sequence

<400> SEQUENCE: 4
```

Met Leu Leu Gln Ala Phe Leu Phe Leu Leu Ala Gly Phe Ala Ala Lys
1               5                   10                  15

Ile Ser Ala Ser
            20

<210> SEQ ID NO 5
<211> LENGTH: 18
<212> TYPE: PRT
<213> ORGANISM: Unknown
<220> FEATURE:
<223> OTHER INFORMATION: Description of Unknown: Higher plant secretion
      signal

<400> SEQUENCE: 5

Met Ala Asn Lys Ser Leu Leu Leu Leu Leu Leu Gly Ser Leu Ala
1               5                   10                  15

Ser Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 6

Met Ala Arg Leu Pro Leu Ala Ala Leu Gly
1               5                   10

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Ala Asn Lys Leu Leu Leu Leu Leu Leu Leu Leu Leu Pro Leu
1               5                   10                  15

Ala Ala Ser Gly
            20

<210> SEQ ID NO 8
<211> LENGTH: 2615
<212> TYPE: DNA
<213> ORGANISM: Saccharomyces cerevisiae

<400> SEQUENCE: 8
gaattcccca acatggtgga gcacgacact ctcgtctact ccaagaatat caaagataca      60
gtctcagaag accaaagggc tattgagact tttcaacaaa gggtaatatc gggaaacctc     120
ctcggattcc attgcccagc tatctgtcac ttcatcaaaa ggacagtaga aaaggaaggt     180
ggcacctaca aatgccatca ttgcgataaa ggaaaggcta tcgttcaaga tgcctctgcc     240
gacagtggtc ccaaagatgg accccccaccc acgaggagca tcgtggaaaa agaagacgtt     300
ccaaccacgt cttcaaagca gtggattga tgtgaacatg gtggagcacg acactctcgt     360
ctactccaag aatatcaaag atacagtctc agaagaccaa agggctattg agactttca     420 acaaagggta atatcgggaa acctcctcgg attccattgc ccagctatct gtcacttcat     480
caaaaggaca gtagaaaagg aaggtggcac ctacaaatgc catcattgcg ataaaggaaa     540

```
ggctatcgtt caagatgcct ctgccgacag tggtcccaaa gatggacccc cacccacgag    600
gagcatcgtg gaaaagaag acgttccaac cacgtcttca aagcaagtgg attgatgtga    660
tatctccact gacgtaaggg atgacgcaca atcccactat ccttcgcaag acccttcctc    720
tatataagga agttcatttc atttggagag acacgctga aatcaccagt ctctctctac     780
aaatctatct ctggcgcgcc atatcaatgc ttcttcaggc cttctttttt cttcttgctg    840
gttttgctgc caagatcagc gcctctatga cgaacgaaac ctcggataga ccacttgtgc    900
actttacacc aaacaagggc tggatgaatg accccaatgg actgtggtac gacgaaaaag    960
atgccaagtg gcatctgtac tttcaataca acccgaacga tactgtctgg gggacgccat   1020
tgttttgggg ccacgccacg tccgacgacc tgaccaattg ggaggaccaa ccaatagcta   1080
tcgctccgaa gaggaacgac tccggagcat tctcgggttc catggtggtt gactacaaca   1140
atacttccgg cttttcaac gataccattg acccgagaca acgctgcgtg ccatatggaa    1200
cttacaacac accggagtcc gaggagcagt acatctcgta tagcctggac ggtggataca   1260
cttttacaga gtatcagaag aaccctgtgc ttgctgcaaa ttcgactcag ttccgagatc   1320
cgaaggtctt ttggtacgag ccctcgcaga agtggatcat gacagcggca aagtcacagg   1380
actacaagat cgaaatttac tcgtctgacg accttaaatc ctggaagctc gaatccgcgt   1440
tcgcaaacga gggctttctc ggctaccaat acgaatgccc aggcctgata gaggtcccaa   1500
cagagcaaga tcccagcaag tcctactggg tgatgtttat ttccattaat ccaggagcac   1560
cggcaggagg ttcttttaat cagtacttcg tcggaagctt taacggaact catttcgagg   1620
catttgataa ccaatcaaga gtagttgatt ttggaaagga ctactatgcc ctgcagactt   1680
tcttcaatac tgacccgacc tatgggagcg ctcttggcat tgcgtgggct tctaactggg   1740
agtattccgc attcgttcct acaaacccct tggaggtcctc catgtcgctc gtgaggaaat   1800
tctctctcaa cactgagtac caggccaacc cggaaaccga actcataaac ctgaaagccg   1860
aaccgatcct gaacattagc aacgctggcc cctggagccg gtttgcaacc aacaccacgt   1920
tgacgaaagc caacagctac aacgtcgatc tttcgaatag caccggtaca cttgaatttg   1980
aactggtgta tgccgtcaat accacccaaa cgatctcgaa gtcggtgttc gcggacctct   2040
ccctctggtt taaaggcctg gaagaccccg aggagtacct cagaatgggt ttcgaggttt   2100
ctgcgtcctc cttcttcctt gatcgcggga acagcaaagt aaaatttgtt aaggagaacc   2160
catattttac caacaggatg agcgttaaca accaaccatt caagagcgaa aacgacctgt   2220
cgtactacaa agtgtatggt ttgcttgatc aaaatatcct ggaactctac ttcaacgatg   2280
gtgatgtcgt gtccaccaac acatacttca tgacaaccgg gaacgcactg ggctccgtga   2340
acatgacgac gggtgtggat aacctgttct acatcgacaa attccaggtg agggaagtca   2400
agtgagatct gtcgatcgac aagctcgagt ttctccataa taatgtgtga gtagttccca   2460
gataagggaa ttagggttcc tatagggttt cgctcatgtg ttgagcatat aagaaaccct   2520
tagtatgtat ttgtatttgt aaaatacttc tatcaataaa atttctaatt cctaaaacca   2580
aaatccagta ctaaaatcca gatcccccga attaa                              2615
```

<210> SEQ ID NO 9  
<211> LENGTH: 22  
<212> TYPE: DNA  
<213> ORGANISM: Artificial Sequence  
<220> FEATURE:  
<223> OTHER INFORMATION: Description of Artificial Sequence: Synthetic primer

```
<400> SEQUENCE: 9
tgttgaagaa tgagccggcg ac                                              22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagtgagcta ttacgcactc                                                 20

<210> SEQ ID NO 11
<211> LENGTH: 541
<212> TYPE: DNA
<213> ORGANISM: Prototheca kruegani

<400> SEQUENCE: 11
tgttgaagaa tgagccggcg agttaaaaag agtggcatgg ttaagaaaaa tactctggag     60
ccatagcgaa agcaagttta gtaagcttag gtcattcttt ttagacccga aaccgagtga    120
tctacccatg atcagggtga agtgttagta aaataacatg gaggcccgaa ccgactaatg    180
ttgaaaaatt agcggatgaa ttgtgggtag gggcgaaaaa ccaatcgaac tcggagttag    240
ctggttctcc ccgaaatgcg tttaggcgca gcagtagcag tacaaataga ggggtaaagc    300
actgtttctt tgtgggctt cgaaagttgt acctcaaagt ggcaaactct gaatactcta    360
tttagatatc tactagtgag accttggggg ataagctcct tggtcaaaag ggaaacagcc    420
cagatcacca gttaaggccc caaaatgaaa atgatagtga ctaaggatgt gggtatgtca    480
aaacctccag caggttagct tagaagcagc aatccttttca agagtgcgta atagctcact    540
g                                                                    541

<210> SEQ ID NO 12
<211> LENGTH: 573
<212> TYPE: DNA
<213> ORGANISM: Prototheca wickerhamii

<400> SEQUENCE: 12
tgttgaagaa tgagccggcg acttaaaata aatggcaggc taagagattt aataactcga     60
aacctaagcg aaagcaagtc ttaatagggc gtcaatttaa caaaacttta aataaattat    120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctagggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573

<210> SEQ ID NO 13
<211> LENGTH: 541
<212> TYPE: DNA
<213> ORGANISM: Prototheca stagnora
```

<400> SEQUENCE: 13

```
tgttgaagaa tgagccggcg agttaaaaaa aatggcatgg ttaaagatat ttctctgaag    60
ccatagcgaa agcaagtttt acaagctata gtcatttttt ttagacccga aaccgagtga   120
tctacccatg atcagggtga agtgttggtc aaataacatg gaggcccgaa ccgactaatg   180
gtgaaaaatt agcggatgaa ttgtgggtag gggcgaaaaa ccaatcgaac tcggagttag   240
ctggttctcc ccgaaatgcg tttaggcgca gcagtagcaa cacaaataga ggggtaaagc   300
actgttttctt ttgtgggctt cgaaagttgt acctcaaagt ggcaaactct gaatactcta   360
tttagatatc tactagtgag accttggggg ataagctcct tggtcaaaag ggaaacagcc   420
cagatcacca gttaaggccc caaaatgaaa atgatagtga ctaaggacgt gagtatgtca   480
aaacctccag caggttagct tagaagcagc aatcctttca agagtgcgta atagctcact   540
g                                                                  541
```

<210> SEQ ID NO 14
<211> LENGTH: 541
<212> TYPE: DNA
<213> ORGANISM: Prototheca moriformis

<400> SEQUENCE: 14

```
tgttgaagaa tgagccggcg agttaaaaag agtggcatgg ttaaagataa ttctctggag    60
ccatagcgaa agcaagttta acaagctaaa gtcacccttt ttagacccga aaccgagtga   120
tctacccatg atcagggtga agtgttggta aaataacatg gaggcccgaa ccgactaatg   180
gtgaaaaatt agcggatgaa ttgtgggtag gggcgaaaaa ccaatcgaac tcggagttag   240
ctggttctcc ccgaaatgcg tttaggcgca gcagtagcaa cacaaataga ggggtaaagc   300
actgttttctt ttgtgggctt cgaaagttgt acctcaaagt ggcaaactct gaatactcta   360
tttagatatc tactagtgag accttggggg ataagctcct tggtcaaaag ggaaacagcc   420
cagatcacca gttaaggccc caaaatgaaa atgatagtga ctaaggatgt gggtatgtta   480
aaacctccag caggttagct tagaagcagc aatcctttca agagtgcgta atagctcact   540
g                                                                  541
```

<210> SEQ ID NO 15
<211> LENGTH: 573
<212> TYPE: DNA
<213> ORGANISM: Prototheca moriformis

<400> SEQUENCE: 15

```
tgttgaagaa tgagccggcg acttaaaata aatggcaggc taagagaatt aataactcga    60
aacctaagcg aaagcaagtc ttaatagggc gctaatttaa caaaacatta aataaaatct   120
aaagtcattt attttagacc cgaacctgag tgatctaacc atggtcagga tgaaacttgg   180
gtgacaccaa gtggaagtcc gaaccgaccg atgttgaaaa atcggcggat gaactgtggt   240
tagtggtgaa ataccagtcg aactcagagc tagctggttc tccccgaaat gcgttgaggc   300
gcagcaatat atctcgtcta tctagggta aagcactgtt tcggtgcggg ctatgaaaat   360
ggtaccaaat cgtggcaaac tctgaatact agaaatgacg atatattagt gagactatgg   420
gggataagct ccatagtcga gagggaaaca gcccagacca ccagttaagg ccccaaaatg   480
ataatgaagt ggtaaaggag gtgaaaatgc aaatacaacc aggaggttgg cttagaagca   540
gccatccttt aaagagtgcg taatagctca ctg                                573
```

<210> SEQ ID NO 16
<211> LENGTH: 573
<212> TYPE: DNA
<213> ORGANISM: Prototheca wickerhamii

<400> SEQUENCE: 16

```
tgttgaagaa tgagccgtcg acttaaaata aatggcaggc taagagaatt aataactcga      60
aacctaagcg aaagcaagtc ttaatagggc gctaatttaa caaaacatta ataaaatct     120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                  573
```

<210> SEQ ID NO 17
<211> LENGTH: 541
<212> TYPE: DNA
<213> ORGANISM: Prototheca moriformis

<400> SEQUENCE: 17

```
tgttgaagaa tgagccggcg agttaaaaag agtggcgtgg ttaaagaaaa ttctctggaa      60
ccatagcgaa agcaagttta acaagcttaa gtcactttt ttagacccga aaccgagtga     120
tctacccatg atcagggtga agtgttggta aaataacatg gaggcccgaa ccgactaatg    180
gtgaaaaatt agcggatgaa ttgtgggtag gggcgaaaaa ccaatcgaac tcggagttag    240
ctggttctcc ccgaaatgcg tttaggcgca gcagtagcaa cacaaataga ggggtaaagc    300
actgttttctt ttgtgggctc cgaaagttgt acctcaaagt ggcaaactct gaatactcta    360
tttagatatc tactagtgag accttggggg ataagctcct tggtcgaaag ggaaacagcc    420
cagatcacca gttaaggccc caaaatgaaa atgatagtga ctaaggatgt gagtatgtca    480
aaacctccag caggttagct tagaagcagc aatcctttca agagtgcgta atagctcact    540
g                                                                     541
```

<210> SEQ ID NO 18
<211> LENGTH: 541
<212> TYPE: DNA
<213> ORGANISM: Prototheca zopfii

<400> SEQUENCE: 18

```
tgttgaagaa tgagccggcg agttaaaaag agtggcatgg ttaaagaaaa ttctctggag      60
ccatagcgaa agcaagttta acaagcttaa gtcactttt ttagacccga aaccgagtga     120
tctacccatg atcagggtga agtgttggta aaataacatg gaggcccgaa ccgactaatg    180
gtgaaaaatt agcggatgaa ttgtgggtag gggcgaaaaa ccaatcgaac tcggagttag    240
ctggttctcc ccgaaatgcg tttaggcgca gcagtagcaa cacaaataga ggggtaaagc    300
actgttttctt tcgtgggctt cgaaagttgt acctcaaagt ggcaaactct gaatactcta    360
tttagatatc tactagtgag accttggggg ataagctcct tggtcaaaag ggaaacagcc    420
cagatcacca gttaaggccc caaaatgaaa atgatagtga ctaaggatgt gagtatgtca    480
```

```
aaacctccag caggttagct tagaagcagc aatcctttca agagtgcgta atagctcact       540
g                                                                      541
```

<210> SEQ ID NO 19
<211> LENGTH: 565
<212> TYPE: DNA
<213> ORGANISM: Prototheca moriformis

<400> SEQUENCE: 19

```
tgttgaagaa tgagccggcg acttagaaaa ggtggcatgg ttaaggaaat attccgaagc        60
cgtagcaaaa gcgagtctga ataggggcgat aaaatatatt aatatttaga atctagtcat      120
tttttctaga cccgaacccg ggtgatctaa ccatgaccag gatgaagctt gggtgatacc      180
aagtgaaggt ccgaaccgac cgatgttgaa aaatcggcgg atgagttgtg gttagcggtg      240
aaataccagt cgaacccgga gctagctggt tctccccgaa atgcgttgag gcgcagcagt      300
acatctagtc tatctagggg taaagcactg tttcggtgcg ggctgtgaga acggtaccaa      360
atcgtggcaa actctgaata ctagaaatga cgatgtagta gtgagactgt ggggggataag      420 ctccattgtc aagagggaaa cagcccagac caccagctaa ggccccaaaa tggtaatgta      480
gtgacaaagg aggtgaaaat gcaaatacaa ccaggaggtt ggcttagaag cagccatcct      540
ttaaagagtg cgtaatagct cactg                                            565
```

<210> SEQ ID NO 20
<211> LENGTH: 550
<212> TYPE: PRT
<213> ORGANISM: Cichorium intybus

<400> SEQUENCE: 20

```
Met Ser Asn Ser Ser Asn Ala Ser Glu Ser Leu Phe Pro Ala Thr Ser
1               5                   10                  15

Glu Gln Pro Tyr Arg Thr Ala Phe His Phe Gln Pro Gln Asn Trp
            20                  25                  30

Met Asn Asp Pro Asn Gly Pro Met Cys Tyr Asn Gly Val Tyr His Leu
        35                  40                  45

Phe Tyr Gln Tyr Asn Pro Phe Gly Pro Leu Trp Asn Leu Arg Met Tyr
    50                  55                  60

Trp Ala His Ser Val Ser His Asp Leu Ile Asn Trp Ile His Leu Asp
65                  70                  75                  80

Leu Ala Phe Ala Pro Thr Glu Pro Phe Asp Ile Asn Gly Cys Leu Ser
                85                  90                  95

Gly Ser Ala Thr Val Leu Pro Gly Asn Lys Pro Ile Met Leu Tyr Thr
            100                 105                 110

Gly Ile Asp Thr Glu Asn Arg Gln Val Gln Asn Leu Ala Val Pro Lys
        115                 120                 125

Asp Leu Ser Asp Pro Tyr Leu Arg Glu Trp Val Lys His Thr Gly Asn
    130                 135                 140

Pro Ile Ile Ser Leu Pro Glu Glu Ile Gln Pro Asp Asp Phe Arg Asp
145                 150                 155                 160

Pro Thr Thr Thr Trp Leu Glu Glu Asp Gly Thr Trp Arg Leu Leu Val
                165                 170                 175

Gly Ser Gln Lys Asp Lys Thr Gly Ile Ala Phe Leu Tyr His Ser Gly
            180                 185                 190

Asp Phe Val Asn Trp Thr Lys Ser Asp Ser Pro Leu His Lys Val Ser
        195                 200                 205
```

```
Gly Thr Gly Met Trp Glu Cys Val Asp Phe Phe Pro Val Trp Val Asp
    210                 215                 220

Ser Thr Asn Gly Val Asp Thr Ser Ile Ile Asn Pro Ser Asn Arg Val
225                 230                 235                 240

Lys His Val Leu Lys Leu Gly Ile Gln Asp His Gly Lys Asp Cys Tyr
                245                 250                 255

Leu Ile Gly Lys Tyr Ser Ala Asp Lys Glu Asn Tyr Val Pro Glu Asp
            260                 265                 270

Glu Leu Thr Leu Ser Thr Leu Arg Leu Asp Tyr Gly Met Tyr Tyr Ala
        275                 280                 285

Ser Lys Ser Phe Phe Asp Pro Val Lys Asn Arg Arg Ile Met Thr Ala
290                 295                 300

Trp Val Asn Glu Ser Asp Ser Glu Ala Asp Val Ile Ala Arg Gly Trp
305                 310                 315                 320

Ser Gly Val Gln Ser Phe Pro Arg Ser Leu Trp Leu Asp Lys Asn Gln
                325                 330                 335

Lys Gln Leu Leu Gln Trp Pro Ile Glu Glu Ile Glu Met Leu His Gln
            340                 345                 350

Asn Glu Val Ser Phe His Asn Lys Lys Leu Asp Gly Gly Ser Ser Leu
        355                 360                 365

Glu Val Leu Gly Ile Thr Ala Ser Gln Ala Asp Val Lys Ile Ser Phe
    370                 375                 380

Lys Leu Ala Asn Leu Glu Ala Glu Leu Asp Pro Ser Trp Val
385                 390                 395                 400

Asp Pro Gln Leu Ile Cys Ser Glu Asn Asp Ala Ser Lys Lys Gly Lys
                405                 410                 415

Phe Gly Pro Phe Gly Leu Leu Ala Leu Ala Ser Ser Asp Leu Arg Glu
            420                 425                 430

Gln Thr Ala Ile Phe Phe Arg Val Phe Arg Lys Asn Gly Arg Tyr Val
        435                 440                 445

Val Leu Met Cys Ser Asp Gln Ser Arg Ser Ser Met Lys Asn Gly Ile
    450                 455                 460

Glu Lys Arg Thr Tyr Gly Ala Phe Val Asp Ile Asp Pro Gln Gln Asp
465                 470                 475                 480

Glu Ile Ser Leu Arg Thr Leu Ile Asp His Ser Ile Val Glu Ser Phe
                485                 490                 495

Gly Gly Arg Gly Lys Thr Cys Ile Thr Thr Arg Val Tyr Pro Thr Leu
            500                 505                 510

Ala Ile Gly Glu Gln Ala Arg Leu Phe Ala Phe Asn His Gly Thr Glu
        515                 520                 525

Ser Val Glu Ile Ser Glu Leu Ser Ala Trp Ser Met Lys Lys Ala Gln
    530                 535                 540

Met Lys Val Glu Glu Pro
545                 550

<210> SEQ ID NO 21
<211> LENGTH: 581
<212> TYPE: PRT
<213> ORGANISM: Schizosaccharomyces pombe

<400> SEQUENCE: 21

Met Phe Leu Lys Tyr Ile Leu Ala Ser Gly Ile Cys Leu Val Ser Leu
1               5                   10                  15

Leu Ser Ser Thr Asn Ala Ala Pro Arg His Leu Tyr Val Lys Arg Tyr
            20                  25                  30
```

```
Pro Val Ile Tyr Asn Ala Ser Asn Ile Thr Glu Val Ser Asn Ser Thr
         35                  40                  45

Thr Val Pro Pro Pro Phe Val Asn Thr Thr Ala Pro Asn Gly Thr
 50                  55                  60

Cys Leu Gly Asn Tyr Asn Glu Tyr Leu Pro Ser Gly Tyr Tyr Asn Ala
 65                  70                  75                  80

Thr Asp Arg Pro Lys Ile His Phe Thr Pro Ser Ser Gly Phe Met Asn
                 85                  90                  95

Asp Pro Asn Gly Leu Val Tyr Thr Gly Gly Val Tyr His Met Phe Phe
                100                 105                 110

Gln Tyr Ser Pro Lys Thr Leu Thr Ala Gly Glu Val His Trp Gly His
                115                 120                 125

Thr Val Ser Lys Asp Leu Ile His Trp Glu Asn Tyr Pro Ile Ala Ile
                130                 135                 140

Tyr Pro Asp Glu His Glu Asn Gly Val Leu Ser Leu Pro Phe Ser Gly
145                 150                 155                 160

Ser Ala Val Val Asp Val His Asn Ser Ser Gly Leu Phe Ser Asn Asp
                165                 170                 175

Thr Ile Pro Glu Glu Arg Ile Val Leu Ile Tyr Thr Asp His Trp Thr
                180                 185                 190

Gly Val Ala Glu Arg Gln Ala Ile Ala Tyr Thr Thr Asp Gly Gly Tyr
                195                 200                 205

Thr Phe Lys Lys Tyr Ser Gly Asn Pro Val Leu Asp Ile Asn Ser Leu
                210                 215                 220

Gln Phe Arg Asp Pro Lys Val Ile Trp Asp Phe Asp Ala Asn Arg Trp
225                 230                 235                 240

Val Met Ile Val Ala Met Ser Gln Asn Tyr Gly Ile Ala Phe Tyr Ser
                245                 250                 255

Ser Tyr Asp Leu Ile His Trp Thr Glu Leu Ser Val Phe Ser Thr Ser
                260                 265                 270

Gly Tyr Leu Gly Leu Gln Tyr Glu Cys Pro Gly Met Ala Arg Val Pro
                275                 280                 285

Val Glu Gly Thr Asp Glu Tyr Lys Trp Val Leu Phe Ile Ser Ile Asn
                290                 295                 300

Pro Gly Ala Pro Leu Gly Gly Ser Val Val Gln Tyr Phe Val Gly Asp
305                 310                 315                 320

Trp Asn Gly Thr Asn Phe Val Pro Asp Asp Gly Gln Thr Arg Phe Val
                325                 330                 335

Asp Leu Gly Lys Asp Phe Tyr Ala Ser Ala Leu Tyr His Ser Ser Ser
                340                 345                 350

Ala Asn Ala Asp Val Ile Gly Val Gly Trp Ala Ser Asn Trp Gln Tyr
                355                 360                 365

Thr Asn Gln Ala Pro Thr Gln Val Phe Arg Ser Ala Met Thr Val Ala
                370                 375                 380

Arg Lys Phe Thr Leu Arg Asp Val Pro Gln Asn Pro Met Thr Asn Leu
385                 390                 395                 400

Thr Ser Leu Ile Gln Thr Pro Leu Asn Val Ser Leu Leu Arg Asp Glu
                405                 410                 415

Thr Leu Phe Thr Ala Pro Val Ile Asn Ser Ser Ser Leu Ser Gly
                420                 425                 430

Ser Pro Ile Thr Leu Pro Ser Asn Thr Ala Phe Glu Phe Asn Val Thr
                435                 440                 445
```

```
Leu Ser Ile Asn Tyr Thr Glu Gly Cys Thr Thr Gly Tyr Cys Leu Gly
    450                 455                 460

Arg Ile Ile Ile Asp Ser Asp Pro Tyr Arg Leu Gln Ser Ile Ser
465                 470                 475                 480

Val Asp Val Asp Phe Ala Ala Ser Thr Leu Val Ile Asn Arg Ala Lys
                485                 490                 495

Ala Gln Met Gly Trp Phe Asn Ser Leu Phe Thr Pro Ser Phe Ala Asn
            500                 505                 510

Asp Ile Tyr Ile Tyr Gly Asn Val Thr Leu Tyr Gly Ile Val Asp Asn
            515                 520                 525

Gly Leu Leu Glu Leu Tyr Val Asn Asn Gly Glu Lys Thr Tyr Thr Asn
530                 535                 540

Asp Phe Phe Leu Gln Gly Ala Thr Pro Gly Gln Ile Ser Phe Ala
545                 550                 555                 560

Ala Phe Gln Gly Val Ser Phe Asn Asn Val Thr Val Thr Pro Leu Lys
                565                 570                 575

Thr Ile Trp Asn Cys
            580

<210> SEQ ID NO 22
<211> LENGTH: 550
<212> TYPE: PRT
<213> ORGANISM: Pichia anomala

<400> SEQUENCE: 22

Met Ile Gln Leu Ser Pro Leu Leu Leu Pro Leu Phe Ser Val Phe
1               5                   10                  15

Asn Ser Ile Ala Asp Ala Ser Thr Glu Tyr Leu Arg Pro Gln Ile His
                20                  25                  30

Leu Thr Pro Asp Gln Gly Trp Met Asn Asp Pro Asn Gly Met Phe Tyr
            35                  40                  45

Asp Arg Lys Asp Lys Leu Trp His Val Tyr Phe Gln His Asn Pro Asp
50                  55                  60

Lys Lys Ser Ile Trp Ala Thr Pro Val Thr Trp Gly His Ser Thr Ser
65                  70                  75                  80

Lys Asp Leu Leu Thr Trp Asp Tyr His Gly Asn Ala Leu Glu Pro Glu
                85                  90                  95

Asn Asp Asp Glu Gly Ile Phe Ser Gly Ser Val Val Asp Arg Asn
            100                 105                 110

Asn Thr Ser Gly Phe Phe Asn Asp Ser Thr Asp Pro Glu Gln Arg Ile
        115                 120                 125

Val Ala Ile Tyr Thr Asn Asn Ala Gln Leu Gln Thr Gln Glu Ile Ala
130                 135                 140

Tyr Ser Leu Asp Lys Gly Tyr Ser Phe Ile Lys Tyr Asp Gln Asn Pro
145                 150                 155                 160

Val Ile Asn Val Asn Ser Ser Gln Gln Arg Asp Pro Lys Val Leu Trp
                165                 170                 175

His Asp Glu Ser Asn Gln Trp Ile Met Val Val Ala Lys Thr Gln Glu
            180                 185                 190

Phe Lys Val Gln Ile Tyr Gly Ser Pro Asp Leu Lys Lys Trp Asp Leu
        195                 200                 205

Lys Ser Asn Phe Thr Ser Asn Gly Tyr Leu Gly Phe Gln Tyr Glu Cys
210                 215                 220

Pro Gly Leu Phe Lys Leu Pro Ile Glu Asn Pro Leu Asn Asp Thr Val
225                 230                 235                 240
```

```
Thr Ser Lys Trp Val Leu Leu Ala Ile Asn Pro Gly Ser Pro Leu
                245                 250                 255

Gly Gly Ser Ile Asn Glu Tyr Phe Ile Gly Asp Phe Asp Gly Thr Thr
            260                 265                 270

Phe His Pro Asp Asp Gly Ala Thr Arg Phe Met Asp Ile Gly Lys Asp
        275                 280                 285

Phe Tyr Ala Phe Gln Ser Phe Asp Asn Thr Glu Pro Glu Asp Gly Ala
    290                 295                 300

Leu Gly Leu Ala Trp Ala Ser Asn Trp Gln Tyr Ala Asn Thr Val Pro
305                 310                 315                 320

Thr Glu Asn Trp Arg Ser Ser Met Ser Leu Val Arg Asn Tyr Thr Leu
                325                 330                 335

Lys Tyr Val Asp Val Asn Pro Glu Asn Tyr Gly Leu Thr Leu Ile Gln
            340                 345                 350

Lys Pro Val Tyr Asp Thr Lys Glu Thr Arg Leu Asn Glu Thr Leu Lys
        355                 360                 365

Thr Leu Glu Thr Ile Asn Glu Tyr Glu Val Asn Asp Leu Lys Leu Asp
    370                 375                 380

Lys Ser Ser Phe Val Ala Thr Asp Phe Asn Thr Glu Arg Asn Ala Thr
385                 390                 395                 400

Gly Val Phe Glu Phe Asp Leu Lys Phe Thr Gln Thr Asp Leu Lys Met
                405                 410                 415

Gly Tyr Ser Asn Met Thr Thr Gln Phe Gly Leu Tyr Ile His Ser Gln
            420                 425                 430

Thr Val Lys Gly Ser Gln Glu Thr Leu Gln Leu Val Phe Asp Thr Leu
        435                 440                 445

Ser Thr Thr Trp Tyr Ile Asp Arg Thr Thr Gln His Ser Phe Gln Arg
    450                 455                 460

Asn Ser Pro Val Phe Thr Glu Arg Ile Ser Thr Tyr Val Glu Lys Ile
465                 470                 475                 480

Asp Thr Thr Asp Gln Gly Asn Val Tyr Thr Leu Tyr Gly Val Val Asp
                485                 490                 495

Arg Asn Ile Leu Glu Leu Tyr Phe Asn Asp Gly Ser Ile Ala Met Thr
            500                 505                 510

Asn Thr Phe Phe Phe Arg Glu Gly Lys Ile Pro Thr Ser Phe Glu Val
        515                 520                 525

Val Cys Asp Ser Glu Lys Ser Phe Ile Thr Ile Asp Glu Leu Ser Val
    530                 535                 540

Arg Glu Leu Ala Arg Lys
545                 550

<210> SEQ ID NO 23
<211> LENGTH: 533
<212> TYPE: PRT
<213> ORGANISM: Debaryomyces occidentalis

<400> SEQUENCE: 23

Met Val Gln Val Leu Ser Val Leu Val Ile Pro Leu Leu Thr Leu Phe
1               5                   10                  15

Phe Gly Tyr Val Ala Ser Ser Ser Ile Asp Leu Ser Val Asp Thr Ser
            20                  25                  30

Glu Tyr Asn Arg Pro Leu Ile His Phe Thr Pro Glu Lys Gly Trp Met
        35                  40                  45

Asn Asp Pro Asn Gly Leu Phe Tyr Asp Lys Thr Ala Lys Leu Trp His
```

-continued

```
            50                  55                  60
Leu Tyr Phe Gln Tyr Asn Pro Asn Ala Thr Ala Trp Gly Gln Pro Leu
65                  70                  75                  80

Tyr Trp Gly His Ala Thr Ser Asn Asp Leu Val His Trp Asp Glu His
                85                  90                  95

Glu Ile Ala Ile Gly Pro Glu His Asp Asn Gly Ile Phe Ser Gly
                    100                 105                 110

Ser Ile Val Val Asp His Asn Asn Thr Ser Gly Phe Phe Asn Ser Ser
                115                 120                 125

Ile Asp Pro Asn Gln Arg Ile Val Ala Ile Tyr Thr Asn Asn Ile Pro
130                 135                 140

Asp Leu Gln Thr Gln Asp Ile Ala Phe Ser Leu Asp Gly Gly Tyr Thr
145                 150                 155                 160

Phe Thr Lys Tyr Glu Asn Asn Pro Val Ile Asp Val Ser Ser Asn Gln
                165                 170                 175

Phe Arg Asp Pro Lys Val Phe Trp His Glu Arg Phe Lys Ser Met Asp
                180                 185                 190

His Gly Cys Ser Glu Ile Ala Arg Val Lys Ile Gln Ile Phe Gly Ser
                195                 200                 205

Ala Asn Leu Lys Asn Trp Val Leu Asn Ser Asn Phe Ser Ser Gly Tyr
                210                 215                 220

Tyr Gly Asn Gln Tyr Gly Met Ser Arg Leu Ile Glu Val Pro Ile Glu
225                 230                 235                 240

Asn Ser Asp Lys Ser Lys Trp Val Met Phe Leu Ala Ile Asn Pro Gly
                    245                 250                 255

Ser Pro Leu Gly Gly Ser Ile Asn Gln Tyr Phe Val Gly Asp Phe Asp
                260                 265                 270

Gly Phe Gln Phe Val Pro Asp Asp Ser Gln Thr Arg Phe Val Asp Ile
                275                 280                 285

Gly Lys Asp Phe Tyr Ala Phe Gln Thr Phe Ser Glu Val Glu His Gly
                290                 295                 300

Val Leu Gly Leu Ala Trp Ala Ser Asn Trp Gln Tyr Ala Asp Gln Val
305                 310                 315                 320

Pro Thr Asn Pro Trp Arg Ser Ser Thr Ser Leu Ala Arg Asn Tyr Thr
                    325                 330                 335

Leu Arg Tyr Val Ile Gln Met Leu Lys Leu Thr Ala Asn Ile Asp Lys
                340                 345                 350

Ser Val Leu Pro Asp Ser Ile Asn Val Asp Lys Leu Lys Lys
                355                 360                 365

Asn Val Lys Leu Thr Asn Lys Lys Pro Ile Lys Thr Asn Phe Lys Gly
370                 375                 380

Ser Thr Gly Leu Phe Asp Phe Asn Ile Thr Phe Lys Val Leu Asn Leu
385                 390                 395                 400

Asn Val Ser Pro Gly Lys Thr His Phe Asp Ile Leu Ile Asn Ser Gln
                    405                 410                 415

Glu Leu Asn Ser Ser Val Asp Ser Ile Lys Ile Gly Phe Asp Ser Ser
                420                 425                 430

Gln Ser Leu Phe Tyr Ile Asp Arg His Ile Pro Asn Val Glu Phe Pro
                435                 440                 445

Arg Lys Gln Phe Phe Thr Asp Lys Leu Ala Ala Tyr Leu Glu Pro Leu
                450                 455                 460

Asp Tyr Asp Gln Asp Leu Arg Val Phe Ser Leu Tyr Gly Ile Val Asp
465                 470                 475                 480
```

```
Lys Asn Ile Ile Glu Leu Tyr Phe Asn Asp Gly Thr Val Ala Met Thr
                485                 490                 495

Asn Thr Phe Phe Met Gly Glu Gly Lys Tyr Pro His Asp Ile Gln Ile
            500                 505                 510

Val Thr Asp Thr Glu Glu Pro Leu Phe Glu Leu Glu Ser Val Ile Ile
        515                 520                 525

Arg Glu Leu Asn Lys
    530

<210> SEQ ID NO 24
<211> LENGTH: 654
<212> TYPE: PRT
<213> ORGANISM: Oryza sativa

<400> SEQUENCE: 24

Met Ala Thr Ser Arg Leu Thr Pro Ala Tyr Asp Leu Lys Asn Ala Ala
1               5                   10                  15

Ala Ala Val Tyr Thr Pro Leu Pro Glu Gln Pro His Ser Ala Glu Val
            20                  25                  30

Glu Ile Arg Asp Arg Lys Pro Phe Lys Ile Ile Ser Ala Ile Ile Leu
        35                  40                  45

Ser Ser Leu Leu Leu Leu Ala Leu Ile Leu Val Ala Val Asn Tyr Gln
    50                  55                  60

Ala Pro Pro Ser His Ser Ser Gly Asp Asn Ser Gln Pro Ala Ala Val
65                  70                  75                  80

Met Pro Pro Ser Arg Gly Val Ser Gln Gly Val Ser Glu Lys Ala Phe
                85                  90                  95

Arg Gly Ala Ser Gly Ala Gly Asn Gly Val Ser Phe Ala Trp Ser Asn
            100                 105                 110

Leu Met Leu Ser Trp Gln Arg Thr Ser Tyr His Phe Gln Pro Val Lys
        115                 120                 125

Asn Trp Met Asn Asp Pro Asn Gly Pro Leu Tyr Tyr Lys Gly Trp Tyr
    130                 135                 140

His Leu Phe Tyr Gln Tyr Asn Pro Asp Ser Ala Val Trp Gly Asn Ile
145                 150                 155                 160

Thr Trp Gly His Ala Val Ser Thr Asp Leu Ile Asn Trp Leu His Leu
                165                 170                 175

Pro Phe Ala Met Val Pro Asp Gln Trp Tyr Asp Val Asn Gly Val Trp
            180                 185                 190

Thr Gly Ser Ala Thr Ile Leu Pro Asp Gly Arg Ile Val Met Leu Tyr
        195                 200                 205

Thr Gly Asp Thr Asp Asp Tyr Val Gln Asp Gln Asn Leu Ala Phe Pro
    210                 215                 220

Ala Asn Leu Ser Asp Pro Leu Leu Val Asp Trp Val Lys Tyr Pro Asn
225                 230                 235                 240

Asn Pro Val Ile Tyr Pro Pro Gly Ile Gly Val Lys Asp Phe Arg
                245                 250                 255

Asp Pro Thr Thr Ala Gly Thr Ala Gly Met Gln Asn Gly Gln Arg Leu
            260                 265                 270

Val Thr Ile Gly Ser Lys Val Gly Lys Thr Gly Ile Ser Leu Val Tyr
        275                 280                 285

Glu Thr Thr Asn Phe Thr Thr Phe Lys Leu Leu Tyr Gly Val Leu His
    290                 295                 300

Ala Val Pro Gly Thr Gly Met Trp Glu Cys Val Asp Leu Tyr Pro Val
```

```
            305                 310                 315                 320
Ser Thr Thr Gly Glu Asn Gly Leu Asp Thr Ser Val Asn Gly Leu Gly
                325                 330                 335

Val Lys His Val Leu Lys Thr Ser Leu Asp Asp Lys His Asp Tyr
            340                 345                 350

Tyr Ala Leu Gly Thr Tyr Asp Pro Val Lys Asn Lys Trp Thr Pro Asp
                355                 360                 365

Asn Pro Asp Leu Asp Val Gly Ile Gly Leu Arg Leu Asp Tyr Gly Lys
            370                 375                 380

Tyr Tyr Ala Ala Arg Thr Phe Tyr Asp Gln Asn Lys Gln Arg Ile
385                 390                 395                 400

Leu Trp Gly Trp Ile Gly Glu Thr Asp Leu Glu Ala Val Asp Leu Met
                405                 410                 415

Lys Gly Trp Ala Ser Leu Gln Ala Ile Pro Arg Thr Ile Val Phe Asp
            420                 425                 430

Lys Lys Thr Gly Thr Asn Val Leu Gln Arg Pro Glu Glu Val Glu
            435                 440                 445

Ser Trp Ser Ser Gly Asp Pro Ile Thr Gln Arg Arg Ile Phe Glu Pro
    450                 455                 460

Gly Ser Val Val Pro Ile His Val Ser Gly Ala Thr Gln Leu Asp Ile
465                 470                 475                 480

Thr Ala Ser Phe Glu Val Asp Glu Thr Leu Leu Glu Thr Thr Ser Glu
                485                 490                 495

Ser His Asp Ala Gly Tyr Asp Cys Ser Asn Ser Gly Ala Gly Thr
            500                 505                 510

Arg Gly Ser Leu Gly Pro Phe Gly Leu Leu Val Val Ala Asp Glu Lys
            515                 520                 525

Leu Ser Glu Leu Thr Pro Val Tyr Leu Tyr Val Ala Lys Gly Gly Asp
            530                 535                 540

Gly Lys Ala Lys Ala His Leu Cys Ala Tyr Gln Thr Arg Ser Ser Met
545                 550                 555                 560

Ala Ser Gly Val Glu Lys Glu Val Tyr Gly Ser Ala Val Pro Val Leu
                565                 570                 575

Asp Gly Glu Asn Tyr Ser Ala Arg Ile Leu Ile Asp His Ser Ile Val
            580                 585                 590

Glu Ser Phe Ala Gln Ala Gly Arg Thr Cys Val Arg Ser Arg Asp Tyr
    595                 600                 605

Pro Thr Lys Asp Ile Tyr Gly Ala Ala Arg Cys Phe Phe Asn Asn
    610                 615                 620

Ala Thr Glu Ala Ser Val Arg Ala Ser Leu Lys Ala Trp Gln Met Lys
625                 630                 635                 640

Ser Phe Ile Arg Pro Tyr Pro Phe Ile Pro Asp Gln Lys Ser
                645                 650

<210> SEQ ID NO 25
<211> LENGTH: 690
<212> TYPE: PRT
<213> ORGANISM: Allium cepa

<400> SEQUENCE: 25

Met Ser Ser Asp Asp Leu Glu Ser Pro Pro Ser Ser Tyr Leu Pro Ile
1               5                   10                  15

Pro Pro Ser Asp Glu Phe His Asp Gln Pro Pro Leu Arg Ser Trp
            20                  25                  30
```

```
Leu Arg Leu Leu Ser Ile Pro Leu Ala Leu Met Phe Leu Phe Leu
         35                  40                  45

Ala Thr Phe Leu Ser Asn Leu Glu Ser Pro Ser Asp Ser Gly Leu
 50                  55                  60

Val Ser Asp Pro Val Thr Phe Asp Val Asn Pro Ala Val Val Arg Arg
 65                      70                  75                  80

Gly Lys Asp Ala Gly Val Ser Asp Lys Thr Ser Gly Val Asp Ser Gly
                     85                  90                  95

Phe Val Leu Asp Pro Val Ala Val Asp Ala Asn Ser Val Val His
             100                 105                 110

Arg Gly Lys Asp Ala Gly Val Ser Asp Lys Thr Ser Gly Val Asp Ser
             115                 120                 125

Gly Leu Leu Lys Asp Ser Pro Leu Gly Pro Tyr Pro Trp Thr Asn Gln
 130                 135                 140

Met Leu Ser Trp Gln Arg Thr Gly Phe His Phe Gln Pro Val Lys Asn
 145                 150                 155                 160

Trp Met Asn Asp Pro Asn Gly Pro Leu Tyr Tyr Lys Gly Trp Tyr His
                 165                 170                 175

Phe Phe Tyr Gln Tyr Asn Pro Glu Gly Ala Val Trp Gly Asn Ile Ala
             180                 185                 190

Trp Gly His Ala Val Ser Arg Asp Leu Val His Trp Thr His Leu Pro
 195                 200                 205

Leu Ala Met Val Pro Asp Gln Trp Tyr Asp Ile Asn Gly Val Trp Thr
 210                 215                 220

Gly Ser Ala Thr Ile Leu Pro Asp Gly Gln Ile Val Met Leu Tyr Thr
225                 230                 235                 240

Gly Ala Thr Asn Glu Ser Val Gln Val Gln Asn Leu Ala Val Pro Ala
                 245                 250                 255

Asp Gln Ser Asp Thr Leu Leu Leu Arg Trp Lys Lys Ser Glu Ala Asn
                 260                 265                 270

Pro Ile Leu Val Pro Pro Gly Ile Gly Asp Lys Asp Phe Arg Asp
             275                 280                 285

Pro Thr Thr Ala Trp Tyr Glu Pro Ser Asp Asp Thr Trp Arg Ile Val
 290                 295                 300

Ile Gly Ser Lys Asp Ser Ser His Ser Gly Ile Ala Ile Val Tyr Ser
305                 310                 315                 320

Thr Lys Asp Phe Ile Asn Tyr Lys Leu Ile Pro Gly Ile Leu His Ala
                 325                 330                 335

Val Glu Arg Val Gly Met Trp Glu Cys Val Asp Phe Tyr Pro Val Ala
                 340                 345                 350

Thr Ala Asp Ser Ser His Ala Asn His Gly Leu Asp Pro Ser Ala Arg
                 355                 360                 365

Pro Ser Pro Ala Val Lys His Val Leu Lys Ala Ser Met Asp Asp Asp
 370                 375                 380

Arg His Asp Tyr Tyr Ala Ile Gly Thr Tyr Asp Pro Ala Gln Asn Thr
385                 390                 395                 400

Trp Val Pro Asp Asp Ala Ser Val Asp Val Gly Ile Gly Leu Arg Tyr
                 405                 410                 415

Asp Trp Gly Lys Phe Tyr Ala Ser Lys Thr Phe Tyr Asp His Ala Lys
                 420                 425                 430

Lys Arg Arg Ile Leu Trp Ser Trp Ile Gly Glu Thr Asp Ser Glu Thr
             435                 440                 445

Ala Asp Ile Ala Lys Gly Trp Ala Ser Leu Gln Gly Val Pro Arg Thr
```

```
            450                 455                 460
Val Leu Leu Asp Val Lys Thr Gly Ser Asn Leu Ile Thr Trp Pro Val
465                 470                 475                 480

Val Glu Ile Glu Ser Leu Arg Thr Arg Pro Arg Asp Phe Ser Gly Ile
                485                 490                 495

Thr Val Asp Ala Gly Ser Thr Phe Lys Leu Asp Val Gly Ala Ala
            500                 505                 510

Gln Leu Asp Ile Glu Ala Glu Phe Lys Ile Ser Ser Glu Glu Leu Glu
            515                 520                 525

Ala Val Lys Glu Ala Asp Val Ser Tyr Asn Cys Ser Ser Ser Gly Gly
530                 535                 540

Ala Ala Glu Arg Gly Val Leu Gly Pro Phe Gly Leu Val Leu Ala
545                 550                 555                 560

Asn Gln Asp Leu Thr Glu Gln Thr Ala Thr Tyr Phe Tyr Val Ser Arg
                565                 570                 575

Gly Met Asp Gly Gly Leu Asn Thr His Phe Cys Gln Asp Glu Lys Arg
            580                 585                 590

Ser Ser Lys Ala Ser Asp Ile Val Lys Arg Ile Val Gly His Ser Val
            595                 600                 605

Pro Val Leu Asp Gly Glu Ser Phe Ala Leu Arg Ile Leu Val Asp His
            610                 615                 620

Ser Ile Val Glu Ser Phe Ala Gln Gly Gly Arg Ala Ser Ala Thr Ser
625                 630                 635                 640

Arg Val Tyr Pro Thr Glu Ala Ile Tyr Asn Asn Ala Arg Val Phe Val
                645                 650                 655

Phe Asn Asn Ala Thr Gly Ala Lys Val Thr Ala Gln Ser Leu Lys Val
            660                 665                 670

Trp His Met Ser Thr Ala Ile Asn Glu Ile Tyr Asp Pro Ala Thr Ser
            675                 680                 685

Val Met
    690

<210> SEQ ID NO 26
<211> LENGTH: 501
<212> TYPE: PRT
<213> ORGANISM: Beta vulgaris
<220> FEATURE:
<221> NAME/KEY: MOD_RES
<222> LOCATION: (382)..(382)
<223> OTHER INFORMATION: Any amino acid

<400> SEQUENCE: 26

Leu Phe Tyr Gln Tyr Asn Pro Asn Gly Val Ile Trp Gly Pro Val
1                5                  10                  15

Trp Gly His Ser Thr Ser Lys Asp Leu Val Asn Trp Val Pro Gln Pro
                20                  25                  30

Leu Thr Met Glu Pro Glu Met Ala Ala Asn Ile Asn Gly Ser Trp Ser
            35                  40                  45

Gly Ser Ala Thr Ile Leu Pro Gly Asn Lys Pro Ala Ile Leu Phe Thr
50                  55                  60

Gly Leu Asp Pro Lys Tyr Glu Gln Val Gln Val Leu Ala Tyr Pro Lys
65                  70                  75                  80

Asp Thr Ser Asp Pro Asn Leu Lys Glu Trp Phe Leu Ala Pro Gln Asn
                85                  90                  95

Pro Val Met Phe Pro Thr Pro Gln Asn Gln Ile Asn Ala Thr Ser Phe
            100                 105                 110
```

```
Arg Asp Pro Thr Thr Ala Trp Arg Leu Pro Asp Gly Val Trp Arg Leu
            115                 120                 125

Leu Ile Gly Ser Lys Arg Gly Gln Arg Gly Leu Ser Leu Leu Phe Arg
        130                 135                 140

Ser Arg Asp Phe Val His Trp Val Gln Ala Lys His Pro Leu Tyr Ser
145                 150                 155                 160

Asp Lys Leu Ser Gly Met Trp Glu Cys Pro Asp Phe Phe Pro Val Tyr
                165                 170                 175

Ala Asn Gly Asp Gln Met Gly Val Asp Thr Ser Ile Ile Gly Ser His
            180                 185                 190

Val Lys His Val Leu Lys Asn Ser Leu Asp Ile Thr Lys His Asp Ile
        195                 200                 205

Tyr Thr Ile Gly Asp Tyr Asn Ile Lys Lys Asp Ala Tyr Thr Pro Asp
    210                 215                 220

Ile Gly Tyr Met Asn Asp Ser Ser Leu Arg Tyr Asp Tyr Gly Lys Tyr
225                 230                 235                 240

Tyr Ala Ser Lys Thr Phe Phe Asp Asp Ala Lys Lys Glu Arg Ile Leu
                245                 250                 255

Leu Gly Trp Ala Asn Glu Ser Ser Val Glu Asp Ile Lys Lys
            260                 265                 270

Gly Trp Ser Gly Ile His Thr Ile Pro Arg Lys Ile Trp Leu Asp Lys
        275                 280                 285

Leu Gly Lys Gln Leu Ile Gln Trp Pro Ile Ala Asn Ile Glu Lys Leu
    290                 295                 300

Arg Gln Lys Pro Val Asn Ile Tyr Arg Lys Val Leu Lys Gly Gly Ser
305                 310                 315                 320

Gln Ile Glu Val Ser Gly Ile Thr Ala Ala Gln Ala Asp Val Glu Ile
                325                 330                 335

Ser Phe Lys Ile Lys Asp Leu Lys Asn Val Glu Lys Phe Asp Ala Ser
            340                 345                 350

Trp Thr Ser Pro Gln Leu Leu Cys Ser Lys Lys Gly Ala Ser Val Lys
        355                 360                 365

Gly Gly Leu Gly Pro Phe Gly Leu Leu Thr Leu Ala Ser Xaa Gly Leu
    370                 375                 380

Glu Glu Tyr Thr Ala Val Phe Phe Arg Ile Phe Lys Ala Tyr Asp Asn
385                 390                 395                 400

Lys Phe Val Val Leu Met Cys Ser Asp Gln Ser Arg Ser Ser Leu Asn
                405                 410                 415

Pro Thr Asn Asp Lys Thr Thr Tyr Gly Thr Phe Val Asp Val Asn Pro
            420                 425                 430

Ile Arg Glu Gly Leu Ser Leu Arg Val Leu Ile Asp His Ser Val Val
        435                 440                 445

Glu Ser Phe Gly Ala Lys Gly Lys Asn Val Ile Thr Ala Arg Val Tyr
    450                 455                 460

Pro Thr Leu Ala Ile Asn Glu Lys Ala His Leu Tyr Val Phe Asn Arg
465                 470                 475                 480

Gly Thr Ser Asn Val Glu Ile Thr Gly Leu Thr Ala Trp Ser Met Lys
                485                 490                 495

Lys Ala Asn Ile Ala
            500

<210> SEQ ID NO 27
<211> LENGTH: 518
```

<212> TYPE: PRT
<213> ORGANISM: Bifidobacterium breve

<400> SEQUENCE: 27

```
Met Thr Asp Phe Thr Pro Glu Thr Pro Val Leu Thr Pro Ile Arg Asp
1               5                   10                  15

His Ala Ala Glu Leu Ala Lys Ala Glu Ala Gly Val Ala Glu Met Ala
            20                  25                  30

Ala Lys Arg Asn Asn Arg Trp Tyr Pro Lys Tyr His Ile Ala Ser Asn
        35                  40                  45

Gly Gly Trp Ile Asn Asp Pro Asn Gly Leu Cys Phe Tyr Lys Gly Arg
    50                  55                  60

Trp His Val Phe Tyr Gln Leu His Pro Tyr Gly Thr Gln Trp Gly Pro
65                  70                  75                  80

Met His Trp Gly His Val Ser Ser Thr Asp Met Leu Asn Trp Lys Arg
                85                  90                  95

Glu Pro Ile Met Phe Ala Pro Ser Leu Glu Gln Glu Lys Asp Gly Val
            100                 105                 110

Phe Ser Gly Ser Ala Val Ile Asp Asp Asn Gly Asp Leu Arg Phe Tyr
        115                 120                 125

Tyr Thr Gly His Arg Trp Ala Asn Gly His Asp Asn Thr Gly Gly Asp
    130                 135                 140

Trp Gln Val Gln Met Thr Ala Leu Pro Asp Asn Asp Glu Leu Thr Ser
145                 150                 155                 160

Ala Thr Lys Gln Gly Met Ile Ile Asp Cys Pro Thr Asp Lys Val Asp
                165                 170                 175

His His Tyr Arg Asp Pro Lys Val Trp Lys Thr Gly Asp Thr Trp Tyr
            180                 185                 190

Met Thr Phe Gly Val Ser Ser Glu Asp Lys Arg Gly Gln Met Trp Leu
        195                 200                 205

Phe Ser Ser Lys Asp Met Val Arg Trp Glu Tyr Glu Arg Val Leu Phe
    210                 215                 220

Gln His Pro Asp Pro Asp Val Phe Met Leu Glu Cys Pro Asp Phe Phe
225                 230                 235                 240

Pro Ile Lys Asp Lys Asp Gly Asn Glu Lys Trp Val Ile Gly Phe Ser
                245                 250                 255

Ala Met Gly Ser Lys Pro Ser Gly Phe Met Asn Arg Asn Val Asn Asn
            260                 265                 270

Ala Gly Tyr Met Ile Gly Thr Trp Glu Pro Gly Gly Glu Phe Lys Pro
        275                 280                 285

Glu Thr Glu Phe Arg Leu Trp Asp Cys Gly His Asn Tyr Tyr Ala Pro
    290                 295                 300

Gln Ser Phe Asn Val Asp Gly Arg Gln Ile Val Tyr Gly Trp Met Ser
305                 310                 315                 320

Pro Phe Val Gln Pro Ile Pro Met Glu Asp Asp Gly Trp Cys Gly Gln
                325                 330                 335

Leu Thr Leu Pro Arg Glu Ile Thr Leu Asp Asp Gly Asp Val Val
            340                 345                 350

Thr Ala Pro Val Ala Glu Met Glu Gly Leu Arg Glu Asp Thr Leu Asp
        355                 360                 365

His Gly Ser Ile Thr Leu Asp Met Asp Gly Glu Gln Val Ile Ala Asp
    370                 375                 380

Asp Ala Glu Ala Val Glu Ile Glu Met Thr Ile Asp Leu Ala Ala Ser
385                 390                 395                 400
```

```
Thr Ala Asp Arg Ala Gly Leu Lys Ile His Ala Thr Glu Asp Gly Ala
                405                 410                 415
Tyr Thr Tyr Val Ala Tyr Asp Gln Ile Gly Arg Val Val Val Asp
        420                 425                 430
Arg Gln Ala Met Ala Asn Gly Asp His Gly Tyr Arg Ala Ala Pro Leu
            435                 440                 445
Thr Asp Ala Glu Leu Ala Ser Gly Lys Leu Asp Leu Arg Val Phe Val
450                 455                 460
Asp Arg Gly Ser Val Glu Val Tyr Val Asn Gly His Gln Val Leu
465                 470                 475                 480
Ser Ser Tyr Ser Tyr Ala Ser Glu Gly Pro Arg Ala Ile Lys Leu Val
                485                 490                 495
Ala Glu Phe Gly Asn Leu Lys Val Glu Ser Leu Lys Leu His His Met
                500                 505                 510
Lys Ser Ile Gly Leu Glu
        515

<210> SEQ ID NO 28
<211> LENGTH: 532
<212> TYPE: PRT
<213> ORGANISM: Saccharomyces cerevisiae

<400> SEQUENCE: 28

Met Leu Leu Gln Ala Phe Leu Phe Leu Leu Ala Gly Phe Ala Ala Lys
1               5                   10                  15
Ile Ser Ala Ser Met Thr Asn Glu Thr Ser Asp Arg Pro Leu Val His
            20                  25                  30
Phe Thr Pro Asn Lys Gly Trp Met Asn Asp Pro Asn Gly Leu Trp Tyr
        35                  40                  45
Asp Glu Lys Asp Ala Lys Trp His Leu Tyr Phe Gln Tyr Asn Pro Asn
    50                  55                  60
Asp Thr Val Trp Gly Thr Pro Leu Phe Trp Gly His Ala Thr Ser Asp
65                  70                  75                  80
Asp Leu Thr Asn Trp Glu Asp Gln Pro Ile Ala Ile Ala Pro Lys Arg
                85                  90                  95
Asn Asp Ser Gly Ala Phe Ser Gly Ser Met Val Val Asp Tyr Asn Asn
            100                 105                 110
Thr Ser Gly Phe Phe Asn Asp Thr Ile Asp Pro Arg Gln Arg Cys Val
        115                 120                 125
Ala Ile Trp Thr Tyr Asn Thr Pro Glu Ser Glu Glu Gln Tyr Ile Ser
    130                 135                 140
Tyr Ser Leu Asp Gly Gly Tyr Thr Phe Thr Glu Tyr Gln Lys Asn Pro
145                 150                 155                 160
Val Leu Ala Ala Asn Ser Thr Gln Phe Arg Asp Pro Lys Val Phe Trp
                165                 170                 175
Tyr Glu Pro Ser Gln Lys Trp Ile Met Thr Ala Ala Lys Ser Gln Asp
            180                 185                 190
Tyr Lys Ile Glu Ile Tyr Ser Ser Asp Asp Leu Lys Ser Trp Lys Leu
        195                 200                 205
Glu Ser Ala Phe Ala Asn Glu Gly Phe Leu Gly Tyr Gln Tyr Glu Cys
    210                 215                 220
Pro Gly Leu Ile Glu Val Pro Thr Glu Gln Asp Pro Ser Lys Ser Tyr
225                 230                 235                 240
Trp Val Met Phe Ile Ser Ile Asn Pro Gly Ala Pro Ala Gly Gly Ser
```

```
                    245                 250                 255
Phe Asn Gln Tyr Phe Val Gly Ser Phe Asn Gly Thr His Phe Glu Ala
                260                 265                 270

Phe Asp Asn Gln Ser Arg Val Val Asp Phe Gly Lys Asp Tyr Tyr Ala
            275                 280                 285

Leu Gln Thr Phe Phe Asn Thr Asp Pro Thr Tyr Gly Ser Ala Leu Gly
        290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530

<210> SEQ ID NO 29
<211> LENGTH: 512
<212> TYPE: PRT
<213> ORGANISM: Zymomonas mobilis

<400> SEQUENCE: 29

Met Glu Ser Pro Ser Tyr Lys Asn Leu Ile Lys Ala Glu Asp Ala Gln
1               5                   10                  15

Lys Lys Ala Gly Lys Arg Leu Leu Ser Ser Glu Trp Tyr Pro Gly Phe
            20                  25                  30

His Val Thr Pro Leu Thr Gly Trp Met Asn Asp Pro Asn Gly Leu Ile
        35                  40                  45

Phe Phe Lys Gly Glu Tyr His Leu Phe Tyr Gln Tyr Tyr Pro Phe Ala
    50                  55                  60

Pro Val Trp Gly Pro Met His Trp Gly His Ala Lys Ser Arg Asp Leu
65                  70                  75                  80
```

-continued

```
Val His Trp Glu Thr Leu Pro Val Ala Leu Ala Pro Gly Asp Leu Phe
                85                  90                  95

Asp Arg Asp Gly Cys Phe Ser Gly Cys Ala Val Asp Asn Asn Gly Val
            100                 105                 110

Leu Thr Leu Ile Tyr Thr Gly His Ile Val Leu Ser Asn Asp Ser Pro
        115                 120                 125

Asp Ala Ile Arg Glu Val Gln Cys Met Ala Thr Ser Ile Asp Gly Ile
    130                 135                 140

His Phe Gln Lys Glu Gly Ile Val Leu Glu Lys Ala Pro Met Pro Gln
145                 150                 155                 160

Val Ala His Phe Arg Asp Pro Arg Val Trp Lys Glu Asn Asp His Trp
                165                 170                 175

Phe Met Val Val Gly Tyr Arg Thr Asp Asp Glu Lys His Gln Gly Ile
            180                 185                 190

Gly His Val Ala Leu Tyr Arg Ser Glu Asn Leu Lys Asp Trp Ile Phe
        195                 200                 205

Val Lys Thr Leu Leu Gly Asp Asn Ser Gln Leu Pro Leu Gly Lys Arg
    210                 215                 220

Ala Phe Met Trp Glu Cys Pro Asp Phe Phe Ser Leu Gly Asn Arg Ser
225                 230                 235                 240

Val Leu Met Phe Ser Pro Gln Gly Leu Lys Ala Ser Gly Tyr Lys Asn
                245                 250                 255

Arg Asn Leu Phe Gln Asn Gly Tyr Ile Leu Gly Lys Trp Gln Ala Pro
            260                 265                 270

Gln Phe Thr Pro Glu Thr Ser Phe Gln Glu Leu Asp Tyr Gly His Asp
        275                 280                 285

Phe Tyr Ala Ala Gln Arg Phe Glu Ala Lys Asp Gly Arg Gln Ile Leu
    290                 295                 300

Ile Ala Trp Phe Asp Met Trp Glu Asn Gln Lys Pro Ser Gln Arg Asp
305                 310                 315                 320

Gly Trp Ala Gly Cys Met Thr Leu Pro Arg Lys Leu Asp Leu Ile Asp
                325                 330                 335

Asn Lys Ile Val Met Thr Pro Val Arg Glu Met Glu Ile Leu Arg Gln
            340                 345                 350

Ser Glu Lys Ile Glu Ser Val Val Thr Leu Ser Asp Ala Glu His Pro
        355                 360                 365

Phe Thr Met Asp Ser Pro Leu Gln Glu Ile Glu Leu Ile Phe Asp Leu
    370                 375                 380

Glu Lys Ser Ser Ala Tyr Gln Ala Gly Leu Ala Leu Arg Cys Asn Gly
385                 390                 395                 400

Lys Gly Gln Glu Thr Leu Leu Tyr Ile Asp Arg Ser Gln Asn Arg Ile
                405                 410                 415

Ile Leu Asp Arg Asn Arg Ser Gly Gln Asn Val Lys Gly Ile Arg Ser
            420                 425                 430

Cys Pro Leu Pro Asn Thr Ser Lys Val Arg Leu His Ile Phe Leu Asp
        435                 440                 445

Arg Ser Ser Ile Glu Ile Phe Val Gly Asp Asp Gln Thr Gln Gly Leu
    450                 455                 460

Tyr Ser Ile Ser Ser Arg Ile Phe Pro Asp Asp Ser Leu Lys Gly
465                 470                 475                 480

Arg Leu Phe Ala Ile Glu Gly Tyr Ala Val Phe Asp Ser Phe Lys Arg
                485                 490                 495

Trp Thr Leu Gln Asp Ala Asn Leu Ala Ala Phe Ser Ser Asp Ala Cys
```

<210> SEQ ID NO 30
<211> LENGTH: 987
<212> TYPE: DNA
<213> ORGANISM: Chlorella luteoviridis

<400> SEQUENCE: 30

| | | | | | |
|---|---|---|---|---|---|
| tgttgaagaa | tgagccggcg | acttatagga | agtggcttgg | ttaaggatac | tttccgaagc | 60 |
| ctaagcgaaa | gcaagttgta | acaatagcga | tatacctctt | tgtaggtcag | tcacttctta | 120 |
| tggacccgaa | cccgggtgat | ctaaccatga | ccaggatgaa | gcttgggtaa | caccaagtga | 180 |
| aggtccgaac | tcttcgatct | ttaaaaatcg | tgagatgagt | tatggttagg | ggtaaatctg | 240 |
| gcagttttgc | cccgcaaaag | ggtaaccttt | tgtaattact | gactcataac | ggtgaagcct | 300 |
| aaggcgttag | ctatggtaat | accgtgggaa | gtttcaatac | cttcttgcat | atttttttatt | 360 |
| tgcacccttta | gtgcaaacag | tgtaaagaaa | gcgttttgaa | accccttaac | gactaatttt | 420 |
| ttgcttttgc | aagaacgtca | gcactcacca | atacactttc | cgttttttttc | ttttattaat | 480 |
| taaagcaaca | taaaaatata | ttttatagct | ttaatcataa | aactatgtta | gcacttcgtg | 540 |
| ctaatgtgct | aatgtgctaa | tcaaatgaaa | agtgttctta | aaagtgagtt | gaaggtagag | 600 |
| tctaatcttg | cctgaaaggg | caagctgcac | attttttttt | gaatgtgcaa | caatggaaat | 660 |
| gccaatcgaa | ctcggagcta | gctggttctc | cccgaaatgt | gttgaggcgc | agcgattcat | 720 |
| gattagtacg | gtgtaggggt | aaagcactgt | ttcggtgcgg | gctgtgaaaa | cggtaccaaa | 780 |
| tcgtggcaaa | ctaagaatac | tacgcttgta | taccatggat | cagtgagact | atggggggata | 840 |
| agctccatag | tcaagaggga | aacagcccag | atcaccagtt | aaggccccaa | aatgacagct | 900 |
| aagtggcaaa | ggaggtgaaa | gtgcagaaac | aaccaggagg | tttgcccaga | agcagccatc | 960 |
| ctttaaagag | tgcgtaatag | ctcactg | | | | 987 |

<210> SEQ ID NO 31
<211> LENGTH: 1412
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

| | | | | | |
|---|---|---|---|---|---|
| gaattcgagt | ttaggtccag | cgtccgtggg | gggggacggg | ctgggagctt | gggccgggaa | 60 |
| gggcaagacg | atgcagtccc | tctgggagt | cacagccgac | tgtgtgtgtt | gcactgtgcg | 120 |
| gcccgcagca | ctcacacgca | aaatgcctgg | ccgacaggca | ggccctgtcc | agtgcaacat | 180 |
| ccacggtccc | tctcatcagg | ctcacctttgc | tcattgacat | aacggaatgc | gtaccgctct | 240 |
| ttcagatctg | tccatccaga | gaggggagca | ggctccccac | cgacgctgtc | aaacttgctt | 300 |
| cctgcccaac | cgaaaacatt | attgtttgag | gggggggggg | gggggcaga | ttgcatggcg | 360 |
| ggatatctcg | tgaggaacat | cactgggaca | ctgtggaaca | cagtgagtgc | agtatgcaga | 420 |
| gcatgtatgc | taggggtcag | cgcaggaagg | gggcctttcc | cagtctccca | tgccactgca | 480 |
| ccgtatccac | gactcaccag | gaccagcttc | ttgatcggct | tccgctcccg | tggacaccag | 540 |
| tgtgtagcct | ctggactcca | ggtatgcgtg | caccgcaaag | gccagccgat | cgtgccgatt | 600 |
| cctggggtgg | aggatatgag | tcagccaact | tgggctcag | agtgcacact | ggggcacgat | 660 |
| acgaaacaac | atctacaccg | tgtcctccat | gctgacacac | cacagcttcg | ctccacctga | 720 |

| | |
|---|---|
| atgtgggcgc atgggcccga atcacagcca atgtcgctgc tgccataatg tgatccagac | 780 |
| cctctccgcc cagatgccga gcggatcgtg ggcgctgaat agattcctgt ttcgatcact | 840 |
| gtttgggtcc tttcctttc gtctcggatg cgcgtctcga acaggctgc gtcgggcttt | 900 |
| cggatccctt ttgctccctc cgtcaccatc ctgcgcgcgg gcaagttgct tgaccctggg | 960 |
| ctggtaccag ggttggaggg tattaccgcg tcaggccatt cccagcccgg attcaattca | 1020 |
| aagtctgggc caccaccctc cgccgctctg tctgatcact ccacattcgt gcatacacta | 1080 |
| cgttcaagtc ctgatccagg cgtgtctcgg acaaggtgt gcttgagttt gaatctcaag | 1140 |
| gacccactcc agcacagctg ctggttgacc ccgccctcgc aactccctac catgtctgct | 1200 |
| ggtaggtcca gggatctttg ccatgcacac aggacccccgt ttgtgggggt ccccggtgca | 1260 |
| tgctgtcgct gtgcaggcgc cggtgtgggg cctgggcccc gcgggagctc aactcctccc | 1320 |
| catatgcctg ccgtccctcc cacccaccgc gacctggccc cctttgcaga ggaaggcgaa | 1380 |
| gtcagcgcca tcgtgtgcga taatggatcc gg | 1412 |

<210> SEQ ID NO 32
<211> LENGTH: 1627
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

| | |
|---|---|
| gaattcgccc ttgagtttag gtccagcgtc cgtgggggggg gcgtgagact ccccctgac | 60 |
| cttcgtatgg cagggactcc tacttgccaa gtaatcagtt gacaatgcca cttcaatgct | 120 |
| cgttgtggta cactgacgcg ggtctaacat actgggaagc atgaattgcc gacatggact | 180 |
| cagttggaga cagtaacagc tctttgtgtt ctatcttcag gaacacattt ggcagcgcac | 240 |
| ccatacagtg gcgcacacgc agctgtacct gatgtggctc tattcccaca tgtttcaact | 300 |
| tgatccaaaa gtcactcaga ctctcagcag ctagacttga tcgcatcttt ggccatgaag | 360 |
| atgcttgcgc aactctagga atgggacgag aaaagagcct gctctgatcg gatatttcca | 420 |
| ttctctggat gggactgaga tgattctgaa gaaatgctgc tcgacttatt tggaagaaca | 480 |
| gcacctgacg catgctttga ggctgctgtg gctgggatgt gctgtatttg tcagcattga | 540 |
| gcatctacgg gtagatggcc ataaccacgc gctgcctatc atgcgggtggg ttgtgtggaa | 600 |
| aacgtacaat ggacagaaat caatcccatt gcgagcctag cgtgcagcca tgcgctccct | 660 |
| ctgtagcccc gctccaagac aaagccagcc aatgccagaa cccacataga gagggtatct | 720 |
| tcctaatgac ctcgcccatc atttcctcca aattaactat aatgccttga ttgtggagtt | 780 |
| ggctttggct tgcagctgct cgcgctggca cttttgtagg cagcacaggg tatgccagcg | 840 |
| ccgaactttg tgcccttgag caggccacaa gggcacaaga ctacaccatg cagctggtat | 900 |
| acttggaact gataccattc ttaccaagca aggcacagca cagcctgcac cgactcactt | 960 |
| tgcttgagcg gggcacagcg ccgcgactga tcctgcgagc tgtggggagt tccgactgtt | 1020 |
| ctggacctcg gtctctgaaa gatgtgtacg atgggatcaa gtcattcaag tatgctcttc | 1080 |
| acatgagcaa tcgggggaga cacggtgcc ctaaaggtgt tcatctgatt caagtgtagt | 1140 |
| ggggggggtgc tgtttgtccc ggggcgcccc ccgctcccg accccggaga agggccccag | 1200 |
| aggactcggc cgcccacaga ggaataaccg gcgtggctc ggccctgcgc ctccctcttt | 1260 |
| caatatttca cctggtgttc agtgcacgga cacgtaaaga actagataca atggccgagg | 1320 |

```
gaaagacggt gagagcttgg cgttggtgga ccgggcagca tcagaaactc ctcttccccg    1380
cccgccttga aactcactgt aactccctcc tcttcccctt cgcagcatct gtctatcgtt    1440
atcgtgagtg aaagggactg ccatgtgtcg ggtcgttgac cacggtcggc tcgggcgctg    1500
ctgcccgcgt cgcgaacgtt ccctgcaaac gccgcgcagc cgtcccttt tctgccgccg     1560 ccccacccccc tcgctccccc cttcaatcac accgcagtgc ggacatgtcg attccggcaa   1620
gtccacc                                                              1627
```

<210> SEQ ID NO 33
<211> LENGTH: 570
<212> TYPE: DNA
<213> ORGANISM: Chlorella protothecoides

<400> SEQUENCE: 33

```
gaattccctg caggaagaag gccggcagca gctggtactt gtccttcacc tccttgatcg     60
gctgggtgag cttggccggg tcgcagtcgt cgatgccggc atcgcccagc acgctgtgcg    120
gggagccggc atcgacaacc ttggcactgc tcaccttggt caccggcatg ggtcatggc     180 gctgcagacc agcggcctgt cagcatgctg caggcatctg tgttttgtag tagatacttt    240
ctgatgcatc accacgcgtt tggaaggtcc ccaagcccct tcaacagtct cgacatatga    300
cactcgcgcc ctcttcctcg tcccgtggcc tgatgagggt acgcaggtac cgcagctgcg    360
ccccgtcccg ccagttgccc tggccccgcc gggcccaatc tgttcattgc cgctccctgg    420
cagccgtgaa cttcacacta ccgctctctg tgaccttcag cacagcagga atcgccattt    480
caccggcggt cgttgctgcg gagcctcagc tgatctcgcc tgcgagaccc cacagtttga    540
atttgcggtc cccacacaac ctctgacgcc                                     570
```

<210> SEQ ID NO 34
<211> LENGTH: 568
<212> TYPE: DNA
<213> ORGANISM: Chlorella protothecoides
<220> FEATURE:
<221> NAME/KEY: modified_base
<222> LOCATION: (133)..(133)
<223> OTHER INFORMATION: a, c, t, g, unknown or other

<400> SEQUENCE: 34

```
gaattccctc aggaagaagg ccggcagcag ctggtacttg tccttcacct ccttgatcgg     60
ctgggtgagc ttcgcaggat cgcagtcgtc gatgccggca tcgcccagca cgctgtgcgg    120
ggagccggca tcnacaacct tggcactgct ccccttggtc accggcatgg gtcatggcg     180 ctgcagccca gcggcctgtc agcatgctgc aggcatctgt gtattgtagt aggtacttcc    240
tgatgcatca acacacgttt ggaagctccc caagccccttt caacagtctc gacgtatgac    300
actcgcgccc tcttcctcgc cccgtggcct gatgagggta cgcaggtacc acagctgcgc    360 ccgtcccgc cagttgccct ggccggccg ggcccaatct gttcattgcc gctccctggt     420
agccgtgaac tcacattacc gctctctgtg accttcagca cagcaggaat cgccatttca    480
ccggcggtcg ttgctgcgga gcctcagctg atctcgcctg cgagacccca gtttgaat      540 ttgcggtccc cacacaacct ctgacgcc                                       568
```

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
tgacctaggt gattaattaa ctcgaggcag cagcagctcg gatagtatcg           50

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctacgagctc aagctttcca tttgtgttcc catcccacta cttcc                45

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gatcagaatt ccgcctgcaa cgcaagggca gc                              32

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcatactagt ggcgggacgg agagagggcg                                 30

<210> SEQ ID NO 39
<211> LENGTH: 1568
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaattccttt cttgcgctat gacacttcca gcaaaaggta gggcgggctg cgagacggct    60
tcccggcgct gcatgcaaca ccgatgatgc ttcgaccccc cgaagctcct tcggggctgc   120
atgggcgctc cgatgccgct ccagggcgag cgctgtttaa atagccaggc cccgattgc    180 aaagacatta tagcgagcta ccaaagccat attcaaacac ctagatcact accacttcta   240
cacaggccac tcgagcttgt gatcgcactc cgctaagggg gcgcctcttc ctcttcgttt   300
cagtcacaac ccgcaaacgg cgcgccatat caatgattga acaagatgga ttgcacgcag   360
gttctccggc cgcttgggtg gagaggctat tcggctatga ctgggcacaa cagacaatcg   420
gctgctctga tgccgccgtg ttccggctgt cagcgcaggg gcgcccggtt ctttttgtca   480
agaccgacct gtccggtgcc ctgaatgaac tgcaggacga ggcagcgcgg ctatcgtggc   540
tggccacgac gggcgttcct tgcgcagctg tgctcgacgt tgtcactgaa gcgggaaggg   600
actggctgct attgggcgaa gtgccggggc aggatctcct gtcatctcac cttgctcctg   660
ccgagaaagt atccatcatg gctgatgcaa tgcggcggct gcatacgctt gatccggcta   720

| | |
|---|---:|
| cctgcccatt cgaccaccaa gcgaaacatc gcatcgagcg agcacgtact cggatggaag | 780 |
| ccggtcttgt cgatcaggat gatctggacg aagagcatca ggggctcgcg ccagccgaac | 840 |
| tgttcgccag gctcaaggcg cgcatgcccg acggcgagga tctcgtcgtg acccatggcg | 900 |
| atgcctgctt gccgaatatc atggtggaaa atggccgctt ttctggattc atcgactgtg | 960 |
| gccggctggg tgtggcggac cgctatcagg acatagcgtt ggctacccgt gatattgctg | 1020 |
| aagagcttgg cggcgaatgg gctgaccgct tcctcgtgct ttacggtatc gccgctcccg | 1080 |
| attcgcagcg catcgccttc tatcgccttc ttgacgagtt cttctaagat ctgtcgatcg | 1140 |
| acaagtgact cgaggcagca gcagctcgga tagtatcgac acactctgga cgctggtcgt | 1200 |
| gtgatggact gttgccgcca cacttgctgc cttgacctgt gaatatccct gccgctttta | 1260 |
| tcaaacagcc tcagtgtgtt tgatcttgtg tgtacgcgct tttgcgagtt gctagctgct | 1320 |
| tgtgctattt gcgaatacca cccccagcat ccccttccct cgtttcatat cgcttgcatc | 1380 |
| ccaaccgcaa cttatctacg ctgtcctgct atccctcagc gctgctcctg ctcctgctca | 1440 |
| ctgcccctcg cacagccttg gtttgggctc cgcctgtatt ctcctggtac tgcaacctgt | 1500 |
| aaaccagcac tgcaatgctg atgcacggga agtagtggga tgggaacaca atggaaagc | 1560 |
| ttgagctc | 1568 |

<210> SEQ ID NO 40
<211> LENGTH: 2571
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (997)..(999)
<223> OTHER INFORMATION: a, c, t, g, unknown or other

<400> SEQUENCE: 40

| | |
|---|---:|
| gaattccgcc tgcaacgcaa gggcagccac agccgctccc acccgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggacgtg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg ggcatgccac agcacgggca ccggggagtg | 420 |
| gaatggcacc accaagtgtg tgcgagccag catcgccgcc tggctgtttc agctacaacg | 480 |
| gcaggagtca tccaactaac catagctgat caacactgca atcatcggcg gctgatgcaa | 540 |
| gcatcctgca agacacatgc tgtgcgatgc tgcgctgctg cctgctgcgc acgccgttga | 600 |
| gttggcagca gctcagccat gcactggatc aggctgggct gccactgcaa tgtggtggat | 660 |
| aggatgcaag tggagcgaat accaaaccct ctggctgctt gctgggttgc atggcatcgc | 720 |
| accatcagca ggagcgcatg cgaagggact ggccccatgc acgccatgcc aaaccggagc | 780 |
| gcaccgagtg tccacactgt caccaggccc gcaagctttg cagaaccatg ctcatggacg | 840 |
| catgtagcgc tgacgtccct tgacggcgct cctctcgggt gtgggaaacg caatgcagca | 900 |
| caggcagcag aggcggcggc agcagagcgg cggcagcagc ggcgggggcc acccttcttg | 960 |
| cggggtcgcg ccccagccag cggtgatgcg ctgatcnnnc caaacgagtt cacattcatt | 1020 |

```
tgcagcctgg agaagcgagg ctggggcctt tgggctggtg cagcccgcaa tggaatgcgg    1080
gaccgccagg ctagcagcaa aggcgcctcc cctactccgc atcgatgttc catagtgcat    1140
tggactgcat ttgggtgggg cggccggctg tttctttcgt gttgcaaaac gcgccacgtc    1200
agcaacctgt cccgtgggtc ccccgtgccg atgaaatcgt gtgcacgccg atcagctgat    1260
tgcccggctc gcgaagtagg cgccctcttt ctgctcgccc tctctccgtc ccgccactag    1320
tggcgcgcca tatcaatgat tgaacaagat ggattgcacg caggttctcc ggccgcttgg    1380
gtggagaggc tattcggcta tgactgggca acagacaa tcggctgctc tgatgccgcc     1440
gtgttccggc tgtcagcgca ggggcgcccg gttcttttg tcaagaccga cctgtccggt     1500
gccctgaatg aactgcagga cgaggcagcg cggctatcgt ggctggccac gacgggcgtt    1560
ccttgcgcag ctgtgctcga cgttgtcact gaagcgggaa gggactggct gctattgggc    1620
gaagtgccgg ggcaggatct cctgtcatct caccttgctc ctgccgagaa agtatccatc    1680
atggctgatg caatgcggcg gctgcatacg cttgatccgg ctacctgccc attcgaccac    1740
caagcgaaac atcgcatcga gcgagcacgt actcggatgg aagccggtct tgtcgatcag    1800
gatgatctgg acgaagagca tcaggggctc gcgccagccg aactgttcgc caggctcaag    1860
gcgcgcatgc ccgacggcga ggatctcgtc gtgacccatg gcgatgcctg cttgccgaat    1920
atcatggtgg aaaatggccg cttttctgga ttcatcgact gtggccggct gggtgtggcg    1980
gaccgctatc aggacatagc gttggctacc cgtgatattg ctgaagagct tggcggcgaa    2040
tgggctgacc gcttcctcgt gctttacggt atcgccgctc ccgattcgca gcgcatcgcc    2100
ttctatcgcc ttcttgacga gttcttctaa gatctgtcga tcgacaagtg actcgaggca    2160
gcagcagctc ggatagtatc gacacactct ggacgctggt cgtgtgatgg actgttgccg    2220
ccacacttgc tgccttgacc tgtgaatatc cctgccgctt ttatcaaaca gcctcagtgt    2280
gtttgatctt gtgtgtacgc gcttttgcga gttgctagct gcttgtgcta tttgcgaata    2340 ccaccccag catccccttc cctcgtttca tatcgcttgc atcccaaccg caacttatct     2400
acgctgtcct gctatccctc agcgctgctc ctgctcctgc tcactgcccc tcgcacagcc    2460
ttggtttggg ctccgcctgt attctcctgg tactgcaacc tgtaaaccag cactgcaatg    2520
ctgatgcacg ggaagtagtg ggatgggaac acaaatggaa agcttgagct c             2571
```

<210> SEQ ID NO 41
<211> LENGTH: 2550
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (997)..(999)
<223> OTHER INFORMATION: a, c, t, g, unknown or other

<400> SEQUENCE: 41

```
gaattccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggacgtg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
```

```
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaactaac catagctgat caacactgca atcatcggcg gctgatgcaa    540
gcatcctgca agacacatgc tgtgcgatgc tgcgctgctg cctgctgcgc acgccgttga    600
gttggcagca gctcagccat gcactggatc aggctgggct gccactgcaa tgtggtggat    660
aggatgcaag tggagcgaat accaaaccct ctggctgctt gctgggttgc atggcatcgc    720
accatcagca ggagcgcatg cgaagggact ggccccatgc acgccatgcc aaaccggagc    780
gcaccgagtg tccacactgt caccaggccc gcaagctttg cagaaccatg ctcatggacg    840
catgtagcgc tgacgtccct tgacggcgct cctctcgggt gtgggaaacg caatgcagca    900
caggcagcag aggcggcggc agcagagcgg cggcagcagc ggcgggggcc acccttcttg    960
cggggtcgcg ccccagccag cggtgatgcg ctgatcnnnc aaacgagtt cacattcatt   1020 tgcagcctgg agaagcgagg ctggggcctt gggctggtg cagcccgcaa tggaatgcgg   1080
gaccgccagg ctagcagcaa aggcgcctcc cctactccgc atcgatgttc catagtgcat   1140
tggactgcat ttgggtgggg cggccggctg tttctttcgt gttgcaaaac gcgccacgtc   1200
agcaacctgt cccgtgggtc ccccgtgccg atgaaatcgt gtgcacgccg atcagctgat   1260
tgcccggctc gcgaagtagg cgccctcttt ctgctcgccc tctctccgtc ccgccactag   1320
tggcgcgcca tatcaatgat cgagcaggac ggcctccacg ccggctcccc cgccgcctgg   1380
gtggagcgcc tgttcggcta cgactgggcc cagcagacca tcggctgctc cgacgccgcc   1440
gtgttccgcc tgtccgccca gggccgcccc gtgctgttcg tgaagaccga cctgtccggc   1500
gccctgaacg agctgcagga cgaggccgcc cgcctgtcct ggctggccac caccggcgtg   1560
ccctgcgccg ccgtgctgga cgtggtgacc gaggccggcc gcgactggct gctgctgggc   1620
gaggtgcccg ccaggacct gctgtcctcc cacctggccc ccgccgagaa ggtgtccatc   1680
atggccgacg ccatgcgccg cctgcacacc ctggaccccg ccacctgccc cttcgaccac   1740
caggccaagc accgcatcga gcgcgcccgc acccgcatgg aggccggcct ggtgaccag   1800 gacgacctgg acgaggagca ccagggcctg gcccccgccc agctgttcgc ccgcctgaag   1860
gcccgcatgc ccgacggcga ggacctggtg gtgacccacg gcgacgcctg cctgcccaac   1920
atcatggtgg agaacggccg cttctccggc ttcatcgact gcggccgcct gggcgtggcc   1980
gaccgctacc aggacatcgc cctggccacc gcgacatcg ccgaggagct gggcggcgag   2040
tgggccgacc gcttcctggt gctgtacggc atcgccgccc ccgactccca gcgcatcgcc   2100
ttctaccgcc tgctggacga gttcttctga ctcgaggcag cagcagctcg atagtatcg    2160 acacactctg gacgctggtc gtgtgatgga ctgttgccgc cacacttgct gccttgacct   2220
gtgaatatcc ctgccgcttt tatcaaacag cctcagtgtg tttgatcttg tgtgtacgcg   2280
cttttgcgag ttgctagctg cttgtgctat ttgcgaatac cacccccagc atcccttcc   2340 ctcgtttcat atcgcttgca tcccaaccgc aacttatcta cgctgtcctg ctatccctca   2400
gcgctgctcc tgctcctgct cactgcccct cgcacagcct tggtttgggc tccgcctgta   2460
ttctcctggt actgcaacct gtaaaccagc actgcaatgc tgatgcacgg gaagtagtgg   2520
gatgggaaca caaatggaaa gcttgagctc                                    2550
```

<210> SEQ ID NO 42
<211> LENGTH: 1547
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 42

```
gaattccttt cttgcgctat gacacttcca gcaaaaggta gggcgggctg cgagacggct      60
tcccggcgct gcatgcaaca ccgatgatgc ttcgaccccc cgaagctcct tcggggctgc     120
atgggcgctc cgatgccgct ccagggcgag cgctgtttaa atagccaggc ccccgattgc     180
aaagacatta tagcgagcta ccaaagccat attcaaacac ctagatcact accacttcta     240
cacaggccac tcgagcttgt gatcgcactc cgctaagggg gcgcctcttc ctcttcgttt     300
cagtcacaac ccgcaaacgg cgcgccatat caatgatcga gcaggacggc ctccacgccg     360
gctcccccgc cgcctgggtg gagcgcctgt tcggctacga ctgggcccag cagaccatcg     420
gctgctccga cgccgccgtg ttccgcctgt ccgcccaggg ccgccccgtg ctgttcgtga     480
agaccgacct gtccggcgcc ctgaacgagc tgcaggacga ggccgcccgc ctgtcctggc     540
tggccaccac cggcgtgccc tgcgccgccg tgctggacgt ggtgaccgag gccggccgcg     600
actggctgct gctgggcgag gtgcccggcc aggacctgct gtcctcccac ctggcccccg     660
ccgagaaggt gtccatcatg gccgacgcca tgcgccgcct gcacaccctg accccgcca     720
cctgccccct cgaccaccag gccaagcacc gcatcgagcg cgcccgcacc cgcatggagg     780
ccggcctggt ggaccaggac gacctggacg aggagcacca gggcctggcc ccgccgagc     840
tgttcgcccg cctgaaggcc cgcatgcccg acgcgagga cctggtggtg acccacggcg     900
acgcctgcct gcccaacatc atggtggaga acggccgctt ctccggcttc atcgactgcg     960
gccgcctggg cgtggccgac cgctaccagg acatcgccct ggccaccgc gacatcgccg    1020
aggagctggg cggcgagtgg gccgaccgct tcctggtgct gtacggcatc gccgccccg    1080
actcccagcg catcgccttc taccgcctgc tggacgagtt cttctgactc gaggcagcag    1140
cagctcggat agtatcgaca cactctggac gctggtcgtg tgatggactg ttgccgccac    1200
acttgctgcc ttgacctgtg aatatccctg ccgcttttat caaacagcct cagtgtgttt    1260
gatcttgtgt gtacgcgctt ttgcgagttg ctagctgctt gtgctatttg cgaataccac    1320
ccccagcatc cccttccctc gtttcatatc gcttgcatcc caaccgcaac ttatctacgc    1380
tgtcctgcta tccctcagcg ctgctcctgc tcctgctcac tgcccctcgc acagccttgg    1440
tttgggctcc gcctgtattc tcctggtact gcaacctgta aaccagcact gcaatgctga    1500
tgcacgggaa gtagtgggat gggaacacaa atgaaagct tgagctc                  1547
```

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 43

```
gccgcgactg gctgctgctg g                                                21
```

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aggtcctcgc cgtcgggcat g                                          21

<210> SEQ ID NO 45
<211> LENGTH: 1292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atcaaaggca tagattcaca tttgttggca ttgcagagca atcatcgcgc aggacgaaca      60
tcgctcacca agcacgtact gggcatccgg aggcctccgc aaattcctgc aacaggactc    120
gctgatcagt tcgcccaagg tctacgacgc tccctatcgg cgctagactt caacacatat    180
ttcactgtca cagcctcggc atgcatcagg cctcagtctc caccatgaag accatccagt    240
ctcggcacgc cggtcccatc ggacatgtgc agtcgggtcg ccgatcggcg gggcgcgcgg    300
gatcccgcat ggcgaccccc gtggccgcag ctaccgtcgc agcccctcgc tcggccctca    360
acctctcccc caccatcatt cgacaggagg tgctccactc cgccagcgcc cagcaactag    420
actgcgtggc ctccctggcg cccgtcttcg agtcccagat cctcccccctc ctgacgcccg    480 tggacgagat gtggcagccc accgacttcc tccccgcctc gaactcggag gcattcttcg    540
accagatcgg cgacctgcgg gcgcgatcgg cggccatccc cgacgacctg ctggtctgcc    600
tggtggggga catgatcacg gaggaggccc tgcccaccta catggccatg ctgaacaccc    660
tggacgtcgt gcgcgatgag acagggcaca gccagcaccc ctacgccaag tggaccaggg    720
cttggatcgc ggaggagaac cgccatggcg acctgctgaa caagtacatg tggctgacgg    780
ggcgggtggg acatgctggc ggtggagcgc accatccagc catgctggcg gtggagcgca    840
ccatccagcg cctcatctca tcgggcatgg acccgggcac ggagaaccac ccctaccacg    900
cctttgtgtt caccagcttc caggagcgcg ccaccaagct gagccacggc tccaccgccc    960
gcctggcggt cgccgccggg gacgaggccc tggccaagat ctgcgggacc attgcgcggg   1020
acgagtcgcg ccacgaggcg gcgtacacgc ggaccatgga tgccatcttc cagcgcgacc   1080
ccagcggggc catggtggcg tttgcgcaca tgatgatgcg caagatcacc atgcccgccc   1140
acctcatgga cgacggccag cacggcgcgc gcaacggggg ggcgcaactt gttcgacgac   1200
tttgcggcag tggcggagcg ggcaggggtg tacaccgccg cgactacat cggcatcctg   1260 cgccacctca tccggcgctg ggacgtggag gg                                1292

<210> SEQ ID NO 46
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met His Gln Ala Ser Val Ser Thr Met Lys Thr Ile Gln Ser Arg His
1               5                   10                  15

Ala Gly Pro Ile Gly His Val Gln Ser Gly Arg Arg Ser Ala Gly Arg
            20                  25                  30

Ala Gly Ser Arg Met Ala Thr Pro Val Ala Ala Ala Thr Val Ala Ala

```
            35                  40                  45
Pro Arg Ser Ala Leu Asn Leu Ser Pro Thr Ile Ile Arg Gln Glu Val
 50                  55                  60

Leu His Ser Ala Ser Ala Gln Gln Leu Asp Cys Val Ala Ser Leu Ala
 65                  70                  75                  80

Pro Val Phe Glu Ser Gln Ile Leu Pro Leu Thr Pro Val Asp Glu
                 85                  90                  95

Met Trp Gln Pro Thr Asp Phe Leu Pro Ala Ser Asn Ser Glu Ala Phe
                100                 105                 110

Phe Asp Gln Ile Gly Asp Leu Arg Ala Arg Ser Ala Ala Ile Pro Asp
                115                 120                 125

Asp Leu Leu Val Cys Leu Val Gly Asp Met Ile Thr Glu Glu Ala Leu
                130                 135                 140

Pro Thr Tyr Met Ala Met Leu Asn Thr Leu Asp Val Val Arg Asp Glu
145                 150                 155                 160

Thr Gly His Ser Gln His Pro Tyr Ala Lys Trp Thr Arg Ala Trp Ile
                165                 170                 175

Ala Glu Glu Asn Arg His Gly Asp Leu Leu Asn Lys Tyr Met Trp Leu
                180                 185                 190

Thr Gly Arg Val Gly His Ala Gly Gly Ala His His Pro Ala Met
                195                 200                 205

Leu Ala Val Glu Arg Thr Ile Gln Arg Leu Ile Ser Ser Gly Met Asp
210                 215                 220

Pro Gly Thr Glu Asn His Pro Tyr His Ala Phe Val Phe Thr Ser Phe
225                 230                 235                 240

Gln Glu Arg Ala Thr Lys Leu Ser His Gly Ser Thr Ala Arg Leu Ala
                245                 250                 255

Val Ala Ala Gly Asp Glu Ala Leu Ala Lys Ile Cys Gly Thr Ile Ala
                260                 265                 270

Arg Asp Glu Ser Arg His Glu Ala Ala Tyr Thr Arg Thr Met Asp Ala
                275                 280                 285

Ile Phe Gln Arg Asp Pro Ser Gly Ala Met Val Ala Phe Ala His Met
290                 295                 300

Met Met Arg Lys Ile Thr Met Pro Ala His Leu Met Asp Asp Gly Gln
305                 310                 315                 320

His Gly Ala Arg Asn Gly Gly Ala Gln Leu Val Arg Arg Leu Cys Gly
                325                 330                 335

Ser Gly Gly Ala Gly Arg Gly Val His Arg Arg Leu His Arg His
                340                 345                 350

Pro Ala Pro Pro His Pro Ala Leu Gly Arg Gly Gly
                355                 360

<210> SEQ ID NO 47
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
attatacatc ggcatcgtct caggtttcac gatctgcatg ctatctatgg gactgtgact      60
ccgccggcca ggttgtggtg cgcgagaatc ctccccgctc ctgccttctc atttccctga     120
cgggagtcgc cgctgagcac cgggcggatc atgggcgtcg gcacactcca aaccccatat     180
```

```
acatgtggtc gtgcattcac gcatagcgca cggtatgtcc cgcgacgcgc ggctcgaagc    240
cgtggccatc cgacgcgctg cacggccgag gtgagggcac gccccctccgc caatggcgcg   300
cagcccatga ccgccttcga cttccggcag tacatgcagc agcgcgccgc gctggtggac    360
gcagcgctgg aacctgcagt gccgctgcag taccccgaga agatcaacga ggccatgcgg    420
tacagcctgc tggccggggg caagcgcgtg cgccccgcgc tctgcctcgc tgcctgcgag    480
ctcgtgggcg gccccctgga ggcggccatg cccgccgcct cgccatgga gatgatccac     540
accatgagcc tcatccacga cgacctcccc gccatggaca cgacgactt ccggcgcggc     600
cagcccgcca accacaaggc ctatggcgag gagattgcga tcctggcggg cgacgcgctg    660
ctgtcgctga gctttgagca catcgcgcgc gagacgcgag gcgtggaccc ggtgcgcgtc    720
ctggccgcca tctcggagtg gcgcgcggtg ggcagccgcg ggctggtggc ggggcaggtg    780
gtggacctgg gtttcgaggg cggcggcgtg gggctggccc cgctgcgcta catccacgag    840
cacaaaaccg cggcgctgct ggaggcggcg gtggtgtccg gcgcgctgct gggcggcgcg    900
gaggaggcgg acctggagcg cctgcgcacc tacaaccgcg ccatcggcct cgctttccag    960
gtggtggggg acatcctgga catcccgggg accagcgagg agctgggcaa gaccgcgggc   1020
aaggacctga gctcccccaa aaccccctac ccgtccctgg tggggctggc caggtccaaa   1080
aaaattgcgg acgaactgat tgaggacgcg aaaacccaac tcacccagta cgagccggcc   1140
cgagcggcgc ccctcgtaac cctggccgaa aacatttgaa accggaagaa ctgactgggg   1200
gccccccctg ccccagata cggcggggct cctccatcca gttttgggat gggaggagcg    1260
acaaccgacc ccgtaaccct gtgacgcgtt tgccttgcat acgtacgcat gccttgaaac   1320
ccatccatga ccctcaacaa tacctggttg tgtgtagctt ggtcctgaaa aaaaaaaaa    1380
aaaaaaaaaa aaaaa                                                    1395

<210> SEQ ID NO 48
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Val Gly Thr Leu Gln Thr Pro Tyr Thr Cys Gly Arg Ala Phe
1               5                   10                  15

Thr His Ser Ala Arg Tyr Val Pro Arg Arg Ala Ala Arg Ser Arg Gly
            20                  25                  30

His Pro Thr Arg Cys Thr Ala Glu Val Arg Ala Arg Pro Ser Ala Asn
        35                  40                  45

Gly Ala Gln Pro Met Thr Ala Phe Asp Phe Arg Gln Tyr Met Gln Gln
    50                  55                  60

Arg Ala Ala Leu Val Asp Ala Leu Asp Leu Ala Val Pro Leu Gln
65                  70                  75                  80

Tyr Pro Glu Lys Ile Asn Glu Ala Met Arg Tyr Ser Leu Leu Ala Gly
                85                  90                  95

Gly Lys Arg Val Arg Pro Ala Leu Cys Leu Ala Ala Cys Glu Leu Val
            100                 105                 110

Gly Gly Pro Leu Glu Ala Ala Met Pro Ala Ala Cys Ala Met Glu Met
        115                 120                 125

Ile His Thr Met Ser Leu Ile His Asp Asp Leu Pro Ala Met Asp Asn
    130                 135                 140
```

```
Asp Asp Phe Arg Arg Gly Gln Pro Ala Asn His Lys Ala Tyr Gly Glu
145                 150                 155                 160

Glu Ile Ala Ile Leu Ala Gly Asp Ala Leu Leu Ser Leu Ser Phe Glu
            165                 170                 175

His Ile Ala Arg Glu Thr Arg Gly Val Asp Pro Val Arg Val Leu Ala
        180                 185                 190

Ala Ile Ser Glu Trp Arg Ala Val Gly Ser Arg Gly Leu Val Ala Gly
    195                 200                 205

Gln Val Val Asp Leu Gly Phe Glu Gly Gly Val Gly Leu Ala Pro
210                 215                 220

Leu Arg Tyr Ile His Glu His Lys Thr Ala Ala Leu Leu Glu Ala Ala
225                 230                 235                 240

Val Val Ser Gly Ala Leu Leu Gly Gly Ala Glu Glu Ala Asp Leu Glu
                245                 250                 255

Arg Leu Arg Thr Tyr Asn Arg Ala Ile Gly Leu Ala Phe Gln Val Val
            260                 265                 270

Gly Asp Ile Leu Asp Ile Pro Gly Thr Ser Glu Glu Leu Gly Lys Thr
        275                 280                 285

Ala Gly Lys Asp Leu Ser Ser Pro Lys Thr Pro Tyr Pro Ser Leu Val
    290                 295                 300

Gly Leu Ala Arg Ser Lys Lys Ile Ala Asp Glu Leu Ile Glu Asp Ala
305                 310                 315                 320

Lys Thr Gln Leu Thr Gln Tyr Glu Pro Ala Arg Ala Ala Pro Leu Val
                325                 330                 335

Thr Leu Ala Glu Asn Ile
            340

<210> SEQ ID NO 49
<211> LENGTH: 833
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
cagatgccat gcgccctcgg gccgcgggcc tgagggtcca cgcagcgtcc tcggtggccc      60
agacgcacca ggccgccccc ccggcggaca ggaggttcga cgactaccag ccccgcaccg     120
ccatcctctt ccccggccag ggcgcgcaga gcgtgggcat ggcgggagag ctggcgaagg     180
ccgtccccgc cgccgcggcg ctgttcgacg ccgcctccga ccagctcggc tatgacctgc     240
tccgcgtgtg cgttgagggc cccaaggcgc gcctggacag caccgccgtc agccagcccg     300
ccatctacgt ggccagcctg gcggcggtgg agaagctgcg cgcggagggc ggggaggagg     360
cactggccgc catcgacgtc gctgccggtc tgtccttggg cgagtacacc gcgctggcct     420
ttgccggcgc cttctccttc gccgacgggc tgcgcctggt ggccctgcgc ggcgccagca     480
tgcaggccgc cgccgacgcc gcaccctcgg gcatggtctc cgtcatcggt ctgccctccg     540
acgcggtggc cgcgctgtgc gaggccgcca cgcgcaggt ggcccccgac caggccgtgc     600
gcatcgccaa ctacctctgc gacggcaact acgccgtcag cggtgggctg agggctgcg      660 cggcggtgga gggcctggcc aaggcccaca aggcgcgcat gacggtgcgc ctggcggtgg     720
cgggcgcctt ccacaccccc ttcatgcagc cggcggtgga ggcgctgagc gcgggcgctg     780
gcggacacgc cgctggtcgc gccgcgcatc cccgtggtca gcaacgggac gcc            833
```

<210> SEQ ID NO 50
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Met Arg Pro Arg Ala Ala Gly Leu Arg Val His Ala Ala Ser Ser Val
1               5                   10                  15

Ala Gln Thr His Gln Ala Ala Pro Pro Ala Asp Arg Arg Phe Asp Asp
            20                  25                  30

Tyr Gln Pro Arg Thr Ala Ile Leu Phe Pro Gly Gln Gly Ala Gln Ser
        35                  40                  45

Val Gly Met Ala Gly Glu Leu Ala Lys Ala Val Pro Ala Ala Ala Ala
    50                  55                  60

Leu Phe Asp Ala Ala Ser Asp Gln Leu Gly Tyr Asp Leu Leu Arg Val
65                  70                  75                  80

Cys Val Glu Gly Pro Lys Ala Arg Leu Asp Ser Thr Ala Val Ser Gln
                85                  90                  95

Pro Ala Ile Tyr Val Ala Ser Leu Ala Ala Val Glu Lys Leu Arg Ala
            100                 105                 110

Glu Gly Gly Glu Glu Ala Leu Ala Ala Ile Asp Val Ala Ala Gly Leu
        115                 120                 125

Ser Leu Gly Glu Tyr Thr Ala Leu Ala Phe Ala Gly Ala Phe Ser Phe
    130                 135                 140

Ala Asp Gly Leu Arg Leu Val Ala Leu Arg Gly Ala Ser Met Gln Ala
145                 150                 155                 160

Ala Ala Asp Ala Ala Pro Ser Gly Met Val Ser Val Ile Gly Leu Pro
                165                 170                 175

Ser Asp Ala Val Ala Ala Leu Cys Glu Ala Ala Asn Ala Gln Val Ala
            180                 185                 190

Pro Asp Gln Ala Val Arg Ile Ala Asn Tyr Leu Cys Asp Gly Asn Tyr
        195                 200                 205

Ala Val Ser Gly Gly Leu Glu Gly Cys Ala Ala Val Glu Gly Leu Ala
    210                 215                 220

Lys Ala His Lys Ala Arg Met Thr Val Arg Leu Ala Val Ala Gly Ala
225                 230                 235                 240

Phe His Thr Pro Phe Met Gln Pro Ala Val Glu Ala Leu Ser Ala Gly
                245                 250                 255

Ala Gly Gly His Ala Ala Gly Arg Ala Ala His Pro Arg Gly Gln Gln
            260                 265                 270

Arg Asp Ala
        275
```

<210> SEQ ID NO 51
<211> LENGTH: 787
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
tgtccatctc cccccaccct ccatccaacc atcgtcgacg gcatgcaggc gctgtgttct    60
caccccgcgt ccctcacggc gcgtgcggta ccccatgggc gggccagccc agcacagcgg   120
```

```
gtgtccagcg ccggcccggc ctacaccggc ctgtcccggc acaccctggg ctgccccagc    180 accccaccc tccagtcccg cgccgcggtc cagacccgcg gctcctcctc cggctccacc     240
acgcgcatga ccaccaccgc ccagcgcaag atcaaggtgg ccatcaacgg gttcggccgc   300
atcggccgcc agttcctgcg ctgcgtggag gggcgcgagg actcgctgct ggagatcgtg   360
gccgtgaacg actccggcgg cgtgaagcag gccagccacc tgctcaagta cgactccacc   420
atgggcacct tcaacgccga catcaagatc tcgggcgagg gcaccttctc cgtcaacggc   480
cgcgacatcc gcgtcgtctc ctcccgcgac cccctggccc tgccctgggg cgagctgggc   540
gtggacctgg tgatcgaggg gacgggagtg tttgtggacc gcaagggtgc cagcaagcac   600
ctgcaggcgg ggccaagaa ggtcatcatc accgcgccgg ccaagggctc cgacgtgccc    660
acctacgtca tgggcgtgaa cgcggaccag tactccaact ccgacgacat catctccaac   720
gcctcctgca ccaccaactg cctggcgccc tttgtcaagg tgctcaacga ccgcttcggc   780
atcgtga                                                             787
```

<210> SEQ ID NO 52
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Met Gln Ala Leu Cys Ser His Pro Ala Ser Leu Thr Ala Arg Ala Val
1               5                   10                  15

Pro His Gly Arg Ala Ser Pro Ala Gln Arg Val Ser Ser Ala Gly Pro
            20                  25                  30

Ala Tyr Thr Gly Leu Ser Arg His Thr Leu Gly Cys Pro Ser Thr Pro
        35                  40                  45

Thr Leu Gln Ser Arg Ala Ala Val Gln Thr Arg Gly Ser Ser Ser Gly
    50                  55                  60

Ser Thr Thr Arg Met Thr Thr Thr Ala Gln Arg Lys Ile Lys Val Ala
65                  70                  75                  80

Ile Asn Gly Phe Gly Arg Ile Gly Arg Gln Phe Leu Arg Cys Val Glu
                85                  90                  95

Gly Arg Glu Asp Ser Leu Leu Glu Ile Val Ala Val Asn Asp Ser Gly
            100                 105                 110

Gly Val Lys Gln Ala Ser His Leu Leu Lys Tyr Asp Ser Thr Met Gly
        115                 120                 125

Thr Phe Asn Ala Asp Ile Lys Ile Ser Gly Glu Gly Thr Phe Ser Val
    130                 135                 140

Asn Gly Arg Asp Ile Arg Val Val Ser Ser Arg Asp Pro Leu Ala Leu
145                 150                 155                 160

Pro Trp Gly Glu Leu Gly Val Asp Leu Val Ile Glu Gly Thr Gly Val
                165                 170                 175

Phe Val Asp Arg Lys Gly Ala Ser Lys His Leu Gln Ala Gly Ala Lys
            180                 185                 190

Lys Val Ile Ile Thr Ala Pro Ala Lys Gly Ser Asp Val Pro Thr Tyr
        195                 200                 205

Val Met Gly Val Asn Ala Asp Gln Tyr Ser Asn Ser Asp Asp Ile Ile
    210                 215                 220

Ser Asn Ala Ser Cys Thr Thr Asn Cys Leu Ala Pro Phe Val Lys Val
```

```
                    225                 230                 235                 240

Leu Asn Asp Arg Phe Gly Ile Val
                245

<210> SEQ ID NO 53
<211> LENGTH: 860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gatgttgaga atagtagctt gctgccttgt cgccatgcag agcgtgtgcg cgcagtcggt        60
ttcatgcaag ggggccttca cccagtccct gcggaccccc cgatgcagca ggagccagct       120
cgtctgccgg gctgatggca aggccggagc cttcatcaag accgtaaaga gcggtgctgc       180
cgctctggct gcctccctcc tcctgtctgg gggtgcgggc gcactgacct ttgatgagct       240
gcagggcctg acctacctgc aggtgaaggg ctctggcatc gccaacacct gccccaccct       300
gtctggcggc tcctccaaca tcaaggacct gaagagcggg acctactccg tcaacaagat       360
gtgcctggag cccacgtcct tcaaggtcaa ggaggaggca cagttcaaga acggcgaggc       420
cgactttgtg cccaccaagc tcgtcacgcg tctgacctac accctggacg agatctctgg       480
ccagatgaag atcgacggca gcggcggcgt ggagttcaag gaggaggatg catcgacta       540 tgctgcagtc accgtgcagc ttccgggcgg ggagcgcgtg cccttcctct tcaccatcaa       600
ggagcttgac gccaagggga ctgccgacgg cttcaagggc gagttcaccg tgccctccta       660
ccgtgggtcc tccttcctgg accccaaggg ccgcggcgcc tccaccggct acgacaacgc       720
cgtggccctg cccgccgccg gcgattccga ggagttggag aaggagaaca acaagtccac       780
caaggctctg aagggggagg ccatcttctc catcgccaag gtggacgccg gacagggga       840 ggtggcgggc atctttgagt                                                  860

<210> SEQ ID NO 54
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gln Ser Val Cys Ala Gln Ser Val Ser Cys Lys Gly Ala Phe Thr
1               5                   10                  15

Gln Ser Leu Arg Thr Pro Arg Cys Ser Arg Ser Gln Leu Val Cys Arg
            20                  25                  30

Ala Asp Gly Lys Ala Gly Ala Phe Ile Lys Thr Val Lys Ser Gly Ala
        35                  40                  45

Ala Ala Leu Ala Ala Ser Leu Leu Leu Ser Gly Gly Ala Gly Ala Leu
    50                  55                  60

Thr Phe Asp Glu Leu Gln Gly Leu Thr Tyr Leu Gln Val Lys Gly Ser
65                  70                  75                  80

Gly Ile Ala Asn Thr Cys Pro Thr Leu Ser Gly Gly Ser Ser Asn Ile
                85                  90                  95

Lys Asp Leu Lys Ser Gly Thr Tyr Ser Val Asn Lys Met Cys Leu Glu
            100                 105                 110

Pro Thr Ser Phe Lys Val Lys Glu Glu Ala Gln Phe Lys Asn Gly Glu
```

```
                  115                 120                 125
Ala Asp Phe Val Pro Thr Lys Leu Val Thr Arg Leu Thr Tyr Thr Leu
    130                 135                 140

Asp Glu Ile Ser Gly Gln Met Lys Ile Asp Gly Ser Gly Gly Val Glu
145                 150                 155                 160

Phe Lys Glu Glu Asp Gly Ile Asp Tyr Ala Ala Val Thr Val Gln Leu
                165                 170                 175

Pro Gly Gly Glu Arg Val Pro Phe Leu Phe Thr Ile Lys Glu Leu Asp
            180                 185                 190

Ala Lys Gly Thr Ala Asp Gly Phe Lys Gly Glu Phe Thr Val Pro Ser
        195                 200                 205

Tyr Arg Gly Ser Ser Phe Leu Asp Pro Lys Gly Arg Gly Ala Ser Thr
    210                 215                 220

Gly Tyr Asp Asn Ala Val Ala Leu Pro Ala Ala Gly Asp Ser Glu Glu
225                 230                 235                 240

Leu Glu Lys Glu Asn Asn Lys Ser Thr Lys Ala Leu Lys Gly Glu Ala
                245                 250                 255

Ile Phe Ser Ile Ala Lys Val Asp Ala Gly Thr Gly Glu Val Ala Gly
            260                 265                 270

Ile Phe Glu
        275

<210> SEQ ID NO 55
<211> LENGTH: 818
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
ataatcggaa cccagctgca cgcaccatca gtgcggcagc atgcagaccg tcgcagccag     60
ctatggcgta ttggcgccct ccggctccag cgtgacccgg ggctcgacca gcagcaagca    120
gcacttcacc accctcactc cctttttccgg cttcaggcgc ctgaatcatg tggatcgggc   180
ggggcaggcg gggtctggga gcccccagac cctgcagcag gccgtgggca aggccgtgcg   240
ccggtcgcgg ggccgcacca ccagcgccgt gcgcgtgacc cgcatgatgt ttgagcggtt   300
caccgagaag gccatcaagg tggtcatgct cgcgcaggag gaggctcgcc gtctgggcca   360
caacttcgtg gggacggagc aaatcctgct ggggttgatt ggggagtcca caggcatcgc   420
cgccaaggtc ctcaagtcga tgggcgtcac gctgaaagat gcgcgtgtgg aggtcgagaa   480
gatcatcggc cgggggagcg gctttgtggc cgtggagatc cccttcaccc ccgcgccaa    540 gcgtgtgctg gagctgtccc tggaggaggc tcgccagctc ggccacaact acattggcac   600
ggagcacatc ctgctgggcc tgctgcgcga gggtgagggc gtggcctccc gcgtgctgga   660
gaccctgggc gccgaccccc agaagatccg cactcaggtg gtacgcatgg tgggtgagtc   720
gcaggagccc gtgggcacca cggtgggcgg agggtccacc ggctccaaca agatgcccac   780
cctggaggag tacggcacca acctgaccgc ccaggccg                           818

<210> SEQ ID NO 56
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 56

Met Gln Thr Val Ala Ala Ser Tyr Gly Val Leu Ala Pro Ser Gly Ser
1               5                   10                  15

Ser Val Thr Arg Gly Ser Thr Ser Ser Lys Gln His Phe Thr Thr Leu
            20                  25                  30

Thr Pro Phe Ser Gly Phe Arg Arg Leu Asn His Val Asp Arg Ala Gly
        35                  40                  45

Gln Ala Gly Ser Gly Ser Pro Gln Thr Leu Gln Gln Ala Val Gly Lys
    50                  55                  60

Ala Val Arg Arg Ser Arg Gly Arg Thr Thr Ser Ala Val Arg Val Thr
65                  70                  75                  80

Arg Met Met Phe Glu Arg Phe Thr Glu Lys Ala Ile Lys Val Val Met
                85                  90                  95

Leu Ala Gln Glu Glu Ala Arg Arg Leu Gly His Asn Phe Val Gly Thr
            100                 105                 110

Glu Gln Ile Leu Leu Gly Leu Ile Gly Glu Ser Thr Gly Ile Ala Ala
        115                 120                 125

Lys Val Leu Lys Ser Met Gly Val Thr Leu Lys Asp Ala Arg Val Glu
    130                 135                 140

Val Glu Lys Ile Ile Gly Arg Gly Ser Gly Phe Val Ala Val Glu Ile
145                 150                 155                 160

Pro Phe Thr Pro Arg Ala Lys Arg Val Leu Glu Leu Ser Leu Glu Glu
                165                 170                 175

Ala Arg Gln Leu Gly His Asn Tyr Ile Gly Thr Glu His Ile Leu Leu
            180                 185                 190

Gly Leu Leu Arg Glu Gly Glu Gly Val Ala Ser Arg Val Leu Glu Thr
        195                 200                 205

Leu Gly Ala Asp Pro Gln Lys Ile Arg Thr Gln Val Val Arg Met Val
    210                 215                 220

Gly Glu Ser Gln Glu Pro Val Gly Thr Thr Val Gly Gly Gly Ser Thr
225                 230                 235                 240

Gly Ser Asn Lys Met Pro Thr Leu Glu Glu Tyr Gly Thr Asn Leu Thr
                245                 250                 255

Ala Gln Ala

<210> SEQ ID NO 57
<211> LENGTH: 2357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
ctttcttgcg ctatgacact tccagcaaaa ggtagggcgg gctgcgagac ggcttcccgg    60
cgctgcatgc aacaccgatg atgcttcgac cccccgaagc tccttcgggg ctgcatgggc   120
gctccgatgc cgctccaggg cgagcgctgt ttaaatagcc aggcccccga ttgcaaagac   180
attatagcga gctaccaaag ccatattcaa acacctagat cactaccact tctacacagg   240
ccactcgagc ttgtgatcgc actccgctaa gggggcgcct cttcctcttc gtttcagtca   300
caacccgcaa acggcgcgcc atatcaatgc ttcttcaggc cttttttttt cttcttgctg   360
gttttgctgc caagatcagc gcctctatga cgaacgaaac ctcggataga ccacttgtgc   420
actttacacc aaacaagggc tggatgaatg accccaatgg actgtggtac gacgaaaaag   480

| | |
|---|---|
| atgccaagtg gcatctgtac tttcaataca acccgaacga tactgtctgg gggacgccat | 540 |
| tgttttgggg ccacgccacg tccgacgacc tgaccaattg ggaggaccaa ccaatagcta | 600 |
| tcgctccgaa gaggaacgac tccggagcat tctcgggttc catggtggtt gactacaaca | 660 |
| atacttccgg cttttcaac gataccattg acccgagaca acgctgcgtg gccatatgga | 720 |
| cttacaacac accggagtcc gaggagcagt acatctcgta tagcctggac ggtggataca | 780 |
| cttttacaga gtatcagaag aaccctgtgc ttgctgcaaa ttcgactcag ttccgagatc | 840 |
| cgaaggtctt ttggtacgag ccctcgcaga gtggatcat gacagcggca aagtcacagg | 900 |
| actacaagat cgaaatttac tcgtctgacg accttaaatc ctggaagctc gaatccgcgt | 960 |
| tcgcaaacga gggctttctc ggctaccaat acgaatgccc aggcctgata gaggtcccaa | 1020 |
| cagagcaaga tcccagcaag tcctactggg tgatgtttat ttccattaat ccaggagcac | 1080 |
| cggcaggagg ttcttttaat cagtacttcg tcggaagctt taacggaact catttcgagg | 1140 |
| catttgataa ccaatcaaga gtagttgatt ttggaaagga ctactatgcc ctgcagactt | 1200 |
| tcttcaatac tgacccgacc tatgggagcg ctcttggcat tgcgtgggct tctaactggg | 1260 |
| agtattccgc attcgttcct acaaacccct tggaggtcctc catgtcgctc gtgaggaaat | 1320 |
| tctctctcaa cactgagtac caggccaacc cggaaaccga actcataaac ctgaaagccg | 1380 |
| aaccgatcct gaacattagc aacgctggcc cctggagccg gtttgcaacc aacaccacgt | 1440 |
| tgacgaaagc caacagctac aacgtcgatc tttcgaatag caccggtaca cttgaatttg | 1500 |
| aactggtgta tgccgtcaat accacccaaa cgatctcgaa gtcggtgttc gcggacctct | 1560 |
| ccctctggtt taaaggcctg gaagacccg aggagtacct cagaatgggt ttcgaggttt | 1620 |
| ctgcgtcctc cttcttcctt gatcgcggga acagcaaagt aaaatttgtt aaggagaacc | 1680 |
| catattttac caacaggatg agcgttaaca accaaccatt caagagcgaa aacgacctgt | 1740 |
| cgtactacaa agtgtatggt ttgcttgatc aaaatatcct ggaactctac ttcaacgatg | 1800 |
| gtgatgtcgt gtccaccaac acatacttca tgacaaccgg gaacgcactg gctccgtga | 1860 |
| acatgacgac gggtgtggat aacctgttct acatcgacaa attccaggtg agggaagtca | 1920 |
| agtgagatct gtcgatcgac aagctcgagg cagcagcagc tcggatagta tcgacacact | 1980 |
| ctggacgctg gtcgtgtgat ggactgttgc cgccacactt gctgccttga cctgtgaata | 2040 |
| tccctgccgc ttttatcaaa cagcctcagt gtgtttgatc ttgtgtgtac gcgcttttgc | 2100 |
| gagttgctag ctgcttgtgc tatttgcgaa taccaccccc agcatcccct tccctcgttt | 2160 |
| catatcgctt gcatcccaac cgcaacttat ctacgctgtc ctgctatccc tcagcgctgc | 2220 |
| tcctgctcct gctcactgcc cctcgcacag ccttggtttg ggctccgcct gtattctcct | 2280 |
| ggtactgcaa cctgtaaacc agcactgcaa tgctgatgca cgggaagtag tgggatggga | 2340 |
| acacaaatgg aaagctt | 2357 |

<210> SEQ ID NO 58
<211> LENGTH: 2335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

| | |
|---|---|
| ctttcttgcg ctatgacact tccagcaaaa ggtagggcgg gctgcgagac ggcttcccgg | 60 |
| cgctgcatgc aacaccgatg atgcttcgac cccccgaagc tccttcgggg ctgcatgggc | 120 |

```
gctccgatgc cgctccaggg cgagcgctgt ttaaatagcc aggccccga ttgcaaagac      180 attatagcga gctaccaaag ccatattcaa acacctagat cactaccact tctacacagg      240
ccactcgagc ttgtgatcgc actccgctaa gggggcgcct cttcctcttc gtttcagtca      300
caacccgcaa acgcgcgcc atgctgctgc aggccttcct gttcctgctg ccggcttcg       360 ccgccaagat cagcgcctcc atgacgaacg agacgtccga ccgcccctg gtgcacttca      420 cccccaacaa gggctggatg aacgacccca cggcctgtg gtacgacgag aaggacgcca      480
agtggcacct gtacttccag tacaacccga cgacaccgt ctgggggacg cccttgttct      540
ggggccacgc cacgtccgac gacctgacca actgggagga ccagcccatc gccatcgccc      600
cgaagcgcaa cgactccggc gccttctccg gctccatggt ggtggactac aacaacacct      660
ccggcttctt caacgacacc atcgaccgc gccagcgctg cgtggccatc tggacctaca      720
acaccccgga gtccgaggag cagtacatct cctacagcct ggacggcggc tacaccttca      780
ccgagtacca gaagaacccc gtgctggccg ccaactccac ccagttccgc gacccgaagg      840
tcttctggta cgagccctcc cagaagtgga tcatgaccgc ggccaagtcc caggactaca      900
agatcgagat ctactcctcc gacgacctga agtcctggaa gctggagtcc gcgttcgcca      960
acgagggctt cctcggctac cagtacgagt gccccggcct gatcgaggtc cccaccgagc     1020
aggaccccag caagtcctac tgggtgatgt tcatctccat caaccccggc gccccggccg     1080
gcggctcctt caaccagtac ttcgtcggca gcttcaacgg cacccacttc gaggccttcg     1140
acaaccagtc ccgcgtggtg gacttcggca aggactacta cgccctgcag accttcttca     1200
acaccgaccc gacctacggg agcgccctgg gcatcgcgtg ggcctccaac tgggagtact     1260
ccgccttcgt gcccaccaac ccctggcgct cctccatgtc cctcgtgcgc aagttctccc     1320
tcaacaccga gtaccaggcc aacccggaga cggagctgat caacctgaag gccgagccga     1380
tcctgaacat cagcaacgcc ggcccctgga gccggttcgc caccaacacc acgttgacga     1440
aggccaacag ctacaacgtc gacctgtcca acagcaccgg caccctggag ttcgagctgg     1500
tgtacgccgt caacaccacc cagacgatct ccaagtccgt gttcgcggac ctctccctct     1560
ggttcaaggg cctggaggac cccgaggagt acctccgcat gggcttcgag gtgtccgcgt     1620
cctccttctt cctggaccgc gggaacagca aggtgaagtt cgtgaaggag aaccccctat     1680
tcaccaaccg catgagcgtg aacaaccagc ccttcaagag cgagaacgac ctgtcctact     1740
acaaggtgta cggcttgctg gaccagaaca tcctggagct gtacttcaac gacggcgacg     1800
tcgtgtccac caacacctac ttcatgacca ccgggaacgc cctgggctcc gtgaacatga     1860 cgacggggt ggacaacctg ttctacatcg acaagttcca ggtgcgcgag gtcaagtgat      1920
taattaactc gaggcagcag cagctcggat agtatcgaca cactctggac gctggtcgtg     1980
tgatggactg ttgccgccac acttgctgcc ttgacctgtg aatatccctg ccgcttttat     2040
caaacagcct cagtgtgttt gatcttgtgt gtacgcgctt ttgcgagttg ctagctgctt     2100
gtgctatttg cgaataccac ccccagcatc cccttccctc gtttcatatc gcttgcatcc     2160
caaccgcaac ttatctacgc tgtcctgcta ccctcagcg ctgctcctgc tcctgctcac      2220
tgcccctcgc acagccttgg tttgggctcc gcctgtattc tcctggtact gcaacctgta     2280
aaccagcact gcaatgctga tgcacgggaa gtagtgggat gggaacacaa atgga           2335
```

<210> SEQ ID NO 59
<211> LENGTH: 382
<212> TYPE: PRT

<213> ORGANISM: Cinnamomum camphorum

<400> SEQUENCE: 59

```
Met Ala Thr Thr Ser Leu Ala Ser Ala Phe Cys Ser Met Lys Ala Val
1               5                   10                  15
Met Leu Ala Arg Asp Gly Arg Gly Met Lys Pro Arg Ser Ser Asp Leu
            20                  25                  30
Gln Leu Arg Ala Gly Asn Ala Gln Thr Ser Leu Lys Met Ile Asn Gly
        35                  40                  45
Thr Lys Phe Ser Tyr Thr Glu Ser Leu Lys Lys Leu Pro Asp Trp Ser
    50                  55                  60
Met Leu Phe Ala Val Ile Thr Thr Ile Phe Ser Ala Ala Glu Lys Gln
65                  70                  75                  80
Trp Thr Asn Leu Glu Trp Lys Pro Lys Pro Asn Pro Pro Gln Leu Leu
            85                  90                  95
Asp Asp His Phe Gly Pro His Gly Leu Val Phe Arg Arg Thr Phe Ala
        100                 105                 110
Ile Arg Ser Tyr Glu Val Gly Pro Asp Arg Ser Thr Ser Ile Val Ala
    115                 120                 125
Val Met Asn His Leu Gln Glu Ala Ala Leu Asn His Ala Lys Ser Val
130                 135                 140
Gly Ile Leu Gly Asp Gly Phe Gly Thr Thr Leu Glu Met Ser Lys Arg
145                 150                 155                 160
Asp Leu Ile Trp Val Val Lys Arg Thr His Val Ala Val Glu Arg Tyr
            165                 170                 175
Pro Ala Trp Gly Asp Thr Val Glu Val Glu Cys Trp Val Gly Ala Ser
        180                 185                 190
Gly Asn Asn Gly Arg Arg His Asp Phe Leu Val Arg Asp Cys Lys Thr
    195                 200                 205
Gly Glu Ile Leu Thr Arg Cys Thr Ser Leu Ser Val Met Met Asn Thr
210                 215                 220
Arg Thr Arg Arg Leu Ser Lys Ile Pro Glu Glu Val Arg Gly Glu Ile
225                 230                 235                 240
Gly Pro Ala Phe Ile Asp Asn Val Ala Val Lys Asp Glu Glu Ile Lys
            245                 250                 255
Lys Pro Gln Lys Leu Asn Asp Ser Thr Ala Asp Tyr Ile Gln Gly Gly
        260                 265                 270
Leu Thr Pro Arg Trp Asn Asp Leu Asp Ile Asn Gln His Val Asn Asn
    275                 280                 285
Ile Lys Tyr Val Asp Trp Ile Leu Glu Thr Val Pro Asp Ser Ile Phe
290                 295                 300
Glu Ser His His Ile Ser Ser Phe Thr Ile Glu Tyr Arg Arg Glu Cys
305                 310                 315                 320
Thr Met Asp Ser Val Leu Gln Ser Leu Thr Thr Val Ser Gly Gly Ser
            325                 330                 335
Ser Glu Ala Gly Leu Val Cys Glu His Leu Leu Gln Leu Glu Gly Gly
        340                 345                 350
Ser Glu Val Leu Arg Ala Lys Thr Glu Trp Arg Pro Lys Leu Thr Asp
    355                 360                 365
Ser Phe Arg Gly Ile Ser Val Ile Pro Ala Glu Ser Ser Val
370                 375                 380
```

<210> SEQ ID NO 60
<211> LENGTH: 1240

<212> TYPE: DNA
<213> ORGANISM: Cinnamomum camphorum

<400> SEQUENCE: 60

```
ggcgcgccat ggccaccacc tccctggcct ccgccttctg cagcatgaag gccgtgatgc      60
tggcccgcga cggccgcggc atgaagcccc gctccagcga cctgcagctg cgcgccggca     120
acgcccagac ctccctgaag atgatcaacg gcaccaagtt ctcctacacc gagagcctga     180
agaagctgcc cgactggtcc atgctgttcg ccgtgatcac caccatcttc tccgccgccg     240
agaagcagtg gaccaacctg gagtggaagc ccaagcccaa ccccccccag ctgctggacg     300
accacttcgg ccccacggc ctggtgttcc gccgcacctt cgccatccgc agctacgagg      360
tgggccccga ccgctccacc agcatcgtgg ccgtgatgaa ccacctgcag gaggccgccc     420
tgaaccacgc caagtccgtg ggcatcctgg gcgacggctt cggcaccacc ctggagatgt     480
ccaagcgcga cctgatctgg gtggtgaagc gcacccacgt ggccgtggag cgctaccccg     540
cctggggcga caccgtggag gtggagtgct gggtgggcgc ctccggcaac aacggccgcc     600
gccacgactt cctggtgcgc gactgcaaga ccggcgagat cctgacccgc tgcacctccc     660
tgagcgtgat gatgaacacc cgcacccgcc gcctgagcaa gatccccgag gaggtgcgcg     720
gcgagatcgg ccccgccttc atcgacaacg tggccgtgaa ggacgaggag atcaagaagc     780
cccagaagct gaacgactcc accgccgact acatccaggg cggcctgacc cccgctgga    840
acgacctgga catcaaccag cacgtgaaca acatcaagta cgtggactgg atcctggaga     900
ccgtgcccga cagcatcttc gagagccacc acatctcctc cttcaccatc gagtaccgcc     960
gcgagtgcac catggacagc gtgctgcagt ccctgaccac cgtgagcggc ggctcctccg    1020
aggccggcct ggtgtgcgag cacctgctgc agctggaggg cggcagcgag gtgctgcgcg    1080
ccaagaccga gtggcgcccc aagctgaccg actccttccg cggcatcagc gtgatccccg    1140
ccgagtccag cgtgatggac tacaaggacc acgacggcga ctacaaggac cacgacatcg    1200
actacaagga cgacgacgac aagtgactcg agttaattaa                          1240
```

<210> SEQ ID NO 61
<211> LENGTH: 415
<212> TYPE: PRT
<213> ORGANISM: Cuphea hookeriana

<400> SEQUENCE: 61

```
Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125
```

```
Glu Ser Thr Val Gln Asp Gly Leu Val Phe Arg Gln Ser Phe Ser Ile
            130                 135                 140
Arg Ser Tyr Glu Ile Gly Thr Asp Arg Thr Ala Ser Ile Glu Thr Leu
145                 150                 155                 160
Met Asn His Leu Gln Glu Thr Ser Leu Asn His Cys Lys Ser Thr Gly
                165                 170                 175
Ile Leu Leu Asp Gly Phe Gly Arg Thr Leu Glu Met Cys Lys Arg Asp
            180                 185                 190
Leu Ile Trp Val Ile Lys Met Gln Ile Lys Val Asn Arg Tyr Pro
        195                 200                 205
Ala Trp Gly Asp Thr Val Glu Ile Asn Thr Arg Phe Ser Arg Leu Gly
210                 215                 220
Lys Ile Gly Met Gly Arg Asp Trp Leu Ile Ser Asp Cys Asn Thr Gly
225                 230                 235                 240
Glu Ile Leu Val Arg Ala Thr Ser Ala Tyr Ala Met Met Asn Gln Lys
                245                 250                 255
Thr Arg Arg Leu Ser Lys Leu Pro Tyr Glu Val His Gln Glu Ile Val
            260                 265                 270
Pro Leu Phe Val Asp Ser Pro Val Ile Glu Asp Ser Asp Leu Lys Val
        275                 280                 285
His Lys Phe Lys Val Lys Thr Gly Asp Ser Ile Gln Lys Gly Leu Thr
    290                 295                 300
Pro Gly Trp Asn Asp Leu Asp Val Asn Gln His Val Ser Asn Val Lys
305                 310                 315                 320
Tyr Ile Gly Trp Ile Leu Glu Ser Met Pro Thr Glu Val Leu Glu Thr
                325                 330                 335
Gln Glu Leu Cys Ser Leu Ala Leu Glu Tyr Arg Arg Glu Cys Gly Arg
            340                 345                 350
Asp Ser Val Leu Glu Ser Val Thr Ala Met Asp Pro Ser Lys Val Gly
        355                 360                 365
Val Arg Ser Gln Tyr Gln His Leu Leu Arg Leu Glu Asp Gly Thr Ala
    370                 375                 380
Ile Val Asn Gly Ala Thr Glu Trp Arg Pro Lys Asn Ala Gly Ala Asn
385                 390                 395                 400
Gly Ala Ile Ser Thr Gly Lys Thr Ser Asn Gly Asn Ser Val Ser
                405                 410                 415

<210> SEQ ID NO 62
<211> LENGTH: 1339
<212> TYPE: DNA
<213> ORGANISM: Cuphea hookeriana

<400> SEQUENCE: 62
ggcgcgccat ggtggccgcc gccgcctcca gcgccttctt ccccgtgccc gccccggcg        60 cctcccccaa gcccggcaag ttcggcaact ggccctccag cctgagcccc tccttcaagc      120
ccaagtccat ccccaacggc ggcttccagg tgaaggccaa cgacagcgcc caccccaagg      180
ccaacggctc cgccgtgagc ctgaagagcg gcagcctgaa cacccaggag gacacctcct      240
ccagcccccc ccccgcacc ttcctgcacc agctgcccga ctggagccgc ctgctgaccg       300
ccatcaccac cgtgttcgtg aagtccaagc gccccgacat gcacgaccgc aagtccaagc      360
gccccgacat gctggtggac agcttcggcc tggagtccac cgtgcaggac ggcctggtgt      420
tccgccagtc cttctccatc cgctcctacg agatcggcac cgaccgcacc gccagcatcg      480
agaccctgat gaaccaccctg caggagacct ccctgaacca ctgcaagagc accggcatcc      540
```

```
tgctggacgg cttcggccgc accctggaga tgtgcaagcg cgacctgatc tgggtggtga    600
tcaagatgca gatcaaggtg aaccgctacc ccgcctgggg cgacaccgtg gagatcaaca    660
cccgcttcag ccgcctgggc aagatcggca tgggccgcga ctggctgatc tccgactgca    720
acaccggcga gatcctggtg cgcgccacca gcgcctacgc catgatgaac cagaagaccc    780
gccgcctgtc caagctgccc tacgaggtgc accaggagat cgtgcccctg ttcgtggaca    840
gccccgtgat cgaggactcc gacctgaagg tgcacaagtt caaggtgaag accggcgaca    900
gcatccagaa gggcctgacc cccggctgga cgacctgga cgtgaaccag cacgtgtcca    960
acgtgaagta catcggctgg atcctggaga gcatgcccac cgaggtgctg gagacccagg   1020
agctgtgctc cctggccctg gagtaccgcc gcgagtgcgg ccgcgactcc gtgctggaga   1080
gcgtgaccgc catggacccc agcaaggtgg gcgtgcgctc ccagtaccag cacctgctgc   1140
gcctggagga cggcaccgcc atcgtgaacg gcgccaccga gtggcgcccc aagaacgccg   1200
gcgccaacgg cgccatctcc accggcaaga ccagcaacgg caactccgtg tccatggact   1260
acaaggacca cgacggcgac tacaaggacc acgacatcga ctacaaggac gacgacgaca   1320
agtgactcga gttaattaa                                                1339
```

<210> SEQ ID NO 63
<211> LENGTH: 382
<212> TYPE: PRT
<213> ORGANISM: Umbellularia sp.

<400> SEQUENCE: 63

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220
```

-continued

```
Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
            245                 250                 255

Lys Leu Gln Lys Leu Asn Asp Ser Thr Ala Asp Tyr Ile Gln Gly Gly
        260                 265                 270

Leu Thr Pro Arg Trp Asn Asp Leu Asp Val Asn Gln His Val Asn Asn
    275                 280                 285

Leu Lys Tyr Val Ala Trp Val Phe Glu Thr Val Pro Asp Ser Ile Phe
290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380
```

<210> SEQ ID NO 64
<211> LENGTH: 1240
<212> TYPE: DNA
<213> ORGANISM: Umbellularia sp.

<400> SEQUENCE: 64

```
ggcgcgccat ggccaccacc agcctggcct ccgccttctg ctccatgaag gccgtgatgc    60
tggcccgcga cggccgcggc atgaagcccc gcagctccga cctgcagctg cgcgccggca   120
acgcccccac ctccctgaag atgatcaacg gcaccaagtt cagctacacc gagagcctga   180
agcgcctgcc cgactggtcc atgctgttcg ccgtgatcac caccatcttc agcgccgccg   240
agaagcagtg gaccaacctg gagtggaagc ccaagcccaa gctgccccag ctgctggacg   300
accacttcgg cctgcacggc ctggtgttcc gccgcacctt cgccatccgc tcctacgagg   360
tgggccccga ccgcagcacc tccatcctgg ccgtgatgaa ccacatgcag gaggccaccc   420
tgaaccacgc caagagcgtg ggcatcctgg gcgacggctt cggcaccacc ctggagatgt   480
ccaagcgcga cctgatgtgg gtggtgcgcc gcacccacgt ggccgtggag cgctacccca   540
cctgggggcga caccgtggag gtggagtgct ggatcggcgc cagcggcaac aacggcatgc   600
gccgcgactt cctggtgcgc gactgcaaga ccggcgagat cctgacccgc tgcacctccc   660
tgagcgtgct gatgaacacc cgcacccgcc gcctgagcac catccccgac gaggtgcgcg   720
gcgagatcgg ccccgccttc atcgacaacg tggccgtgaa ggacgacgag atcaagaagc   780
tgcagaagct gaacgactcc accgccgact acatccaggg cggcctgacc cccgctgga   840
acgacctgga cgtgaaccag cacgtgaaca acctgaagta cgtggcctgg gtgttcgaga   900
ccgtgcccga cagcatcttc gagtcccacc acatcagctc cttcaccctg gagtaccgcc   960
gcgagtgcac ccgcgactcc gtgctgcgca gcctgaccac cgtgagcggc ggcagctccg  1020
aggccggcct ggtgtgcgac cacctgctgc agctggaggg cggcagcgag gtgctgcgcg  1080
cccgcaccga gtggcgcccc aagctgaccg actccttccg cggcatcagc gtgatccccg  1140
ccgagccccg cgtgatggac tacaaggacc acgacgcgca ctacaaggac cacgacatcg  1200
actacaagga cgacgacgac aagtgactcg agttaattaa                        1240
```

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccgccgtgct ggacgtggtg                                           20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggtggcgggg tccagggtgt                                           20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cggccggcgg ctccttcaac                                           20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggcgctcccg taggtcgggt                                           20

<210> SEQ ID NO 69
<211> LENGTH: 1335
<212> TYPE: DNA
<213> ORGANISM: Chlorella sorokiniana

<400> SEQUENCE: 69
cgcctgcaac gcaagggcag ccacagccgc tcccacccgc cgctgaaccg acacgtgctt    60
gggcgcctgc cgcctgcctg ccgcatgctt gtgctggtga ggctgggcag tgctgccatg   120
ctgattgagg cttggttcat cgggtggaag cttatgtgtg tgctgggctt gcatgccggg   180
caatgcgcat ggtggcaaga gggcggcagc acttgctgga gctgccgcgg tgcctccagg   240
tggttcaatc gcggcagcca gagggatttc agatgatcgc gcgtacaggt tgagcagcag   300
tgtcagcaaa ggtagcagtt tgccagaatg atcggttcag ctgttaatca atgccagcaa   360
gagaaggggt caagtgcaaa cacgggcatg ccacagcacg ggcaccgggg agtggaatgg   420
caccaccaag tgtgtgcgag ccagcatcgc cgcctggctg tttcagctac aacggcagga   480
gtcatccaac gtaaccatga gctgatcaac actgcaatca tcgggcgggc gtgatgcaag   540

| catgcctggc | gaagacacat | ggtgtgcgga | tgctgccggc | tgctgcctgc | tgcgcacgcc | 600 |

| gttgagttgg | cagcaggctc | agccatgcac | tggatggcag | ctgggctgcc | actgcaatgt | 660 |

| ggtggatagg | atgcaagtgg | agcgaatacc | aaaccctctg | gctgcttgct | gggttgcatg | 720 |

| gcatcgcacc | atcagcagga | gcgcatgcga | agggactggc | cccatgcacg | ccatgccaaa | 780 |

| ccggagcgca | ccgagtgtcc | acactgtcac | caggcccgca | agctttgcag | aaccatgctc | 840 |

| atggacgcat | gtagcgctga | cgtcccttga | cggcgctcct | ctcgggtgtg | ggaaacgcaa | 900 |

| tgcagcacag | gcagcagagg | cggcggcagc | agagcggcgg | cagcagcggc | ggggggccacc | 960 |

| cttcttgcgg | ggtcgcgccc | cagccagcgg | tgatgcgctg | atcccaaacg | agttcacatt | 1020 |

| catttgcatg | cctggagaag | cgaggctggg | gcctttgggc | tggtgcagcc | cgcaatggaa | 1080 |

| tgcgggaccg | ccaggctagc | agcaaaggcg | cctcccctac | tccgcatcga | tgttccatag | 1140 |

| tgcattggac | tgcatttggg | tggggcggcc | ggctgtttct | ttcgtgttgc | aaaacgcgcc | 1200 |

| agctcagcaa | cctgtcccgt | gggtcccccg | tgccgatgaa | atcgtgtgca | cgccgatcag | 1260 |

| ctgattgccc | ggctcgcgaa | gtaggcgccc | tcctttctgc | tcgccctctc | tccgtcccgc | 1320 |

| cactagtggc | gcgcc | | | | | 1335 |

<210> SEQ ID NO 70
<211> LENGTH: 1146
<212> TYPE: DNA
<213> ORGANISM: Umbellularia californica

<400> SEQUENCE: 70

| atggccacca | ccagcctggc | ctccgccttc | tgctccatga | aggccgtgat | gctggcccgc | 60 |

| gacggccgcg | gcatgaagcc | ccgcagctcc | gacctgcagc | tgcgcgccgg | caacgccccc | 120 |

| acctcccctga | agatgatcaa | cggcaccaag | ttcagctaca | ccgagagcct | gaagcgcctg | 180 |

| cccgactggt | ccatgctgtt | cgccgtgatc | accaccatct | tcagcgccgc | cgagaagcag | 240 |

| tggaccaacc | tggagtggaa | gcccaagccc | aagctgcccc | agctgctgga | cgaccacttc | 300 |

| ggcctgcacg | gcctggtgtt | ccgccgcacc | ttcgccatcc | gctcctacga | ggtgggcccc | 360 |

| gaccgcagca | cctccatcct | ggccgtgatg | aaccacatgc | aggaggccac | cctgaaccac | 420 |

| gccaagagcg | tgggcatcct | gggcgacggc | ttcggcacca | ccctggagat | gtccaagcgc | 480 |

| gacctgatgt | gggtggtgcg | ccgcacccac | gtggccgtgg | agcgctaccc | cacctggggc | 540 |

| gacaccgtgg | aggtggagtg | ctggatcggc | gccagcggca | acaacggcat | gcgccgcgac | 600 |

| ttcctggtgc | gcgactgcaa | gaccggcgag | atcctgaccc | gctgcacctc | cctgagcgtg | 660 |

| ctgatgaaca | cccgcacccg | ccgcctgagc | accatccccg | acgaggtgcg | cggcgagatc | 720 |

| ggccccgcct | tcatcgacaa | cgtggccgtg | aaggacgacg | agatcaagaa | gctgcagaag | 780 |

| ctgaacgact | ccaccgccga | ctacatccag | ggcggcctga | ccccccgctg | gaacgacctg | 840 |

| gacgtgaacc | agcacgtgaa | caacctgaag | tacgtggcct | gggtgttcga | gaccgtgccc | 900 |

| gacagcatct | tcgagtccca | ccacatcagc | tccttcaccc | tggagtaccg | ccgcgagtgc | 960 |

| acccgcgact | ccgtgctgcg | cagcctgacc | accgtgagcg | gcggcagctc | cgaggccggc | 1020 |

| ctggtgtgcg | accacctgct | gcagctggag | ggcggcagca | aggtgctgcg | cgcccgcacc | 1080 |

| gagtggcgcc | ccaagctgac | cgactccttc | cgcggcatca | gcgtgatccc | cgccgagccc | 1140 |

| cgcgtg | | | | | | 1146 |

<210> SEQ ID NO 71
<211> LENGTH: 1146

```
<212> TYPE: DNA
<213> ORGANISM: Cinnamomum camphora

<400> SEQUENCE: 71
atggccacca cctccctggc ctccgccttc tgcagcatga aggccgtgat gctggcccgc      60
gacggccgcg gcatgaagcc ccgctccagc gacctgcagc tgcgcgccgg caacgcccag     120
acctccctga agatgatcaa cggcaccaag ttctcctaca ccgagagcct gaagaagctg     180
cccgactggt ccatgctgtt cgccgtgatc accaccatct ctccgccgc cgagaagcag      240
tggaccaacc tggagtggaa gcccaagccc aaccccccc agctgctgga cgaccacttc      300
ggcccccacg gctggtgtt ccgccgcacc ttcgccatcc gcagctacga ggtgggcccc      360
gaccgctcca ccagcatcgt ggccgtgatg aaccacctgc aggaggccgc cctgaaccac     420
gccaagtccg tgggcatcct gggcgacggc ttcggcacca ccctggagat gtccaagcgc     480
gacctgatct gggtggtgaa gcgcacccac gtggccgtgg agcgctaccc cgcctgggc      540
gacaccgtgg aggtggagtg ctgggtgggc gcctccggca caacggccg ccgccacgac      600
ttcctggtgc gcgactgcaa gaccggcgag atcctgaccc gctgcacctc cctgagcgtg     660
atgatgaaca cccgcacccg ccgcctgagc aagatccccg aggaggtgcg cggcgagatc     720
ggccccgcct tcatcgacaa cgtggccgtg aaggacgagg agatcaagaa gccccagaag     780
ctgaacgact ccaccgccga ctacatccag ggcggcctga cccccgctg gaacgacctg      840
gacatcaacc agcacgtgaa caacatcaag tacgtggact ggatcctgga gaccgtgccc     900
gacagcatct cgagagcca ccacatctcc tccttcacca tcgagtaccg ccgcgagtgc      960
accatggaca gcgtgctgca gtccctgacc accgtgagcg gcggctcctc cgaggccggc    1020
ctggtgtgcg agcacctgct gcagctggag ggcggcagcg aggtgctgcg cgccaagacc    1080
gagtggcgcc ccaagctgac cgactccttc gcggcatca gcgtgatccc cgccgagtcc    1140
agcgtg                                                               1146

<210> SEQ ID NO 72
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atggactaca aggaccacga cggcgactac aaggaccacg acatcgacta caaggacgac      60
gacgacaagt ga                                                         72

<210> SEQ ID NO 73
<211> LENGTH: 408
<212> TYPE: DNA
<213> ORGANISM: Chlorella vulgaris

<400> SEQUENCE: 73
ctcgaggcag cagcagctcg gatagtatcg acacactctg gacgctggtc gtgtgatgga      60
ctgttgccgc cacacttgct gccttgacct gtgaatatcc ctgccgcttt tatcaaacag     120
cctcagtgtg tttgatcttg tgtgtacgcg cttttgcgag ttgctagctg cttgtgctat     180
ttgcgaatac caccccagc atcccttcc ctcgtttcat atcgcttgca tcccaaccgc       240
aacttatcta cgctgtcctg ctatcccctca gcgctgctcc tgctcctgct cactgcccct    300
cgcacagcct tggtttgggc tccgcctgta ttctcctggt actgcaacct gtaaaccagc    360
```
actgcaatgc tgatgcacgg gaagtagtgg gatgggaaca caaatgga        408

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctgggcgacg gcttcggcac        20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aagtcgcggc gcatgccgtt        20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
taccccgcct ggggcgacac        20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cttgctcagg cggcgggtgc        20

<210> SEQ ID NO 78
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
atggtggccg ccgccgcctc cagcgccttc ttccccgtgc ccgcccccgg cgcctccccc        60
aagcccggca agttcggcaa ctggcccctcc agcctgagcc cctccttcaa gcccaagtcc       120
atccccaacg gcggcttcca ggtgaaggcc aacgacagcg cccaccccaa ggccaacggc       180
tccgccgtga gcctgaagag cggcagcctg aacacccagg aggacacctc ctccagcccc       240 ccccccgca ccttcctgca ccagctgccc gactggagcc gctgctgac cgccatcacc       300 accgtgttcg tgaagtccaa cgccccgac atgcacgacc gcaagtccaa cgccccgac       360 atgctggtgg acagcttcgg cctggagtcc accgtgcagg acggcctggt gttccgccag       420

```
tccttctcca tccgctccta cgagatcggc accgaccgca ccgccagcat cgagaccctg      480
atgaaccacc tgcaggagac ctccctgaac cactgcaaga gcaccggcat cctgctggac      540
ggcttcggcc gcaccctgga gatgtgcaag cgcgacctga tctgggtggt gatcaagatg      600
cagatcaagg tgaaccgcta ccccgcctgg ggcgacaccg tggagatcaa cacccgcttc      660
agccgcctgg gcaagatcgg catgggccgc gactggctga tctccgactg caacaccggc      720
gagatcctgt gcgcgccac cagcgcctac gccatgatga accagaagac cgccgcctg       780 tccaagctgc cctacgaggt gcaccaggag atcgtgcccc tgttcgtgga cagccccgtg      840
atcgaggact ccgacctgaa ggtgcacaag ttcaaggtga agaccggcga cagcatccag      900
aagggcctga cccccggctg aacgacctg acgtgaacc agcacgtgtc aacgtgaag       960 tacatcggct ggatcctgga gagcatgccc accgaggtgc tggagaccca ggagctgtgc     1020
tccctggccc tggagtaccg ccgcgagtgc ggccgcgact ccgtgctgga gagcgtgacc     1080
gccatggacc ccagcaaggt gggcgtgcgc tcccagtacc agcacctgct cgcctggag     1140 gacggcaccg ccatcgtgaa cggcgccacc gagtggcgcc caagaacgc cggcgccaac     1200 ggcgccatct ccaccggcaa gaccagcaac ggcaactccg tgtccatgga ctacaaggac     1260
cacgacggcg actacaagga ccacgacatc gactacaagg acgacgacga caagtga         1317
```

<210> SEQ ID NO 79
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
atggccaccg catccacttt ctcggcgttc aatgcccgct gcggcgacct cgtcgctcg       60 gcgggctccg ggccccggcg cccagcgagg ccctccccg tgcgcgggcg cgcccagctg      120
cccgactgga gccgcctgct gaccgccatc accacgtgt tcgtgaagtc aagcgcccc      180 gacatgcacg accgcaagtc caagcgcccc gacatgctgg tggacagctt cggcctggag     240
tccaccgtgc aggacggcct ggtgttccgc cagtccttct ccatccgctc ctacgagatc     300
ggcaccgacc gcaccgccag catcgagacc ctgatgaacc acctgcagga gacctccctg     360
aaccactgca gagcaccgg catcctgctg gacggcttcg gccgcaccct ggagatgtgc     420
aagcgcgacc tgatctgggt ggtgatcaag atgcagatca aggtgaaccg ctaccccgcc     480
tggggcgaca ccgtggagat caacacccgc ttcagccgcc tgggcaagat cggcatgggc     540
cgcgactggc tgatctccga ctgcaacacc ggcgagatcc tgtgcgcgc caccagcgcc     600 tacgccatga tgaaccagaa gaccgccgc ctgtccaagc tgccctacga ggtgcaccag     660
gagatcgtgc cctgttcgt ggacagcccc gtgatcgagg actccgacct gaaggtgcac     720
aagttcaagg tgaagaccgg cgacagcatc cagaagggcc tgaccccgg ctggaacgac     780 ctggacgtga accagcacgt gtccaacgtg aagtacatcg gctggatcct ggagagcatg     840
cccaccgagg tgctggagac ccaggagctg tgctccctgg ccctggagta ccgccgcgag     900
tgcggccgcg actccgtgct ggagagcgtg accgccatgg accccagcaa ggtgggcgtg     960
cgctcccagt accagcacct gctcgcctg gaggacggca ccgccatcgt gaacggcgcc    1020
accgagtggc gccccaagaa cgccggcgcc aacggcgcca tctccaccgg caagaccagc    1080
aacggcaact ccgtgtccat ggactacaag gaccacgacg gcgactacaa ggaccacgac    1140
```

```
atcgactaca aggacgacga cgacaagtga                                    1170
```

<210> SEQ ID NO 80
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
atggctatca agacgaacag gcagcctgtg gagaagcctc cgttcacgat cgggacgctg     60
cgcaaggcca tccccgcgca ctgtttcgag cgctcggcgc ttcgtgggcg cgcccagctg    120
cccgactgga gccgcctgct gaccgccatc accaccgtgt tcgtgaagtc caagcgcccc    180
gacatgcacg accgcaagtc caagcgcccc gacatgctgg tggacagctt cggcctggag    240
tccaccgtgc aggacggcct ggtgttccgc cagtccttct ccatccgctc ctacgagatc    300
ggcaccgacc gcaccgccag catcgagacc ctgatgaacc acctgcagga gacctccctg    360
aaccactgca agagcaccgg catcctgctg gacggcttcg ccgcaccct ggagatgtgc    420 aagcgcgacc tgatctgggt ggtgatcaag atgcagatca aggtgaaccg ctaccccgcc    480
tggggcgaca ccgtggagat caacacccgc ttcagccgcc tgggcaagat cggcatgggc    540
cgcgactggc tgatctccga ctgcaacacc ggcgagatcc tggtgcgcgc caccagcgcc    600
tacgccatga tgaaccagaa gacccgccgc ctgtccaagc tgccctacga ggtgcaccag    660
gagatcgtgc ccctgttcgt ggacagcccc gtgatcgagg actccgacct gaaggtgcac    720
aagttcaagg tgaagaccgg cgacagcatc cagaagggcc tgacccccgg ctggaacgac    780
ctggacgtga accagcacgt gtccaacgtg aagtacatcg gctggatcct ggagagcatg    840
cccaccgagg tgctggagac ccaggagctg tgctccctgg ccctggagta ccgccgcgag    900
tgcggccgcg actccgtgct ggagagcgtg accgccatgg accccagcaa ggtgggcgtg    960
cgctcccagt accagcacct gctgcgcctg gaggacggca ccgccatcgt gaacggcgcc   1020
accgagtggc gccccaagaa cgccggcgcc aacggcgcca tctccaccgg caagaccagc   1080
aacggcaact ccgtgtccat ggactacaag gaccacgacg gcgactacaa ggaccacgac   1140
atcgactaca aggacgacga cgacaagtga                                    1170
```

<210> SEQ ID NO 81
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atgacgttcg ggtcgccct cccggccatg ggccgcggtg tctcccttcc ccggcccagg     60
gtcgcggtgc gcgcccagtc ggcgagtcag gttttggaga gcgggcgcgc ccagctgccc    120
gactggagcc gctgctgac cgccatcacc accgtgttcg tgaagtccaa gcgccccgac    180
atgcacgacc gcaagtccaa gcgccccgac atgctggtgg acagcttcgg cctggagtcc    240
accgtgcagg acggcctggt gttccgccag tccttctcca tccgctccta cgagatcggc    300
accgaccgca ccgccagcat cgagaccctg atgaaccacc tgcaggagac ctccctgaac    360
cactgcaaga gcaccggcat cctgctggac ggcttcggcc gcaccctgga gatgtgcaag    420
```

```
cgcgacctga tctgggtggt gatcaagatg cagatcaagg tgaaccgcta ccccgcctgg      480
ggcgacaccg tggagatcaa cacccgcttc agccgcctgg gcaagatcgg catgggccgc      540
gactggctga tctccgactg caacaccggc gagatcctgg tgcgcgccac cagcgcctac      600
gccatgatga accagaagac ccgccgcctg tccaagctgc cctacgaggt gcaccaggag      660
atcgtgcccc tgttcgtgga cagccccgtg atcgaggact ccgacctgaa ggtgcacaag      720
ttcaaggtga agaccggcga cagcatccag aagggcctga ccccggctg aacgacctg       780 gacgtgaacc agcacgtgtc caacgtgaag tacatcggct ggatcctgga gagcatgccc      840
accgaggtgc tggagaccca ggagctgtgc tccctggccc tggagtaccg ccgcgagtgc      900
ggccgcgact ccgtgctgga gagcgtgacc gccatggacc ccagcaaggt gggcgtgcgc      960
tcccagtacc agcacctgct gcgcctggag gacggcaccg ccatcgtgaa cggcgccacc     1020
gagtggcgcc ccaagaacgc cggcgccaac ggcgccatct ccaccggcaa gaccagcaac     1080
ggcaactccg tgtccatgga ctacaaggac cacgacggcg actacaagga ccacgacatc     1140
gactacaagg acgacgacga caagtga                                         1167
```

<210> SEQ ID NO 82
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
atgacgttcg gggtcgccct cccggccatg ggccgcggtg tctcccttcc ccggcccagg       60
gtcgcggtgc gcgcccagtc ggcgagtcag gttttggaga gcgggcgcgc ccccgactgg      120
tccatgctgt tcgccgtgat caccaccatc ttcagcgccg ccgagaagca gtggaccaac      180
ctggagtgga agcccaagcc caagctgccc agctgctgg acgaccactt cggcctgcac       240
ggcctggtgt tccgccgcac cttcgccatc cgctcctacg aggtgggccc cgaccgcagc      300
acctccatcc tggccgtgat gaaccacatg caggaggcca ccctgaacca cgccaagagc      360
gtgggcatcc tgggcgacgg cttcggcacc accctggaga tgtccaagcg cgacctgatg      420
tgggtggtgc gccgcaccca cgtggccgtg gagcgctacc ccacctgggg cgacaccgtg      480
gaggtggagt gctggatcgg cgccagcggc aacaacggca tgcgccgcga cttcctggtg      540
cgcgactgca agaccggcga gatcctgacc cgctgcacct ccctgagcgt gctgatgaac      600
acccgcaccc gccgcctgag caccatcccc gacgaggtgc gcggcgagat cggccccgcc      660
ttcatcgaca acgtggccgt gaaggacgac gagatcaaga agctgcagaa gctgaacgac      720
tccaccgccg actacatcca gggcggcctg accccccgct ggaacgacct ggacgtgaac      780
cagcacgtga acaacctgaa gtacgtggcc tgggtgttcg agaccgtgcc cgacagcatc      840
ttcgagtccc accacatcag ctccttcacc ctggagtacc gccgcgagtg cacccgcgac      900
tccgtgctgc gcagcctgac caccgtgagc ggcggcagct ccgaggccgg cctggtgtgc      960
gaccacctgc tgcagctgga gggcggcagc gaggtgctgc gcgcccgcac cgagtggcgc     1020
cccaagctga ccgactcctt ccgcggcatc agcgtgatcc ccgccgagcc ccgcgtgatg     1080
gactacaagg accacgacgg cgactacaag gaccacgaca tcgactacaa ggacgacgac     1140
gacaagtga                                                             1149
```

<210> SEQ ID NO 83

<211> LENGTH: 1146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

| | |
|---|---|
| atggcttccg cggcattcac catgtcggcg tgccccgcga tgactggcag ggcccctggg | 60 |
| gcacgtcgct ccggacggcc agtcgccacc cgcctgaggg ggcgcgcccc cgactggtcc | 120 |
| atgctgttcg ccgtgatcac caccatcttc agcgccgccg agaagcagtg gaccaacctg | 180 |
| gagtggaagc ccaagcccaa gctgcccag ctgctggacg accacttcgg cctgcacggc | 240 |
| ctggtgttcc gccgcacctt cgccatccgc tcctacgagg tgggccccga ccgcagcacc | 300 |
| tccatcctgg ccgtgatgaa ccacatgcag gaggccaccc tgaaccacgc caagagcgtg | 360 |
| ggcatcctgg gcgacggctt cggcaccacc ctggagatgt ccaagcgcga cctgatgtgg | 420 |
| gtggtgcgcc gcacccacgt ggccgtggag cgctaccca cctggggcga caccgtggag | 480 |
| gtggagtgct ggatcggcgc cagcggcaac aacggcatgc ccgcgactt cctggtgcgc | 540 |
| gactgcaaga ccggcgagat cctgacccgc tgcacctccc tgagcgtgct gatgaacacc | 600 |
| cgcacccgcc gcctgagcac catccccgac gaggtgcgcg gcgagatcgg ccccgccttc | 660 |
| atcgacaacg tggccgtgaa ggacgacgag atcaagaagc tgcagaagct gaacgactcc | 720 |
| accgccgact acatccaggg cggcctgacc cccgctgga cgacctgga cgtgaaccag | 780 |
| cacgtgaaca acctgaagta cgtggcctgg gtgttcgaga ccgtgcccga cagcatcttc | 840 |
| gagtcccacc acatcagctc cttcacccctg gagtaccgcc gcgagtgcac ccgcgactcc | 900 |
| gtgctgcgca gcctgaccac cgtgagcggc ggcagctccg aggccggcct ggtgtgcgac | 960 |
| cacctgctgc agctggaggg cggcagcgag gtgctgcgcg cccgcaccga gtggcgcccc | 1020 |
| aagctgaccg actccttccg cggcatcagc gtgatcccg ccgagcccg cgtgatggac | 1080 |
| tacaaggacc acgacggcga ctacaaggac cacgacatcg actacaagga cgacgacgac | 1140 |
| aagtga | 1146 |

<210> SEQ ID NO 84
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

| | |
|---|---|
| atggccaccg catccacttt ctcggcgttc aatgcccgct gcggcgacct gcgtcgctcg | 60 |
| gcgggctccg ggccccggcg cccagcgagg cccctcccg tgcgcgggcg cgccccgac | 120 |
| tggtccatgc tgttcgccgt gatcaccacc atcttcagcg ccgccgagaa gcagtggacc | 180 |
| aacctggagt ggaagcccaa gcccaagctg ccccagctgc tggacgacca cttcggcctg | 240 |
| cacggcctgg tgttccgccg caccttcgcc atccgctcct acgaggtggg ccccgaccgc | 300 |
| agcacctcca tcctggccgt gatgaaccac atgcaggagg ccaccctgaa ccacgccaag | 360 |
| agcgtgggca tcctgggcga cggcttcggc accaccctgg agatgtccaa gcgcgacctg | 420 |
| atgtgggtgg tgcgccgcac ccacgtggcc gtggagcgct accccacctg ggcgacacc | 480 |
| gtggaggtgg agtgctggat cggcgccagc ggcaacaacg gcatgcgccg cgacttcctg | 540 |
| gtgcgcgact gcaagaccgg cgagatcctg acccgctgca cctccctgag cgtgctgatg | 600 |

```
aacacccgca cccgccgcct gagcaccatc cccgacgagg tgcgcggcga gatcggcccc    660
gccttcatcg acaacgtggc cgtgaaggac gacgagatca agaagctgca gaagctgaac    720
gactccaccg ccgactacat ccagggcggc ctgaccccc gctggaacga cctggacgtg     780
aaccagcacg tgaacaacct gaagtacgtg gcctgggtgt tcgagaccgt gcccgacagc    840
atcttcgagt cccaccacat cagctccttc accctggagt accgccgcga gtgcacccgc    900
gactccgtgc tgcgcagcct gaccaccgtg agcggcggca gctccgaggc cggcctggtg    960
tgcgaccacc tgctgcagct ggagggcggc agcgaggtgc tgcgcgcccg caccgagtgg   1020
cgccccaagc tgaccgactc cttccgcggc atcagcgtga tccccgccga gccccgcgtg   1080
atggactaca aggaccacga cggcgactac aaggaccacg acatcgacta caaggacgac   1140
gacgacaagt gatga                                                   1155
```

<210> SEQ ID NO 85
<211> LENGTH: 1152
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
atggctatca agacgaacag gcagcctgtg gagaagcctc cgttcacgat cgggacgctg     60
cgcaaggcca tccccgcgca ctgtttcgag cgctcggcgc ttcgtgggcg cgccccgac    120 tggtccatgc tgttcgccgt gatcaccacc atcttcagcg ccgccgagaa gcagtggacc    180
aacctggagt ggaagcccaa gcccaagctg ccccagctgc tggacgacca cttcggcctg    240
cacggcctgg tgttccgccg caccttcgcc atccgctcct acgaggtggg ccccgaccgc    300
agcacctcca tcctggccgt gatgaaccac atgcaggagg ccaccctgaa ccacgccaag    360
agcgtgggca tcctgggcga cggcttcggc accaccctgg agatgtccaa gcgcgacctg    420
atgtgggtgg tgcgccgcac ccacgtggcc gtggagcgct accccacctg ggcgacacc    480 gtggaggtgg agtgctggat cggcgccagc ggcaacaacg gcatgcgccg cgacttcctg    540
gtgcgcgact gcaagaccgg cgagatcctg acccgctgca cctccctgag cgtgctgatg    600
aacacccgca cccgccgcct gagcaccatc cccgacgagg tgcgcggcga gatcggcccc    660
gccttcatcg acaacgtggc cgtgaaggac gacgagatca agaagctgca gaagctgaac    720
gactccaccg ccgactacat ccagggcggc ctgaccccc gctggaacga cctggacgtg     780
aaccagcacg tgaacaacct gaagtacgtg gcctgggtgt tcgagaccgt gcccgacagc    840
atcttcgagt cccaccacat cagctccttc accctggagt accgccgcga gtgcacccgc    900
gactccgtgc tgcgcagcct gaccaccgtg agcggcggca gctccgaggc cggcctggtg    960
tgcgaccacc tgctgcagct ggagggcggc agcgaggtgc tgcgcgcccg caccgagtgg   1020
cgccccaagc tgaccgactc cttccgcggc atcagcgtga tccccgccga gccccgcgtg   1080
atggactaca aggaccacga cggcgactac aaggaccacg acatcgacta caaggacgac   1140
gacgacaagt ga                                                      1152
```

<210> SEQ ID NO 86
<211> LENGTH: 1155
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

| | | |
|---|---|---|
| atggccaccg catccacttt ctcggcgttc aatgcccgct gcggcgacct gcgtcgctcg | 60 |
| gcgggctccg ggccccggcg cccagcgagg cccctcccg tgcgcgggcg cgccccgac | 120 |
| tggtccatgc tgttcgccgt gatcaccacc atcttctccg ccgccgagaa gcagtggacc | 180 |
| aacctggagt ggaagcccaa gcccaacccc ccccagctgc tggacgacca cttcggcccc | 240 |
| cacggcctgg tgttccgccg caccttcgcc atccgcagct acgaggtggg ccccgaccgc | 300 |
| tccaccagca tcgtggccgt gatgaaccac ctgcaggagg ccgccctgaa ccacgccaag | 360 |
| tccgtgggca tcctgggcga cggcttcggc accaccctgg agatgtccaa gcgcgacctg | 420 |
| atctgggtgg tgaagcgcac ccacgtggcc gtggagcgct accccgcctg ggcgacacc | 480 |
| gtggaggtgg agtgctgggt gggcgcctcc ggcaacaacg gccgccgcca cgacttcctg | 540 |
| gtgcgcgact gcaagaccgg cgagatcctg acccgctgca cctccctgag cgtgatgatg | 600 |
| aacacccgca cccgccgcct gagcaagatc cccgaggagg tgcgcggcga gatcggcccc | 660 |
| gccttcatcg acaacgtggc cgtgaaggac gaggagatca agaagcccca gaagctgaac | 720 |
| gactccaccc ccgactacat ccagggcggc ctgacccccc gctggaacga cctggacatc | 780 |
| aaccagcacg tgaacaacat caagtacgtg gactggatcc tggagaccgt gcccgacagc | 840 |
| atcttcgaga gccaccacat ctcctccttc accatcgagt accgccgcga gtgcaccatg | 900 |
| gacagcgtgc tgcagtccct gaccaccgtg agcggcggct cctccgaggc cggcctggtg | 960 |
| tgcgagcacc tgctgcagct ggagggcggc agcgaggtgc tgcgcgccaa gaccgagtgg | 1020 |
| cgccccaagc tgaccgactc cttccgcggc atcagcgtga tccccgccga gtccagcgtg | 1080 |
| atggactaca aggaccacga cggcgactac aaggaccacg acatcgacta caaggacgac | 1140 |
| gacgacaagt gatga | 1155 |

<210> SEQ ID NO 87
<211> LENGTH: 1893
<212> TYPE: DNA
<213> ORGANISM: Artificial Sequence
<220> FEATURE:
<223> OTHER INFORMATION: Description of Artificial Sequence: Synthetic
 polynucleotide

<400> SEQUENCE: 87

| | | |
|---|---|---|
| gaattccttt cttgcgctat gacacttcca gcaaaaggta gggcgggctg cgagacggct | 60 |
| tcccggcgct gcatgcaaca ccgatgatgc ttcgaccccc cgaagctcct tcggggctgc | 120 |
| atgggcgctc cgatgccgct ccagggcgag cgctgtttaa atagccaggc cccgattgc | 180 |
| aaagacatta tagcgagcta ccaaagccat attcaaacac ctagatcact accacttcta | 240 |
| cacaggccac tcgagcttgt gatcgcactc cgctaagggg gcgcctcttc ctcttcgttt | 300 |
| cagtcacaac ccgcaaacac tagtatggcc accgcatcca cttttctcgg cgttcaatgcc | 360 |
| cgctgcggcg acctgcgtcg ctcggcgggc tccgggcccc ggcgcccagc gaggcccctc | 420 |
| cccgtgcgcg ggcgcgcccc cgactggtcc atgctgttcg ccgtgatcac caccatcttc | 480 |
| tccgccgccg agaagcagtg gaccaacctg gagtggaagc caagcccaa cccccccag | 540 |
| ctgctggacg accacttcgg ccccacggc ctggtgttcc gccgcacctt cgccatccgc | 600 |
| agctacgagg tgggccccga ccgctccacc agcatcgtgg ccgtgatgaa ccacctgcag | 660 |
| gaggccgccc tgaaccacgc caagtccgtg ggcatcctgg gcgacggctt cggcaccacc | 720 |

| | |
|---|---|
| ctggagatgt ccaagcgcga cctgatctgg gtggtgaagc gcacccacgt ggccgtggag | 780 |
| cgctaccccg cctggggcga caccgtggag gtggagtgct gggtgggcgc ctccggcaac | 840 |
| aacggccgcc gccacgactt cctggtgcgc gactgcaaga ccggcgagat cctgacccgc | 900 |
| tgcacctccc tgagcgtgat gatgaacacc cgcacccgcc gcctgagcaa gatccccgag | 960 |
| gaggtgcgcg gcgagatcgg ccccgccttc atcgacaacg tggccgtgaa ggacgaggag | 1020 |
| atcaagaagc cccagaagct gaacgactcc accgccgact acatccaggg cggcctgacc | 1080 |
| ccccgctgga acgacctgga catcaaccag cacgtgaaca acatcaagta cgtggactgg | 1140 |
| atcctggaga ccgtgcccga cagcatcttc gagagccacc acatctcctc cttcaccatc | 1200 |
| gagtaccgcc gcgagtgcac catggacagc gtgctgcagt ccctgaccac cgtgagcggc | 1260 |
| ggctcctccg aggccggcct ggtgtgcgag cacctgctgc agctggaggg cggcagcgag | 1320 |
| gtgctgcgcg ccaagaccga gtggcgcccc aagctgaccg actccttccg cggcatcagc | 1380 |
| gtgatccccg ccgagtccag cgtgatggac tacaaggacc acgacggcga ctacaaggac | 1440 |
| cacgacatcg actacaagga cgacgacgac aagtgatgac tcgaggcagc agcagctcgg | 1500 |
| atagtatcga cacactctgg acgctggtcg tgtgatggac tgttgccgcc acacttgctg | 1560 |
| ccttgacctg tgaatatccc tgccgctttt atcaaacagc ctcagtgtgt ttgatcttgt | 1620 |
| gtgtacgcgc ttttgcgagt tgctagctgc ttgtgctatt tgcgaatacc accccagca | 1680 |
| tccccttccc tcgtttcata tcgcttgcat cccaaccgca acttatctac gctgtcctgc | 1740 |
| tatccctcag cgctgctcct gctcctgctc actgcccctc gcacagcctt ggtttgggct | 1800 |
| ccgcctgtat tctcctggta ctgcaacctg taaaccagca ctgcaatgct gatgcacggg | 1860 |
| aagtagtggg atgggaacac aaatggaaag ctt | 1893 |

<210> SEQ ID NO 88
<211> LENGTH: 1887
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 88

| | |
|---|---|
| gaattccttt cttgcgctat gacacttcca gcaaaaggta gggcgggctg cgagacggct | 60 |
| tcccggcgct gcatgcaaca ccgatgatgc ttcgaccccc cgaagctcct tcggggctgc | 120 |
| atgggcgctc cgatgccgct ccagggcgag cgctgtttaa atagccaggc ccccgattgc | 180 |
| aaagacatta tagcgagcta ccaaagccat attcaaacac ctagatcact accacttcta | 240 |
| cacaggccac tcgagcttgt gatcgcactc cgctaagggg gcgcctcttc ctcttcgttt | 300 |
| cagtcacaac ccgcaaacac tagtatggct tccgcggcat tcaccatgtc ggcgtgcccc | 360 |
| gcgatgactg gcagggcccc tggggcacgt cgctccggac ggccagtcgc caccccgcctg | 420 |
| aggggggcgcg ccccgactg gtccatgctg ttcgccgtga tcaccaccat cttctccgcc | 480 |
| gccgagaagc agtggaccaa cctggagtgg aagcccaagc caacccccc ccagctgctg | 540 |
| gacgaccact tcggccccca cggcctggtg ttcgccgcca ccttcgccat cgcagctac | 600 |
| gaggtgggcc ccgaccgctc caccagcatc gtggccgtga tgaaccacct gcaggaggcc | 660 |
| gccctgaacc acgccaagtc cgtgggcatc ctgggcgacg gcttcggcac caccctggag | 720 |
| atgtccaagc gcgacctgat ctgggtggtg aagcgcaccc acgtggccgt ggagcgctac | 780 |
| cccgcctggg gcgacaccgt ggaggtggag tgctgggtgg gcgcctccgg caacaacggc | 840 |

```
cgccgccacg acttcctggt gcgcgactgc aagaccggcg agatcctgac ccgctgcacc      900
tccctgagcg tgatgatgaa cacccgcacc cgccgcctga gcaagatccc cgaggaggtg      960
cgcggcgaga tcggccccgc cttcatcgac aacgtggccg tgaaggacga ggagatcaag     1020
aagccccaga agctgaacga ctccaccgcc gactacatcc agggcggcct gaccccccgc     1080
tggaacgacc tggacatcaa ccagcacgtg aacaacatca agtacgtgga ctggatcctg     1140
gagaccgtgc ccgacagcat cttcgagagc caccacatct cctccttcac catcgagtac     1200
cgccgcgagt gcaccatgga cagcgtgctg cagtccctga ccaccgtgag cggcggctcc     1260
tccgaggccg gcctggtgtg cgagcacctg ctgcagctgg agggcggcag cgaggtgctg     1320
cgcgccaaga ccgagtggcg ccccaagctg accgactcct tccgcggcat cagcgtgatc     1380
cccgccgagt ccagcgtgat ggactacaag gaccacgacg gcgactacaa ggaccacgac     1440
atcgactaca aggacgacga cgacaagtga tgactcgagg cagcagcagc tcggatagta     1500
tcgacacact ctggacgctg gtcgtgtgat ggactgttgc cgccacactt gctgccttga     1560
cctgtgaata tccctgccgc ttttatcaaa cagcctcagt gtgtttgatc ttgtgtgtac     1620
gcgcttttgc gagttgctag ctgcttgtgc tatttgcgaa taccacccc agcatcccct      1680 tccctcgttt catatcgctt gcatcccaac cgcaacttat ctacgctgtc ctgctatccc     1740
tcagcgctgc tcctgctcct gctcactgcc cctcgcacag ccttggtttg ggctccgcct     1800
gtattctcct ggtactgcaa cctgtaaacc agcactgcaa tgctgatgca cgggaagtag     1860
tgggatggga acacaaatgg aaagctt                                          1887
```

<210> SEQ ID NO 89
<211> LENGTH: 3631
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
gaattccgcc tgcaacgcaa gggcagccac agccgctccc accgccgct gaaccgacac        60 gtgcttgggc gcctgccgcc tgcctgccgc atgcttgtgc tggtgaggct gggcagtgct      120
gccatgctga ttgaggcttg gttcatcggg tggaagctta tgtgtgtgct gggcttgcat      180
gccgggcaat gcgcatggtg gcaagagggc ggcagcactt gctggagctg ccgcggtgcc      240
tccaggtggt tcaatcgcgg cagccagagg gatttcagat gatcgcgcgt acaggttgag      300
cagcagtgtc agcaaaggta gcagtttgcc agaatgatcg gttcagctgt taatcaatgc      360
cagcaagaga aggggtcaag tgcaaacacg ggcatgccac agcacgggca ccggggagtg      420
gaatggcacc accaagtgtg tgcgagccag catcgccgcc tggctgtttc agctacaacg      480
gcaggagtca tccaacgtaa ccatgagctg atcaacactg caatcatcgg gcgggcgtga      540
tgcaagcatg cctggcgaag acacatggtg tgcggatgct gccggctgct gcctgctgcg      600
cacgccgttg agttggcagc aggctcagcc atgcactgga tggcagctgg gctgccactg      660
caatgtggtg gataggatgc aagtggagcg aataccaaac cctctggctg cttgctgggt      720
tgcatggcat cgcaccatca gcaggagcgc atgcgaaggg actggcccca tgcacgccat      780
gccaaaccgg agcgcaccga gtgtccacac tgtcaccagg cccgcaagct tgcagaacc      840 atgctcatgg acgcatgtag cgctgacgtc cctgacggc gctcctctcg ggtgtgggaa      900
acgcaatgca gcacaggcag cagaggcggc ggcagcagag cggcggcagc agcggcgggg      960
```

```
gccacccttc ttgcggggtc gcgccccagc cagcggtgat gcgctgatcc caaacgagtt    1020
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttgggtggg gcggccggct gtttcttcg tgttgcaaaa      1200 cgcgccagct cagcaacctg tcccgtgggt cccccgtgcc gatgaaatcg tgtgcacgcc    1260
gatcagctga ttgcccggct cgcgaagtag gcgccctcct ttctgctcgc cctctctccg    1320
tcccgccact agtatgctgc tgcaggcctt cctgttcctg ctggccggct cgccgccaa      1380 gatcagcgcc tccatgacga acgagacgtc cgaccgcccc ctggtgcact tcaccccaa      1440 caagggctgg gggcgcgcca gccaccacgt gtacaagcgc ctgacccaga gcaccaacac    1500
caagtccccc agcgtgaacc agccctaccg caccggcttc cacttccagc cccccaagaa    1560
ctggatgaac gaccccaacg gccccatgat ctacaagggc atctaccacc tgttctacca    1620
gtggaacccc aagggcgccg tgtggggcaa catcgtgtgg gcccactcca ccagcaccga    1680
cctgatcaac tgggaccccc accccccgc catcttcccc agcgcccct cgacatcaa       1740 cggctgctgg tccggcagcg ccaccatcct gcccaacggc aagcccgtga tcctgtacac    1800
cggcatcgac cccaagaacc agcaggtgca gaacatcgcc gagcccaaga acctgtccga    1860
cccctacctg cgcgagtgga gaagagccc cctgaacccc ctgatggccc ccgacgccgt    1920
gaacggcatc aacgcctcca gcttccgcga ccccaccacc gcctggctgg ccaggacaa      1980 gaagtggcgc gtgatcatcg gctccaagat ccaccgccgc ggcctggcca tcacctacac    2040
cagcaaggac ttcctgaagt gggagaagtc ccccgagccc ctgcactacg acgacggcag    2100
cggcatgtgg gagtgccccg acttcttccc cgtgacccgc ttcggcagca acggcgtgga    2160
gacctccagc ttcggcgagc ccaacgagat cctgaagcac gtgctgaaga tctccctgga    2220
cgacaccaag cacgactact acaccatcgg cacctacgac cgcgtgaagg acaagttcgt    2280
gcccgacaac ggcttcaaga tggacggcac cgccccccgc tacgactacg caagtacta     2340 cgccagcaag accttcttcg actccgccaa gaaccgccgc atcctgtggg gctggaccaa    2400
cgagtcctcc agcgtggagg acgacgtgga gaagggctgg tccggcatcc agaccatccc    2460
ccgcaagatc tggctggacc gcagcggcaa gcagctgatc cagtggcccg tgcgcgaggt    2520
ggagcgcctg cgcaccaagc aggtgaagaa cctgcgcaac aaggtgctga agtccggcag    2580
ccgcctggag gtgtacggcg tgaccgccgc ccaggccgac gtggaggtgc tgttcaaggt    2640
gcgcgacctg gagaaggccg acgtgatcga gccctcctgg accgaccccc agctgatctg    2700
cagcaagatg aacgtgtccg tgaagtccgg cctgggcccc ttcggcctga tggtgctggc    2760
cagcaagaac ctggaggagt acaccctccgt gtacttccgc atcttcaagg cccgccagaa    2820
cagcaacaag tacgtggtgc tgatgtgctc cgaccagtcc cgcagctccc tgaaggagga    2880
caacgacaag accacctacg cgccttcgt ggacatcaac cccaccagc ccctgagcct       2940 gcgcgccctg atcgaccact ccgtggtgga gagcttcggc ggcaagggcc gcgcctgcat    3000
cacctcccgc gtgtacccca agctggccat cggcaagtcc agccacctgt cgccttcaa     3060 ctacggctac cagtccgtgg acgtgctgaa cctgaacgcc tggagcatga actccgccca    3120
gatcagcatg gactacaagg accacgacgg cgactacaag gaccacgaca tcgactacaa    3180
ggacgacgac gacaagtgat taattaaccg gctcgaggca gcagcagctc ggatagtatc    3240
gacacactct ggacgctggt cgtgtgatgg actgttgccg ccacacttgc tgccttgacc    3300
tgtgaatatc cctgccgctt ttatcaaaca gcctcagtgt gtttgatctt gtgtgtacgc    3360
```

-continued

```
gcttttgcga gttgctagct gcttgtgcta tttgcgaata ccaccccag catcccttc    3420 cctcgtttca tatcgcttgc atcccaaccg caacttatct acgctgtcct gctatccctc    3480
agcgctgctc ctgctcctgc tcactgcccc tcgcacagcc ttggtttggg ctccgcctgt    3540
attctcctgg tactgcaacc tgtaaaccag cactgcaatg ctgatgcacg ggaagtagtg    3600
ggatgggaac acaaatggaa agcttgagct c                                   3631
```

<210> SEQ ID NO 90
<211> LENGTH: 621
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
                20                  25                  30

Phe Thr Pro Asn Lys Gly Trp Gly Arg Ala Ser His His Val Tyr Lys
            35                  40                  45

Arg Leu Thr Gln Ser Thr Asn Thr Lys Ser Pro Ser Val Asn Gln Pro
        50                  55                  60

Tyr Arg Thr Gly Phe His Phe Gln Pro Pro Lys Asn Trp Met Asn Asp
65                  70                  75                  80

Pro Asn Gly Pro Met Ile Tyr Lys Gly Ile Tyr His Leu Phe Tyr Gln
                85                  90                  95

Trp Asn Pro Lys Gly Ala Val Trp Gly Asn Ile Val Trp Ala His Ser
            100                 105                 110

Thr Ser Thr Asp Leu Ile Asn Trp Asp Pro His Pro Pro Ala Ile Phe
        115                 120                 125

Pro Ser Ala Pro Phe Asp Ile Asn Gly Cys Trp Ser Gly Ser Ala Thr
    130                 135                 140

Ile Leu Pro Asn Gly Lys Pro Val Ile Leu Tyr Thr Gly Ile Asp Pro
145                 150                 155                 160

Lys Asn Gln Gln Val Gln Asn Ile Ala Glu Pro Lys Asn Leu Ser Asp
                165                 170                 175

Pro Tyr Leu Arg Glu Trp Lys Lys Ser Pro Leu Asn Pro Leu Met Ala
            180                 185                 190

Pro Asp Ala Val Asn Gly Ile Asn Ala Ser Ser Phe Arg Asp Pro Thr
        195                 200                 205

Thr Ala Trp Leu Gly Gln Asp Lys Lys Trp Arg Val Ile Ile Gly Ser
    210                 215                 220

Lys Ile His Arg Arg Gly Leu Ala Ile Thr Tyr Thr Ser Lys Asp Phe
225                 230                 235                 240

Leu Lys Trp Glu Lys Ser Pro Glu Pro Leu His Tyr Asp Asp Gly Ser
                245                 250                 255

Gly Met Trp Glu Cys Pro Asp Phe Phe Pro Val Thr Arg Phe Gly Ser
            260                 265                 270

Asn Gly Val Glu Thr Ser Ser Phe Gly Glu Pro Asn Glu Ile Leu Lys
        275                 280                 285

His Val Leu Lys Ile Ser Leu Asp Asp Thr Lys His Asp Tyr Tyr Thr
    290                 295                 300
```

Ile Gly Thr Tyr Asp Arg Val Lys Asp Lys Phe Val Pro Asp Asn Gly
305                 310                 315                 320

Phe Lys Met Asp Gly Thr Ala Pro Arg Tyr Asp Tyr Gly Lys Tyr Tyr
            325                 330                 335

Ala Ser Lys Thr Phe Phe Asp Ser Ala Lys Asn Arg Arg Ile Leu Trp
            340                 345                 350

Gly Trp Thr Asn Glu Ser Ser Val Glu Asp Val Glu Lys Gly
            355                 360                 365

Trp Ser Gly Ile Gln Thr Ile Pro Arg Lys Ile Trp Leu Asp Arg Ser
            370                 375                 380

Gly Lys Gln Leu Ile Gln Trp Pro Val Arg Glu Val Glu Arg Leu Arg
385                 390                 395                 400

Thr Lys Gln Val Lys Asn Leu Arg Asn Lys Val Leu Lys Ser Gly Ser
            405                 410                 415

Arg Leu Glu Val Tyr Gly Val Thr Ala Ala Gln Ala Asp Val Glu Val
            420                 425                 430

Leu Phe Lys Val Arg Asp Leu Glu Lys Ala Asp Val Ile Glu Pro Ser
            435                 440                 445

Trp Thr Asp Pro Gln Leu Ile Cys Ser Lys Met Asn Val Ser Val Lys
450                 455                 460

Ser Gly Leu Gly Pro Phe Gly Leu Met Val Leu Ala Ser Lys Asn Leu
465                 470                 475                 480

Glu Glu Tyr Thr Ser Val Tyr Phe Arg Ile Phe Lys Ala Arg Gln Asn
            485                 490                 495

Ser Asn Lys Tyr Val Val Leu Met Cys Ser Asp Gln Ser Arg Ser Ser
            500                 505                 510

Leu Lys Glu Asp Asn Asp Lys Thr Thr Tyr Gly Ala Phe Val Asp Ile
            515                 520                 525

Asn Pro His Gln Pro Leu Ser Leu Arg Ala Leu Ile Asp His Ser Val
530                 535                 540

Val Glu Ser Phe Gly Gly Lys Gly Arg Ala Cys Ile Thr Ser Arg Val
545                 550                 555                 560

Tyr Pro Lys Leu Ala Ile Gly Lys Ser Ser His Leu Phe Ala Phe Asn
            565                 570                 575

Tyr Gly Tyr Gln Ser Val Asp Val Leu Asn Leu Asn Ala Trp Ser Met
            580                 585                 590

Asn Ser Ala Gln Ile Ser Met Asp Tyr Lys Asp His Asp Gly Asp Tyr
            595                 600                 605

Lys Asp His Asp Ile Asp Tyr Lys Asp Asp Asp Lys
610                 615                 620

<210> SEQ ID NO 91
<211> LENGTH: 997
<212> TYPE: DNA
<213> ORGANISM: Prototheca moriformis

<400> SEQUENCE: 91
cctgtcgatc gaagagaagg agacatgtgt acattattgg tgtgagggcg ctgaatcggc     60 catttttaa aatgatcacg ctcatgccaa tagacgcggc acataacgac gttcaaaccc    120
ccgccaaagc cgcggacaac cccatccctc cacaccccc acacaaagaa cccgccaccg    180
cttaccttgc ccacgaggta ggcctttcgt tgcgcaaaac cggcctcggt gatgaatgca    240
tgcccgttcc tgacgagcgc tgcccgggcc aacacgctct tttgctgcgt ctcctcaggc    300
ttgggggcct ccttgggctt gggtgccgcc atgatctgcg cgcatcagag aaacgttgct    360

```
ggtaaaaagg agcgcccggc tgcgcaatat atatataggc atgccaacac agcccaacct    420
cactcgggag cccgtcccac caccccccaag tcgcgtgcct tgacggcata ctgctgcaga    480
agcttcatga gaatgatgcc gaacaagagg ggcacgagga cccaatcccg gacatccttg    540
tcgataatga tctcgtgagt ccccatcgtc cgcccgacgc tccggggagc ccgccgatgc    600
tcaagacgag agggccctcg accaggaggg gctggcccgg gcgggcactg gcgtcgaagg    660
tgcgcccgtc gttcgcctgc agtcctatgc cacaaaacaa gtcttctgac ggggtgcgtt    720
tgctcccgtg cgggcaggca acagaggtat tcaccctggt catggggaga tcggcgatcg    780
agctgggata agagatactt ctggcaagca atgacaactt gtcaggaccg gaccgtgcca    840
tatatttctc acctagcgcc gcaaaaccta acaatttggg agtcactgtg ccactgagtt    900
cgactggtag ctgaatggag tcgctgctcc actaaacgaa ttgtcagcac cgccagccgg    960
ccgaggaccc gagtcatagc gagggtagta gcgcgcc                             997
```

```
<210> SEQ ID NO 92
<211> LENGTH: 753
<212> TYPE: DNA
<213> ORGANISM: Prototheca moriformis

<400> SEQUENCE: 92
actaattgca atcgtgcagt aatcatcgat atggtcacaa gtagatcccc tactgacacc     60
ctctcgtaca tgtaggcaat gtcatcggcg ccgtcctgct gaccgatgcc gacgtagcag    120
agcagacccg ggccgatctg ggatacgagc cggccctcca cctgcgctcg aggtggaatc    180
aagtaaataa ccaatacact tttcgacacc acacagagtt gcacggacgg tggcgtacct    240
ctacgctcgc gctcttcacg cgctggacga ccgcacgcat gagcccgggt ggcttggtct    300
gggctgcaaa aatgcacaac aaacaagtat cagacgctca tggatgcaca cgcgctccca    360
agcacgctca gactaaatat tacagtagct cgtatctgat aagatatcga gacataccgc    420
tcaactcacc cgcaaactgc gccccgccag gtgatgcgca cagggcccca ccatgcgatc    480
catcgcatcg ctcctcgagg gcgctatcac gtggccggag agcgttcaca gcgtacgcca    540
ctgtatctgg gcggtatgcg gtccgtcaac atggagacag ataccccgcac caccaccttg    600 caagctcttc catattggaa gtagaaaatt gtaattgtat catcgcacga ggggccaact    660
tgccgtcggc gagctgggcg acgaacacca cctggacgtt gtcgagactc gctcgtgccg    720
tgcgccgggc cgctgggtat ccagaccgtc gcc                                  753
```

```
<210> SEQ ID NO 93
<211> LENGTH: 1122
<212> TYPE: DNA
<213> ORGANISM: Prototheca moriformis

<400> SEQUENCE: 93
caacgacaac cagcaggcaa ctcggtcagc gacccaacac gcgagtcaaa ttgttgcgtg     60
ttcttgcctt gtctatttac tgtgatagca agactgtcgg tcagtcaata ccgcggtgcg    120
cacgtcgggg tgccaagcct agcagagcac gggacggctg gtgctgtgcg ccagctcagc    180
tcgcttcgcg accaattgta ggaccggcaa agtcaccaaa acatgccagc ggtgcgattc    240
aattggtcat gagctctaca aaattgtttt gtgcgtcgcg caggtatcca acggcgcggc    300
agagaaagtt tgcagctct cgatttcatc tcggaaaaat ggggagaatt tatgacacac    360
aagtgcgcag gcggcccagg cggccagcat attctggcgt gacctgggcc gcccacaaaa    420
```

| | |
|---|---|
| tgcttggatg cactctaaaa taattatatt tgccatgaac aagggaagag ttaccgcacc | 480 |
| cagccctaga cttgggcgcc cgagcaaggt tacgtcaagc caccttcgcc catcgcccaa | 540 |
| ctccgtattc cccgacagcc gcacgtggcc ctcgccggaa tgaaccctga atcggcatca | 600 |
| cgccacgcgt tcgccaatcg ttccgctctc tggcttcatc ggcctgcgcc ttcacgtcgt | 660 |
| ggtcacgaca gtgcattcat acttccattt gcacctcggc acacactttt acgcatcgcc | 720 |
| taccttgct gcggcagtct agggtcactt tgcagccatg gacagtgct acaccaccgt | 780 |
| cggtgcgcaa agctatttca agtgaaccgt gggcggaaaa aaggaatgta cactgtctca | 840 |
| accgactcct acaattgttt accatgcaga tcagagctcg acggccatca tcgagcaggt | 900 |
| gtggggcctt ggtggcgcgg cgcggggccc cagggcgtcg caggcattga tggcactctg | 960 |
| agactttcgc acgcgcatga gggacccccat caagagaaga gtgtgtcttt atgtccccat | 1020 |
| tcatgatgat gtatcttgtg attgtcgcag tttggcaagt ttaaccggat cgccgctcca | 1080 |
| ggtgtggcgt ggcggatttt tctaggggtg cttgagcagt cg | 1122 |

```
<210> SEQ ID NO 94
<211> LENGTH: 574
<212> TYPE: DNA
<213> ORGANISM: Prototheca moriformis

<400> SEQUENCE: 94
```

| | |
|---|---|
| ggcccagggc cctgcggatg ccccacacca gatctagcct ctcttatgcc atgcccgcct | 60 |
| cgctgcccgt cgtatccccc cgccgatccg cgcgtagggg accgcggcct gacccacgcc | 120 |
| acgaaagagc tttgctcctc aatttctcgc caacagaacc gtatcaaacg ctcaacgcct | 180 |
| atcccgaaca atccgtattc acaccaaatc gagtataccg gactggtttg cctagtcttg | 240 |
| aaggaaatga tcccgtccat gctcggaagg gggagcgggc ggaggatcct actcatctct | 300 |
| gaaatgggat tggtccgaag atgggttggg caagcacgtg ccaaacccca gcgagttgct | 360 |
| gacgagcagg ctcatccaat cccccggcga atcctccctc acgccccgca tgcatacaag | 420 |
| tccctcccac acgccccctc ccatccattt tcgcctggtc cgaacgcgag cggcgtcgag | 480 |
| gcggaccact tgctccgcag cgccgtctgg gtctccaccc cacagcggct ttgctgccag | 540 |
| aggcaccccc cttgccccac ctcctcttgc agcc | 574 |

```
<210> SEQ ID NO 95
<211> LENGTH: 1096
<212> TYPE: DNA
<213> ORGANISM: Prototheca moriformis

<400> SEQUENCE: 95
```

| | |
|---|---|
| ccaggcaggc ggtagggttg ccgattgctt gagcgaattg gaagatataa tttttttgtgg | 60 |
| tgtccctgga cgctgtttgt ggcgctcctt tttggagaag attgcgtggg ggagctttcc | 120 |
| atgtaccacg cttccttctg aaaggattct ggccgagtcc tgatgagccc aaagaaaaca | 180 |
| cctgcctttc agtgctggca ctctgaaaac gtcaacagat gattatacat gtcacaaaag | 240 |
| gcagccgatt aggaacggga gctctggccg ttcgtttggc tgcctgggct gattgaagtg | 300 |
| atccaccctg ttcgaatgaa ggcggtcgag tcgaattatc gaccggagct gtcgggaagg | 360 |
| cgtccggggc agagtgaggt gctgcggcct ggttgtcgtt caaaaagacc ccggtagccc | 420 |
| aacaatcacg aacgaaagga atataattgc ttgcatacta tacattcagt ttctatgtgg | 480 |
| cgggtagaca agtctcatgg gcttctaaag gctgtccctt gaaggctact tataaaaact | 540 |
| tgctgcgcca tggcacggat cgcgcttgcg caggctgcaa ccctgcgcgc aaggtcaaat | 600 |

```
acacagcaaa agatactaac agaatttcta aaaacattta aatatttgtt tcgaccagcc      660
aattgtggtc gtaggcacgc aaaagacttt gttttgcgcc caccgagcat ccacgctggc      720
agtcaagcca gtccgatgtg cattgcgtgg cagcatcgag gagcatcaaa aacctcgtgc      780
acgcttttct gtcaatcatc atcaaccact ccaccatgta tacccgatgc atcgcggtgc      840
gcagcgcgcc acgcgtccca gacccgccca aaaacccagc agcggcgaaa gcaaatcttc      900
acttgcccga aaccccgagc agcggcattc acacgtgggc gaaaaccccca cttgccctaa      960 caggcgtatg tctgctgtca cgatgcctga caacggtatt atagatatac actgattaat     1020
gtttgagtgt gtgcgagtcg cgaatcagga atgaattgct agtaggcact ccgaccgggc     1080
gggggccgag ggacca                                                    1096
```

<210> SEQ ID NO 96
<211> LENGTH: 1075
<212> TYPE: DNA
<213> ORGANISM: Prototheca moriformis

<400> SEQUENCE: 96

```
ggccgacagg acgcgcgtca aaggtgctgg gcgtgtatgc cctggtcggc aggtcgttgc       60
tgttgctgcg ctcgtggttc cgcaaccctg attttggcgt cttattctgg cgtggcaagc      120
gctgacgccc gcgagccggg ccggcggcga tgcggtgtct cacggctgcc gagctccaag      180
ggaggcaaga gcgcccggat cagctgaagg gctttacacg caaggtacag ccgctcctgc      240
aaggctgcgt ggtggacttg aacctgtagg tcctctgctg aagttcctcc actacctcac      300
caggcccagc agaccaaagc acaggctttt caggtccgtg tcatccactc taaaacactc      360
gactacgacc tactgatggc cctagattct tcatcaacaa tgcctgagac acttgctcag      420
aattgaaact ccctgaaggg accaccagag gccctgagtt gttccttccc cccgtggcga      480
gctgccagcc aggctgtacc tgtgatcgag gctggcggga aaataggctt cgtgtgctca      540
ggtcatggga ggtgcaggac agctcatgaa acgccaacaa tcgcacaatt catgtcaagc      600
taatcagcta tttcctcttc acgagctgta attgtcccaa aattctggtc taccgggggt      660
gatccttcgt gtacgggccc ttccctcaac cctaggtatg cgcgcatgcg gtcgccgcgc      720
aactcgcgcg agggccgagg gtttgggacg ggccgtcccg aaatgcagtt gcacccggat      780
gcgcggcgcc tttcttgcga taatttatgc aatggactgc tctgcaaatt tctgggtctg      840
tcgccaaccc taggatcagc ggcgtaggat ttcgtaatca ttcgtcctga tggggagcta      900
ccgactaccc taatatcagc ccggctgcct gacgccagcg tccactttg cgtacacatt      960 ccattcgtgc ccaagacatt tcattgtggt gcgaagcgtc cccagttacg ctcacctgtt     1020
tcccgacctc cttactgttc tgtcgacaga gcgggcccac aggccggtcg cagcc          1075
```

<210> SEQ ID NO 97
<211> LENGTH: 772
<212> TYPE: DNA
<213> ORGANISM: Prototheca moriformis

<400> SEQUENCE: 97

```
tcaccagcgg acaaagcacc ggtgtatcag gtccgtgtca tccactctaa agagctcgac       60
tacgacctac tgatggccct agattcttca tcaaaaacgc ctgagacact tgcccaggat      120
tgaaactccc tgaagggacc accaggggcc ctgagttgtt ccttcccccc gtggcgagct      180
gccagccagg ctgtacctgt gatcggggct ggcgggaaaa caggcttcgt gtgctcaggt      240
```

| | |
|---|---|
| tatgggaggt gcaggacagc tcattaaacg ccaacaatcg cacaattcat ggcaagctaa | 300 |
| tcagttattt cccattaacg agctataatt gtcccaaaat tctggtctac cgggggtgat | 360 |
| ccttcgtgta cgggcccttc cctcaaccct aggtatgcgc acatgcggtc gccgcgcaac | 420 |
| gcgcgcgagg gccgagggtt tgggacgggc cgtcccgaaa tgcagttgca cccggatgcg | 480 |
| tggcaccttt tttgcgataa tttatgcaat ggactgctct gcaaaattct ggctctgtcg | 540 |
| ccaaccctag gatcagcggt gtaggatttc gtaatcattc gtcctgatgg ggagctaccg | 600 |
| actgccctag tatcagcccg actgcctgac gccagcgtcc acttttgtgc acacattcca | 660 |
| ttcgtgccca agacatttca ttgtggtgcg aagcgtcccc agttacgctc acctgatccc | 720 |
| caacctcctt attgttctgt cgacagagtg ggcccagagg ccggtcgcag cc | 772 |

<210> SEQ ID NO 98
<211> LENGTH: 991
<212> TYPE: DNA
<213> ORGANISM: Protoheca moriformis

<400> SEQUENCE: 98

| | |
|---|---|
| cgaaggggtc tgcatcgatt cgcgcggtct ggaggccagc gtgactgctc gcgaaaatgc | 60 |
| tctgccgtgt cgggctctgg ctgggcggc cagagatctc accgtgccac acgcaactgc | 120 |
| cgcactctgt gcccgccacc tggcgcgcac atgcgacctc ttccccgtca taccctctcc | 180 |
| tcatgtgatc tttccacacg agtgacgcag gtgcgcggag tggagggaat caggacgttt | 240 |
| tcaaggtacc tgctcgagcc gtaccaacag ctgccgcccg gcaaggaaga gatcgaggca | 300 |
| gagattgccc ggctggaggc ccggataacg gagctcaaga gcaagctgtc cgagtgagac | 360 |
| cgcccaggtg cacgtgtcga ctcgctatga catgtactcg acacaacatg aggaattcat | 420 |
| cgaatttgta ggaagcgggc attggtacgg gagtgggaaa gcgaaaaaac ctccctccgg | 480 |
| cagtgccatc tgccggagtc gaacgttgat agggttctcg tgacagggtg tgacctctca | 540 |
| gccttgcatc aattaaacgc tatagacatt atcagtaacc gtgaatcccg cattggatgc | 600 |
| cacccgcgcg accattgggg acctgcatta cagatctagg tgagatgaca gcgaggcaac | 660 |
| ttcggcccgc ggcccagctt gcggcgcacc aatattggtc acgggaagcc acacaccgac | 720 |
| cataaatgaa tacttgtaag ctatgtcaac cgatcaatgg cgtcgaaagt gtgccacgag | 780 |
| gatccatctg gcggggcggc gtggcgcaca agccgcagtcg caatttctcg gacccatctg | 840 |
| acctaggccc agcgccgcgg gagaaatccc cggcgggtcc tccacgcagt aaccctaatg | 900 |
| agtatcgagc gccgaccatt tacaccatcg cccccgaaat ccttccgaca ttattattat | 960 |
| cttttagatc ttggaacaga ctctgccaac c | 991 |

<210> SEQ ID NO 99
<211> LENGTH: 1347
<212> TYPE: DNA
<213> ORGANISM: Prototheca moriformis

<400> SEQUENCE: 99

| | |
|---|---|
| agagagcgga ggtggggttg tgaggtgggg ttgctgacca ggagctcgcg tcgccgagcg | 60 |
| cgactcgcac acggtccagt tacccccccc tccgcccaaa cgcaagcctc ccatcttgat | 120 |
| gcctttccgg ccacctatac tatttcttag ttcgctgtaa catccagacc gtcctgaata | 180 |
| ataacaatgc cctgtgtcaa gtgcattcct aaaaaaattc tgtcccaacc aacaatccca | 240 |
| cctgaaatac caccagccct gcccagtaca ctcttccaat accatctccc tacctccacg | 300 |
| cgcaagcgac ccccatgcgc gaccaggctc gaaagtgatt tatgacttga gacgagcgag | 360 |

```
tggcggcgcg gtcgactgcc ttttcatcac gtgccgtacg tcggcgaccg ctagggcttt       420
gcacggcaac gcacggcttc gccaacccga ccagccagga cctcgactac tctaccgcga       480
attcgcctca agaagtcgcc aaatgtgcca tacaccattc cttacagcac tgttcaaact       540
tgatgccaat tttgacattc gggttgctcg ttggctgcgc ccacatcggc cgtgagtgca       600
gcaggcggga tcggacacgg aggacgcggc gtcacgcccc gaacgcagcc cgtaactcta       660
catcaacacg acgtgttgcg taatcccgcc cggctgcgca tcgtgccaac ccattcgcga       720
tggatggtcg gaaaatggtg tgccaactgc cctgagggag gctctcgcga aacgggcacg       780
tccctgaaac cgaaactgtg gccttgtcgt cggccacgca agcacgtgga ccctaaacac       840
caagaaaatc agtaaacaag gttgacatcc tctacgggcg aattgtttgc ccaacccttc       900
atcgcacact gccattataa tgcatctagc tcggcgacaa gtttagaaaa ggcaggctgc       960
attgttccat ttcgccgtgg cggcgtgggt gcccatttta cgaggtttgg gctcccgggc      1020
agcgaccgag ccaggtcgag tccctctcgc cgtcgacaa tgttgcgaac cccacaagcg      1080
gctaacaaca acttgatggt acctgtacac tgccaattcc ttcttccccg gccgaggttt      1140
acacgtgatg gccatggctt cgcattcagg ccgacttccc attccgactt ccagagggt      1200 ccgcggacgc tgggggttgg ctgcctgagg cccacccttt gttccccgcg tcccgacaaa      1260
cacaattgcg ttacataagg gggagccgcc cccgttcaga gtgcagaaat ctttcactat      1320
attttccagt cgtcagcgaa atcaagt                                          1347

<210> SEQ ID NO 100
<211> LENGTH: 1180
<212> TYPE: DNA
<213> ORGANISM: Prototheca moriformis

<400> SEQUENCE: 100
gatggtgggg tgtctgcctt gggctgggtg atggaggctg gtggtgcgcg ggtttcctga        60
tgcattctat ctacgcagtg tcatggtgtc cattccacac accagtacac ccttacacta       120
aggatccatc cctccttccc tcttcaggac tacatggacc ccacgagcta ccgaccgggc       180
tttctcaaaa acgtcaaggt catgtttgac atgcgggacg tggtggacga cgtgcaaggt       240
gcgtccggag tgcgcgcaaa tgagcaagtc gggcaatgtg tcggggtggg caccggggct       300
ggagatccgc gatccccgag aaaacgccgt accaccccc gcgctattcc ctcgattgcg       360
cgcagatgtg gtgaccgaca cggggggacaa cctggcggac atggggcgcc ggacctggaa       420
gcacgccaag tcgcacacgg ggaggctcgt gcagtccccc catcgtacc tcaagggtct       480 ctttggtcgc gatccaaagt acgctggtgg catggcatgc ccgaaatgaa catcatgtgt       540
gatctccgat tgccaatggc cacctccacg gaccaccttg caggcggaag cgcaatccag       600
ggcccgagcc tgacgaggac ggagactcct cgtccagcgc ggggtccccg acccgacgca       660
gcagccgacc cctgctaacc cggcaacgat cggaccagca accttgctgt agttccgatc       720
cgtgatgacg ggcattgccg ccgctcgatc cgctttgatg actgtctatt atttgcgcgg       780
agccccctcg gaaccctacc ccgctcttgc aagccccttg catcggagat cctcgtgcgc       840
ccgccatgac cccactggat tgcccaacat ccttctttat cgtgtaaaat gtgattcctc       900
ggctgcaatc gactggcctt cgcttctggc cccaagaggg ctcgaacgtg cggcagcgag       960
ggcgctgaca cacccaagcc ctagggcttt caacgtcggc tgccaggccg ataggggga      1020 tcgcctcctt tccaccaccc acctacgagg gattcgagtc ggcttccagc tcagctattc      1080
```

| | |
|---|---|
| ggccgcgccc ccggccctgc agacgtcctc cagtttccga acaggtcgct ctcagaacac | 1140 |
| ctgccgcggc tgcgatacgg caggctctca aagcgtcgac | 1180 |

<210> SEQ ID NO 101
<211> LENGTH: 1263
<212> TYPE: DNA
<213> ORGANISM: Prototheca moriformis

<400> SEQUENCE: 101

| | |
|---|---|
| cgcgtggagc ggtgcgtgcg gatgccgcgc gcctgccaag gccttttgta tgcctggcct | 60 |
| gggaagtttc ctgactgaag catcttcaag atgctctctc acgaccagcg acaccaacac | 120 |
| cgtcactttt tgcccctcct gccgcaggtg ccactttcta ctttgacgtc ttctccaggc | 180 |
| ggtacattgc gggactgagc gccaattcgg ccaagaacag cgctgtcgac ttgaggaggc | 240 |
| aggggtccgt cgactctgcc gagtgacacg ccttcgaccc gactgtacta cggcctgctg | 300 |
| aagagtgggt ctcgccggcc ggcgtgaccg ccctgtgcc cacaatcgac catctattcg | 360 |
| ctccttgtca tctggcgccg tcaattgccc gcgacttgac ggcaactggc tcgatcgagt | 420 |
| cgtattgaaa aagcacgttt tgtcctacag ggccgcggtc cgttaccaac gtggttctcg | 480 |
| ttaggttttc gtcgggcggt ggtgcgcgaa ctgtccgatg ccatcccggc aaaccccagc | 540 |
| aaggtcgcca gtctggttct gacgcaatag agtgcgtttt gggccagtct aaaaattcgt | 600 |
| ctggcatgac gtggctccac atcgtacccg gagcctgcct tggtaatgtg aggcaccggt | 660 |
| gccaactcca ttatggcagg catcgagcgc gcaggtgagt acatgacctt ccgtgaattg | 720 |
| ggaaggcgag cttgtgtaac gcctgcgatc gtgccagtga ggcatcgtaa actcaaaata | 780 |
| ttttgtagaa agtgtctgat gcctggtgag gctgcgtagg gcaagggcaa gcccttggca | 840 |
| gatgggtaat gggtccggac ctcacaacag caaccccgcg tcccccttag ggcccctgag | 900 |
| gctcgatggc agggccagcg agcccgcggc caaagggcgc catcccacgg tcgcccaacg | 960 |
| actccacggg tcctatacct catcttgaat ggcactaaaa actatagaat atcgggcact | 1020 |
| ggtgggcgtc tggggtacag ctggccgagc gcagtggcaa accctaggtc ccgcctcaag | 1080 |
| ggcgattccc gggtcaatga cacgcaagca agatacacatg gcgcggtccg cctcgcggct | 1140 |
| ccacacccag gccctagttt cgcaacccat aaatatcgcc ccgataccat cataagccag | 1200 |
| caaataattt tttatcagag ttccaaacct cctcagctgt gggaaaccag cccactctga | 1260 |
| acg | 1263 |

<210> SEQ ID NO 102
<211> LENGTH: 1400
<212> TYPE: DNA
<213> ORGANISM: Prototheca moriformis

<400> SEQUENCE: 102

| | |
|---|---|
| ccgagcagtt catggccaag tacaaggact agagaccgga ggtcggtagg ctgaatggag | 60 |
| ctggcgtcgt cgtgcgcgac gtgcacgcga tgcgatacta cgaccccaca aacgcatgcc | 120 |
| tcccatcttg atgcctttcc ggccatttat actatttctc atttcgctgt aacatcttga | 180 |
| ataatagaat tgccctgtgt caagtggatt ccaagaaata ttctgtccca acaaaacaac | 240 |
| ccaacctgaa acaaccctca ataccacca gccctgccca cctgcccagt cacttttcc | 300 |
| aataccatct ccctaccttc acgcgcaagc ggcacccatg cgcgaccagg ctcgaaagga | 360 |
| tttcacgact caggacgagc gagtggcggc gcgaccgcct gcctgttcgt cacgtgccgt | 420 |
| acgtcggcga ccgctagagc tttgcctggc aaccccggc ttcgtcaacc cggccagcca | 480 |

```
ggatctcgac cactctaccg cgaaatcgcc tcaagaagtc gccaaaagtg ccgtacacca      540
tgcttcgcag cgctgttcaa acttgatgcc aatcttgaca atcaggttgc tcgttggctg      600
cgtccacatc ggccgtgatt gcagcaggcg gggatcggac acggaggacg cggcgtcacg      660
ccgcgaacgc agcccgtaac tctacatcaa cgcgatatgt tgcgtaatcc cgcccggctg      720
cgcattgtga caacccattc gcgatggatg gtcggaaaat ggtgtgccaa ctgccctgag      780
ggactctctc gcgaaacggg cacgtccctg tatccgaaac tgtggcatgg ccttgtcgac      840
cacgcaagca cgtggaccct aacaccacga aaataagtaa aaaggttga catcctctac       900 gagcgaattg tttgctcgac ccttcatcgc acactgtcat tataatgcat ctagctcggc      960
gacaagttta aaaaggcag gctgcattat tccattttgc cgtggcggca tgggtgccca      1020 tttatgagg tttgggctct tgggcagcga ccgagccagg ttgagtccct ctcgcccgtc      1080
gacaacgttc caaagcccat aagtggctaa taaacaactt gatggtacct gtacactgcc      1140
agttccttct tccccggccg aggtttacac gtgatggcca tggcttcgcg tttcaggctg      1200
acttcccatt ccgactttcc agagggtccg cggacgccgg gggttggctg cgtgaggccc      1260
accccttgtt ccccgcgtcc cgacaaacac aattgcgtta cataaggggg aagccgcccc      1320
ccgttcagag tgcaaacatc tttcattata tttttcagtc gtcagcgaaa tcaagtatgt      1380
cgctgacagg catgaaggcc                                                   1400
```

<210> SEQ ID NO 103
<211> LENGTH: 3681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
gcccttttgtc atcgttggca tgcttttttgc gtatgtacca tatgttgaat gtataatacg       60
aacggttgac cgtctgagat gcgagctttg ggtcttgtca aatgcgtggc cgcacggctc      120
cctcgcaccc agccccgagg cgtcgcgcac ctggcgagga gcagacccac gccaagaaag      180
tctagtccag catgtaacaa catcaggcaa tgtgacgttt tcggttcccg atttctctgc      240 cgctcttttga cggcaggcac gggcgagcaa ccggcggcgc tcgcgtcagg cacgatggat      300
gcggcgctgc ccacctgtca atgtaccccca ccagtctgtc gatcgctaca agcaaccttg      360
tgctccacat tcccacttgc agacagtcta gtcgattttg ccaagctgga tgtgaggatt       420
ggccatatct tggaggccaa gattcacccg gatgctgatg ggtacgtacg cgagccaggc      480
aggcagctgc gttgactttc tgattggcac aaagctttgg ctactctcaa taccaaccac      540
gtgccccttc tgcacacctg cttccttctg atgaccactc gccacgcatg tcgcagtctg      600
tacgtcgagc agatcgacct cggcgaggag ggggcccctc gcaccatcgt gagtggcctg      660
gtccggcacg tgaccctgga ggaccttgtc ggccggcggg tggtggtgct ggccaacctc      720
aagcctcgga gcatgcgcgg ggtcaaatcg gctgggatgc tgctctgcgc cgccaacgcg      780
gatcacaccg cggtggagcc gctgcgggtc ccggacgccg ccgtgacggg ggagcgggtc      840
tgggcggggg acgaggcact cctgtccacg gagcctgcca cacccaatca ggtaaggaca      900
cgttattggt gcgcatggtg cgaatgcgtg gtctgacctg ctgtgggtat gtgttgtggg      960
attggaaacc gaatgagggc cgttcaggat tgagcccttg gccccaccct gctcatcctc      1020
tcacgcccgc aggtccagaa gaagaaaatc tgggaggcag tacagccgct gctgagagtg      1080
```

```
aacgcccagg ggatcgctac tgtggcagga gaggctatgg tgaccagtgc ggggccactg    1140
accgcgccca cgctggttga cgccgcgatt tcctgacgcg agcgactgat tcttgacctt    1200
tgagaagcca ccacagcacc attttcattg ttcatccttg atttcagtac gacttctcac    1260
catttcagta ctgtaggacc cccaaaatag tgtgatcacg ctcgcaaggc acctgtgtga    1320
tcacggggaa gggcgaattc ctttcttgcg ctatgacact tccagcaaaa ggtagggcgg    1380
gctgcgagac ggcttcccgg cgctgcatgc aacaccgatg atgcttcgac ccccgaagc    1440 tccttcgggg ctgcatgggc gctccgatgc cgctccaggg cgagcgctgt taaatagcc    1500 aggcccccga ttgcaaagac attatagcga gctaccaaag ccatattcaa acacctagat    1560
cactaccact tctacacagg ccactcgagc ttgtgatcgc actccgctaa ggggcgcct    1620 cttcctcttc gtttcagtca caacccgcaa acggcgcgcc atgctgctgc aggccttcct    1680
gttcctgctg gccggcttcg ccgccaagat cagcgcctcc atgacgaacg agacgtccga    1740 ccgcccctg gtgcacttca cccccaacaa gggctggatg aacgacccca acggcctgtg    1800
gtacgacgag aaggacgcca agtggcacct gtacttccag tacaacccga cgacaccgt    1860 ctggggacg cccttgttct ggggccacgc cacgtccgac gacctgacca actgggagga    1920
ccagcccatc gccatcgccc cgaagcgcaa cgactccggc gccttctccg gctccatggt    1980
ggtggactac aacaacacct ccggcttctt caacgacacc atcgaccgc gccagcgctg    2040 cgtggccatc tggacctaca acaccccgga gtccgaggag cagtacatct cctacagcct    2100
ggacggcggc tacaccttca ccgagtacca gaagaacccc gtgctggccg ccaactccac    2160
ccagttccgc gacccgaagg tcttctggta cgagccctcc cagaagtgga tcatgaccgc    2220
ggccaagtcc caggactaca agatcgagat ctactcctcc gacgacctga agtcctggaa    2280
gctggagtcc gcgttcgcca acgagggctt cctcggctac cagtacgagt gccccggcct    2340
gatcgaggtc cccaccgagc aggacccag caagtcctac tgggtgatgt tcatctccat    2400
caaccccggc gccccggccg gcggctcctt caaccagtac ttcgtcggca gcttcaacgg    2460
cacccacttc gaggccttcg acaaccagtc ccgcgtggtg gacttcggca aggactacta    2520
cgccctgcag accttcttca acaccgaccc gacctacggg agcgcccggg catcgcgtg    2580 ggcctccaac tgggagtact ccgccttcgt gcccaccaac ccctggcgct cctccatgtc    2640
cctcgtgcgc aagttctccc tcaacaccga gtaccaggcc aacccggaga cggagctgat    2700
caacctgaag gccgagccga tcctgaacat cagcaacgcc ggcccctgga gccggttcgc    2760
caccaacacc acgttgacga aggccaacag ctacaacgtc gacctgtcca acagcaccgg    2820
caccctggag ttcgagctgg tgtacgccgt caacaccacc cagacgatct ccaagtccgt    2880
gttcgcggac ctctccctct ggttcaaggg cctggaggac cccgaggagt acctccgcat    2940
gggcttcgag gtgtccgcgt cctccttctt cctggaccgc gggaacagca aggtgaagtt    3000
cgtgaaggag aaccctact tcaccaaccg catgagcgtg aacaaccagc ccttcaagag    3060
cgagaacgac ctgtcctact acaaggtgta cggcttgctg gaccagaaca tcctggagct    3120
gtacttcaac gacggcgacg tcgtgtccac caacacctac ttcatgacca ccgggaacgc    3180
cctgggctcc gtgaacatga cgacgggggt ggacaacctg ttctacatcg acaagttcca    3240
ggtgcgcgag gtcaagtgat taattaactc gaggcagcag cagctcggat agtatcgaca    3300
cactctggac gctggtcgtg tgatggactg ttgccgccac acttgctgcc ttgacctgtg    3360
aatatccctg ccgcttttat caaacagcct cagtgtgttt gatcttgtgt gtacgcgctt    3420
```

```
ttgcgagttg ctagctgctt gtgctatttg cgaataccac ccccagcatc cccttccctc    3480
gtttcatatc gcttgcatcc caaccgcaac ttatctacgc tgtcctgcta tccctcagcg    3540
ctgctcctgc tcctgctcac tgcccctcgc acagccttgg tttgggctcc gcctgtattc    3600
tcctggtact gcaacctgta aaccagcact gcaatgctga tgcacgggaa gtagtgggat    3660
gggaacacaa atggaaagct t                                              3681

<210> SEQ ID NO 104
<211> LENGTH: 3850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
tttggccccg ctttccagct ccggatctgc tggcgtccgc cgcgagacgt gacatcgcac      60
gtcgccggga gcgccagctt gatcacttgg caggggccg tgctctacaa ataccaggcc     120
ccgcggcggt cagttcgcac atccaatacc tgccgagcca tcttgcctac acttttatc     180 gactcctcta ctctgttcgc gagagcgctc ggtccaggct tggaattcgc cgaattcagc    240
tcgatcagtc gcttctgcaa ctgatctcgg ccgttcgcag actgcctttt ctcagcttgt    300
caggtagcga gttgttgttt tatatttatt cgatttcatc tgtgttgcat gtcttgttcg    360
tgctgtgcgt tctttctggg ccgcgctgtc gggtcgcatg ggctagctgt actcatgtta    420
gtcatgccgg tccgaccttg ttcgaggaag gccccacact gagcgtgccc tctttctaca    480
ccccttgtgc agaaattaga tagaaagcag aattcctttc ttgcgctatg acacttccag    540
caaaaggtag ggcgggctgc gagacggctt cccggcgctg catgcaacac cgatgatgct    600 tcgaccccc gaagctcctt cggggctgca tgggcgctcc gatgccgctc cagggcgagc    660
gctgtttaaa tagccaggcc cccgattgca aagacattat agcgagctac caaagccata    720
ttcaaacacc tagatcacta ccacttctac acaggccact cgagcttgtg atcgcactcc    780
gctaaggggg cgcctcttcc tcttcgtttc agtcacaacc cgcaaacggc gcgccatgct    840
gctgcaggcc ttcctgttcc tgctggccgg cttcgccgcc aagatcagcg cctccatgac    900
gaacgagacg tccgaccgcc ccctggtgca cttcacccc aacaagggct ggatgaacga    960
ccccaacggc ctgtggtacg acgagaagga cgccaagtgg cacctgtact ccagtacaa    1020 cccgaacgac accgtctggg ggacgccctt gttctggggc cacgccacgt ccgacgacct    1080
gaccaactgg gaggaccagc ccatcgccat cgccccgaag cgcaacgact ccggcgcctt    1140
ctccggctcc atggtggtgg actacaacaa cacctccggc ttcttcaacg acaccatcga    1200
cccgcgccag cgctgcgtgg ccatctggac ctacaacacc ccggagtccg aggagcagta    1260
catctcctac agcctggacg gcggctacac cttcaccgag taccagaaga accccgtgct    1320
ggccgccaac tccacccagt tccgcgaccc gaaggtcttc tggtacgagc cctcccagaa    1380
gtggatcatg accgcggcca gtcccagga ctacaagatc gagatctact cctccgacga    1440
cctgaagtcc tggaagctgg agtccgcgtt cgccaacgag ggcttcctcg gctaccagta    1500
cgagtgcccc ggcctgatcg aggtcccac cgagcaggac cccagcaagt cctactgggt    1560
gatgttcatc tccatcaacc ccggcgcccc ggccggcggc tccttcaacc agtacttcgt    1620
cggcagcttc aacggcaccc acttcgaggc cttcgacaac cagtcccgcg tggtggactt    1680
cggcaaggac tactacgccc tgcagacctt cttcaacacc gacccgacct acgggagcgc    1740
```

```
cctgggcatc gcgtgggcct ccaactggga gtactccgcc ttcgtgccca ccaacccctg    1800
gcgctcctcc atgtccctcg tgcgcaagtt ctccctcaac accgagtacc aggccaaccc    1860
ggagacggag ctgatcaacc tgaaggccga gccgatcctg aacatcagca cgccggccc     1920 ctggagccgg ttcgccacca acaccacgtt gacgaaggcc aacagctaca acgtcgacct    1980
gtccaacagc accggcaccc tggagttcga gctggtgtac gccgtcaaca ccacccagac    2040
gatctccaag tccgtgttcg cggacctctc cctctggttc aagggcctgg aggaccccga    2100
ggagtacctc cgcatgggct tcgaggtgtc cgcgtcctcc ttcttcctgg accgcgggaa    2160
cagcaaggtg aagttcgtga aggagaaccc ctacttcacc aaccgcatga gcgtgaacaa    2220
ccagcccttc aagagcgaga cgacctgtc ctactacaag gtgtacggct tgctggacca     2280
gaacatcctg gagctgtact caacgacgg cgacgtcgtg tccaccaaca cctacttcat     2340
gaccaccggg aacgccctgg gctccgtgaa catgacgacg ggggtggaca acctgttcta    2400
catcgacaag ttccaggtgc gcgaggtcaa gtgattaatt aactcgaggc agcagcagct    2460
cggatagtat cgacacactc tggacgctgg tcgtgtgatg gactgttgcc gccacacttg    2520
ctgccttgac ctgtgaatat ccctgccgct tttatcaaac agcctcagtg tgtttgatct    2580
tgtgtgtacg cgcttttgcg agttgctagc tgcttgtgct atttgcgaat ccaccccca    2640 gcatcccctt ccctcgtttc atatcgcttg catcccaacc gcaacttatc tacgctgtcc    2700
tgctatccct cagcgctgct cctgctcctg ctcactgccc ctcgcacagc cttggtttgg    2760
gctccgcctg tattctcctg gtactgcaac ctgtaaacca gcactgcaat gctgatgcac    2820
gggaagtagt gggatgggaa cacaaatgga ccgacgcc cccggcccag gtccagttct      2880
cctgggtctt ccagaggccc gtcgccatgt aaagtggcag agattggcgc ctgattcgat    2940
ttggatccaa ggatctccaa tcggtgatgg ggactgagtg cccaactacc acccttgcac    3000
tatcgtcctc gcactattta ttcccacctt ctgctcgccc tgccgggcga ttgcgggcgt    3060
ttctgccctt gacgtatcaa tttcgcccct gctggcgcga ggattcttca ttctaataag    3120
aactcactcc cgccagctct gtacttttcc tgcggggccc ctgcatggct tgttcccaat    3180
gcttgctcga tcgacggcgc ccattgccca cggcgctgcc gcatccatgt gaagaaacac    3240
ggaagagtgc gaagactgga agtgaattaa gagtataaga agaggtacca agggattctc    3300
aggtgctctt aggaacggct tttccttcgc caagagaaac tgctactgct cgtgtcgcca    3360
cggtggtcaa gccgcccat ctgcgatcca ccaggcccat ccgcggactc gcgatcagcc     3420
tgctggatcc ggactgccga cctgaccgct cgcatccacc attacaaccc tccaattgga    3480
caccactccc acgtcctaaa gttcaccatg caagctgatc gatcgcattc gccgatgcac    3540
tcgcctgcca cagaggtgtg cgcttcggac tagcgtgcag gcgccccgag gccaccagca    3600
tgcaccgatg gaagcgggca cggccgctgc tccaggtcgc tggctcgctc agacccatag    3660
caacctccgc tgcgtcccta aatgtcacac agagcgtctt tgatgggtac ggatgggaga    3720
gaatctgatt gggcattgct ggtgcagtgc aggaagatgg caagtgcaca gtcagtcatg    3780
ctgtacaaac tggtgcctcg tagtattgac tcgtatagtg catagtatca tgcatggtcg    3840
ttacttgcaa                                                          3850

<210> SEQ ID NO 105
<211> LENGTH: 3108
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 105

| | | | | | |
|---|---|---|---|---|---|
| tttggccccg | ctttccagct | ccggatctgc | tggcgtccgc | cgcgagacgt | gacatcgcac | 60 |
| gtcgccggga | gcgccagctt | gatcacttgg | caggggggccg | tgctctacaa | ataccaggcc | 120 |
| ccgcggcggt | cagttcgcac | atccaatacc | tgccgagcca | tcttgcctac | acttttatc | 180 |
| gactcctcta | ctctgttcgc | gagagcgctc | ggtccaggct | tggaattcgc | cgaattcagc | 240 |
| tcgatcagtc | gcttctgcaa | ctgatctcgg | ccgttcgcag | actgcttttt | ctcagcttgt | 300 |
| caggtagcga | gttgttgttt | tatatttatt | cgatttcatc | tgtgttgcat | gtcttgttcg | 360 |
| tgctgtgcgt | tctttctggg | ccgcgctgtc | gggtcgcatg | ggctagctgt | actcatgtta | 420 |
| gtcatgccgg | tccgaccttg | ttcgaggaag | gccccacact | gagcgtgccc | tctttctaca | 480 |
| ccccttgtgc | agaaattaga | tagaaagcaa | tgctgctgca | ggccttcctg | ttcctgctgg | 540 |
| ccggcttcgc | cgccaagatc | agcgcctcca | tgacgaacga | gacgtccgac | cgcccctgg | 600 |
| tgcacttcac | ccccaacaag | ggctggatga | acgaccccaa | cggcctgtgg | tacgacgaga | 660 |
| aggacgccaa | gtggcacctg | tacttccagt | acaacccgaa | cgacaccgtc | tggggacgc | 720 |
| ccttgttctg | gggccacgcc | acgtccgacg | acctgaccaa | ctgggaggac | cagcccatcg | 780 |
| ccatcgcccc | gaagcgcaac | gactccggcg | ccttctccgg | ctccatggtg | gtggactaca | 840 |
| acaacacctc | cggcttcttc | aacgaccacca | tcgacccgcg | ccagcgctgc | gtggccatct | 900 |
| ggacctacaa | caccccggag | tccgaggagc | agtacatctc | ctacagcctg | acggcggct | 960 |
| acaccttcac | cgagtaccag | aagaaccccg | tgctggccgc | caactccacc | cagttccgcg | 1020 |
| acccgaaggt | cttctggtac | gagccctccc | agaagtggat | catgaccgcg | gccaagtccc | 1080 |
| aggactacaa | gatcgagatc | tactcctccg | acgacctgaa | gtcctggaag | ctggagtccg | 1140 |
| cgttcgccaa | cgagggcttc | ctcggctacc | agtacgagtg | ccccggcctg | atcgaggtcc | 1200 |
| ccaccgagca | ggaccccagc | aagtcctact | gggtgatgtt | catctccatc | aaccccggcg | 1260 |
| ccccggccgg | cggctccttc | aaccagtact | tcgtcggcag | cttcaacggc | acccacttcg | 1320 |
| aggccttcga | caaccagtcc | cgcgtggtgg | acttcggcaa | ggactactac | gccctgcaga | 1380 |
| ccttcttcaa | caccgacccg | acctacggga | gcgccctggg | catcgcgtgg | gcctccaact | 1440 |
| gggagtactc | cgccttcgtg | cccaccaacc | cctggcgctc | ctccatgtcc | ctcgtgcgca | 1500 |
| agttctcccct | caacaccgag | taccaggcca | acccggagac | ggagctgatc | aacctgaagg | 1560 |
| ccgagccgat | cctgaacatc | agcaacgccg | gccctggag | ccggttcgcc | accaacacca | 1620 |
| cgttgacgaa | ggccaacagc | tacaacgtcg | acctgtccaa | cagcaccggc | accctggagt | 1680 |
| tcgagctggt | gtacgccgtc | aacaccaccc | agacgatctc | caagtccgtg | ttcgcggacc | 1740 |
| tctcccctctg | gttcaagggc | ctggaggacc | ccgaggagta | cctccgcatg | ggcttcgagg | 1800 |
| tgtccgcgtc | ctccttcttc | ctggaccgcg | ggaacagcaa | ggtgaagttc | gtgaaggaga | 1860 |
| accccctactt | caccaaccgc | atgagcgtga | acaaccagcc | cttcaagagc | gagaacgacc | 1920 |
| tgtcctacta | caaggtgtac | ggcttgctgg | accagaacat | cctggagctg | tacttcaacg | 1980 |
| acggcgacgt | cgtgtccacc | aacacctact | tcatgaccac | cggaacgcc | ctgggctccg | 2040 |
| tgaacatgac | gacgggggtg | gacaacctgt | tctacatcga | caagttccag | gtgcgcgagg | 2100 |
| tcaagtgacc | gacacgcccc | cggcccaggt | ccagttctcc | tgggtcttcc | agaggcccgt | 2160 |
| cgccatgtaa | agtggcagag | attggcgcct | gattcgattt | ggatccaagg | atctccaatc | 2220 |
| ggtgatgggg | actgagtgcc | caactaccac | ccttgcacta | tcgtcctcgc | actatttatt | 2280 |

```
cccaccttct gctcgccctg ccgggcgatt gcgggcgttt ctgcccttga cgtatcaatt    2340
tcgcccctgc tggcgcgagg attcttcatt ctaataagaa ctcactcccg ccagctctgt    2400
acttttcctg cggggcccct gcatggcttg ttcccaatgc ttgctcgatc gacggcgccc    2460 attgccacg gcgctgccgc atccatgtga agaaacacgg aagagtgcga agactggaag    2520
tgaattaaga gtataagaag aggtaccaag ggattctcag gtgctcttag aacggcttt    2580 tccttcgcca agagaaactg ctactgctcg tgtcgccacg tggtcaagc cgccccatct    2640 gcgatccacc aggcccatcc gcggactcgc gatcagcctg ctggatccgg actgccgacc    2700
tgaccgctcg catccaccat acaaccctc caattggaca ccactccac gtcctaaagt    2760 tcaccatgca agctgatcga tcgcattcgc cgatgcactc gcctgccaca gaggtgtgcg    2820
cttcggacta gcgtgcaggc gccccgaggc caccagcatg caccgatgga agcgggcacg    2880
gccgctgctc caggtcgctg gctcgctcag acccatagca acctccgctg cgtccctaaa    2940
tgtcacacag agcgtctttg atgggtacgg atgggagaga atctgattgg gcattgctgg    3000
tgcagtgcag gaagatggca agtgcacagt cagtcatgct gtacaaactg gtgcctcgta    3060
gtattgactc gtatagtgca tagtatcatg catggtcgtt acttgcaa    3108

<210> SEQ ID NO 106
<211> LENGTH: 559
<212> TYPE: DNA
<213> ORGANISM: Chlorella luteoviridis

<400> SEQUENCE: 106
tgttgaagaa tgagccggcg acttatagga agtggcgtgg ttaaggaatt ttccgaagcc      60
caagcgaaag caagttttaa aaatagcgat atttgtcact ttttatggac ccgaaccccgg    120 gtgatctaac cgtgaccagg atgaagcttg ggtaacacca agtgaaggtc cgaactcttc    180 gatcttttaaa aatcgtgaga tgagttgcgg ttagtaggtg aaatgccaat cgaactcgga    240
gctagctggt tctccccgaa atgtgttgag gcgcagcgat gaatgacaaa acaaatagta    300
cggtgtaggg gtaaagcact gtttcggtgc gggctgcgaa agcggtacca atcgtggca    360 aactcagaat actacgcttg tataccattc atcagtgaga ctgtgggga taagctccat    420 agtcaagagg gaaacagccc agatcaccag ttaaggcccc aaaatgacag ctaagtggca    480
aaggaggtga aagtgcagaa acaaccagga ggtttgccca aagcagcca tcctttaaag    540 agtgcgtaat agctcactg                                                 559

<210> SEQ ID NO 107
<211> LENGTH: 1841
<212> TYPE: DNA
<213> ORGANISM: Cuphea palustris

<400> SEQUENCE: 107
gaattccttt cttgcgctat gacacttcca gcaaaaggta gggcgggctg cgagacggct     60
tcccggcgct gcatgcaaca ccgatgatgc ttcgaccccc cgaagctcct tcggggctgc    120
atgggcgctc cgatgccgct ccagggcgag cgctgtttaa atagccaggc ccccgattgc    180
aaagacatta tagcgagcta ccaaagccat attcaaacac ctagatcact accacttcta    240
cacaggccac tcgagcttgt gatcgcactc cgctaagggg gcgcctcttc ctcttcgttt    300
cagtcacaac ccgcaaacac tagtatggcc accgcatcca ctttctcggc gttcaatgcc    360
cgctgcggcg acctgcgtcg ctcggcgggc tccgggcccc ggcgcccagc gaggcccctc    420
```

```
cccgtgcgcg ggcgcgccag catgctgctg tcggcggtga ccacggtctt cggcgtggcc      480
gagaagcagt ggcccatgct ggaccgcaag tccaagcgcc ccgacatgct ggtcgagccc      540
ctgggcgtgg accgcatcgt ctacgacggc gtgagcttcc gccagtcgtt ctccatccgc      600
agctacgaga tcggcgccga ccgcaccgcc tcgatcgaga cgctgatgaa catgttccag      660
gagacctccc tgaaccactg caagatcatc ggcctgctga cgacggcttc ggccgcacg       720
cccgagatgt gcaagcgcga cctgatctgg gtcgtgacca agatgcagat cgaggtgaac      780
cgctacccca cgtggggcga caccatcgag gtcaacacgt gggtgagcgc ctcgggcaag      840
cacggcatgg gccgcgactg gctgatctcc gactgccaca ccggcgagat cctgatccgc      900
gcgacgagcg tctgggcgat gatgaaccag aagacccgcc gcctgtcgaa gatcccctac      960
gaggtgcgcc aggagatcga gcccagttc gtcgactccg cccccgtgat cgtggacgac      1020
cgcaagttcc acaagctgga cctgaagacg ggcgacagca tctgcaacgg cctgaccccc     1080
cgctggacgg acctgacgt gaaccagcac gtcaacaacg tgaagtacat cggctggatc      1140
ctgcagtcgg tccccaccga ggtgttcgag acgcaggagc tgtgcggcct gaccctggag     1200
taccgccgcg agtgcggccg cgactccgtg ctggagagcg tcacggccat ggaccctcg      1260
aaggagggcg accgctccct gtaccagcac ctgctgcgcc tggaggacgg cgcggacatc     1320
gtgaagggcc gcaccgagtg gcgccccaag aacgccggcg ccaagggcgc catcctgacg     1380
ggcaagacca gcaacggcaa ctcgatctcc tgactcgagt taattaactc gaggcagcag     1440
cagctcggat agtatcgaca cactctggac gctggtcgtg tgatggactg ttgccgccac     1500
acttgctgcc ttgacctgtg aatatccctg ccgcttttat caaacagcct cagtgtgttt     1560
gatcttgtgt gtacgcgctt ttgcgagttg ctagctgctt gtgctatttg cgaataccac     1620
ccccagcatc cccttccctc gtttcatatc gcttgcatcc caaccgcaac ttatctacgc     1680
tgtcctgcta tccctcagcg ctgctcctgc tcctgctcac tgcccctcgc acagccttgg     1740
tttgggctcc gcctgtattc tcctggtact gcaacctgta aaccagcact gcaatgctga     1800
tgcacgggaa gtagtgggat gggaacacaa atggaaagct t                         1841
```

<210> SEQ ID NO 108
<211> LENGTH: 1010
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
ggcgcgccca gctgcccgac tggagcatgc tgctggccgc gatcaccacc ctgttcctgg       60
cggccgagaa gcagtggatg atgctggact ggaagcccaa cgccccgac atgctggtgg      120
accccttcgg cctgggccgc ttcgtgcagg acggcctggt gttccgcaac aacttcagca     180
tccgcagcta cgagatcggc gcggaccgca ccgccagcat cgagaccctg atgaaccacc     240
tgcaggagac cgccctgaac cacgtgaaga gcgtgggcct gctggaggac ggcctgggca     300
gcacccgcga tgagcctg cgcaacctga tctgggtggt gaccaagatg caggtggcgg       360
tggaccgcta cccacctgg ggcgacgagg tgcaggtgag cagctgggcg accgccatcg      420
gcaagaacgg catgccgcc gagtggatcg tgaccgactt ccgcaccggc gagaccctgc      480
tgcgcgccac cagcgtgtgg gtgatgatga acaagctgac ccgccgcatc agcaagatcc     540
ccgaggaggt gtggcacgag atcggcccca gcttcatcga cgcgcccccc ctgcccaccg     600
```

```
tggaggacga cggccgcaag ctgacccgct tcgacgagag cagcgccgac ttcatccgca    660
agggcctgac cccccgctgg agcgacctgg acatcaacca gcacgtgaac aacgtgaagt    720
acatcggctg gctgctggag agcgcgcccc ccgagatcca cgagagccac gagatcgcca    780
gcctgaccct ggagtaccgc cgcgagtgcg ccgcgacga cgtgctgaac agcgccacca    840
aggtgagcga cagcagccag ctgggcaaga gcgccgtgga gtgcaaccac ctggtgcgcc    900
tgcagaacgg cggcgagatc gtgaagggcc gcaccgtgtg cgcccccaag cgcccctgt     960 acaacgacgg cgccgtggtg gacgtgcccg ccaagaccag ctgactcgag             1010

<210> SEQ ID NO 109
<211> LENGTH: 5472
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
ggtacccttt cttgcgctat gacacttcca gcaaaaggta gggcgggctg cgagacggct     60
tcccggcgct gcatgcaaca ccgatgatgc ttcgaccccc cgaagctcct tcggggctgc    120
atgggcgctc cgatgccgct ccagggcgag cgctgtttaa atagccaggc ccccgattgc    180
aaagacatta tagcgagcta ccaaagccat attcaaacac ctagatcact accacttcta    240
cacaggccac tcgagcttgt gatcgcactc cgctaagggg cgcctcttc ctcttcgttt     300 cagtcacaac ccgcaaactc tagaatatca atgctgctgc aggccttcct gttcctgctg    360
gccggcttcg ccgccaagat cagcgcctcc atgacgaacg agacgtccga ccgccccctg    420
gtgcacttca cccccaacaa gggctggatg aacgaccccca acggcctgtg gtacgacgag    480
aaggacgcca agtggcacct gtacttccag tacaacccga cgacaccgt ctggggggacg    540 cccttgttct ggggccacgc cacgtccgac gacctgacca ctgggaagga ccagcccatc    600
gccatcgccc gaagcgcaa cgactccggc gccttctccg gctccatggt ggtggactac    660
aacaacacct ccggcttctt caacgacacc atcgacccgc gccagcgctg cgtggccatc    720
tggacctaca acacccccgga gtccgaggag cagtacatct cctacagcct ggacggcggc    780 tacacctica ccgagtacca gaagaacccc gtgctggccg ccaactccac ccagttccgc    840
gacccgaagg tcttctggta cgagccctcc cagaagtgga tcatgaccgc ggccaagtcc    900
caggactaca gatcgagat ctactcctcc gacgacctga gtcctggaa gctggagtcc    960 gcgttcgcca acgagggctt cctcggctac cagtacgagt gccccggcct gatcgaggtc    1020
cccaccgagc aggaccccag caagtcctac tgggtgatgt tcatctccat caaccccggc   1080
gccccggccc gcggctcctt caaccagtac ttcgtcggca gcttcaacgg caccactc    1140 gaggccttcg acaaccagtc ccgcgtggtg gacttcggca aggactacta cgccctgcag   1200
accttcttca acaccgaccc gacctacggg agcgccctgg catcgcgtg ggcctccaac   1260 tgggagtact ccgccttcgt gcccaccaac ccctggcgct cctccatgtc cctcgtgcgc   1320
aagttctccc tcaacaccga gtaccaggcc aacccggaga cggagctgat caacctgaag   1380
gccgagccga tcctgaacat cagcaacgcc ggccctga ccggttcgc caccaacacc   1440 acgttgacga aggccaacag ctacaacgtc gacctgtcca acagcaccgg caccctggag   1500
ttcgagctgg tgtacgccgt caacaccacc agacgatct ccaagtccgt gttcgcggac   1560
ctctccctct ggttcaaggg cctggaggac cccgaggagt acctccgcat gggcttcgag   1620
```

```
gtgtccgcgt cctccttctt cctggaccgc gggaacagca aggtgaagtt cgtgaaggag    1680 aaccccctact tcaccaaccg catgagcgtg aacaaccagc ccttcaagag cgagaacgac    1740
ctgtcctact acaaggtgta cggcttgctg gaccagaaca tcctggagct gtacttcaac    1800
gacggcgacg tcgtgtccac caacacctac ttcatgacca ccgggaacgc cctgggctcc    1860
gtgaacatga cgacggggt ggacaacctg ttctacatcg acaagttcca ggtgcgcgag    1920
gtcaagtgac aattggcagc agcagctcgg atagtatcga cacactctgg acgctggtcg    1980
tgtgatggac tgttgccgcc acacttgctg ccttgacctg tgaatatccc tgccgctttt    2040
atcaaacagc ctcagtgtgt tgatcttgt gtgtacgcgc ttttgcgagt gctagctgc     2100 ttgtgctatt tgcgaatacc accccagca tcccttccc tcgtttcata tcgcttgcat     2160
cccaaccgca acttatctac gctgtcctgc tatccctcag cgctgctcct gctcctgctc    2220
actgcccctc gcacagcctt ggtttgggct ccgcctgtat tctcctggta ctgcaacctg    2280
taaaccagca ctgcaatgct gatgcacggg aagtagtggg atgggaacac aaatggagga    2340
tcccgcgtct cgaacagagc gcgcagagga acgctgaagg tctcgcctct gtcgcacctc    2400
agcgcggcat acaccacaat aaccacctga cgaatgcgct tggttcttcg tccattagcg    2460
aagcgtccgg ttcacacacg tgccacgttg gcgaggtggc aggtgacaat gatcggtgga    2520
gctgatggtc gaaacgttca cagcctaggg atatcgaatt ccgcctgcaa cgcaagggca    2580
gccacagccg ctcccacccg ccgctgaacc gacacgtgct tgggcgcctg ccgcctgcct    2640
gccgcatgct tgtgctggtg aggctgggca tgctgccat gctgattgag cttggttca     2700 tcgggtggaa gcttatgtgt gtgctgggct tgcatgccgg gcaatgcgca tggtggcaag    2760
agggcggcag cacttgctgg agctgccgcg gtgcctccag gtggttcaat cgcggcagcc    2820 agagggatt cagatgatcg cgcgtacagg ttgagcagca gtgtcagcaa aggtagcagt    2880
ttgccagaat gatcggttca gctgttaatc aatgccagca agagaagggg tcaagtgcaa    2940
acacgggcat gccacagcac gggcaccggg gagtggaatg gcaccaccaa gtgtgtgcga    3000
gccagcatcg ccgcctggct gttcagcta caacggcagg agtcatccaa cgtaaccatg    3060
agctgatcaa cactgcaatc atcgggcggg cgtgatgcaa gcatgcctgg cgaagacaca    3120
tggtgtgcgg atgctgccgg ctgctgcctg ctgcgcacgc cgttgagttg gcagcaggct    3180
cagccatgca ctgatggca gctgggctgc cactgcaatg tggtggatag gatgcaagtg    3240
gagcgaatac caaaccctct ggctgcttgc tgggttgcat ggcatcgcac catcagcagg    3300
agcgcatgcg aagggactgg ccccatgcac gccatgccaa accggagcgc accgagtgtc    3360
cacactgtca ccaggcccgc aagctttgca gaaccatgct catggacgca tgtagcgctg    3420 acgtccttg acgcgctcc tctcgggtgt gggaaacgca atgcagcaca ggcagcagag    3480
gcggcggcag cagagcggcg gcagcagcgg cgggggccac ccttcttgcg ggtcgcgcc    3540 ccagccagcg gtgatgcgct gatcccaaac gagttcacat tcatttgcat gcctggagaa    3600
gcgaggctgg ggccttttggg ctggtgcagc ccgcaatgga atgcgggacc gccaggctag    3660
cagcaaaggc gcctccccta ctccgcatcg atgttccata gtgcattgga ctgcatttgg    3720
gtggggcggc cggctgtttc tttcgtgttg caaaacgcgc cagctcagca acctgtcccg    3780
tgggtccccc gtgccgatga aatcgtgtgc acgccgatca gctgattgcc cggctcgcga    3840
agtaggcgcc ctcctttctg ctcgccctct ctccgtcccg ccactagtat ggccaccgca    3900
tccactttct cggcgttcaa tgcccgctgc ggcgacctgc gtcgctcggc gggctccggg    3960
ccccggcgcc cagcgaggcc cctccccgtg cgcgggcgcg cccagctgcc cgactggagc    4020
```

```
cgcctgctga ccgccatcac caccgtgttc gtgaagtcca agcgccccga catgcacgac    4080
cgcaagtcca agcgccccga catgctggtg gacagcttcg gcctggagtc caccgtgcag    4140
gacggcctgg tgttccgcca gtccttctcc atccgctcct acgagatcgg caccgaccgc    4200
accgccagca tcgagaccct gatgaaccac ctgcaggaga cctccctgaa ccactgcaag    4260
agcaccggca tcctgctgga cggcttcggc cgcaccctgg agatgtgcaa gcgcgacctg    4320
atctgggtgg tgatcaagat gcagatcaag gtgaaccgct accccgcctg ggcgacacc    4380
gtggagatca caccccgctt cagccgcctg gcaagatcg gcatgggccg cgactggctg    4440
atctccgact gcaacaccgg cgagatcctg gtgcgcgcca ccagcgccta cgccatgatg    4500
aaccagaaga cccgccgcct gtccaagctg ccctacgagg tgcaccagga gatcgtgccc    4560
ctgttcgtgg acagccccgt gatcgaggac tccgacctga aggtgcacaa gttcaaggtg    4620
aagaccggcg acagcatcca agggcctg accccggct ggaacgacct ggacgtgaac    4680
cagcacgtgt ccaacgtgaa gtacatcggc tggatcctgg agagcatgcc caccgaggtg    4740
ctggagaccc aggagctgtg ctccctggcc ctggagtacc gccgcgagtg cggccgcgac    4800
tccgtgctgg agagcgtgac cgccatggac cccagcaagg tgggcgtgcg ctcccagtac    4860
cagcacctgc tgcgcctgga ggacggcacc gccatcgtga acggcgccac cgagtggcgc    4920
cccaagaacg ccgcgccaa cggcgccatc tccaccggca agaccagcaa cggcaactcc    4980
gtgtccatgg actacaagga ccacgacggc gactacaagg accacgacat cgactacaag    5040
gacgacgacg acaagtgact cgaggcagca gcagctcgga tagtatcgac acactctgga    5100
cgctggtcgt gtgatggact gttgccgcca cacttgctgc cttgacctgt gaatatccct    5160
gccgcttta tcaaacagcc tcagtgtgtt tgatcttgtg tgtacgcgct tttgcgagtt    5220
gctagctgct tgtgctattt gcgaatacca ccccagcat ccccttccct cgtttcatat    5280
cgcttgcatc ccaaccgcaa cttatctacg ctgtcctgct atccctcagc gctgctcctg    5340
ctcctgctca ctgcccctcg cacagccttg gtttgggctc cgcctgtatt ctcctggtac    5400
tgcaacctgt aaaccagcac tgcaatgctg atgcacggga agtagtggga tgggaacaca    5460
aatggaaagc tt                                                       5472
```

<210> SEQ ID NO 110
<211> LENGTH: 5451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
ggtacccttt cttgcgctat gacacttcca gcaaaaggta gggcgggctg cgagacggct     60
tcccggcgct gcatgcaaca ccgatgatgc ttcgaccccc cgaagctcct tcggggctgc    120
atgggcgctc cgatgccgct ccagggcgag cgctgtttaa atagccaggc ccccgattgc    180
aaagacatta tagcgagcta ccaaagccat attcaaacac ctagatcact accacttcta    240
cacaggccac tcgagcttgt gatcgcactc cgctaagggg gcgcctcttc ctcttcgttt    300
cagtcacaac ccgcaaactc tagaatatca atgctgctgc aggccttcct gttcctgctg    360
gccggcttcg ccgccaagat cagcgcctcc atgacgaacg agacgtccga ccgccccctg    420
gtgcacttca cccccaacaa gggctggatg aacgaccca acggcctgtg gtacgacgag    480
aaggacgcca agtggcacct gtacttccag tacaacccga acgacaccgt ctggggacg    540
```

```
cccttgttct ggggccacgc cacgtccgac gacctgacca actgggagga ccagcccatc    600
gccatcgccc cgaagcgcaa cgactccggc gccttctccg gctccatggt ggtggactac    660
aacaacacct ccggcttctt caacgacacc atcgacccgc gccagcgctg cgtggccatc    720
tggacctaca cacccccgga gtccgaggag cagtacatct cctacagcct ggacggcggc    780
tacaccttca ccgagtacca gaagaacccc gtgctggccg ccaactccac ccagttccgc    840
gacccgaagg tcttctggta cgagccctcc cagaagtgga tcatgaccgc ggccaagtcc    900
caggactaca agatcgagat ctactcctcc gacgacctga agtcctggaa gctggagtcc    960
gcgttcgcca acgagggctt cctcggctac cagtacgagt gccccggcct gatcgaggtc   1020
cccaccgagc aggaccccag caagtcctac tgggtgatgt tcatctccat caaccccggc   1080
gccccggccg gcggctcctt caaccagtac ttcgtcggca gcttcaacgg cacccacttc   1140
gaggccttcg acaaccagtc ccgcgtggtg gacttcggca aggactacta cgccctgcag   1200
accttcttca acaccgaccc gacctacggg agcgccctgg gcatcgcgtg ggcctccaac   1260
tgggagtact ccgccttcgt gcccaccaac ccctggcgct cctccatgtc cctcgtgcgc   1320
aagttctccc tcaacaccga gtaccaggcc aacccggaga cggagctgat caacctgaag   1380
gccgagccga tcctgaacat cagcaacgcc ggcccctgga gccggttcgc caccaacacc   1440
acgttgacga aggccaacag ctacaacgtc gacctgtcca acagcaccgg caccctggag   1500
ttcgagctgg tgtacgccgt caacaccacc cagacgatct ccaagtccgt gttcgcggac   1560
ctctcccctct ggttcaaggg cctggaggac cccgaggagt acctccgcat gggcttcgag   1620
gtgtccgcgt cctccttctt cctggaccgc gggaacagca aggtgaagtt cgtgaaggag   1680
aaccccctact tcaccaaccg catgagcgtg aacaaccagc ccttcaagag cgagaacgac   1740
ctgtcctact acaaggtgta cggcttgctg gaccagaaca tcctggagct gtacttcaac   1800
gacggcgacg tcgtgtccac caacacctac ttcatgacca ccgggaacgc cctgggctcc   1860
gtgaacatga cgacggggggt ggacaacctg ttctacatcg acaagttcca ggtgcgcgag   1920
gtcaagtgac aattggcagc agcagctcgg atagtatcga cacactctgg acgctggtcg   1980
tgtgatggac tgttgccgcc acacttgctg ccttgacctg tgaatatccc tgccgctttt   2040
atcaaacagc ctcagtgtgt ttgatcttgt gtgtacgcgc ttttgcgagt gctagctgc    2100
ttgtgctatt tgcgaatacc accccagca tcccccttccc tcgtttcata tcgcttgcat   2160
cccaaccgca acttatctac gctgtcctgc tatccctcag cgctgctcct gctcctgctc   2220
actgcccctc gcacagcctt ggtttgggct ccgcctgtat tctcctggta ctgcaacctg   2280
taaaccagca ctgcaatgct gatgcacggg aagtagtggg atgggaacac aaatggagga   2340
tcccgcgtct cgaacagagc gcgcagagga acgctgaagg tctcgcctct gtcgcacctc   2400
agcgcggcat acaccacaat aaccacctga cgaatgcgct tggttcttcg tccattagcg   2460
aagcgtccgg ttcacacacg tgccacgttg gcgaggtggc aggtgacaat gatcggtgga   2520
gctgatggtc gaaacgttca cagcctaggg atatcgaatt ccgcctgcaa cgcaagggca   2580
gccacagccg ctcccacccg ccgctgaacc gacacgtgct tgggcgcctg ccgcctgcct   2640
gccgcatgct tgtgctggtg aggctgggca gtgctgccat gctgattgag gcttggttca   2700
tcgggtggaa gcttatgtgt gtgctgggct tgcatgccgg gcaatgcgca tggtggcaag   2760
agggcggcag cacttgctgg agctgccgcg gtgcctccag gtggttcaat cgcggcagcc   2820
agagggattt cagatgatcg cgcgtacagg ttgagcagca gtgtcagcaa aggtagcagt   2880
```

```
ttgccagaat gatcggttca gctgttaatc aatgccagca agagaagggg tcaagtgcaa    2940
acacgggcat gccacagcac gggcaccggg gagtggaatg gcaccaccaa gtgtgtgcga    3000
gccagcatcg ccgcctggct gtttcagcta aacggcagg agtcatccaa cgtaaccatg     3060
agctgatcaa cactgcaatc atcgggcggg cgtgatgcaa gcatgcctgg cgaagacaca    3120
tggtgtgcgg atgctgccgg ctgctgcctg ctgcgcacgc cgttgagttg gcagcaggct    3180
cagccatgca ctggatggca gctgggctgc cactgcaatg tggtggatag gatgcaagtg    3240
gagcgaatac caaaccctct ggctgcttgc tgggttgcat ggcatcgcac catcagcagg    3300
agcgcatgcg aagggactgg ccccatgcac gccatgccaa accggagcgc accgagtgtc    3360
cacactgtca ccaggcccgc aagctttgca gaaccatgct catggacgca tgtagcgctg    3420
acgtcccttg acggcgctcc tctcgggtgt gggaaacgca atgcagcaca ggcagcagag    3480
gcggcggcag cagagcggcg gcagcagcgg cgggggccac ccttcttgcg gggtcgcgcc    3540
ccagccagcg gtgatgcgct gatcccaaac gagttcacat tcatttgcat gcctggagaa    3600
gcgaggctgg ggcctttggg ctggtgcagc ccgcaatgga atgcgggacc gccaggctag    3660
cagcaaaggc gcctcccta ctccgcatcg atgttccata gtgcattgga ctgcatttgg     3720
gtggggcggc cggctgtttc tttcgtgttg caaaacgcgc cagctcagca acctgtcccg    3780
tgggtccccc gtgccgatga aatcgtgtgc acgccgatca gctgattgcc cggctcgcga    3840
agtaggcgcc ctccttttctg ctcgccctct ctccgtcccg ccactagtat gacgttcggg   3900
gtcgccctcc cggccatggg ccgcggtgtc tcccttcccc ggcccagggt cgcggtgcgc    3960
gcccagtcgg cgagtcaggt tttggagagc gggcgcgccc ccgactggtc catgctgttc    4020
gccgtgatca ccaccatctt cagcgccgcc gagaagcagt ggaccaacct ggagtggaag    4080
cccaagccca agctgcccca gctgctggac gaccacttcg gcctgcacgg cctggtgttc    4140
cgccgcacct tcgccatccg ctcctacgag gtgggccccg accgcagcac ctccatcctg    4200
gccgtgatga accacatgca ggaggccacc ctgaaccacg ccaagagcgt gggcatcctg    4260
ggcgacggct tcggcaccac cctggagatg tccaagcgcg acctgatgtg ggtggtgcgc    4320
cgcacccacg tggccgtgga gcgctacccc acctgggggcg acaccgtgga ggtggagtgc    4380
tggatcggcg ccagcggcaa caacggcatg cgccgcgact tcctggtgcg cgactgcaag    4440
accggcgaga tcctgacccg ctgcacctcc ctgagcgtgc tgatgaacac ccgcacccgc    4500
cgcctgagca ccatccccga cgaggtgcgc ggcgagatcg gccccgcctt catcgacaac    4560
gtggccgtga aggacgacga gatcaagaag ctgcagaagc tgaacgactc caccgccgac    4620
tacatccagg gcggcctgac ccccgctgg aacgacctgg acgtgaacca gcacgtgaac     4680
aacctgaagt acgtggcctg ggtgttcgag accgtgcccg acagcatctt cgagtcccac    4740
cacatcagct cccttcaccct ggagtaccgc cgcgagtgca cccgcgactc cgtgctgcgc    4800
agcctgacca ccgtgagcgg cggcagctcc gaggccggcc tggtgtgcga ccacctgctg    4860
cagctggagg cgcagcgcga ggtgctgcgc gcccgcaccg agtggcgccc caagctgacc    4920
gactccttcc gcggcatcag cgtgatcccc gccgagcccc gcgtgatgga ctacaaggac    4980
cacgacggcg actacaagga ccacgacatc gactacaagg acgacgacga caagtgactc    5040
gaggcagcag cagctcggat agtatcgaca cactctggac gctggtcgtg tgatggactg    5100
ttgccgccac acttgctgcc ttgacctgtg aatatccctg ccgcttttat caaacagcct    5160
cagtgtgttt gatcttgtgt gtacgcgctt ttgcgagttg ctagctgctt gtgctatttg    5220
cgaataccac ccccagcatc cccttccctc gtttcatatc gcttgcatcc caaccgcaac    5280
```

```
ttatctacgc tgtcctgcta tccctcagcg ctgctcctgc tcctgctcac tgcccctcgc    5340
acagccttgg tttgggctcc gcctgtattc tcctggtact gcaacctgta aaccagcact    5400
gcaatgctga tgcacgggaa gtagtgggat gggaacacaa atggaaagct t             5451
```

<210> SEQ ID NO 111
<211> LENGTH: 5454
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
ggtacccttt cttgcgctat gacacttcca gcaaaaggta gggcgggctg cgagacggct      60
tcccggcgct gcatgcaaca ccgatgatgc ttcgaccccc cgaagctcct tcggggctgc     120
atgggcgctc cgatgccgct ccagggcgag cgctgtttaa atagccaggc ccccgattgc     180
aaagacatta tagcgagcta ccaaagccat attcaaacac ctagatcact accacttcta     240
cacaggccac tcgagcttgt gatcgcactc cgctaagggg cgcctcttc ctcttcgttt      300 cagtcacaac ccgcaaactc tagaatatca atgctgctgc aggccttcct gttcctgctg     360
gccggcttcg ccgccaagat cagcgcctcc atgacgaacg agacgtccga ccgcccctg      420 gtgcacttca cccccaacaa gggctggatg aacgaccca acggcctgtg gtacgacgag      480
aaggacgcca gtggcacct gtacttccag tacaacccga cgacaccgt ctggggggacg      540 cccttgttct ggggccacgc cacgtccgac gacctgacca ctgggaggga ccagcccatc     600
gccatcgccc cgaagcgcaa cgactccggc gccttctccg gctccatggt ggtggactac     660
aacaacacct ccggcttctt caacgacacc atcgacccgc ccagcgctg cgtgccatc      720 tggacctaca caccccgga gtccgaggag cagtacatct cctacagcct ggacggcggc     780
tacaccttca ccgagtacca gaagaacccc gtgctggccg ccaactccac ccagttccgc    840
gacccgaagg tcttctggta cgagccctcc cagaagtgga tcatgaccgc ggccaagtcc    900
caggactaca gatcgagat ctactcctcc gacgacctga gtcctggaa gctggagtcc      960 gcgttcgcca acgagggctt cctcggctac cagtacgagt gccccggcct gatcgaggtc    1020
cccaccgagc aggaccccag caagtcctac tgggtgatgt tcatctccat caaccccggc    1080
gccccggccg gcggctcctt caaccagtac ttcgtcggca gcttcaacgg cacccacttc    1140
gaggccttcg acaaccagtc ccgcgtggtg gacttcggca aggactacta cgccctgcag    1200
accttcttca cacccgaccc gacctacggg agcgccctgg gcatcgcgtg gcctccaac     1260 tgggagtact ccgccttcgt gcccaccaac ccctggcgct cctccatgtc cctcgtcgc    1320 aagttctccc tcaacaccga gtaccaggcc aacccggaga cggagctgat caacctgaag    1380
gccgagccga tcctgaacat cagcaacgcc ggccctgga gccggttcgc caccaacacc    1440
acgttgacga aggccaacag ctacaacgtc gacctgtcca acagcaccgg cacccctggag   1500 ttcgagctgg tgtacgccgt caacaccacc cagacgatct ccaagtccgt gttcgcggac    1560 ctctcccctct ggttcaaggg cctggaggac cccgaggagt acctccgcat gggcttcgag    1620
gtgtccgcgt cctccttctt cctggaccgc gggaacagca aggtgaagtt cgtgaaggag    1680 aaccccctact tcaccaaccg catgagcgtg aacaaccagc ccttcaagag cgagaacgac    1740
ctgtcctact acaaggtgta cggcttgctg gaccagaaca tcctggagct gtacttcaac    1800
gacggcgacg tcgtgtccac caacacctac ttcatgacca ccgggaacgc cctgggctcc    1860
```

```
gtgaacatga cgacgggggt ggacaacctg ttctacatcg acaagttcca ggtgcgcgag   1920
gtcaagtgac aattggcagc agcagctcgg atagtatcga cacactctgg acgctggtcg   1980
tgtgatggac tgttgccgcc acacttgctg ccttgacctg tgaatatccc tgccgctttt   2040
atcaaacagc ctcagtgtgt ttgatcttgt gtgtacgcgc ttttgcgagt tgctagctgc   2100
ttgtgctatt tgcgaatacc accccagca tccccttccc tcgtttcata tcgcttgcat    2160
cccaaccgca acttatctac gctgtcctgc tatcccag cgctgctcct gctcctgctc     2220
actgcccctc gcacagcctt ggtttgggct ccgcctgtat tctcctggta ctgcaacctg   2280
taaaccagca ctgcaatgct gatgcacggg aagtagtggg atgggaacac aaatggagga   2340
tcccgcgtct cgaacagagc gcgcagagga acgctgaagg tctcgcctct gtcgcacctc   2400
agcgcggcat acaccacaat aaccacctga cgaatgcgct tggttcttcg tccattagcg   2460
aagcgtccgg ttcacacacg tgccacgttg gcgaggtggc aggtgacaat gatcggtgga   2520
gctgatggtc gaaacgttca cagcctaggg atatcgaatt ccgcctgcaa cgcaagggca   2580
gccacagccg ctcccacccg ccgctgaacc gacacgtgct tgggcgcctg ccgcctgcct   2640
gccgcatgct tgtgctggtg aggctgggca gtgctgccat gctgattgag gcttggttca   2700
tcgggtggaa gcttatgtgt gtgctgggct tgcatgccgg gcaatgcgca tggtggcaag   2760
agggcggcag cacttgctgg agctgccgcg gtgcctccag gtggttcaat cgcggcagcc   2820
agagggattt cagatgatcg cgcgtacagg ttgagcagca gtgtcagcaa aggtagcagt   2880
ttgccagaat gatcggttca gctgttaatc aatgccagca agagaagggg tcaagtgcaa   2940
acacgggcat gccacagcac gggcaccggg gagtggaatg gcaccaccaa gtgtgtgcga   3000
gccagcatcg ccgcctggct gtttcagcta caacggcagg agtcatccaa cgtaaccatg   3060
agctgatcaa cactgcaatc atcgggcggg cgtgatgcaa gcatgcctgg cgaagacaca   3120
tggtgtgcgg atgctgccgg ctgctgcctg ctgcgcacgc cgttgagttg gcagcaggct   3180
cagccatgca ctggatggca gctgggctgc cactgcaatg tggtggatag gatgcaagtg   3240
gagcgaatac caaaccctct ggctgcttgc tgggttgcat ggcatcgcac catcagcagg   3300
agcgcatgcg aagggactgg ccccatgcac gccatgccaa accggagcgc accgagtgtc   3360
cacactgtca ccaggcccgc aagctttgca gaaccatgct catggacgca tgtagcgctg   3420
acgtcccttg acggcgctcc tctcgggtgt gggaaacgca atgcagcaca ggcagcagag   3480
gcggcggcag cagagcggcg gcagcagcgg cggggccac ccttcttgcg gggtcgcgcc    3540
ccagccagcg tgatgcgct gatcccaaac gagttcacat tcatttgcat gcctggagaa   3600
gcgaggctgg ggccttgg ctggtgcagc ccgcaatgga atgcgggacc gccaggctag    3660
cagcaaaggc gcctcccta ctccgcatcg atgttccata gtgcattgga ctgcatttgg    3720
gtggggcggc cggctgtttc tttcgtgttg caaaacgcgc cagctcagca acctgtcccg   3780
tgggtccccc gtgccgatga aatcgtgtgc acgccgatca gctgattgcc cggctcgcga   3840
agtaggcgcc ctcctttctg ctcgccctct ctccgtcccg ccactagtat ggccaccgca   3900
tccactttct cggcgttcaa tgcccgctgc ggcgacctgc gtcgctcggc gggctccggg   3960
ccccggcgcc cagcgaggcc cctccccgtg cgcgggcgcg ccccgactg gtccatgctg    4020 ttcgccgtga tcaccaccat cttctccgcc gccgagaagc agtggaccaa cctggagtgg   4080
aagcccaagc ccaaccccc ccagctgctg gacgaccact tcggccccca ggcctggtg    4140 ttccgccgca ccttcgccat ccgcagctac gaggtgggcc ccgaccgctc caccagcatc   4200
```

| | |
|---|---|
| gtggccgtga tgaaccacct gcaggaggcc gccctgaacc acgccaagtc cgtgggcatc | 4260 |
| ctgggcgacg gcttcggcac cacccctgga gatgtccaagc gcgacctgat ctgggtggtg | 4320 |
| aagcgcaccc acgtggccgt ggagcgctac cccgcctggg gcgacaccgt ggaggtggag | 4380 |
| tgctgggtgg cgcctccgg caacaacggc cgccgccacg acttcctggt gcgcgactgc | 4440 |
| aagaccggcg agatcctgac ccgctgcacc tccctgagcg tgatgatgaa cacccgcacc | 4500 |
| cgccgcctga gcaagatccc cgaggaggtg cgcggcgaga tcggcccgc cttcatcgac | 4560 |
| aacgtggccg tgaaggacga ggagatcaag aagcccaga agctgaacga ctccaccgcc | 4620 |
| gactacatcc agggcggcct gaccccccgc tggaacgacc tggacatcaa ccagcacgtg | 4680 |
| aacaacatca gtacgtgga ctggatcctg gagaccgtgc ccgacagcat cttcgagagc | 4740 |
| caccacatct cctccttcac catcgagtac cgccgcgagt gcaccatgga cagcgtgctg | 4800 |
| cagtccctga ccaccgtgag cggcggctcc tccgaggccg gcctggtgtg cgagcacctg | 4860 |
| ctgcagctgg agggcggcag cgaggtgctg cgcgccaaga ccgagtggcg ccccaagctg | 4920 |
| accgactcct tccgcggcat cagcgtgatc cccgccgagt ccagcgtgat ggactacaag | 4980 |
| gaccacgacg gcgactacaa ggaccacgac atcgactaca aggacgacga cgacaagtga | 5040 |
| ctcgaggcag cagcagctcg gatagtatcg acacactctg gacgctggtc gtgtgatgga | 5100 |
| ctgttgccgc cacacttgct gccttgacct gtgaatatcc ctgccgcttt tatcaaacag | 5160 |
| cctcagtgtg tttgatcttg tgtgtacgcg cttttgcgag ttgctagctg cttgtgctat | 5220 |
| ttgcgaatac caccccagc atccccttcc ctcgtttcat atcgcttgca tcccaaccgc | 5280 |
| aacttatcta cgctgtcctg ctatccctca gcgctgctcc tgctcctgct cactgccctc | 5340 |
| cgcacagcct tggtttgggc tccgcctgta ttctcctggt actgcaacct gtaaaccagc | 5400 |
| actgcaatgc tgatgcacgg gaagtagtgg gatgggaaca caaatggaaa gctt | 5454 |

<210> SEQ ID NO 112
<211> LENGTH: 2933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

| | |
|---|---|
| agagagcgga ggtgggttg tgaggtgggg ttgctgacca ggagctcgcg tcgccgagcg | 60 |
| cgactcgcac acggtccagt taccccccc tccgcccaaa cgcaagcctc ccatcttgat | 120 |
| gcctttccgg ccacctatac tatttcttag ttcgctgtaa catccagacc gtcctgaata | 180 |
| ataacaatgc cctgtgtcaa gtgcattcct aaaaaaattc tgtcccaacc aacaatccca | 240 |
| cctgaaatac caccagccct gcccagtaca ctcttccaat accatctccc tacctccacg | 300 |
| cgcaagcgac cccatgcgc gaccaggctc gaaagtgatt tatgacttga cgagcgag | 360 |
| tggcggcgcg tcgactgcc ttttcatcac gtgccgtacg tcggcgaccg ctagggcttt | 420 |
| gcacggcaac gcacggcttc gccaacccga ccagccagga cctcgactac tctaccgcga | 480 |
| attcgcctca agaagtcgcc aaatgtgcca tacaccattc cttacagcac tgttcaaact | 540 |
| tgatgccaat tttgacattc gggttgctcg ttggctgcgc ccacatcggc cgtgagtgca | 600 |
| gcaggcggga tcggacacgg aggacgcggc gtcacgcccc gaacgcagcc cgtaactcta | 660 |
| catcaacacg acgtgttgcg taatcccgcc cggctgcgca tcgtgccaac ccattcgcga | 720 |
| tggatggtcg gaaaatggtg tgccaactgc cctgagggag gctctcgcga aacgggcacg | 780 |

| | |
|---|---|
| tccctgaaac cgaaactgtg gccttgtcgt cggccacgca agcacgtgga ccctaaacac | 840 |
| caagaaaatc agtaaacaag gttgacatcc tctacgggcg aattgtttgc ccaacccttc | 900 |
| atcgcacact gccattataa tgcatctagc tcggcgacaa gtttagaaaa ggcaggctgc | 960 |
| attgttccat ttcgccgtgg cggcgtgggt gcccatttta cgaggtttgg gctcccgggc | 1020 |
| agcgaccgag ccaggtcgag tccctctcgc ccgtcgacaa tgttgcgaac cccacaagcg | 1080 |
| gctaacaaca acttgatggt acctgtacac tgccaattcc ttcttccccg gccgaggttt | 1140 |
| acacgtgatg gccatggctt cgcattcagg ccgacttccc attccgactt tccagagggt | 1200 |
| ccgcggacgc tggggttgg ctgcctgagg cccacccttt gttccccgcg tcccgacaaa | 1260 |
| cacaattgcg ttacataagg gggagccgcc cccgttcaga gtgcagaaat ctttcactat | 1320 |
| attttccagt cgtcagcgaa atcaagtact agtatggcca ccgcatccac tttctcggcg | 1380 |
| ttcaatgccc gctgcggcga cctgcgtcgc tcggcgggct ccgggccccg cgcccagcg | 1440 |
| aggcccctcc ccgtgcgcgg gcgcgccccc gactggtcca tgctgttcgc cgtgatcacc | 1500 |
| accatcttct ccgccgccga gaagcagtgg accaacctgg agtggaagcc caagcccaac | 1560 |
| cccccccagc tgctggacga ccacttcggc ccccacggcc tggtgttccg ccgcaccttc | 1620 |
| gccatccgca gctacgaggt gggccccgac cgctccacca gcatcgtggc cgtgatgaac | 1680 |
| cacctgcagg aggccgccct gaaccacgcc aagtccgtgg gcatcctggg cgacggcttc | 1740 |
| ggcaccaccc tggagatgtc caagcgcgac ctgatctggg tggtgaagcg cacccacgtg | 1800 |
| gccgtggagc gctaccccgc ctggggcgac accgtggagg tggagtgctg ggtgggcgcc | 1860 |
| tccggcaaca acgccgccg ccacgacttc ctggtgcgcg actgcaagac cggcgagatc | 1920 |
| ctgacccgct gcacctccct gagcgtgatg atgaacaccc gcacccgccg cctgagcaag | 1980 |
| atccccgagg aggtgcgcgg cgagatcggc cccgccttca tcgacaacgt ggccgtgaag | 2040 |
| gacgaggaga tcaagaagcc ccagaagctg aacgactcca ccgccgacta catccagggc | 2100 |
| ggcctgaccc ccgctggaa cgacctggac atcaaccagc acgtgaacaa catcaagtac | 2160 |
| gtggactgga tcctggagac cgtgcccgac agcatcttcg agagccacca catctcctcc | 2220 |
| ttcaccatcg agtaccgccg cgagtgcacc atggacagcg tgctgcagtc cctgaccacc | 2280 |
| gtgagcggcg gctcctccga ggccggcctg gtgtgcgagc acctgctgca gctggagggc | 2340 |
| ggcagcgagg tgctgcgcgc caagaccgag tggcgcccca agctgaccga ctccttccgc | 2400 |
| ggcatcagcg tgatccccgc cgagtccagc gtgatggact acaaggacca cgacggcgac | 2460 |
| tacaaggacc acgacatcga ctacaaggac gacgacgaca agtgactcga gttaattaac | 2520 |
| tcgaggcagc agcagctcgg atagtatcga cacactctgg acgctggtcg tgtgatggac | 2580 |
| tgttgccgcc acacttgctg ccttgacctg tgaatatccc tgccgctttt atcaaacagc | 2640 |
| ctcagtgtgt ttgatcttgt gtgtacgcgc ttttgcgagt tgctagctgc ttgtgctatt | 2700 |
| tgcgaatacc accccagca tccccttccc tcgtttcata tcgcttgcat cccaaccgca | 2760 |
| acttatctac gctgtcctgc tatccctcag cgctgctcct gctcctgctc actgcccctc | 2820 |
| gcacagcctt ggtttgggct ccgcctgtat tctcctggta ctgcaacctg taaaccagca | 2880 |
| ctgcaatgct gatgcacggg aagtagtggg atgggaacac aaatggaaag ctt | 2933 |

<210> SEQ ID NO 113
<211> LENGTH: 4817
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

| | | | | | |
|---|---|---|---|---|---|
| ggtacccgcc | tgcaacgcaa | gggcagccac | agccgctccc | acccgccgct | gaaccgacac | 60 |
| gtgcttgggc | gcctgccgcc | tgcctgccgc | atgcttgtgc | tggtgaggct | gggcagtgct | 120 |
| gccatgctga | ttgaggcttg | gttcatcggg | tggaagctta | tgtgtgtgct | gggcttgcat | 180 |
| gccgggcaat | gcgcatggtg | gcaagagggc | ggcagcactt | gctggagctg | ccgcggtgcc | 240 |
| tccaggtggt | tcaatcgcgg | cagccagagg | gatttcagat | gatcgcgcgt | acaggttgag | 300 |
| cagcagtgtc | agcaaaggta | gcagtttgcc | agaatgatcg | gttcagctgt | taatcaatgc | 360 |
| cagcaagaga | aggggtcaag | tgcaaacacg | ggcatgccac | agcacgggca | ccggggagtg | 420 |
| gaatggcacc | accaagtgtg | tgcgagccag | catcgccgcc | tggctgtttc | agctacaacg | 480 |
| gcaggagtca | tccaacgtaa | ccatgagctg | atcaacactg | caatcatcgg | gcgggcgtga | 540 |
| tgcaagcatg | cctggcgaag | acacatggtg | tgcggatgct | gccggctgct | gcctgctgcg | 600 |
| cacgccgttg | agttggcagc | aggctcagcc | atgcactgga | tggcagctgg | gctgccactg | 660 |
| caatgtggtg | gataggatgc | aagtggagcg | aataccaaac | cctctggctg | cttgctgggt | 720 |
| tgcatggcat | cgcaccatca | gcaggagcgc | atgcgaaggg | actggcccca | tgcacgccat | 780 |
| gccaaaccgg | agcgcaccga | gtgtccacac | tgtcaccagg | cccgcaagct | ttgcagaacc | 840 |
| atgctcatgg | acgcatgtag | cgctgacgtc | ccttgacggc | gctcctctcg | ggtgtgggaa | 900 |
| acgcaatgca | gcacaggcag | cagaggcggc | ggcagcagag | cggcggcagc | agcggcgggg | 960 |
| gccacccttc | ttgcggggtc | gcgccccagc | cagcggtgat | gcgctgatcc | caaacgagtt | 1020 |
| cacattcatt | tgcatgcctg | gagaagcgag | gctggggcct | ttgggctggt | gcagcccgca | 1080 |
| atggaatgcg | ggaccgccag | gctagcagca | aaggcgcctc | ccctactccg | catcgatgtt | 1140 |
| ccatagtgca | ttggactgca | tttgggtggg | gcggccggct | gtttcttctcg | tgttgcaaaa | 1200 |
| cgcgccagct | cagcaacctg | tcccgtgggt | ccccgtgcc | gatgaaatcg | tgtgcacgcc | 1260 |
| gatcagctga | ttgcccggct | cgcgaagtag | gcgccctcct | ttctgctcgc | cctctctccg | 1320 |
| tcccgcctct | agaatatcaa | tgatcgagca | ggacggcctc | cacgccggct | ccccgccgc | 1380 |
| ctgggtggag | cgcctgttcg | gctacgactg | ggcccagcag | accatcggct | gctccgacgc | 1440 |
| cgccgtgttc | cgcctgtccg | cccagggccg | ccccgtgctg | ttcgtgaaga | ccgacctgtc | 1500 |
| cggcgccctg | aacgagctgc | aggacgaggc | cgcccgcctg | tcctggctgg | ccaccaccgg | 1560 |
| cgtgccctgc | gccgccgtgc | tggacgtggt | gaccgaggcc | ggccgcgact | ggctgctgct | 1620 |
| gggcgaggtg | cccggccagg | acctgctgtc | ctcccacctg | gcccccgccg | agaaggtgtc | 1680 |
| catcatggcc | gacgccatgc | gccgcctgca | cacccttggac | cccgccacct | gccccttcga | 1740 |
| ccaccaggcc | aagcaccgca | tcgagcgcgc | ccgcacccgc | atggaggccg | gctggtggga | 1800 |
| ccaggacgac | ctggacgagg | agcaccaggg | cctggccccc | gccagctgt | tcgcccgcct | 1860 |
| gaaggcccgc | atgcccgacg | gcgaggacct | ggtggtgacc | cacggcgacg | cctgcctgcc | 1920 |
| caacatcatg | gtggagaacg | gccgcttctc | cggcttcatc | gactgcggcc | gctgggcgt | 1980 |
| ggccgaccgc | taccaggaca | tcgccctggc | cacccgcgac | atcgccgagg | agctgggcgg | 2040 |
| cgagtgggcc | gaccgcttcc | tggtgctgta | cggcatcgcc | gccccccgact | cccagcgcat | 2100 |
| cgccttctac | cgcctgctgg | acgagttctt | ctgacaattg | gcagcagcag | ctcggatagt | 2160 |
| atcgacacac | tctggacgct | ggtcgtgtga | tggactgttg | ccgccacact | tgctgccttg | 2220 |
| acctgtgaat | atccctgccg | cttttatcaa | acagcctcag | tgtgtttgat | cttgtgtgta | 2280 |

```
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaggta gggcgggctg cgagacggct    2820
tcccggcgct gcatgcaaca ccgatgatgc ttcgacccccc cgaagctcct tcggggctgc   2880
atgggcgctc cgatgccgct ccagggcgag cgctgtttaa atagccaggc cccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacgg cgcgccatgg tggccgccgc cgcctccagc gccttcttcc    3120
ccgtgcccgc ccccggcgcc tccccaagc ccggcaagtt cggcaactgg ccctccagcc     3180
tgagcccctc cttcaagccc aagtccatcc ccaacggcgg cttccaggtg aaggccaacg    3240
acagcgccca ccccaaggcc aacggctccg ccgtgagcct gaagagcggc agcctgaaca    3300
cccaggagga cacctcctcc agccccccc ccgcaccttt cctgcaccag ctgcccgact     3360
ggagccgcct gctgaccgcc atcaccaccg tgttcgtgaa gtccaagcgc cccgacatgc    3420
acgaccgcaa gtccaagcgc cccgacatgc tggtggacag cttcggcctg gagtccaccg    3480
tgcaggacgg cctggtgttc cgccagtcct tctccatccg ctcctacgag atcggcaccg    3540
accgcaccgc cagcatcgag accctgatga accacctgca ggagacctcc ctgaaccact    3600
gcaagagcac cggcatcctg ctggacggct tcggccgcac cctggagatg tgcaagcgcg    3660
acctgatctg ggtggtgatc aagatgcaga tcaaggtgaa ccgctacccc gcctggggcg    3720
acaccgtgga gatcaacacc cgcttcagcc gcctgggcaa gatcggcatg ggccgcgact    3780
ggctgatctc cgactgcaac accggcgaga tcctggtgcg cgccaccagc gcctacgcca    3840
tgatgaacca gaagacccgc cgcctgtcca agctgcccta cgaggtgcac caggagatcg    3900
tgccctgtt cgtggacagc cccgtgatcg aggactccga cctgaaggtg cacaagttca    3960
aggtgaagac cggcgacagc atccagaagg cctgaccccc cggctggaac gacctggacg    4020
tgaaccagca cgtgtccaac gtgaagtaca tcggctggat cctggagagc atgcccaccg    4080
aggtgctgga gacccaggag ctgtgctccc tggccctgga gtaccgccgc gagtgcggcc    4140
gcgactccgt gctggagagc gtgaccgcca tggaccccag caaggtgggc gtgcgctccc    4200
agtaccagca cctgctgcgc ctggaggacg gcaccgccat cgtgaacggc gccaccgagt    4260
ggcgccccaa gaacgccggc gccaacggcg ccatctccac cggcaagacc agcaacggca    4320
actccgtgtc catggactac aaggaccacg acggcgacta caaggaccac gacatcgact    4380
acaaggacga cgacgacaag tgactcgagg cagcagcagc tcggatagta tcgacacact    4440
ctggacgctg gtcgtgtgat ggactgttgc cgccacactt gctgccttga cctgtgaata    4500
tccctgccgc ttttatcaaa cagcctcagt gtgtttgatc ttgtgtgtac gcgcttttgc    4560
gagttgctag ctgcttgtgc tatttgcgaa taccaccccc agcatcccct tccctcgttt    4620
```

-continued

| | |
|---|---|
| catatcgctt gcatcccaac cgcaacttat ctacgctgtc ctgctatccc tcagcgctgc | 4680 |
| tcctgctcct gctcactgcc cctcgcacag ccttggtttg ggctccgcct gtattctcct | 4740 |
| ggtactgcaa cctgtaaacc agcactgcaa tgctgatgca cgggaagtag tgggatggga | 4800 |
| acacaaatgg aaagctt | 4817 |

<210> SEQ ID NO 114
<211> LENGTH: 4665
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 114

| | |
|---|---|
| ggtacccgcc tgcaacgcaa gggcagccac agccgctccc accgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg ggcatgccac agcacgggca ccggggagtg | 420 |
| gaatggcacc accaagtgtg tgcgagccag catcgccgcc tggctgtttc agctacaacg | 480 |
| gcaggagtca tccaacgtaa ccatgagctg atcaacactg caatcatcgg gcgggcgtga | 540 |
| tgcaagcatg cctggcgaag acacatggtg tgcggatgct gccggctgct gcctgctgcg | 600 |
| cacgccgttg agttggcagc aggctcagcc atgcactgga tggcagctgg gctgccactg | 660 |
| caatgtggtg gataggatgc aagtggagcg aataccaaac cctctggctg cttgctgggt | 720 |
| tgcatggcat cgcaccatca gcaggagcgc atgcgaaggg actggcccca tgcacgccat | 780 |
| gccaaaccgg agcgcaccga gtgtccacac tgtcaccagg cccgcaagct tgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccacccttc ttgcggggtc gcgccccagc cagcggtgat gcgctgatcc caaacgagtt | 1020 |
| cacattcatt tgcatgcctg gagaagcgag gctgggcct tgggctggt gcagcccgca | 1080 |
| atggaatgcg ggaccgccag gctagcagca aaggcgcctc ccctactccg catcgatgtt | 1140 |
| ccatagtgca ttggactgca tttgggtggg gcggccggct gtttctttcg tgttgcaaaa | 1200 |
| cgcgccagct cagcaacctg tcccgtgggt cccccgtgcc gatgaaatcg tgtgcacgcc | 1260 |
| gatcagctga ttgcccggct cgcgaagtag gcgcccctcct ttctgctcgc cctctctccg | 1320 |
| tcccgcctct agaatatcaa tgatcgagca ggacggcctc cacgccggct cccccgccgc | 1380 |
| ctgggtggag cgcctgttcg gctacgactg ggcccagcag accatcggct gctccgacgc | 1440 |
| cgccgtgttc cgcctgtccg cccagggccg cccgtgctg ttcgtgaaga ccgacctgtc | 1500 |
| cggcgccctg aacgagctgc aggacgaggc gcccgcctg tcctggctgg ccaccaccgg | 1560 |
| cgtgccctgc gccgccgtgc tggacgtggt gaccgagggc cgccgcgact ggctgctgct | 1620 |
| gggcgaggtg cccggccagg acctgctgtc ctcccacctg gccccgccg agaaggtgtc | 1680 |
| catcatggcc gacgccatgc gccgcctgca cacccctggac cccgcacct gcccttcga | 1740 |
| ccaccaggcc aagcaccgca tcgagcgcgc ccgcacccgc atggaggccg gctggtgga | 1800 |

```
ccaggacgac ctggacgagg agcaccaggg cctggccccc gccgagctgt tcgcccgcct   1860
gaaggcccgc atgcccgacg gcgaggacct ggtggtgacc cacggcgacg cctgcctgcc   1920
caacatcatg gtggagaacg gccgcttctc cggcttcatc gactgcggcc gcctgggcgt   1980
ggccgaccgc taccaggaca tcgccctggc caccccgcga catcgccgagg agctgggcgg   2040 cgagtgggcc gaccgcttcc tggtgctgta cggcatcgcc gcccccgact cccagcgcat   2100
cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgtttaa atagccaggc ccccgattgc   2940
aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatgacg ttcggggtcg ccctcccggc catgggccgc   3120
ggtgtctccc ttccccggcc cagggtcgcg gtgcgcgccc agtcggcgag tcaggttttg   3180
gagagcgggc gcgcccagct gcccgactgg agccgcctgc tgaccgccat caccaccgtg   3240
ttcgtgaagt ccaagcgccc cgacatgcac gaccgcaagt ccaagcgccc cgacatgctg   3300
gtggacagct tcggcctgga gtccaccgtg caggacggcc tggtgttccg ccagtccttc   3360
tccatccgct cctacgagat cggcaccgac cgcaccgcca gcatcgagac cctgatgaac   3420
cacctgcagg agacctccct gaaccactgc aagagcaccg gcatcctgct ggacggcttc   3480
ggccgcaccc tggagatgtg caagcgcgac ctgatctggg tggtgatcaa gatgcagatc   3540
aaggtgaacc gctaccccgc ctggggcgac accgtggaga tcaacacccg cttcagccgc   3600
ctgggcaaga tcggcatggg ccgcgactgg ctgatctccg actgcaacac cggcgagatc   3660
ctggtgcgcg ccaccagcgc ctacgccatg atgaaccaga gacccgccg cctgtccaag   3720 ctgccctacg aggtgcacca ggagatcgtg cccctgttcg tggacagccc cgtgatcgag   3780
gactccgacc tgaaggtgca caagttcaag gtgaagaccg cgacagcat ccagaagggc   3840 ctgacccccg gctggaacga cctggacgtg aaccagcacg tgtccaacgt gaagtacatc   3900
ggctggatcc tggagagcat gcccaccgag gtgctggaga cccaggagct gtgctccctg   3960
gccctggagt accgccgcga gtgcggccgc gactccgtgc tggagagcgt gaccgccatg   4020
gaccccagca aggtgggcgt gcgctcccag taccagcacc tgctgcgcct ggaggacggc   4080
accgccatcg tgaacggcgc caccgagtgg cgccccaaga cgccggcgc caacggcgcc   4140 atctccaccg gcaagaccag caacggcaac tccgtgtcca tggactacaa ggaccacgac   4200
```

```
ggcgactaca aggaccacga catcgactac aaggacgacg acgacaagtg actcgaggca    4260
gcagcagctc ggatagtatc gacacactct ggacgctggt cgtgtgatgg actgttgccg    4320
ccacacttgc tgccttgacc tgtgaatatc cctgccgctt ttatcaaaca gcctcagtgt    4380
gtttgatctt gtgtgtacgc gcttttgcga gttgctagct gcttgtgcta tttgcgaata    4440 ccaccccag catccccttc cctcgtttca tatcgcttgc atcccaaccg caacttatct     4500
acgctgtcct gctatccctc agcgctgctc ctgctcctgc tcactgcccc tcgcacagcc    4560
ttggtttggg ctccgcctgt attctcctgg tactgcaacc tgtaaaccag cactgcaatg    4620
ctgatgcacg ggaagtagtg ggatgggaac acaaatggaa agctt                    4665
```

<210> SEQ ID NO 115
<211> LENGTH: 4668
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc     840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctgggggcct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttctttcg tgttgcaaaa   1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg   1320
tcccgcctct agaatatcaa tgatcgagca ggacggcctc cacgccggct cccccgccgc   1380
ctgggtggag cgcctgttcg gctacgactg ggcccagcag accatcggct gctccgacgc   1440
cgccgtgttc cgcctgtccg cccagggccg cccgtgctg ttcgtgaaga ccgacctgtc    1500
cggcgccctg aacgagctgc aggacgaggc cgcccgcctg tcctggctgg ccaccaccgg   1560
```

```
cgtgccctgc gccgccgtgc tggacgtggt gaccgaggcc ggccgcgact ggctgctgct   1620
gggcgaggtg cccggccagg acctgctgtc ctcccacctg gcccccgccg agaaggtgtc   1680
catcatggcc gacgccatgc gccgcctgca caccctggac cccgccacct gccccttcga   1740
ccaccaggcc aagcaccgca tcgagcgcgc ccgcacccgc atggaggccg gcctggtgga   1800
ccaggacgac ctggacgagg agcaccaggg cctggccccc gccgagctgt tcgcccgcct   1860
gaaggcccgc atgcccgacg cgaggacct ggtggtgacc cacggcgacg cctgcctgcc   1920
caacatcatg gtggagaacg ccgcttctc cggcttcatc gactgcggcc gctgggcgt   1980 ggccgaccgc taccaggaca tcgccctggc cacccgcgac atcgccgagg agctgggcgg   2040
cgagtgggcc gaccgcttcc tggtgctgta cggcatcgcc gcccccgact cccagcgcat   2100
cgccttctac cgcctgctgg acagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acggaagta   2520 gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgttaa atagccaggc ccccgattgc   2940
aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatggct atcaagacga acaggcagcc tgtggagaag   3120
cctccgttca cgatcgggac gctgcgcaag gccatccccg cgcactgttt cgagcgctcg   3180
gcgcttcgtg ggcgcgccca gctgcccgac tggagccgcc tgctgaccgc catcaccacc   3240
gtgttcgtga agtccaagcg ccccgacatg cacgaccgca gtccaagcg ccccgacatg   3300 ctggtggaca gcttcggcct ggagtccacc gtgcaggacg gcctggtgtt ccgccagtcc   3360
ttctccatcc gctcctacga gatcggcacc gaccgcaccg ccagcatcga ccctgatg     3420 aaccacctgc aggagacctc cctgaaccac tgcaagagca ccggcatcct gctggacggc   3480
ttcggccgca ccctggagat gtgcaagcgc gacctgatct gggtggtgat caagatgcag   3540
atcaaggtga accgctaccc cgcctggggc gacaccgtgg agatcaacac ccgcttcagc   3600
cgcctgggca gatcggcat gggcgcgac tggctgatct ccgactgcaa caccggcgag   3660
atcctggtgc gcgccaccag cgcctacgcc atgatgaacc agaagacccg ccgctgtcc   3720 aagctgccct acgaggtgca ccaggagatc gtgcccctgt tcgtggacag ccccgtgatc   3780
gaggactccg acctgaaggt gcacaagttc aaggtgaaga ccggcgacag catccagaag   3840
ggcctgaccc ccggctggaa cgacctggac gtgaaccagc acgtgtccaa cgtgaagtac   3900
```

| | |
|---|---|
| atcggctgga tcctggagag catgcccacc gaggtgctgg agacccagga gctgtgctcc | 3960 |
| ctggccctgg agtaccgccg cgagtgcggc cgcgactccg tgctggagag cgtgaccgcc | 4020 |
| atggacccca gcaaggtggg cgtgcgctcc cagtaccagc acctgctgcg cctggaggac | 4080 |
| ggcaccgcca tcgtgaacgg cgccaccgag tggcgcccca agaacgccgg cgccaacggc | 4140 |
| gccatctcca ccggcaagac cagcaacggc aactccgtgt ccatggacta caaggaccac | 4200 |
| gacggcgact acaaggacca cgacatcgac tacaaggacg acgacgacaa gtgactcgag | 4260 |
| gcagcagcag ctcggatagt atcgacacac tctggacgct ggtcgtgtga tggactgttg | 4320 |
| ccgccacact tgctgccttg acctgtgaat atccctgccg cttttatcaa acagcctcag | 4380 |
| tgtgtttgat cttgtgtgta cgcgcttttg cgagttgcta gctgcttgtg ctatttgcga | 4440 |
| ataccacccc cagcatcccc ttccctcgtt tcatatcgct tgcatcccaa ccgcaactta | 4500 |
| tctacgctgt cctgctatcc ctcagcgctg ctcctgctcc tgctcactgc ccctcgcaca | 4560 |
| gccttggttt gggctccgcc tgtattctcc tggtactgca acctgtaaac cagcactgca | 4620 |
| atgctgatgc acgggaagta gtgggatggg aacacaaatg gaaagctt | 4668 |

<210> SEQ ID NO 116
<211> LENGTH: 4668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

| | |
|---|---|
| ggtacccgcc tgcaacgcaa gggcagccac agccgctccc accgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg ggcatgccac agcacgggca ccggggagtg | 420 |
| gaatggcacc accaagtgtg tgcgagccag catcgccgcc tggctgtttc agctacaacg | 480 |
| gcaggagtca tccaacgtaa ccatgagctg atcaacactg caatcatcgg gcgggcgtga | 540 |
| tgcaagcatg cctggcgaag acacatggtg tgcggatgct gcggctgct gcctgctgcg | 600 |
| cacgccgttg agttggcagc aggctcagcc atgcactgga tggcagctgg gctgccactg | 660 |
| caatgtggtg gataggatgc aagtggagcg aataccaaac cctctggctg cttgctgggt | 720 |
| tgcatggcat cgcaccatca gcaggagcgc atgcgaaggg actggcccca tgcacgccat | 780 |
| gccaaaccgg agcgcaccga gtgtccacac tgtcaccagg cccgcaagct ttgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccaccttc ttgcggggtc gcgcccagc cagcggtgat gcgctgatcc caaacgagtt | 1020 |
| cacattcatt tgcatgcctg gagaagcgag gctgggcct ttgggctggt gcagcccgca | 1080 |
| atggaatgcg ggaccgccag gctagcagca aggcgcctc ccctactccg catcgatgtt | 1140 |
| ccatagtgca ttggactgca tttgggtggg cggccggct gtttcttcg tgttgcaaaa | 1200 |
| cgcgccagct cagcaacctg tccgtgggt cccccgtgcc gatgaaatcg tgtgcacgcc | 1260 |

```
gatcagctga ttgcccggct cgcgaagtag gcgccctcct ttctgctcgc cctctctccg   1320
tcccgcctct agaatatcaa tgatcgagca ggacggcctc cacgccggct ccccgccgc    1380 ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gccccgccg agaaggtgtc    1680 catcatggcc gacgccatgc gccgcctgca caccctggac cccgccacct gcccttcga    1740 ccaccaggcc aagcaccgca tcgagcgcgc ccgcacccgc atggaggccg gctggtgga    1800 ccaggacgac ctggacgagg agcaccaggg cctggccccc gccgagctgt tcgcccgcct   1860
gaaggcccgc atgcccgacg gcgaggacct ggtggtgacc cacggcgacg cctgcctgcc   1920
caacatcatg gtggagaacg gccgcttctc cggcttcatc gactgcggcc gctgggcgt    1980 ggccgaccgc taccaggaca tcgccctggc cacccgcgac atcgccgagg agctgggcgg   2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaggta gggcgggctg cgagacggct    2820
tcccggcgct gcatgcaaca ccgatgatgc ttcgaccccc cgaagctcct tcggggctgc   2880
atgggcgctc cgatgccgct ccagggcgag cgctgtttaa atagccaggc cccgattgc    2940 aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatggcc accgcatcca cttctcggc gttcaatgcc    3120 cgctgcggcg acctgcgtcg ctcggcgggc tccggccccc ggcgcccagc gaggcccctc   3180
cccgtgcgcg ggcgcgccca gctgcccgac tggagccgcc tgctgaccgc catcaccacc   3240
gtgttcgtga agtccaagcg cccccgacatg cacgaccgca agtccaagcg cccccgacatg 3300 ctggtggaca gcttcggcct ggagtccacc gtgcaggacg gcctggtgtt ccgccagtcc   3360
ttctccatcc gctcctacga gatcggcacc gaccgcaccg ccagcatcga ccctgatg     3420 aaccacctgc aggagacctc cctgaaccac tgcaagagca ccggcatcct gctggacggc   3480
ttcggccgca ccctggagat gtgcaagcgc gacctgatct gggtggtgat caagatgcag   3540
atcaaggtga accgctaccc cgcctggggc gacaccgtgg agatcaacac ccgcttcagc   3600
cgcctgggca agatcggcat gggccgcgac tggctgatct ccgactgcaa caccggcgag   3660
```

| | |
|---|---|
| atcctggtgc gcgccaccag cgcctacgcc atgatgaacc agaagacccg ccgcctgtcc | 3720 |
| aagctgccct acgaggtgca ccaggagatc gtgcccctgt tcgtggacag ccccgtgatc | 3780 |
| gaggactccg acctgaaggt gcacaagttc aaggtgaaga ccggcgacag catccagaag | 3840 |
| ggcctgaccc ccggctggaa cgacctggac gtgaaccagc acgtgtccaa cgtgaagtac | 3900 |
| atcggctgga tcctggagag catgcccacc gaggtgctgg agacccagga gctgtgctcc | 3960 |
| ctggccctgg agtaccgccg cgagtgcggc cgcgactccg tgctggagag cgtgaccgcc | 4020 |
| atggacccca gcaaggtggg cgtgcgctcc cagtaccagc acctgctgcg cctggaggac | 4080 |
| ggcaccgcca tcgtgaacgg cgccaccgag tggcgcccca gaacgccgg cgccaacggc | 4140 |
| gccatctcca ccggcaagac cagcaacggc aactccgtgt ccatggacta caaggaccac | 4200 |
| gacggcgact acaaggacca cgacatcgac tacaaggacg acgacgacaa gtgactcgag | 4260 |
| gcagcagcag ctcggatagt atcgacacac tctggacgct ggtcgtgtga tggactgttg | 4320 |
| ccgccacact tgctgccttg acctgtgaat atccctgccg cttttatcaa acagcctcag | 4380 |
| tgtgtttgat cttgtgtgta cgcgcttttg cgagttgcta gctgcttgtg ctatttgcga | 4440 |
| ataccacccc cagcatcccc ttccctcgtt tcatatcgct tgcatcccaa ccgcaactta | 4500 |
| tctacgctgt cctgctatcc ctcagcgctg ctcctgctcc tgctcactgc ccctcgcaca | 4560 |
| gccttggttt gggctccgcc tgtattctcc tggtactgca acctgtaaac cagcactgca | 4620 |
| atgctgatgc acgggaagta gtgggatggg aacacaaatg gaaagctt | 4668 |

<210> SEQ ID NO 117
<211> LENGTH: 4656
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

| | |
|---|---|
| ggtacccgcc tgcaacgcaa gggcagccac agccgctccc acccgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg ggcatgccac agcacgggca ccggggagtg | 420 |
| gaatggcacc accaagtgtg tgcgagccag catcgccgcc tggctgtttc agctacaacg | 480 |
| gcaggagtca tccaacgtaa ccatgagctg atcaacactg caatcatcgg gcgggcgtga | 540 |
| tgcaagcatg cctggcgaag acacatggtg tgcggatgct gccggctgct gcctgctgcg | 600 |
| cacgccgttg agttggcagc aggctcagcc atgcactgga tggcagctgg gctgccactg | 660 |
| caatgtggtg gataggatgc aagtggagcg aataccaaac cctctggctg cttgctgggt | 720 |
| tgcatggcat cgcaccatca gcaggagcgc atgcgaaggg actggcccca tgcacgccat | 780 |
| gccaaaccgg agcgcaccga gtgtccacac tgtcaccagg cccgcaagct tgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccacccttc ttgcggggtc gcgccccagc cagcggtgat gcgctgatcc caaacgagtt | 1020 |

-continued

```
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttgggtggg gcggccggct gtttcttteg tgttgcaaaa    1200 cgcgccagct cagcaacctg tcccgtgggt cccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc     1380 ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc     1680 catcatggcc gacgccatgc gccgcctgca caccctggac cccgccacct gccccttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct     1860 gaaggcccgc atgcccgacg gcgaggacct ggtggtgacc cacggcgacg cctgcctgcc    1920
caacatcatg gtggagaacg gccgcttctc cggcttcatc gactgcggcc gcctgggcgt    1980
ggccgaccgc taccaggaca tcgccctggc cacccgcgac atcgccgagg agctgggcgg    2040
cgagtgggcc gaccgcttcc tggtgctgta cggcatcgcc gccccccgact cccagcgcat    2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc cccgattgc     2940 aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggct tccgcggcat tcaccatgtc ggcgtgcccc    3120
gcgatgactg gcagggcccc tggggcacgt cgctccggac ggccagtcgc cacccgcctg    3180 aggggggcgcg ccccgactg gagccgcctg ctgaccgcca tcaccaccgt gttcgtgaag    3240
tccaagcgcc ccgacatgca cgaccgcaag tccaagcgcc ccgacatgct ggtggacagc    3300
ttcggcctgg agtccaccgt gcaggacggc ctggtgttcc gccagtcctt ctccatccgc    3360
```

| | |
|---|---|
| tcctacgaga tcggcaccga ccgcaccgcc agcatcgaga ccctgatgaa ccacctgcag | 3420 |
| gagacctccc tgaaccactg caagagcacc ggcatcctgc tggacggctt cggccgcacc | 3480 |
| ctggagatgt gcaagcgcga cctgatctgg gtggtgatca agatgcagat caaggtgaac | 3540 |
| cgctaccccg cctggggcga caccgtggag atcaacaccc gcttcagccg cctgggcaag | 3600 |
| atcggcatgg gccgcgactg gctgatctcc gactgcaaca ccggcgagat cctggtgcgc | 3660 |
| gccaccagcg cctacgccat gatgaaccag aagacccgcc gcctgtccaa gctgccctac | 3720 |
| gaggtgcacc aggagatcgt gcccctgttc gtggacagcc ccgtgatcga ggactccgac | 3780 |
| ctgaaggtgc acaagttcaa ggtgaagacc ggcgacagca tccagaaggg cctgaccccc | 3840 |
| ggctggaacg acctggacgt gaaccagcac gtgtccaacg tgaagtacat cggctggatc | 3900 |
| ctggagagca tgcccaccga ggtgctggag acccaggagc tgtgctccct ggccctggag | 3960 |
| taccgccgcg agtgcggccg cgactccgtg ctggagagct gaccgccat ggaccccagc | 4020 |
| aaggtgggcg tgcgctccca gtaccagcac ctgctgcgcc tggaggacgg caccgccatc | 4080 |
| gtgaacggcg ccaccgagtg gcgccccaag aacgccggcg ccaacggcgc catctccacc | 4140 |
| ggcaagacca gcaacggcaa ctccgtgtcc atggactaca aggaccacga cggcgactac | 4200 |
| aaggaccacg acatcgacta caaggacgac gacgacaagt gactcgaggc agcagcagct | 4260 |
| cggatagtat cgacacactc tggacgctgg tcgtgtgatg gactgttgcc gccacacttg | 4320 |
| ctgccttgac ctgtgaatat ccctgccgct tttatcaaac agcctcagtg tgtttgatct | 4380 |
| tgtgtgtacg cgcttttgcg agttgctagc tgcttgtgct atttgcgaat accaccccca | 4440 |
| gcatccccctt ccctcgtttc atatcgcttg catcccaacc gcaacttatc tacgctgtcc | 4500 |
| tgctatccct cagcgctgct cctgctcctg ctcactgccc ctcgcacagc cttggtttgg | 4560 |
| gctccgcctg tattctcctg gtactgcaac ctgtaaacca gcactgcaat gctgatgcac | 4620 |
| gggaagtagt gggatgggaa cacaaatgga aagctt | 4656 |

<210> SEQ ID NO 118
<211> LENGTH: 4721
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

| | |
|---|---|
| ggtacccgcc tgcaacgcaa gggcagccac agccgctccc acccgccgct gaaccgacac | 60 |
| gtgcttgggc gcctgccgcc tgcctgccgc atgcttgtgc tggtgaggct gggcagtgct | 120 |
| gccatgctga ttgaggcttg gttcatcggg tggaagctta tgtgtgtgct gggcttgcat | 180 |
| gccgggcaat gcgcatggtg gcaagagggc ggcagcactt gctggagctg ccgcggtgcc | 240 |
| tccaggtggt tcaatcgcgg cagccagagg gatttcagat gatcgcgcgt acaggttgag | 300 |
| cagcagtgtc agcaaaggta gcagtttgcc agaatgatcg gttcagctgt taatcaatgc | 360 |
| cagcaagaga aggggtcaag tgcaaacacg ggcatgccac agcacgggca ccggggagtg | 420 |
| gaatggcacc accaagtgtg tgcgagccag catcgccgcc tggctgtttc agctacaacg | 480 |
| gcaggagtca tccaacgtaa ccatgagctg atcaacactc caatcatcgg gcgggcgtga | 540 |
| tgcaagcatg cctggcgaag acacatggtg tgcggatgct gccggctgct gcctgctgcg | 600 |
| cacgccgttg agttggcagc aggctcagcc atgcactgga tggcagctgg gctgccactg | 660 |
| caatgtggtg gataggatgc aagtggagcg aataccaaac cctctggctg cttgctgggt | 720 |

-continued

| | |
|---|---|
| tgcatggcat cgcaccatca gcaggagcgc atgcgaaggg actggcccca tgcacgccat | 780 |
| gccaaaccgg agcgcaccga gtgtccacac tgtcaccagg cccgcaagct ttgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccacccttc ttgcggggtc gcgccccagc cagcggtgat gcgctgatcc caaacgagtt | 1020 |
| cacattcatt tgcatgcctg gagaagcgag gctggggcct ttgggctggt gcagcccgca | 1080 |
| atggaatgcg ggaccgccag gctagcagca aaggcgcctc ccctactccg catcgatgtt | 1140 |
| ccatagtgca ttggactgca tttgggtggg cggccggct gtttcttcg tgttgcaaaa | 1200 |
| cgcgccagct cagcaacctg tcccgtgggt cccccgtgcc gatgaaatcg tgtgcacgcc | 1260 |
| gatcagctga ttcccggct cgcgaagtag gcgccctcct ttctgctcgc cctctctccg | 1320 |
| tcccgcctct agaatatcaa tgatcgagca ggacggcctc cacgccggct cccccgccgc | 1380 |
| ctgggtggag cgcctgttcg gctacgactg ggcccagcag accatcggct gctccgacgc | 1440 |
| cgccgtgttc cgcctgtccg cccagggccg ccccgtgctg ttcgtgaaga ccgacctgtc | 1500 |
| cggcgccctg aacgagctgc aggacgaggc cgcccgcctg tcctggctgg ccaccaccgg | 1560 |
| cgtgccctgc gccgccgtgc tggacgtggt gaccgaggcc ggccgcgact ggctgctgct | 1620 |
| gggcgaggtg cccggccagg acctgctgtc ctcccacctg gccccgccg agaaggtgtc | 1680 |
| catcatggcc gacgccatgc gccgcctgca caccctggac cccgccacct gccccttcga | 1740 |
| ccaccaggcc aagcaccgca tcgagcgcgc ccgcacccgc atggaggccg gcctggtgga | 1800 |
| ccaggacgac ctggacgagg agcaccaggg cctggccccc gccgagctgt cgcccgcct | 1860 |
| gaaggcccgc atgcccgacg gcgaggacct ggtggtgacc cacggcgacg cctgcctgcc | 1920 |
| caacatcatg gtggagaacg gccgcttctc cggcttcatc gactgcggcc gctgggcgt | 1980 |
| ggccgaccgc taccaggaca tcgccctggc cacccgcgac atcgccgagg agctgggcgg | 2040 |
| cgagtgggcc gaccgcttcc tggtgctgta cggcatcgcc gccccgact cccagcgcat | 2100 |
| cgccttctac cgcctgctgg acgagttctt ctgacaattg gcagcagcag ctcggatagt | 2160 |
| atcgacacac tctggacgct ggtcgtgtga tggactgttg ccgccacact tgctgccttg | 2220 |
| acctgtgaat atccctgccg cttttatcaa acagcctcag tgtgtttgat cttgtgtgta | 2280 |
| cgcgcttttg cgagttgcta gctgcttgtg ctatttgcga ataccacccc cagcatcccc | 2340 |
| ttccctcgtt tcatatcgct tgcatcccaa ccgcaactta tctacgctgt cctgctatcc | 2400 |
| ctcagcgctg ctcctgctcc tgctcactgc ccctcgcaca gccttggttt gggctccgcc | 2460 |
| tgtattctcc tggtactgca acctgtaaac cagcactgca atgctgatgc acgggaagta | 2520 |
| gtgggatggg aacacaaatg gaggatcccg cgtctcgaac agagcgcgca gaggaacgct | 2580 |
| gaaggtctcg cctctgtcgc acctcagcgc ggcatacacc acaataacca cctgacgaat | 2640 |
| gcgcttggtt cttcgtccat tagcgaagcg tccggttcac acacgtgcca cgttggcgag | 2700 |
| gtggcaggtg acaatgatcg gtggagctga tggtcgaaac gttcacagcc tagggatatc | 2760 |
| gaattccttt cttgcgctat gacacttcca gcaaaggta gggcgggctg cgagacggct | 2820 |
| tcccggcgct gcatgcaaca ccgatgatgc ttcgaccccc cgaagctcct tcggggctgc | 2880 |
| atgggcgctc cgatgccgct ccagggcgag cgctgtttaa atagccaggc cccgattgc | 2940 |
| aaagacatta tagcgagcta ccaaagccat attcaaacac ctagatcact accacttcta | 3000 |
| cacaggccac tcgagcttgt gatcgcactc cgctaagggg gcgcctcttc ctcttcgttt | 3060 |
| cagtcacaac ccgcaaacgg cgcgccatgg ccaccaccag cctggcctcc gccttctgct | 3120 |

```
ccatgaaggc cgtgatgctg gcccgcgacg gccgcggcat gaagcccgc agctccgacc   3180 tgcagctgcg cgccggcaac gcccccacct ccctgaagat gatcaacggc accaagttca   3240
gctacaccga gagcctgaag cgcctgcccg actggtccat gctgttcgcc gtgatcacca   3300
ccatcttcag cgccgccgag aagcagtgga ccaacctgga gtggaagccc aagcccaagc   3360
tgccccagct gctggacgac cacttcggcc tgcacggcct ggtgttccgc cgcaccttcg   3420
ccatccgctc ctacgaggtg gcccccgacc gcagcacctc catcctggcc gtgatgaacc   3480
acatgcagga ggccaccctg aaccacgcca gagcgtggg catcctgggc gacggcttcg   3540
gcaccaccct ggagatgtcc aagcgcgacc tgatgtgggt ggtgcgccgc acccacgtgg   3600
ccgtggagcg ctaccccacc tggggcgaca ccgtggaggt ggagtgctgg atcggcgcca   3660
gcggcaacaa cggcatgcgc cgcgacttcc tggtgcgcga ctgcaagacc ggcgagatcc   3720
tgacccgctg cacctccctg agcgtgctga tgaacacccg caccgccgc ctgagcacca   3780 tccccgacga ggtgcgcggc gagatcggcc ccgccttcat cgacaacgtg gccgtgaagg   3840
acgacgagat caagaagctg cagaagctga acgactccac cgccgactac atccagggcg   3900
gcctgacccc ccgctggaac gacctggacg tgaaccagca cgtgaacaac ctgaagtacg   3960
tggcctgggt gttcgagacc gtgcccgaca gcatcttcga gtcccaccac atcagctcct   4020
tcaccctgga gtaccgccgc gagtgcaccc gcgactccgt gctgcgcagc ctgaccaccg   4080
tgagcggcgg cagctccgag gccggcctgg tgtgcgacca cctgctgcag ctggagggcg   4140
gcagcgaggg gctgcgcgcc cgcaccgagt ggcgcccaa gctgaccgac tccttccgcg   4200
gcatcagcgt gatccccgcc gagccccgcg tgatggacta caaggaccac gacggcgact   4260
acaaggacca cgacatcgac tacaaggacg acgacgacaa gtgatgactc gaggcagcag   4320
cagctcggat agtatcgaca cactctggac gctggtcgtg tgatggactg ttgccgccac   4380
acttgctgcc ttgacctgtg aatatccctg ccgcttttat caaacagcct cagtgtgttt   4440
gatcttgtgt gtacgcgctt ttgcgagttg ctagctgctt gtgctatttg cgaataccac   4500
ccccagcatc cccttccctc gtttcatatc gcttgcatcc caaccgcaac ttatctacgc   4560
tgtcctgcta tccctcagcg ctgctcctgc tcctgctcac tgcccctcgc acagccttgg   4620
tttgggctcc gcctgtattc tcctggtact gcaacctgta aaccagcact gcaatgctga   4680
tgcacgggaa gtagtgggat gggaacacaa atggaaagct t                       4721

<210> SEQ ID NO 119
<211> LENGTH: 4650
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
ggtacccgcc tgcaacgcaa gggcagccac agccgctccc accgccgct gaaccgacac     60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
```

| | |
|---|---|
| gaatggcacc accaagtgtg tgcgagccag catcgccgcc tggctgtttc agctacaacg | 480 |
| gcaggagtca tccaacgtaa ccatgagctg atcaacactg caatcatcgg cgggcgtga | 540 |
| tgcaagcatg cctggcgaag acacatggtg tgcggatgct gccggctgct gcctgctgcg | 600 |
| cacgccgttg agttggcagc aggctcagcc atgcactgga tggcagctgg gctgccactg | 660 |
| caatgtggtg gataggatgc aagtggagcg aataccaaac cctctggctg cttgctgggt | 720 |
| tgcatggcat cgcaccatca gcaggagcgc atgcgaaggg actggcccca tgcacgccat | 780 |
| gccaaaccgg agcgcaccga gtgtccacac tgtcaccagg cccgcaagct tgcagaacc | 840 |
| atgctcatgg acgcatgtag cgctgacgtc ccttgacggc gctcctctcg ggtgtgggaa | 900 |
| acgcaatgca gcacaggcag cagaggcggc ggcagcagag cggcggcagc agcggcgggg | 960 |
| gccacccttc ttgcggggtc gcgcccagc cagcggtgat gcgctgatcc caaacgagtt | 1020 |
| cacattcatt tgcatgcctg agaagcgag gctggggcct ttgggctggt gcagcccgca | 1080 |
| atggaatgcg ggaccgccag gctagcagca aggcgcctc ccctactccg catcgatgtt | 1140 |
| ccatagtgca ttggactgca tttgggtggg gcggccggct gtttctttcg tgttgcaaaa | 1200 |
| cgcgccagct cagcaacctg tcccgtgggt ccccgtgcc gatgaaatcg tgtgcacgcc | 1260 |
| gatcagctga ttgcccggct cgcgaagtag gcgccctcct ttctgctcgc cctctctccg | 1320 |
| tcccgcctct agaatatcaa tgatcgagca ggacggcctc cacgccggct ccccgccgc | 1380 |
| ctgggtggag cgcctgttcg gctacgactg ggcccagcag accatcggct gctccgacgc | 1440 |
| cgccgtgttc cgcctgtccg cccagggccg cccgtgctg ttcgtgaaga ccgacctgtc | 1500 |
| cggcgccctg aacgagctgc aggacgaggc cgcccgcctg tcctggctgg ccaccaccgg | 1560 |
| cgtgccctgc gccgccgtgc tggacgtggt gaccgaggcc ggccgcgact ggctgctgct | 1620 |
| gggcgaggtg cccggccagg acctgctgtc ctcccacctg gcccccgccg agaaggtgtc | 1680 |
| catcatggcc gacgccatgc gccgcctgca caccctggac cccgccacct gccccttcga | 1740 |
| ccaccaggcc aagcaccgca tcgagcgcgc ccgcacccgc atggaggccg gctggtgga | 1800 |
| ccaggacgac ctggacgagg agcaccaggg cctggccccc gccagctgt tcgcccgcct | 1860 |
| gaaggcccgc atgcccgacg gcgaggacct ggtggtgacc cacggcgacg cctgcctgcc | 1920 |
| caacatcatg gtggagaacg gccgcttctc cggcttcatc gactgcggcc gctgggcgt | 1980 |
| ggccgaccgc taccaggaca tcgccctggc cacccgcgac atcgccgagg agctgggcgg | 2040 |
| cgagtgggcc gaccgcttcc tggtgctgta cggcatcgcc gccccgact cccagcgcat | 2100 |
| cgccttctac cgcctgctgg acgagttctt ctgacaattg gcagcagcag ctcggatagt | 2160 |
| atcgacacac tctggacgct ggtcgtgtga tggactgttg ccgccacact tgctgccttg | 2220 |
| acctgtgaat atccctgccg cttttatcaa acagcctcag tgtgtttgat cttgtgtgta | 2280 |
| cgcgcttttg cgagttgcta gctgcttgtg ctatttgcga ataccacccc cagcatcccc | 2340 |
| ttccctcgtt tcatatcgct tgcatcccaa ccgcaactta tctacgctgt cctgctatcc | 2400 |
| ctcagcgctg ctcctgctcc tgctcactgc ccctcgcaca gccttggttt gggctccgcc | 2460 |
| tgtattctcc tggtactgca acctgtaaac cagcactgca atgctgatgc acggaagta | 2520 |
| gtgggatggg aacacaaatg gaggatcccg cgtctcgaac agagcgcgca gaggaacgct | 2580 |
| gaaggtctcg cctctgtcgc acctcagcgc ggcatacacc acaataacca cctgacgaat | 2640 |
| gcgcttggtt cttcgtccat tagcgaagcg tccggttcac acacgtgcca cgttggcgag | 2700 |
| gtggcaggtg acaatgatcg gtggagctga tggtcgaaac gttcacagcc tagggatatc | 2760 |

-continued

```
gaattcctttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc cccgattgc     2940 aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatgacg ttcggggtcg ccctcccggc catgggccgc    3120
ggtgtctccc ttccccggcc cagggtcgcg gtgcgcgccc agtcggcgag tcaggttttg    3180
gagagcgggc gcgccccga ctggtccatg ctgttcgccg tgatcaccac catcttcagc     3240
gccgccgaga agcagtggac caacctggag tggaagccca agcccaagct gccccagctg    3300
ctggacgacc acttcggcct gcacggcctg tgttccgcc gcaccttcgc catccgctcc     3360
tacgaggtgg gccccgaccg cagcacctcc atcctggccg tgatgaacca catgcaggag    3420
gccaccctga accacgccaa gagcgtgggc atcctgggcg acggcttcgg caccaccctg    3480
gagatgtcca gcgcgacct gatgtgggtg gtgcgccgca cccacgtggc cgtggagcgc     3540
taccccacct ggggcgacac cgtggaggtg gagtgctgga tcggcgccag cggcaacaac    3600
ggcatgcgcc gcgacttcct ggtgcgcgac tgcaagaccg gcgagatcct gacccgctgc    3660
acctccctga gcgtgctgat gaacacccgc acccgccgcc tgagcaccat ccccgacgag    3720
gtgcgcggcg agatcggccc cgccttcatc gacaacgtgg ccgtgaagga cgacgagatc    3780
aagaagctgc agaagctgaa cgactccacc gccgactaca tccagggcgg cctgaccccc    3840
cgctggaacg acctggacgt gaaccagcac gtgaacaacc tgaagtacgt ggcctgggtg    3900
ttcgagaccg tgcccgacag catcttcgag tcccaccaca tcagctcctt caccctggag    3960
taccgccgcg agtgcacccg cgactccgtg ctgcgcagcc tgaccaccgt gagcggcggc    4020
agctccgagg ccggcctggt gtgcgaccac ctgctgcagc tggagggcgg cagcgaggtg    4080
ctgcgcgccc gcaccgagtg gcgccccaag ctgaccgact ccttccgcgg catcagcgtg    4140
atccccgccg agcccgcgt gatggactac aaggaccacg acggcgacta caaggaccac    4200
gacatcgact acaaggacga cgacgacaag tgatgactcg aggcagcagc agctcggata    4260
gtatcgacac actctggacg ctggtcgtgt gatggactgt tgccgccaca cttgctgcct    4320
tgacctgtga atatccctgc cgcttttatc aaacagcctc agtgtgtttg atcttgtgtg    4380
tacgcgcttt tgcgagttgc tagctgcttg tgctatttgc gaataccacc cccagcatcc    4440
ccttccctcg tttcatatcg cttgcatccc aaccgcaact tatctacgct gtcctgctat    4500
ccctcagcgc tgctcctgct cctgctcact gcccctcgca cagccttggt ttgggctccg    4560
cctgtattct cctggtactg caacctgtaa accagcactg caatgctgat gcacgggaag    4620
tagtgggatg ggaacacaaa tggaaagctt                                     4650
```

<210> SEQ ID NO 120
<211> LENGTH: 4653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

```
ggtacccgcc tgcaacgcaa gggcagccac agccgctccc accgccgct gaaccgacac       60 gtgcttgggc gcctgccgcc tgcctgccgc atgcttgtgc tggtgaggct gggcagtgct     120
```

```
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctggggcct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttcttccg tgttgcaaaa   1200
cgcgccagct cagcaacctg tcccgtgggt cccccgtgcc gatgaaatcg tgtgcacgcc   1260
gatcagctga ttgcccggct cgcgaagtag gcgccctcct ttctgctcgc cctctctccg   1320
tcccgcctct agaatatcaa tgatcgagca ggacggcctc cacgccggct ccccgccgc    1380 ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gcccccgccg agaaggtgtc   1680
catcatggcc gacgccatgc gccgcctgca cacctggac cccgccacct gccccttcga    1740
ccaccaggcc aagcaccgca tcgagcgcgc ccgcacccgc atggaggccg gctggtggga   1800
ccaggacgac ctggacgagg agcaccaggg cctggccccc gccgagctgt cgcccgcct    1860 gaaggcccgc atgcccgacg gcgaggacct ggtggtgacc cacggcgacg cctgcctgcc   1920
caacatcatg gtggagaacg gccgcttctc cggcttcatc gactgcggcc gcctgggcgt   1980
ggccgaccgc taccaggaca tcgccctggc cacccgcgac atcgccgagg agctgggcgg   2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt   2160
atcgacacac tctggacgct ggtcgtgtga tggactgttg ccgccacact gctgccttg    2220 acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
```

```
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc cccgattgc     2940 aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggct atcaagacga acaggcagcc tgtggagaag    3120
cctccgttca cgatcgggac gctgcgcaag gccatccccg cgcactgttt cgagcgctcg    3180
gcgcttcgtg ggcgcgcccc cgactggtcc atgctgttcg ccgtgatcac caccatcttc    3240
agcgccgccg agaagcagtg gaccaacctg gagtggaagc ccaagcccaa gctgccccag    3300
ctgctggacg accacttcgg cctgcacggc ctggtgttcc gccgcacctt cgccatccgc    3360
tcctacgagg tgggccccga ccgcagcacc tccatcctgg ccgtgatgaa ccacatgcag    3420
gaggccaccc tgaaccacgc caagagcgtg ggcatcctgg cgacggcttc ggcaccacc     3480 ctggagatgt ccaagcgcga cctgatgtgg gtggtgcgcc gcacccacgt ggccgtggag    3540
cgctacccca cctggggcga caccgtggag gtggagtgct ggatcggcgc cagcggcaac    3600
aacggcatgc gccgcgactt cctggtgcgc gactgcaaga ccggcgagat cctgacccgc    3660
tgcacctccc tgagcgtgct gatgaacacc cgcaccccgcc gcctgagcac catcccgac    3720 gaggtgcgcg cgagatcgg ccccgccttc atcgacaacg tggccgtgaa ggacgacgag     3780
atcaagaagc tgcagaagct gaacgactcc accgccgact acatccaggg cggcctgacc    3840
ccccgctgga acgacctgga cgtgaaccag cacgtgaaca acctgaagta cgtggcctgg    3900
gtgttcgaga ccgtgcccga cagcatcttc gagtcccacc acatcagctc cttcaccctg    3960
gagtaccgcc gcgagtgcac ccgcgactcc gtgctgcgca gcctgaccac cgtgagcggc    4020
ggcagctccg aggccggcct ggtgtgcgac cacctgctgc agctggaggg cggcagcgag    4080
gtgctgcgcg cccgcaccga gtggcgcccc aagctgaccg actccttccg cggcatcagc    4140
gtgatccccg ccgagcccg cgtgatggac tacaaggacc acgacggcga ctacaaggac     4200
cacgacatcg actacaagga cgacgacgac aagtgatgac tcgaggcagc agcagctcgg    4260
atagtatcga cacactctgg acgctggtcg tgtgatggac tgttgccgcc acacttgctg    4320
ccttgacctg tgaatatccc tgccgctttt atcaaacagc ctcagtgtgt ttgatcttgt    4380
gtgtacgcgc ttttgcgagt tgctagctgc ttgtgctatt tgcgaatacc acccccagca    4440
tccccttccc tcgtttcata tcgcttgcat cccaaccgca acttatctac gctgtcctgc    4500
tatccctcag cgctgctcct gctcctgctc actgcccctc gcacagcctt ggtttgggct    4560
ccgcctgtat tctcctggta ctgcaacctg taaaccagca ctgcaatgct gatgcacggg    4620
aagtagtggg atgggaacac aaatggaaag ctt                                 4653
```

<210> SEQ ID NO 121  
<211> LENGTH: 4653  
<212> TYPE: DNA  
<213> ORGANISM: Artificial Sequence  
<220> FEATURE:

<223> OTHER INFORMATION: Description of Artificial Sequence: Synthetic polynucleotide

<400> SEQUENCE: 121

```
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga agggtcaag tgcaaacacg gcatgccac agcacgggca ccggggagtg     420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
caatgtggtg gataggatgc aagtggagcg aataccaaac cctctggctg cttgctgggt     720
tgcatggcat cgcaccatca gcaggagcgc atgcgaaggg actggcccca tgcacgccat     780
gccaaaccgg agcgcaccga gtgtccacac tgtcaccagg cccgcaagct ttgcagaacc     840
atgctcatgg acgcatgtag cgctgacgtc ccttgacggc gctcctctcg ggtgtgggaa     900
acgcaatgca gcacaggcag cagaggcggc ggcagcagag cggcggcagc agcggcgggg     960
gccaccttc ttgcggggtc gcgccccagc cagcggtgat gcgctgatcc caaacgagtt    1020
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttgggtggg gcggccggct gtttcttcg tgttgcaaaa    1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc    1380
ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gccccgccg agaaggtgtc    1680
catcatggcc gacgccatgc gccgcctgca caccctggac cccgccacct gcccccttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gctgggcgt    1980
ggccgaccgc taccaggaca tcgccctggc cacccgcgac atcgccgagg agctgggcgg    2040
cgagtgggcc gaccgcttcc tggtgctgta cggcatcgcc gccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
```

```
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggcc accgcatcca ctttctcggc gttcaatgcc    3120
cgctgcggcg acctgcgtcg ctcggcgggc tccgggcccc ggcgcccagc gaggcccctc    3180
cccgtgcgcg ggcgcgcccc cgactggtcc atgctgttcg ccgtgatcac caccatcttc    3240
agcgccgccg agaagcagtg gaccaacctg gagtggaagc ccaagcccaa gctgccccag    3300
ctgctggacg accacttcgg cctgcacggc ctggtgttcc gccgcacctt cgccatccgc    3360
tcctacgagg tgggccccga ccgcagcacc tccatcctgg ccgtgatgaa ccacatgcag    3420
gaggccaccc tgaaccacgc caagagcgtg ggcatcctgg gcgacggctt cggcaccacc    3480
ctggagatgt ccaagcgcga cctgatgtgg gtggtgcgcc gcacccacgt ggccgtggag    3540
cgctacccca cctggggcga caccgtggag gtggagtgct ggatcggcgc cagcggcaac    3600
aacggcatgc gccgcgactt cctggtgcgc gactgcaaga ccggcgagat cctgacccgc    3660
tgcacctccc tgagcgtgct gatgaacacc cgcaccgcc gcctgagcac catccccgac    3720
gaggtgcgcg gcgagatcgg ccccgccttc atcgacaacg tggccgtgaa ggacgacgag    3780
atcaagaagc tgcagaagct gaacgactcc accgccgact acatccaggg cggcctgacc    3840
ccccgctgga acgacctgga cgtgaaccag cacgtgaaca acctgaagta cgtggcctgg    3900
gtgttcgaga ccgtgcccga cagcatcttc gagtcccacc acatcagctc cttcaccctg    3960
gagtaccgcc gcgagtgcac ccgcgactcc gtgctgcgca gcctgaccac cgtgagcggc    4020
ggcagctccg aggccggcct ggtgtgcgac cacctgctgc agctggaggg cggcagcgag    4080
gtgctgcgcg cccgcaccga gtggcgcccc aagctgaccg actccttccg cggcatcagc    4140
gtgatccccg ccgagcccg cgtgatggac tacaaggacc acgacggcga ctacaaggac    4200
cacgacatcg actacaagga cgacgacgac aagtgatgac tcgaggcagc agcagctcgg    4260
atagtatcga cacactctgg acgctggtcg tgtgatggac tgttgccgcc acacttgctg    4320
ccttgacctg tgaatatccc tgccgctttt atcaaacagc ctcagtgtgt ttgatcttgt    4380
gtgtacgcgc ttttgcgagt tgctagctgc ttgtgctatt tgcgaatacc accccagca    4440
tcccccttcc ctcgtttcata tcgcttgcat cccaaccgca acttatctac gctgtcctgc    4500
tatccctcag cgctgctcct gctcctgctc actgccctc gcagagcctt ggtttgggct    4560
ccgcctgtat tctcctggta ctgcaacctg taaaccagca ctgcaatgct gatgcacggg    4620
```

```
aagtagtggg atgggaacac aaatggaaag ctt                                 4653
```

<210> SEQ ID NO 122
<211> LENGTH: 4647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
ggtacccgcc tgcaacgcaa gggcagccac agccgctccc acccgccgct gaaccgacac     60
gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga agggtcaag tgcaaacacg ggcatgccac agcacgggca ccggggagtg     420
gaatggcacc accaagtgtg tgcgagcag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctgggggcct ttgggctggt gcagcccgca   1080
atggaatgcg ggaccgccag gctagcagca aaggcgcctc ccctactccg catcgatgtt   1140
ccatagtgca ttggactgca tttggtgggg gcggccggtc gtttctttcg tgttgcaaaa   1200
cgcgccagct cagcaacctg tcccgtgggt cccccgtgcc gatgaaatcg tgtgcacgcc   1260
gatcagctga ttgcccggct cgcgaagtag gcgcccctcct ttctgctcgc cctctctccg   1320
tcccgcctct agaatatcaa tgatcgagca ggacggcctc cacgccggct cccccgccgc   1380
ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gccccgccg agaaggtgtc    1680
catcatggcc gacgccatgc gccgcctgca caccctggac cccgccacct gccccttcga   1740
ccaccaggcc aagcaccgca tcgagcgcgc ccgcacccgc atggaggccg gctggtgga    1800
ccaggacgac ctggacgagg agcaccaggg cctggcccca gccgagctgt tcgcccgcct   1860
gaaggcccgc atgcccgacg gcgaggacct ggtggtgacc cacggcgacg cctgcctgcc   1920
caacatcatg gtggagaacg gccgcttctc cggcttcatc gactgcgggc gctgggcgt    1980
```

```
ggccgaccgc taccaggaca tcgccctggc caccgcgac atcgccgagg agctgggcgg   2040
cgagtgggcc gaccgcttcc tggtgctgta cggcatcgcc gccccgact cccagcgcat   2100 cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgtttaa atagccaggc ccccgattgc   2940
aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatggct tccgcggcat tcaccatgtc ggcgtgcccc   3120
gcgatgactg gcagggcccc tggggcacgt cgctccggac ggccagtcgc cacccgcctg   3180 aggggcgcg ccccgactg gtccatgctg ttcgccgtga tcaccaccat cttcagcgcc   3240
gccgagaagc agtggaccaa cctggagtgg aagcccaagc caagctgcc ccagctgctg   3300 gacgaccact tcggcctgca cggcctggtg ttccgccgca ccttcgccat ccgctcctac   3360
gaggtgggcc ccgaccgcag cacctccatc ctggccgtga tgaaccacat gcaggaggcc   3420
accctgaacc acgccaagag cgtgggcatc ctgggcgacg gcttcggcac caccctggag   3480
atgtccaagc gcgacctgat gtgggtggtg cgccgcaccc acgtggccgt ggagcgctac   3540
cccacctggg gcgacaccgt ggaggtggag tgctggatcg cgccagcgg caacaacggc   3600 atgcgccgcg acttcctggt gcgcgactgc aagaccggcg agatcctgac ccgctgcacc   3660
tccctgagcg tgctgatgaa cacccgcacc cgccgcctga gcaccatccc cgacgaggtg   3720
cgcggcgaga tcggccccgc cttcatcgac aacgtggccg tgaaggacga cgagatcaag   3780
aagctgcaga agctgaacga ctccaccgcc gactacatcc agggcggcct gaccccccgc   3840
tggaacgacc tggacgtgaa ccagcacgtg aacaacctga gtacgtggc ctgggtgttc   3900 gagaccgtgc ccgacagcat cttcgagtcc caccacatca gctccttcac cctggagtac   3960
cgccgcgagt gcacccgcga ctccgtgctg cgcagcctga ccaccgtgag cggcggcagc   4020
tccgaggccg gctggtgtg cgaccacctg ctgcagctgg agggcggcag cgaggtgctg   4080
cgcgcccgca ccgagtggcg ccccaagctg accgactcct tccgcggcat cagcgtgatc   4140
cccgccgagc ccgcgtgat ggactacaag gaccacgacg gcgactacaa ggaccacgac   4200
atcgactaca aggacgacga cgacaagtga tgactcgagg cagcagcagc tcggatagta   4260
tcgacacact ctggacgctg gtcgtgtgat ggactgttgc cgccacactt gctgccttga   4320
```

```
cctgtgaata tccctgccgc ttttatcaaa cagcctcagt gtgtttgatc ttgtgtgtac    4380
gcgcttttgc gagttgctag ctgcttgtgc tatttgcgaa taccacccc agcatcccct     4440 tccctcgttt catatcgctt gcatcccaac cgcaacttat ctacgctgtc ctgctatccc    4500
tcagcgctgc tcctgctcct gctcactgcc cctcgcacag ccttggtttg gctccgcct     4560 gtattctcct ggtactgcaa cctgtaaacc agcactgcaa tgctgatgca cgggaagtag    4620
tgggatggga acacaaatgg aaagctt                                        4647
```

<210> SEQ ID NO 123
<211> LENGTH: 4721
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgcccagc cagcggtgat gcgctgatcc caaacgagtt    1020
cacattcatt tgcatgcctg gagaagcgag gctggggcct ttgggctggt gcagcccgca    1080
atggaatgcg ggaccgccag gctagcagca aggcgcctc ccctactccg catcgatgtt     1140
ccatagtgca ttggactgca tttggtgggg cggccggct gtttctttcg tgttgcaaaa     1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc    1380 ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
```

```
catcatggcc gacgccatgc gccgcctgca caccctggac cccgccacct gccccttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860
gaaggcccgc atgcccgacg gcgaggacct ggtggtgacc cacggcgacg cctgcctgcc    1920
caacatcatg gtggagaacg gccgcttctc cggcttcatc gactgcggcc gcctgggcgt    1980
ggccgaccgc taccaggaca tcgccctggc caccgcgac atcgccgagg agctgggcgg    2040
cgagtgggcc gaccgcttcc tggtgctgta cggcatcgcc gcccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgacccc cgaagctcct tcggggctgc    2880
atgggcgctc cgatgccgct ccagggcgag cgctgtttaa atagccaggc cccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacgg cgcgccatgg ccaccacctc cctggcctcc gccttctgca    3120
gcatgaaggc cgtgatgctg gcccgcgacg gccgcggcat gaagcccgc tccagcgacc    3180
tgcagctgcg cgccggcaac gcccagacct ccctgaagat gatcaacggc accaagttct    3240
cctacaccga gagcctgaag aagctgcccg actggtccat gctgttcgcc gtgatcacca    3300
ccatcttctc cgccgccgag aagcagtgga ccaacctgga gtggaagccc aagcccaacc    3360
cccccagct gctggacgac cacttcggcc cccacgcct ggtgttccgc cgcaccttcg    3420
ccatccgcag ctacgaggtg ggccccgacc gctccaccag catcgtggcc gtgatgaacc    3480
acctgcagga ggccgccctg aaccacgcca agtccgtggg catcctgggc gacggcttcg    3540
gcaccaccct ggagatgtcc aagcgcgacc tgatctgggt ggtgaagcgc acccacgtgg    3600
ccgtggagcg ctaccccgcc tggggcgaca ccgtggaggt ggagtgctgg gtgggcgcct    3660
ccggcaacaa cggccgccgc cacgacttcc tggtgcgcga ctgcaagacc ggcgagatcc    3720
tgacccgctg cacctccctg agcgtgatga tgaacacccg cacccgccgc ctgagcaaga    3780
tccccgagga ggtgcgcggc gagatcggcc ccgccttcat cgacaacgtg gccgtgaagg    3840
acgaggagat caagaagccc cagaagctga acgactccac cgccgactac atccagggcg    3900
gcctgacccc ccgctggaac gacctggaca tcaaccagca cgtgaacaac atcaagtacg    3960
tggactggat cctggagacc gtgcccgaca gcatcttcga gagccaccac atctcctcct    4020
tcaccatcga gtaccgccgc gagtgcacca tggacagcgt gctgcagtcc ctgaccaccg    4080
```

```
tgagcggcgg ctcctccgag gccggcctgg tgtgcgagca cctgctgcag ctggagggcg    4140
gcagcgaggt gctgcgcgcc aagaccgagt ggcgccccaa gctgaccgac tccttccgcg    4200
gcatcagcgt gatccccgcc gagtccagcg tgatggacta caaggaccac gacggcgact    4260
acaaggacca cgacatcgac tacaaggacg acgacgacaa gtgatgactc gaggcagcag    4320
cagctcggat agtatcgaca cactctggac gctggtcgtg tgatggactg ttgccgccac    4380
acttgctgcc ttgacctgtg aatatccctg ccgcttttat caaacagcct cagtgtgttt    4440
gatcttgtgt gtacgcgctt ttgcgagttg ctagctgctt gtgctatttg cgaataccac    4500
ccccagcatc cccttccctc gtttcatatc gcttgcatcc caaccgcaac ttatctacgc    4560
tgtcctgcta tccctcagcg ctgctcctgc tcctgctcac tgcccctcgc acagccttgg    4620
tttgggctcc gcctgtattc tcctggtact gcaacctgta aaccagcact gcaatgctga    4680
tgcacgggaa gtagtgggat gggaacacaa atggaaagct t                       4721

<210> SEQ ID NO 124
<211> LENGTH: 4650
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg agaagcgag gctggggcct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttcttcg tgttgcaaaa   1200 cgcgccagct cagcaacctg tccgtgggt ccccgtgcc gatgaaatcg tgtgcacgcc   1260
gatcagctga ttgcccggct cgcgaagtag gcgccctcct ttctgctcgc cctctctccg   1320
tcccgcctct agaatatcaa tgatcgagca ggacggcctc cacgccggct ccccgccgc   1380
```

```
ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gcccccgccg agaaggtgtc   1680
catcatggcc gacgccatgc gccgcctgca caccctggac cccgccacct gccccttcga   1740
ccaccaggcc aagcaccgca tcgagcgcgc ccgcacccgc atggaggccg gcctggtgga   1800
ccaggacgac ctggacgagg agcaccaggg cctggccccc gccgagctgt cgcccgcct   1860
gaaggcccgc atgcccgacg gcgaggacct ggtggtgacc cacggcgacg cctgcctgcc   1920
caacatcatg gtggagaacg gccgcttctc cggcttcatc gactgcggcc gcctgggcgt   1980
ggccgaccgc taccaggaca tcgccctggc cacccgcgac atcgccgagg agctgggcgg   2040
cgagtgggcc gaccgcttcc tggtgctgta cggcatcgcc gccccgact cccagcgcat   2100
cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
gtggcaggtg acaatgatcg gtggagctga tggtcgaaac gttcacagcc tagggatatc   2760
gaattccttt cttgcgctat gacacttcca gcaaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgtttaa atagccaggc ccccgattgc   2940
aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatgacg ttcggggtcg ccctcccggc catgggccgc   3120
ggtgtctccc ttccccggcc cagggtcgcg gtgcgcgccc agtcggcgag tcaggttttg   3180
gagagcgggc gcgcccccga ctggtccatg ctgttcgccg tgatcaccac catcttctcc   3240
gccgccgaga agcagtggac caacctggag tggaagccca gcccaacccc ccccagctg   3300
ctggacgacc acttcggccc ccacggcctg gtgttccgcc gcaccttcgc catccgcagc   3360
tacgaggtgg ccccgaccg ctccaccagc atcgtggccg tgatgaacca cctgcaggag   3420
gccgccctga ccacgccaa gtccgtgggc atcctgggcg acggcttcgg caccaccctg   3480
gagatgtcca agcgcgacct gatctgggtg gtgaagcgca cccacgtggc cgtggagcgc   3540
taccccgcct ggggcgacac cgtggaggtg gagtgctggg tgggcgcctc cggcaacaac   3600
ggccgccgcc acgacttcct ggtgcgcgac tgcaagaccg gcgagatcct gacccgctgc   3660
acctccctga gcgtgatgat gaacacccgc accgccgcc tgagcaagat ccccgaggag   3720
```

```
gtgcgcggcg agatcggccc cgccttcatc gacaacgtgg ccgtgaagga cgaggagatc    3780
aagaagcccc agaagctgaa cgactccacc gccgactaca tccagggcgg cctgacccc     3840 cgctggaacg acctggacat caaccagcac gtgaacaaca tcaagtacgt ggactggatc    3900
ctggagaccg tgcccgacag catcttcgag agccaccaca tctcctcctt caccatcgag    3960
taccgccgcg agtgcaccat ggacagcgtg ctgcagtccc tgaccaccgt gagcggcggc    4020
tcctccgagg ccggcctggt gtgcgagcac ctgctgcagc tggagggcgg cagcgaggtg    4080
ctgcgcgcca agaccgagtg cgcgcccaag ctgaccgact ccttccgcgg catcagcgtg    4140
atccccgccg agtccagcgt gatggactac aaggaccacg acggcgacta caaggaccac    4200
gacatcgact acaaggacga cgacgacaag tgatgactcg aggcagcagc agctcggata    4260
gtatcgacac actctggacg ctggtcgtgt gatggactgt tgccgccaca cttgctgcct    4320
tgacctgtga atatccctgc cgcttttatc aaacagcctc agtgtgtttg atcttgtgtg    4380
tacgcgcttt tgcgagttgc tagctgcttg tgctatttgc gaataccacc cccagcatcc    4440
ccttccctcg tttcatatcg cttgcatccc aaccgcaact tatctacgct gtcctgctat    4500
ccctcagcgc tgctcctgct cctgctcact gcccctcgca cagccttggt ttgggctccg    4560
cctgtattct cctggtactg caacctgtaa accagcactg caatgctgat gcacgggaag    4620
tagtgggatg ggaacacaaa tggaaagctt                                    4650
```

<210> SEQ ID NO 125
<211> LENGTH: 4653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

```
ggtacccgcc tgcaacgcaa gggcagccac agccgctccc accgccgct gaaccgacac      60 gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggacg aataccaaac cctctggctg cttgctgggt     720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctggggcct ttgggctggt gcagcccgca   1080
```

-continued

| | |
|---|---|
| atggaatgcg ggaccgccag gctagcagca aaggcgcctc ccctactccg catcgatgtt | 1140 |
| ccatagtgca ttggactgca tttgggtggg gcggccggct gtttcttccg tgttgcaaaa | 1200 |
| cgcgccagct cagcaacctg tcccgtgggt ccccgtgcc gatgaaatcg tgtgcacgcc | 1260 |
| gatcagctga ttcccggct cgcgaagtag gcgccctcct ttctgctcgc cctctctccg | 1320 |
| tcccgcctct agaatatcaa tgatcgagca ggacggcctc cacgccggct ccccgccgc | 1380 |
| ctgggtggag cgcctgttcg gctacgactg ggcccagcag accatcggct gctccgacgc | 1440 |
| cgccgtgttc cgcctgtccg cccagggccg ccccgtgctg ttcgtgaaga ccgacctgtc | 1500 |
| cggcgccctg aacgagctgc aggacgaggc cgcccgcctg tcctggctgg ccaccaccgg | 1560 |
| cgtgccctgc gccgccgtgc tggacgtggt gaccgaggcc ggccgcgact ggctgctgct | 1620 |
| gggcgaggtg cccggccagg acctgctgtc ctcccacctg gccccgccg agaaggtgtc | 1680 |
| catcatggcc gacgccatgc gccgcctgca caccctggac cccgccacct gcccttcga | 1740 |
| ccaccaggcc aagcaccgca tcgagcgcgc ccgcacccgc atggaggccg gcctggtgga | 1800 |
| ccaggacgac ctggacgagg agcaccaggg cctggccccc gccgagctgt cgcccgcct | 1860 |
| gaaggcccgc atgcccgacg gcgaggacct ggtggtgacc cacggcgacg cctgcctgcc | 1920 |
| caacatcatg gtggagaacg gccgcttctc cggcttcatc gactgcggcc gctgggcgt | 1980 |
| ggccgaccgc taccaggaca tcgccctggc cacccgcgac atcgccgagg agctgggcgg | 2040 |
| cgagtgggcc gaccgcttcc tggtgctgta cggcatcgcc gccccgact cccagcgcat | 2100 |
| cgccttctac cgcctgctgg acgagttctt ctgacaattg gcagcagcag ctcggatagt | 2160 |
| atcgacacac tctggacgct ggtcgtgtga tggactgttg ccgccacact tgctgccttg | 2220 |
| acctgtgaat atccctgccg cttttatcaa acagcctcag tgtgtttgat cttgtgtgta | 2280 |
| cgcgcttttg cgagttgcta gctgcttgtg ctatttgcga ataccacccc cagcatcccc | 2340 |
| ttccctcgtt tcatatcgct tgcatcccaa ccgcaactta tctacgctgt cctgctatcc | 2400 |
| ctcagcgctg ctcctgctcc tgctcactgc ccctcgcaca gccttggttt gggctccgcc | 2460 |
| tgtattctcc tggtactgca acctgtaaac cagcactgca atgctgatgc acgggaagta | 2520 |
| gtgggatggg aacacaaatg gaggatcccg cgtctcgaac agagcgcgca gaggaacgct | 2580 |
| gaaggtctcg cctctgtcgc acctcagcgc ggcatacacc acaataacca cctgacgaat | 2640 |
| gcgcttggtt cttcgtccat tagcgaagcg tccggttcac acacgtgcca cgttggcgag | 2700 |
| gtggcaggtg acaatgatcg gtggagctga tggtcgaaac gttcacagcc tagggatatc | 2760 |
| gaattccttt cttgcgctat gacacttcca gcaaaaggta gggcgggctg cgagacggct | 2820 |
| tcccggcgct gcatgcaaca ccgatgatgc ttcgaccccc cgaagctcct tcggggctgc | 2880 |
| atgggcgctc cgatgccgct ccagggcgag cgctgtttaa atagccaggc ccccgattgc | 2940 |
| aaagacatta tagcgagcta ccaaagccat attcaaacac ctagatcact accacttcta | 3000 |
| cacaggccac tcgagcttgt gatcgcactc cgctaagggg gcgcctcttc ctcttcgttt | 3060 |
| cagtcacaac ccgcaaacac tagtatggct atcaagacga acaggcagcc tgtggagaag | 3120 |
| cctccgttca cgatcgggac gctgcgcaag gccatccccg cgcactgttt cgagcgctcg | 3180 |
| gcgcttcgtg ggcgcgcccc cgactggtcc atgctgttcg ccgtgatcac caccatcttc | 3240 |
| tccgccgccg agaagcagtg gaccaacctg gagtggaagc caagcccaa ccccccccag | 3300 |
| ctgctggacg accacttcgg cccccacggc ctggtgttcc gccgcacctt cgccatccgc | 3360 |
| agctacgagg tgggccccga ccgctccacc agcatcgtgg ccgtgatgaa ccacctgcag | 3420 |
| gaggccgccc tgaaccacgc caagtccgtg ggcatcctgg gcgacggctt cggcaccacc | 3480 |

```
ctggagatgt ccaagcgcga cctgatctgg gtggtgaagc gcacccacgt ggccgtggag    3540
cgctaccccg cctggggcga caccgtggag gtggagtgct gggtgggcgc ctccggcaac    3600
aacggccgcc gccacgactt cctggtgcgc gactgcaaga ccggcgagat cctgacccgc    3660
tgcacctccc tgagcgtgat gatgaacacc cgcacccgcc gcctgagcaa gatccccgag    3720
gaggtgcgcg gcgagatcgg ccccgccttc atcgacaacg tggccgtgaa ggacgaggag    3780
atcaagaagc cccagaagct gaacgactcc accgccgact acatccaggg cggcctgacc    3840
ccccgctgga acgacctgga catcaaccag cacgtgaaca acatcaagta cgtggactgg    3900
atcctggaga ccgtgcccga cagcatcttc gagagccacc acatctcctc cttcaccatc    3960
gagtaccgcc gcgagtgcac catggacagc gtgctgcagt ccctgaccac cgtgagcggc    4020
ggctcctccg aggccggcct ggtgtgcgag cacctgctgc agctggaggg cggcagcgag    4080
gtgctgcgcg ccaagaccga gtggcgcccc aagctgaccg actccttccg cggcatcagc    4140
gtgatccccg ccgagtccag cgtgatggac tacaaggacc acgacggcga ctacaaggac    4200
cacgacatcg actacaagga cgacgacgac aagtgatgac tcgaggcagc agcagctcgg    4260
atagtatcga cacactctgg acgctggtcg tgtgatggac tgttgccgcc acacttgctg    4320
ccttgacctg tgaatatccc tgccgctttt atcaaacagc ctcagtgtgt ttgatcttgt    4380
gtgtacgcgc ttttgcgagt tgctagctgc ttgtgctatt tgcgaatacc acccccagca    4440
tccccttccc tcgtttcata tcgcttgcat cccaaccgca acttatctac gctgtcctgc    4500
tatccctcag cgctgctcct gctcctgctc actgccccctc gcacagcctt ggtttgggct    4560
ccgcctgtat tctcctggta ctgcaacctg taaaccagca ctgcaatgct gatgcacggg    4620
aagtagtggg atgggaacac aaatggaaag ctt    4653
```

<210> SEQ ID NO 126
<211> LENGTH: 3669
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
cccgtgatca cacaggtgcc ttgcgagcgt gatcacacta ttttgggggt cctacagtac      60
tgaaatggtg agaagtcgta ctgaaatcaa ggatgaacaa tgaaaatggt gctgtggtgg     120
cttctcaaag gtcaagaatc agtcgctcgc gtcaggaaat cgcggcgtca accagcgtgg     180
gcgcggtcag tggccccgca ctggtcacca tagcctctcc tgccacagta gcgatcccct     240
gggcgttcac tctcagcagc ggctgtactg cctcccagat tttcttcttc tggacctgcg     300
ggcgtgagag gatgagcagg gtggggccaa gggctcaatc ctgaacggcc ctcattcggt     360
ttccaatccc acaacacata cccacagcag gtcagaccac gcattcgcac catgcgcacc     420
aaataacgtg tccttacctg attgggtgtg gcaggctccg tggacaggag tgcctcgtcc     480
cccgcccaga cccgctcccc cgtcacggcg gcgtccggga cccgcagcgg ctccaccgcg     540
gtgtgatccg cgttggcggc gcagagcagc atcccagccg atttgacccc gcgcatgctc     600
cgaggcttga ggttggccag caccaccacc cgccggccga caaggtcctc cagggtcacg     660
tgccggacca ggccactcac gatggtgcga gggccccccct cctcgccgag gtcgatctgc     720
tcgacgtaca gactgcgaca tgcgtggcga gtggtcatca gaaggaagca ggtgtgcaga     780 agggggcacgt ggttggtatt gagagtagcc aaagctttgt gccaatcaga aagtcaacgc     840
```

```
agctgcctgc ctggctcgcg tacaattcct ttcttgcgct atgacacttc cagcaaaagg    900
tagggcgggc tgcgagacgg cttcccggcg ctgcatgcaa caccgatgat gcttcgaccc    960
cccgaagctc cttcggggct gcatgggcgc tccgatgccg ctccagggcg agcgctgttt   1020
aaatagccag gccccgatt gcaaagacat tatagcgagc taccaaagcc atattcaaac   1080
acctagatca ctaccacttc tacacaggcc actcgagctt gtgatcgcac tccgctaagg   1140
gggcgcctct tcctcttcgt ttcagtcaca acccgcaaac ggcgcgccat gctgctgcag   1200
gccttcctgt tcctgctggc cggcttcgcc gccaagatca gcgcctccat gacgaacgag   1260
acgtccgacc gccccctggt gcacttcacc cccaacaagg gctggatgaa cgaccccaac   1320
ggcctgtggt acgacgagaa ggacgccaag tggcacctgt acttccagta caacccgaac   1380
gacaccgtct gggggacgcc cttgttctgg ggccacgcca cgtccgacga cctgaccaac   1440
tgggaggacc agcccatcgc catcgccccg aagcgcaacg actccggcgc cttctccggc   1500
tccatggtgg tggactacaa caacacctcc ggcttcttca acgacaccat cgacccgcgc   1560
cagcgctgcg tggccatctg gacctacaac accccggagt ccgaggagca gtacatctcc   1620
tacagcctgg acgcggcta caccttcacc gagtaccaga gaaccccgt gctggccgcc   1680
aactccaccc agttccgcga cccgaaggtc ttctggtacg agccctccca gaagtggatc   1740
atgaccgcgg ccaagtccca ggactacaag atcgagatct actcctccga cgacctgaag   1800
tcctggaagc tggagtccgc gttcgccaac gagggcttcc tcggctacca gtacgagtgc   1860
cccgccctga tcgaggtccc caccgagcag gaccccagca gtcctactg ggtgatgttc   1920
atctccatca accccggcgc cccggccggc ggctccttca ccagtactt cgtcggcagc   1980
ttcaacggca cccacttcga ggccttcgac aaccagtccc gcgtggtgga cttcggcaag   2040
gactactacg ccctgcagac cttcttcaac accgacccga cctacgggag cgccctgggc   2100
atcgcgtggg cctccaactg ggagtactcc gccttcgtgc ccaccaaccc ctggcgctcc   2160
tccatgtccc tcgtgcgcaa gttctccctc aacaccgagt accaggccaa cccggagacg   2220
gagctgatca acctgaaggc cgagccgatc ctgaacatca gcaacgccgg ccctggagc   2280
cggttcgcca ccaacaccac gttgacgaag gccaacagct acaacgtcga cctgtccaac   2340
agcaccggca ccctggagtt cgagctggtg tacgccgtca acaccaccca gacgatctcc   2400
aagtccgtgt tcgcggacct ctccctctgg ttcaagggcc tggaggaccc cgaggagtac   2460
ctccgcatgg gcttcgaggt gtccgcgtcc tccttcttcc tggaccgcgg gaacagcaag   2520
gtgaagttcg tgaaggagaa cccctacttc accaaccgca tgagcgtgaa caaccagccc   2580
ttcaagagcg agaacgacct gtcctactac aaggtgtacg gcttgctgga ccagaacatc   2640
ctggagctgt acttcaacga cggcgacgtc gtgtccacca caccctactt catgaccacc   2700
gggaacgccc tgggctccgt gaacatgacg acggggtgg acaacctgtt ctacatcgac   2760
aagttccagg tgcgcgaggt caagtgatta ttaactcga ggcagcagca gctcggatag   2820
tatcgacaca ctctggacgc tggtcgtgtg atggactgtt gccgccacac ttgctgcctt   2880
gacctgtgaa tatccctgcc gcttttatca acagcctca gtgtgtttga tcttgtgtgt   2940
acgcgctttt gcgagttgct agctgcttgt gctatttgcg aataccaccc ccagcatccc   3000
cttccctcgt ttcatatcgc ttgcatccca accgcaactt atctacgctg tcctgctatc   3060
cctcagcgct gctcctgctc ctgctcactg ccctcgcac agccttggtt tgggctccgc   3120
ctgtattctc ctggtactgc aacctgtaaa ccagcactgc aatgctgatg cacgggaagt   3180
```

```
agtgggatgg gaacacaaat ggaaagcttg agctcggtac ccgtaccat cagcatccgg    3240 gtgaatcttg gcctccaaga tatggccaat cctcacatcc agcttggcaa aatcgactag    3300
actgtctgca agtgggaatg tggagcacaa ggttgcttgt agcgatcgac agactggtgg    3360
ggtacattga caggtgggca gcgccgcatc catcgtgcct gacgcgagcg ccgccggttg    3420
ctcgcccgtg cctgccgtca aagagcggca gagaaatcgg gaaccgaaaa cgtcacattg    3480
cctgatgttg ttacatgctg gactagactt tcttggcgtg ggtctgctcc tcgccaggtg    3540
cgcgacgcct cggggctggg tgcgagggag ccgtgcggcc acgcatttga caagacccaa    3600
agctcgcatc tcagacggtc aaccgttcgt attatacatt caacatatgg tacatacgca    3660
aaaagcatg                                                            3669
```

<210> SEQ ID NO 127
<211> LENGTH: 39
<212> TYPE: PRT
<213> ORGANISM: Prototheca moriformis

<400> SEQUENCE: 127

Met Thr Phe Gly Val Ala Leu Pro Ala Met Gly Arg Gly Val Ser Leu
1               5                   10                  15

Pro Arg Pro Arg Val Ala Val Arg Ala Gln Ser Ala Ser Gln Val Leu
            20                  25                  30

Glu Ser Gly Arg Ala Gln Leu
        35

<210> SEQ ID NO 128
<211> LENGTH: 40
<212> TYPE: PRT
<213> ORGANISM: Prototheca moriformis

<400> SEQUENCE: 128

Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Gln Leu
        35                  40

<210> SEQ ID NO 129
<211> LENGTH: 36
<212> TYPE: PRT
<213> ORGANISM: Prototheca moriformis

<400> SEQUENCE: 129

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Arg Ala
        35

<210> SEQ ID NO 130
<211> LENGTH: 40
<212> TYPE: PRT
<213> ORGANISM: Chlorella protothecoides

<400> SEQUENCE: 130

Met Ala Thr Ala Ser Thr Phe Ser Ala Phe Asn Ala Arg Cys Gly Asp
1               5                   10                  15

-continued

Leu Arg Arg Ser Ala Gly Ser Gly Pro Arg Arg Pro Ala Arg Pro Leu
            20                  25                  30

Pro Val Arg Gly Arg Ala Gln Leu
        35                  40

<210> SEQ ID NO 131
<211> LENGTH: 87
<212> TYPE: PRT
<213> ORGANISM: Cuphea hookeriana

<400> SEQUENCE: 131

Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His
                85

<210> SEQ ID NO 132
<211> LENGTH: 60
<212> TYPE: PRT
<213> ORGANISM: Umbellularia californica

<400> SEQUENCE: 132

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu
    50                  55                  60

<210> SEQ ID NO 133
<211> LENGTH: 60
<212> TYPE: PRT
<213> ORGANISM: Cinnamomum camphora

<400> SEQUENCE: 133

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu
    50                  55                  60

<210> SEQ ID NO 134
<211> LENGTH: 1104
<212> TYPE: DNA
<213> ORGANISM: Prototheca moriformis

```
<400> SEQUENCE: 134
atggcaccga ccagcctgct tgccagtact ggcgtctctt ccgcttctct gtggtcctct      60
gcgcgctcca gcgcgtgcgc ttttccggtg gatcatgcgg tccgtggcgc accgcagcgg     120
ccgctgccca tgcagcgccg ctgcttccga acagtggcgg tcaggccgc acccgcggta     180 gccgtccgtc cggaacccgc ccaagagttt tgggagcagc ttgagccctg caagatggcg     240
gaggacaagc gcatcttcct ggaggagcac cgcattcggg gcaacgaggt gggcccctcg     300
cagcggctga cgatcacggc ggtggccaac atcctgcagg aggcggcggg caaccacgcg     360
gtggccatgt ggggccggag ctcggagggt ttcgcgacgg acccggagct gcaggaggcg     420
ggtctcatct ttgtgatgac gcgcatgcag atccaaatgt accgctaccc gcgctggggc     480
gacctgatgc aggtggagac ctggttccag acggcgggca agctaggcgc gcagcgcgag     540
tgggtgctgc gcgacaagct gaccggcgag gcgctgggcg cggccacctc cagctgggtc     600
atgatcaaca tccgcacgcg ccggccgtgc cgcatgcccg agctcgtccg cgtcaagtcg     660
gccttcttcg cgcgcgagcc gccgcgcctg gcgctgccgc ccacggtcac gcgcgccaag     720
ctgcccaaca tcgcgacgcc ggcgccgctg cgcgggcacc gccaggtcgc gcgccgcacc     780
gacatggaca tgaacgggca cgtgaacaac gtggcctacc tggcctggtg cctggaggcc     840
gtgcccgagc acgtcttcag cgactaccac ctctaccaga tggagatcga cttcaaggcc     900
gagtgccacg cgggcgacgt catctcctcc caggccgagc agatcccgcc ccaggaggcg     960
ctcacgcaca cggcgccgg ccgcaacccc tcctgcttcg tccatagcat tctgcgcgcc    1020
gagaccgagc tcgtccgcgc gcgaaccaca tggtcggccc ccatcgacgc gcccgccgcc    1080
aagccgccca aggcgagcca ctga                                            1104

<210> SEQ ID NO 135
<211> LENGTH: 1104
<212> TYPE: DNA
<213> ORGANISM: Prototheca moriformis

<400> SEQUENCE: 135
atggcaccga ccagcctgct tgcccgtact ggcgtctctt ccgcttctct gtgctcctct      60
acgcgctccg gcgcgtgcgc ttttccggtg gatcatgcgg tccgtggcgc accgcagcgg     120
ccgctgccca tgcagcgccg ctgcttccga acagtggctg tcaggccgcc acccgcagta     180
gccgtccgtc cggaacccgc ccaagagttt tgggagcagc ttgagccctg caagatggcg     240
gaggacaagc gcatcttcct ggaggagcac cgcattcgtg gcaacgaggt gggcccctcg     300
cagcggctga cgatcacggc ggtggccaac atcctgcagg aggcggcggg caaccacgcg     360
gtggccatgt ggggtcggag ctcggagggt ttcgcgacgg acccggagct gcaggaggcg     420
ggcctcatct ttgtgatgac gcgcatgcag atccaaatgt accgctaccc gcgctggggc     480
gacctgatgc aggtggagac ctggttccag acggcgggca agctaggcgc gcagcgcgag     540
tgggtgctgc gcgacaagct gaccggcgag gcgctgggcg cggccacctc cagctgggtc     600
atgatcaaca tccgcacgcg ccggccgtgc cgcatgcccg agctcgtccg cgtcaagtcg     660
gccttcttcg cgcgcgagcc gccgcgcctg gcgctgccgc ccgcggtcac gcgtgccaag     720
ctgcccaaca tcgcgacgcc ggcgccgctg cgcgggcacc gccaggtcgc gcgccgcacc     780
gacatggaca tgaacgggcc acgtgaacaac gttgcctacc tggcctggtg cctggaggcc     840
gtgcccgagc acgtcttcag cgactaccac ctctaccaga tggagatcga cttcaaggcc     900
gagtgccacg cgggcgacgt catctcctcc caggccgagc agatcccgcc ccaggaggcg     960
```

```
ctcacgcaca acggcgccgg ccgcaacccc tcctgcttcg tccatagcat tctgcgcgcc   1020
gagaccgagc tcgtccgcgc gcgaaccaca tggtcggccc ccatcgacgc gcccgccgcc   1080
aagccgccca aggcgagcca ctga                                         1104
```

<210> SEQ ID NO 136
<211> LENGTH: 367
<212> TYPE: PRT
<213> ORGANISM: Prototheca moriformis

<400> SEQUENCE: 136

```
Met Ala Pro Thr Ser Leu Leu Ala Ser Thr Gly Val Ser Ser Ala Ser
1               5                   10                  15

Leu Trp Ser Ser Ala Arg Ser Ser Ala Cys Ala Phe Pro Val Asp His
                20                  25                  30

Ala Val Arg Gly Ala Pro Gln Arg Pro Leu Pro Met Gln Arg Arg Cys
            35                  40                  45

Phe Arg Thr Val Ala Val Arg Ala Ala Pro Ala Val Arg Pro
    50                  55                  60

Glu Pro Ala Gln Glu Phe Trp Glu Gln Leu Glu Pro Cys Lys Met Ala
65                  70                  75                  80

Glu Asp Lys Arg Ile Phe Leu Glu Glu His Arg Ile Arg Gly Asn Glu
                85                  90                  95

Val Gly Pro Ser Gln Arg Leu Thr Ile Thr Ala Val Ala Asn Ile Leu
            100                 105                 110

Gln Glu Ala Ala Gly Asn His Ala Val Ala Met Trp Gly Arg Ser Ser
        115                 120                 125

Glu Gly Phe Ala Thr Asp Pro Glu Leu Gln Glu Ala Gly Leu Ile Phe
    130                 135                 140

Val Met Thr Arg Met Gln Ile Gln Met Tyr Arg Tyr Pro Arg Trp Gly
145                 150                 155                 160

Asp Leu Met Gln Val Glu Thr Trp Phe Gln Thr Ala Gly Lys Leu Gly
                165                 170                 175

Ala Gln Arg Glu Trp Val Leu Arg Asp Lys Leu Thr Gly Glu Ala Leu
            180                 185                 190

Gly Ala Ala Thr Ser Ser Trp Val Met Ile Asn Ile Arg Thr Arg Arg
        195                 200                 205

Pro Cys Arg Met Pro Glu Leu Val Arg Val Lys Ser Ala Phe Phe Ala
    210                 215                 220

Arg Glu Pro Pro Arg Leu Ala Leu Pro Pro Thr Val Thr Arg Ala Lys
225                 230                 235                 240

Leu Pro Asn Ile Ala Thr Pro Ala Pro Leu Arg Gly His Arg Gln Val
                245                 250                 255

Ala Arg Arg Thr Asp Met Asp Met Asn Gly His Val Asn Asn Val Ala
            260                 265                 270

Tyr Leu Ala Trp Cys Leu Glu Ala Val Pro Glu His Val Phe Ser Asp
        275                 280                 285

Tyr His Leu Tyr Gln Met Glu Ile Asp Phe Lys Ala Glu Cys His Ala
    290                 295                 300

Gly Asp Val Ile Ser Ser Gln Ala Glu Gln Ile Pro Pro Gln Glu Ala
305                 310                 315                 320

Leu Thr His Asn Gly Ala Gly Arg Asn Pro Ser Cys Phe Val His Ser
                325                 330                 335

Ile Leu Arg Ala Glu Thr Glu Leu Val Arg Ala Arg Thr Thr Trp Ser
```

Ala Pro Ile Asp Ala Pro Ala Ala Lys Pro Pro Lys Ala Ser His
            355                 360                 365

<210> SEQ ID NO 137
<211> LENGTH: 367
<212> TYPE: PRT
<213> ORGANISM: Prototheca moriformis

<400> SEQUENCE: 137

Met Ala Pro Thr Ser Leu Leu Ala Arg Thr Gly Val Ser Ala Ser
1               5                   10                  15

Leu Cys Ser Ser Thr Arg Ser Gly Ala Cys Ala Phe Pro Val Asp His
            20                  25                  30

Ala Val Arg Gly Ala Pro Gln Arg Pro Leu Pro Met Gln Arg Arg Cys
            35                  40                  45

Phe Arg Thr Val Ala Val Arg Ala Ala Pro Ala Val Ala Val Arg Pro
50                  55                  60

Glu Pro Ala Gln Glu Phe Trp Glu Gln Leu Glu Pro Cys Lys Met Ala
65                  70                  75                  80

Glu Asp Lys Arg Ile Phe Leu Glu Glu His Arg Ile Arg Gly Asn Glu
                85                  90                  95

Val Gly Pro Ser Gln Arg Leu Thr Ile Thr Ala Val Ala Asn Ile Leu
            100                 105                 110

Gln Glu Ala Ala Gly Asn His Ala Val Ala Met Trp Gly Arg Ser Ser
            115                 120                 125

Glu Gly Phe Ala Thr Asp Pro Glu Leu Gln Glu Ala Gly Leu Ile Phe
130                 135                 140

Val Met Thr Arg Met Gln Ile Gln Met Tyr Arg Tyr Pro Arg Trp Gly
145                 150                 155                 160

Asp Leu Met Gln Val Glu Thr Trp Phe Gln Thr Ala Gly Lys Leu Gly
                165                 170                 175

Ala Gln Arg Glu Trp Val Leu Arg Asp Lys Leu Thr Gly Glu Ala Leu
            180                 185                 190

Gly Ala Ala Thr Ser Ser Trp Val Met Ile Asn Ile Arg Thr Arg Arg
            195                 200                 205

Pro Cys Arg Met Pro Glu Leu Val Arg Val Lys Ser Ala Phe Phe Ala
210                 215                 220

Arg Glu Pro Pro Arg Leu Ala Leu Pro Pro Ala Val Thr Arg Ala Lys
225                 230                 235                 240

Leu Pro Asn Ile Ala Thr Pro Ala Pro Leu Arg Gly His Arg Gln Val
                245                 250                 255

Ala Arg Arg Thr Asp Met Asp Met Asn Gly His Val Asn Asn Val Ala
            260                 265                 270

Tyr Leu Ala Trp Cys Leu Glu Ala Val Pro Glu His Val Phe Ser Asp
            275                 280                 285

Tyr His Leu Tyr Gln Met Glu Ile Asp Phe Lys Ala Glu Cys His Ala
290                 295                 300

Gly Asp Val Ile Ser Ser Gln Ala Glu Gln Ile Pro Pro Gln Glu Ala
305                 310                 315                 320

Leu Thr His Asn Gly Ala Gly Arg Asn Pro Ser Cys Phe Val His Ser
                325                 330                 335

Ile Leu Arg Ala Glu Thr Glu Leu Val Arg Ala Arg Thr Thr Trp Ser
            340                 345                 350

```
Ala Pro Ile Asp Ala Pro Ala Lys Pro Pro Lys Ala Ser His
            355                 360                 365

<210> SEQ ID NO 138
<211> LENGTH: 328
<212> TYPE: PRT
<213> ORGANISM: Cuphea hookeriana

<400> SEQUENCE: 138

Gln Leu Pro Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Val Pro Leu Phe Val Asp Ser Pro
            180                 185                 190

Val Ile Glu Asp Ser Asp Leu Lys Val His Lys Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 139
<211> LENGTH: 322
<212> TYPE: PRT
<213> ORGANISM: Umbellularia californica
```

<400> SEQUENCE: 139

```
Pro Asp Trp Ser Met Leu Phe Ala Val Ile Thr Thr Ile Phe Ser Ala
1               5                   10                  15

Ala Glu Lys Gln Trp Thr Asn Leu Glu Trp Lys Pro Lys Pro Lys Leu
            20                  25                  30

Pro Gln Leu Leu Asp Asp His Phe Gly Leu His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Leu Ala Val Met Asn His Met Gln Glu Ala Thr Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Met Trp Val Val Arg Arg Thr His Val Ala
            100                 105                 110

Val Glu Arg Tyr Pro Thr Trp Gly Asp Thr Val Glu Val Glu Cys Trp
        115                 120                 125

Ile Gly Ala Ser Gly Asn Asn Gly Met Arg Arg Asp Phe Leu Val Arg
    130                 135                 140

Asp Cys Lys Thr Gly Glu Ile Leu Thr Arg Cys Thr Ser Leu Ser Val
145                 150                 155                 160

Leu Met Asn Thr Arg Thr Arg Arg Leu Ser Thr Ile Pro Asp Glu Val
                165                 170                 175

Arg Gly Glu Ile Gly Pro Ala Phe Ile Asp Asn Val Ala Val Lys Asp
            180                 185                 190

Asp Glu Ile Lys Lys Leu Gln Lys Leu Asn Asp Ser Thr Ala Asp Tyr
        195                 200                 205

Ile Gln Gly Gly Leu Thr Pro Arg Trp Asn Asp Leu Asp Val Asn Gln
    210                 215                 220

His Val Asn Asn Leu Lys Tyr Val Ala Trp Val Phe Glu Thr Val Pro
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val
```

<210> SEQ ID NO 140
<211> LENGTH: 345
<212> TYPE: PRT
<213> ORGANISM: Cinnamomum camphora

<400> SEQUENCE: 140

```
Pro Asp Trp Ser Met Leu Phe Ala Val Ile Thr Thr Ile Phe Ser Ala
1               5                   10                  15

Ala Glu Lys Gln Trp Thr Asn Leu Glu Trp Lys Pro Lys Pro Asn Pro
            20                  25                  30
```

```
Pro Gln Leu Leu Asp Asp His Phe Gly Pro His Gly Leu Val Phe Arg
         35                  40                  45

Arg Thr Phe Ala Ile Arg Ser Tyr Glu Val Gly Pro Asp Arg Ser Thr
 50                  55                  60

Ser Ile Val Ala Val Met Asn His Leu Gln Glu Ala Ala Leu Asn His
 65                  70                  75                  80

Ala Lys Ser Val Gly Ile Leu Gly Asp Gly Phe Gly Thr Thr Leu Glu
                 85                  90                  95

Met Ser Lys Arg Asp Leu Ile Trp Val Val Lys Arg Thr His Val Ala
            100                 105                 110

Val Glu Arg Tyr Pro Ala Trp Gly Asp Thr Val Glu Val Glu Cys Trp
        115                 120                 125

Val Gly Ala Ser Gly Asn Asn Gly Arg Arg His Asp Phe Leu Val Arg
    130                 135                 140

Asp Cys Lys Thr Gly Glu Ile Leu Thr Arg Cys Thr Ser Leu Ser Val
145                 150                 155                 160

Met Met Asn Thr Arg Thr Arg Arg Leu Ser Lys Ile Pro Glu Glu Val
                165                 170                 175

Arg Gly Glu Ile Gly Pro Ala Phe Ile Asp Asn Val Ala Val Lys Asp
            180                 185                 190

Glu Glu Ile Lys Lys Pro Gln Lys Leu Asn Asp Ser Thr Ala Asp Tyr
        195                 200                 205

Ile Gln Gly Gly Leu Thr Pro Arg Trp Asn Asp Leu Asp Ile Asn Gln
    210                 215                 220

His Val Asn Asn Ile Lys Tyr Val Asp Trp Ile Leu Glu Thr Val Pro
225                 230                 235                 240

Asp Ser Ile Phe Glu Ser His His Ile Ser Ser Phe Thr Ile Glu Tyr
                245                 250                 255

Arg Arg Glu Cys Thr Met Asp Ser Val Leu Gln Ser Leu Thr Thr Val
            260                 265                 270

Ser Gly Gly Ser Ser Glu Ala Gly Leu Val Cys Glu His Leu Leu Gln
    275                 280                 285

Leu Glu Gly Gly Ser Glu Val Leu Arg Ala Lys Thr Glu Trp Arg Pro
290                 295                 300

Lys Leu Thr Asp Ser Phe Arg Gly Ile Ser Val Ile Pro Ala Glu Ser
305                 310                 315                 320

Ser Val Met Asp Tyr Lys Asp His Asp Gly Asp Tyr Lys Asp His Asp
                325                 330                 335

Ile Asp Tyr Lys Asp Asp Asp Lys
            340                 345

<210> SEQ ID NO 141
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Lys Asp Glu Leu
1

<210> SEQ ID NO 142
<211> LENGTH: 6
<212> TYPE: PRT
<213> ORGANISM: Unknown
```

```
<220> FEATURE:
<223> OTHER INFORMATION: Description of Unknown: Higher plant fatty
      acyl-ACP thioesterase sequence

<400> SEQUENCE: 142

Leu Asp Met Asn Gln His
1               5

<210> SEQ ID NO 143
<211> LENGTH: 6
<212> TYPE: PRT
<213> ORGANISM: Unknown
<220> FEATURE:
<223> OTHER INFORMATION: Description of Unknown: Algal fatty acyl-ACP
      thioesterase sequence

<400> SEQUENCE: 143

Met Asp Met Asn Gly His
1               5
```

US 9,062,294 B2

RENEWABLE FUELS PRODUCED FROM OLEAGINOUS MICROORGANISMS

CROSS-REFERENCE TO RELATED APPLICATIONS

This application is a continuation of U.S. application Ser. No. 13/550,412, filed Jul. 16, 2012, which is a continuation of U.S. application Ser. No. 12/981,409, filed Dec. 29, 2010, now U.S. Pat. No. 8,222,010, which is a continuation of U.S. application Ser. No. 12/628,149, filed Nov. 30, 2009, now U.S. Pat. No. 7,883,882, which claims the benefit under 35 U.S.C. 119(e) of U.S. Provisional Patent Application No. 61/118,590, filed Nov. 28, 2008, U.S. Provisional Patent Application No. 61/118,994, filed Dec. 1, 2008, U.S. Provisional Patent Application No. 61/174,357, filed Apr. 30, 2009, and U.S. Provisional Patent Application No. 61/219,525, filed Jun. 23, 2009. Each of these applications is incorporated herein by reference in its entirety for all purposes.

REFERENCE TO A SEQUENCE LISTING

This application includes an electronic sequence listing in a file named "422843-Sequence.txt", created on Jul. 20, 2012 and containing 348,440 bytes, which is hereby incorporated by reference in its entirety for all purposes.

FIELD OF THE INVENTION

The present invention relates to the production of oils, fuels, and oleochemicals made from microorganisms. In particular, the disclosure relates to oil-bearing microalgae, methods of cultivating them for the production of useful compounds, including lipids, fatty acid esters, fatty acids, aldehydes, alcohols, and alkanes, and methods and reagents for genetically altering them to improve production efficiency and alter the type and composition of the oils produced by them.

BACKGROUND OF THE INVENTION

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years. Fossil fuels are a finite, non-renewable resource.

Increased demand for energy by the global economy has also placed increasing pressure on the cost of hydrocarbons. Aside from energy, many industries, including plastics and chemical manufacturers, rely heavily on the availability of hydrocarbons as a feedstock for their manufacturing processes. Cost-effective alternatives to current sources of supply could help mitigate the upward pressure on energy and these raw material costs.

PCT Pub. No. 2008/151149 describes methods and materials for cultivating microalgae for the production of oil and particularly exemplifies the production of diesel fuel from oil produced by the microalgae *Chlorella protothecoides*. There remains a need for improved methods for producing oil in microalgae, particularly for methods that produce oils with shorter chain length and a higher degree of saturation and without pigments, with greater yield and efficiency. The present invention meets this need.

SUMMARY OF THE INVENTION

The invention provides cells of the genus *Prototheca* comprising an exogenous gene, and in some embodiments the cell is a strain of the species *Prototheca moriformis*, *Prototheca krugani*, *Prototheca stagnora* or *Prototheca zopfii* and in other embodiment the cell has a 23S rRNA sequence with at least 70, 75, 80, 85 or 95% nucleotide identity to one or more of SEQ ID NOs: 11-19. In some cells the exogenous gene is coding sequence and is in operable linkage with a promoter, and in some embodiments the promoter is from a gene endogenous to a species of the genus *Prototheca*. In further embodiments the coding sequence encodes a protein selected from the group consisting of a sucrose invertase, a fatty acyl-ACP thioesterase, a fatty acyl-CoA/aldehyde reductase, a fatty acyl-CoA reductase, a fatty aldehyde reductase, a fatty aldehyde decarbonylase, an acyl carrier protein and a protein that imparts resistance to an antibiotic. Some embodiments of a fatty acyl-ACP thioesterase that has hydrolysis activity towards one or more fatty acyl-ACP substrates of chain length C8, C10, C12 or C14, including acyl-ACP thioesterases with at least 50, 60, 70, 80, or 90% amino acid identity with one or more sequences selected from the group consisting of SEQ ID NOs: 59, 61, 63 and 138-140. In further embodiments the coding sequence comprises a plastid targeting sequence from microalgae, and in some embodiments the microalgae is a species of the genus *Prototheca* or *Chlorella* as well as other genera from the family Chlorellaceae. In some embodiments the plastid targeting sequence has at least 20, 25, 35, 45, or 55% amino acid sequence identity to one or more of SEQ ID NOs: 127-133 and is capable of targeting a protein encoded by an exogenous gene not located in the plastid genome to the plastid. In other embodiments the promoter is upregulated in response to reduction or elimination of nitrogen in the culture media of the cell, such as at least a 3-fold upregulation as determined by transcript abundance in a cell of the genus *Prototheca* when the extracellular environment changes from containing at least 10 mM or 5 mM nitrogen to containing no nitrogen. In further embodiments the promoter comprises a segment of 50 or more nucleotides of one of SEQ ID NOs: 91-102. In other embodiments the cell has a 23S rRNA sequence with at least 70, 75, 80, 85 or 95% nucleotide identity to one or more of SEQ ID NOs: 11-19. In other embodiments the exogenous gene is integrated into a chromosome of the cell.

In additional embodiments of cells of the invention, the cell is of the genus *Prototheca* and comprises an exogenous fatty acyl-ACP thioesterase gene and a lipid profile of at least 4% C8-C14 of total lipids of the cell, an amount of C8 that is at least 0.3% of total lipids of the cell, an amount of C10 that is at least 2% of total lipids of the cell, an amount of C12 that is at least 2% of total lipids of the cell, an amount of C14 that is at least 4% of total lipids of the cell, and an amount of C8-C14 that is 10-30%, 20-30%, or at least 10, 20, or 30% of total lipids of the cell. In some embodiments the cell further comprises an exogenous sucrose invertase gene. In some embodiments the cell is a strain of the species *Prototheca moriformis*, *Prototheca krugani*, *Prototheca stagnora* or *Prototheca zopfii*, and in other embodiment the cell has a 23S rRNA sequence with at least 70, 75, 80, 85 or 95% nucleotide identity to one or more of SEQ ID NOs: 11-19. In other embodiments the exogenous fatty acyl-ACP thioesterase gene is integrated into a chromosome of the cell. Other embodiments of the invention comprise methods of making triglyceride compositions of a lipid profile of at least 4% C8-C14 w/w or area percent of the triglyceride composition, an amount of C8 that is at least 0.3% w/w or area percent, an amount of C10 that is at least 2% w/w or area percent, an amount of C12 that is at least 2% w/w or area percent, an amount of C14 that is at least 4% w/w or area percent, and an amount of C8-C14 that is 10-30%, 20-30%, or at least 10, 20, or 30% w/w or area percent. The invention also comprises methods of making triglyceride compositions comprising cultivating the foregoing cells, wherein the cells also comprise an exogenous gene encoding a sucrose invertase and sucrose is provided as a carbon source. In some embodiments the sucrose invertase has at least 50, 60, 70, 80, or 90% amino acid identity to one or more of SEQ ID NOs: 3, 20-29 and 90.

Embodiments of the invention include triglyceride oil compositions as well as cells containing triglyceride oil compositions comprising a lipid profile of at least 4% C8-C14 and one or more of the following attributes: 0.1-0.4 micrograms/ml total carotenoids, less than 0.4 micrograms/ml total carotenoids, less than 0.001 micrograms/ml lycopene; less than 0.02 micrograms/ml beta carotene, less than 0.02 milligrams of chlorophyll per kilogram of oil; 0.40-0.60 milligrams of gamma tocopherol per 100 grams of oil; 0.2-0.5 milligrams of total tocotrienols per gram of oil, less than 0.4 milligrams of total tocotrienols per gram of oil, 4-8 mg per 100 grams of oil of campesterol, and 40-60 mg per 100 grams of oil of stigmasterol. In some embodiments of the invention the triglyceride oil compositions have a lipid profile of at least 4% C8-C14 w/w or area percent of the triglyceride composition, an amount of C8 that is at least 0.3% w/w or area percent, an amount of C10 that is at least 2% w/w or area percent, an amount of C12 that is at least 2% w/w or area percent, an amount of C14 that is at least 4% w/w or area percent, and an amount of C8-C14 that is 10-30%, 20-30%, or at least 10, 20, or 30% w/w or area percent. In other embodiments the triglyceride oil composition is blended with at least one other composition selected from the group consisting of soy, rapeseed, canola, palm, palm kernel, coconut, corn, waste vegetable, Chinese tallow, olive, sunflower, cotton seed. chicken fat, beef tallow, porcine tallow, microalgae, macroalgae, *Cuphea*, flax, peanut, choice white grease, lard, *Camelina sativa*, mustard seed cashew nut, oats, lupine, kenaf, calendula, hemp, coffee, linseed (flax), hazelnut, euphorbia, pumpkin seed, coriander, camellia, sesame, safflower, rice, tung tree, cocoa, copra, pium poppy, castor beans, pecan, jojoba, jatropha, macadamia, Brazil nuts, avocado, petroleum, or a distillate fraction of any of the preceding oils.

Methods of the invention also include processing the aforementioned oils of by performing one or more chemical reactions from the list consisting of transesterification, hydrogenation, hydrocracking, deoxygenation, isomerization, interesterification, hydroxylation, hydrolysis to yield free fatty acids, and saponification. The invention also includes hydrocarbon fuels made from hydrogenation and isomerization of the aforementioned oils and fatty acid alkyl esters made from transesterification of the aforementioned oils. In some embodiments the hydrocarbon fuel is made from triglyceride isolated from cells of the genus *Prototheca* wherein the ASTM D86 T10-T90 distillation range is at least 25° C. In other embodiments the fatty acid alkyl ester fuel is made from triglyceride isolated from cells of the genus *Prototheca*, wherein the composition has an ASTM D6751 A1 cold soak time of less than 120 seconds.

The invention also includes composition comprising (a) polysaccharide comprising one or more monosaccharides from the list consisting of 20-30 mole percent galactose; 55-65 mole percent glucose; and 5-15 mole percent mannose; (b) protein; and (c) DNA comprising a 23S rRNA sequence with at least 70, 75, 80, 85 or 95% nucleotide identity to one or more of SEQ ID NOs: 11-19; and (d) an exogenous gene. In some embodiments the exogenous gene is selected from a sucrose invertase and a fatty acyl-ACP thioesterase, and in further embodiments the composition further comprises lipid with a lipid profile of at least 4% C8-C14. In other embodiments the composition is formulated for consumption as an animal feed.

The invention includes recombinant nucleic acids encoding promoters that are upregulated in response to reduction or elimination of nitrogen in the culture media of a cell of the genus *Prototheca*, such as at least a 3-fold upregulation as determined by transcript abundance when the extracellular environment changes from containing at least 10 mM or 5 mM nitrogen to containing no nitrogen. In some embodiments the recombinant nucleic acid comprises a segment of 50 or more nucleotides of one of SEQ ID NOs: 91-102. The invention also includes nucleic acid vectors comprising an expression cassette comprising (a) a promoter that is active in a cell of the genus *Prototheca*; and (b) a coding sequence in operable linkage with the promoter wherein the coding sequence contains the most or second most preferred codons of Table 1 for at least 20, 30, 40, 50, 60, or 80% of the codons of the coding sequence. In some vectors the coding sequence comprises a plastid targeting sequence in-frame with a fatty acyl-ACP thioesterase, including thioesterase that have hydrolysis activity towards one or more fatty acyl-ACP substrates of chain length C8, C10, C12 or C14. Some vectors include plastid targeting sequences that encode peptides that are capable of targeting a protein to the plastid of a cell of the genus *Prototheca*, including those from microalgae and those wherein the plastid targeting sequence has at least 20, 25, 35, 45, or 55% amino acid sequence identity to one or more of SEQ ID NOs. 127-133 and is capable of targeting a protein to the plastid of a cell of the genus *Prototheca*. Additional vectors of the invention comprise nucleic acid sequences endogenous to the nuclear genome of a cell of the genus *Prototheca*, wherein the sequence is at least 200 nucleotides long, and some vectors comprise first and second nucleic acid sequences endogenous to the nuclear genome of a cell of the genus *Prototheca*, wherein the first and second sequences (a) are each at least 200 nucleotides long; (b) flank the expression cassette; and (c) are located on the same *Prototheca* chromosome no more than 5, 10, 15, 20, and 50 kB apart.

The invention also includes a recombinant nucleic acid with at least 80, 90, 95 or 98% nucleotide identity to one or both of SEQ ID NOs: 134-135 and a recombinant nucleic acid encoding a protein with at least 80, 90, 95 or 98% amino acid identity to one or both of SEQ ID NOs: 136-137.

The invention also comprises methods of producing triglyceride compositions, comprising (a) culturing a population of cells of the genus *Prototheca* in the presence of a fixed carbon source, wherein: (i) the cells contain an exogenous gene; (ii) the cells accumulate at least 10, 20, 30, 40, 60, or 70% of their dry cell weight as lipid; and (iii) the fixed carbon source is selected from the group consisting of sorghum and depolymerized cellulosic material; and (b) isolating lipid components from the cultured microorganisms. In some embodiments the fixed carbon source is depolymerized cellulosic material selected from the group consisting of corn stover, *Miscanthus*, forage sorghum, sugar beet pulp and sugar cane bagasse, optionally that has been subjected to washing with water prior to the culturing step. In some methods the fixed carbon source is depolymerized cellulosic material and the glucose level of the depolymerized cellulosic material is concentrated to a level of at least 300 g/liter, at least 400 g/liter, at least 500 g/liter, or at least 600 g/liter of prior to the culturing step and is fed to the culture over time as the cells grow and accumulate lipid. In some methods the exogenous gene encodes a fatty acyl-ACP thioesterase that has hydrolysis activity towards one or more fatty acyl-ACP substrates of chain length C8, C10, C12 or C14, and in some methods the triglyceride has a lipid profile of at least 4% C8-C14 and one or more of the following attributes: 0.1-0.4 micrograms/ml total carotenoids; less than 0.02 milligrams of chlorophyll per kilogram of oil; 0.40-0.60 milligrams of gamma tocopherol per 100 grams of oil; 0.2-0.5 milligrams of total tocotrienols per gram of oil, 4-8 mg per 100 grams of oil of campesterol, and 40-60 mg per 100 grams of oil of stigmasterol.

Further methods of the invention include producing a triglyceride composition, comprising: (a) culturing a population of microorganisms in the presence of depolymerized cellulosic material, wherein: (i) the depolymerized cellulosic material is subjected to washing with water prior to the culturing step; (ii) the cells accumulate at least 10, 20, 30, 40, 60, or 70% of their dry cell weight as lipid; and (iii) the depolymerized cellulosic material is concentrated to at least 300, 400, 500, or 600 g/liter of glucose prior to the cultivation step; (iv) the microorganisms are cultured in a fed-batch reaction in which depolymerized cellulosic material of at least 300, 400, 500, or 600 g/liter of glucose is fed to the microorganisms; and (b) isolating lipid components from the cultured microorganisms. In some embodiments the fixed carbon source is depolymerized cellulosic material selected from the group consisting of corn stover, *Miscanthus*, forage sorghum, sugar beet pulp and sugar cane bagasse. In further embodiments the microorganisms are a species of the genus *Prototheca* and contain an exogenous gene, including a fatty acyl-ACP thioesterase that has hydrolysis activity towards one or more fatty acyl-ACP substrates of chain length C8, C10, C12 or C14. A further method of the invention comprises manufacturing triglyceride oil comprising cultivating a cell that has a 23S rRNA sequence with at least 90 or 96% nucleotide identity to SEQ ID NO: 30 in the presence of sucrose as a carbon source.

The invention also includes methods of manufacturing a chemical comprising performing one or more chemical reactions from the list consisting of transesterification, hydrogenation, hydrocracking, deoxygenation, isomerization, interesterification, hydroxylation, hydrolysis, and saponification on a triglyceride oil, wherein the oil has a lipid profile of at least 4% C8-C14 and one or more of the following attributes: 0.1-0.4 micrograms/ml total carotenoids; less than 0.02 milligrams of chlorophyll per kilogram of oil; 0.10-0.60 milligrams of gamma tocopherol per 100 grams of oil; 0.1-0.5 milligrams of total tocotrienols per gram of oil, 1-8 mg per 100 grams of oil of campesterol, and 10-60 mg per 100 grams of oil of stigmasterol. Some methods are performed by manufacturing the oil by cultivating a cell of the genus *Prototheca* that comprises an exogenous fatty acyl-ACP thioesterase gene that encodes a fatty acyl-ACP thioesterase having hydrolysis activity towards one or more fatty acyl-ACP substrates of chain length C8, C10, C12 or C14. In some methods the hydrolysis reaction is selected from the group consisting of saponification, acid hydrolysis, alkaline hydrolysis, enzymatic hydrolysis, catalytic hydrolysis, and hot-compressed water hydrolysis, including a catalytic hydrolysis reaction wherein the oil is split into glycerol and fatty acids. In further methods the fatty acids undergo an amination reaction to produce fatty nitrogen compounds or an ozonolysis reaction to produce mono- and dibasic-acids. In some embodiments the oil undergoes a triglyceride splitting method selected from the group consisting of enzymatic splitting and pressure splitting. In some methods a condensation reaction follows the hydrolysis reaction. Other methods include performing a hydroprocessing reaction on the oil, optionally wherein the product of the hydroprocessing reaction undergoes a deoxygenation reaction or a condensation reaction prior to or simultaneous with the hydroprocessing reaction. Some methods additionally include a gas removal reaction. Additional methods include processing the aforementioned oils by performing a deoxygenation reaction selected from the group consisting of: a hydrogenolysis reaction, hydrogenation, a consecutive hydrogenation-hydrogenolysis reaction, a consecutive hydrogenolysis-hydrogenation reaction, and a combined hydrogenation-hydrogenolysis reaction. In some methods a condensation reaction follows the deoxygenation reaction. Other methods include performing an esterification reaction on the aforementioned oils, optionally an interestification reaction or a transesterification reaction. Other methods include performing a hydroxylation reaction on the aforementioned oils, optionally wherein a condensation reaction follows the hydroxylation reaction.

DETAILED DESCRIPTION OF THE INVENTION

Figure 1:
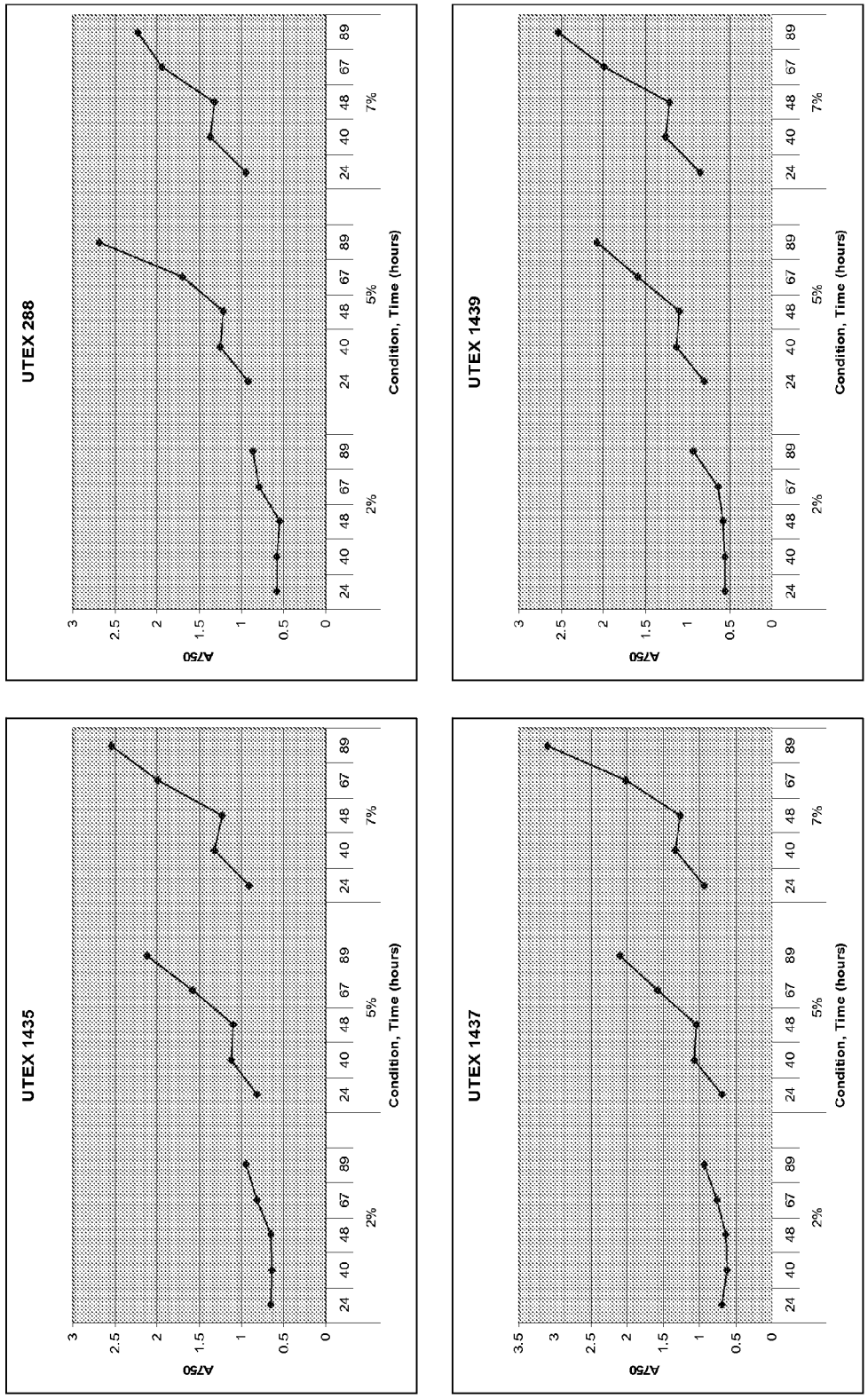
FIGS. 1 and 2 illustrate the growth curves of *Prototheca* species and *Chlorella luteoviridis* strain SAG 2214 grown on sorghum as the carbon source.

The present invention arises from the discovery that *Prototheca* and certain related microorganisms have unexpectedly advantageous properties for the production of oils, fuels, and other hydrocarbon or lipid compositions economically and in large quantities, as well as from the discovery of methods and reagents for genetically altering these microorganisms to improve these properties. The oils produced by these microorganisms can be used in the transportation fuel, petrochemical, and/or food and cosmetic industries, among other applications. Transesterification of lipids yields long-chain fatty acid esters useful as biodiesel. Other enzymatic and chemical processes can be tailored to yield fatty acids, aldehydes, alcohols, alkanes, and alkenes. In some applications, renewable diesel, jet fuel, or other hydrocarbon compounds are produced. The present invention also provides methods of cultivating microalgae for increased productivity and increased lipid yield, and/or for more cost-effective production of the compositions described herein.

This detailed description of the invention is divided into sections for the convenience of the reader. Section I provides definitions of terms used herein. Section 2 provides a description of culture conditions useful in the methods of the invention. Section 3 provides a description of genetic engineering methods and materials. Section 4 provides a description of genetic engineering of *Prototheca* to enable sucrose utilization. Section 5 provides a description of genetic engineering of *Prototheca* to modify lipid biosynthesis. Section 6 describes methods for making fuels and chemicals. Section 7 discloses examples and embodiments of the invention. The detailed description of the invention is followed by examples that illustrate the various aspects and embodiments of the invention.

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Active in microalgae" refers to a nucleic acid that is functional in microalgae. For example, a promoter that has been used to drive an antibiotic resistance gene to impart antibiotic resistance to a transgenic microalgae is active in microalgae.

"Acyl carrier protein" or "ACP" is a protein that binds a growing acyl chain during fatty acid synthesis as a thiol ester at the distal thiol of the 4'-phosphopantetheine moiety and comprises a component of the fatty acid synthase complex.

"Acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

"Area Percent" refers to the area of peaks observed using FAME GC/FID detection methods in which every fatty acid in the sample is converted into a fatty acid methyl ester (FAME) prior to detection. For example, a separate peak is observed for a fatty acid of 14 carbon atoms with no unsaturation (C14:0) compared to any other fatty acid such as C14:1. The peak area for each class of FAME is directly proportional to its percent composition in the mixture and is calculated based on the sum of all peaks present in the sample (i.e. [area under specific peak/total area of all measured peaks]×100). When referring to lipid profiles of oils and cells of the invention, "at least 4% C8-C14" means that at least 4% of the total fatty acids in the cell or in the extracted glycerolipid composition have a chain length that includes 8, 10, 12 or 14 carbon atoms.

"Axenic" is a culture of an organism free from contamination by other living organisms.

"Biodiesel" is a biologically produced fatty acid alkyl ester suitable for use as a fuel in a diesel engine.

"Biomass" is material produced by growth and/or propagation of cells. Biomass may contain cells and/or intracellular contents as well as extracellular material, includes, but is not limited to, compounds secreted by a cell.

"Bioreactor" is an enclosure or partial enclosure in which cells are cultured, optionally in suspension.

"Catalyst" is an agent, such as a molecule or macromolecular complex, capable of facilitating or promoting a chemical reaction of a reactant to a product without becoming a part of the product. A catalyst increases the rate of a reaction, after which, the catalyst may act on another reactant to form the product. A catalyst generally lowers the overall activation energy required for the reaction such that it proceeds more quickly or at a lower temperature. Thus, a reaction equilibrium may be more quickly attained. Examples of catalysts include enzymes, which are biological catalysts; heat, which is a non-biological catalyst; and metals used in fossil oil refining processes.

"Cellulosic material" is the product of digestion of cellulose, including glucose and xylose, and optionally additional compounds such as disaccharides, oligosaccharides, lignin, furfurals and other compounds. Nonlimiting examples of sources of cellulosic material include sugar cane bagasses, sugar beet pulp, corn stover, wood chips, sawdust and switchgrass.

"Co-culture", and variants thereof such as "co-cultivate" and "co-ferment", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

"Cofactor" is any molecule, other than the substrate, required for an enzyme to carry out its enzymatic activity.

"Complementary DNA" or "cDNA" is a DNA copy of mRNA, usually obtained by reverse transcription of messenger RNA (mRNA) or amplification (e.g., via polymerase chain reaction ("PCR")).

"Cultivated", and variants thereof such as "cultured" and "fermented", refer to the intentional fostering of growth (increases in cell size, cellular contents, and/or cellular activity) and/or propagation (increases in cell numbers via mitosis) of one or more cells by use of selected and/or controlled conditions. The combination of both growth and propagation may be termed proliferation. Examples of selected and/or controlled conditions include the use of a defined medium (with known characteristics such as pH, ionic strength, and carbon source), specified temperature, oxygen tension, carbon dioxide levels, and growth in a bioreactor. Cultivate does not refer to the growth or propagation of microorganisms in nature or otherwise without human intervention; for example, natural growth of an organism that ultimately becomes fossilized to produce geological crude oil is not cultivation.

"Cytolysis" is the lysis of cells in a hypotonic environment. Cytolysis is caused by excessive osmosis, or movement of water, towards the inside of a cell (hyperhydration). The cell cannot withstand the osmotic pressure of the water inside, and so it explodes.

"Delipidated meal" and "delipidated microbial biomass" is microbial biomass after oil (including lipids) has been extracted or isolated from it, either through the use of mechanical (i.e., exerted by an expeller press) or solvent extraction or both. Delipidated meal has a reduced amount of oil/lipids as compared to before the extraction or isolation of oil/lipids from the microbial biomass but does contain some residual oil/lipid.

"Expression vector" or "expression construct" or "plasmid" or "recombinant DNA construct" refer to a nucleic acid that has been generated via human intervention, including by recombinant means or direct chemical synthesis, with a series of specified nucleic acid elements that permit transcription and/or translation of a particular nucleic acid in a host cell. The expression vector can be part of a plasmid, virus, or nucleic acid fragment. Typically, the expression vector includes a nucleic acid to be transcribed operably linked to a promoter.

"Exogenous gene" is a nucleic acid that codes for the expression of an RNA and/or protein that has been introduced ("transformed") into a cell. A transformed cell may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome or as an episomal molecule.

"Exogenously provided" refers to a molecule provided to the culture media of a cell culture.

"Expeller pressing" is a mechanical method for extracting oil from raw materials such as soybeans and rapeseed. An expeller press is a screw type machine, which presses material through a caged barrel-like cavity. Raw materials enter one side of the press and spent cake exits the other side while oil seeps out between the bars in the cage and is collected. The machine uses friction and continuous pressure from the screw drives to move and compress the raw material. The oil seeps through small openings that do not allow solids to pass through. As the raw material is pressed, friction typically causes it to heat up.

"Fatty acyl-ACP thioesterase" is an enzyme that catalyzes the cleavage of a fatty acid from an acyl carrier protein (ACP) during lipid synthesis.

"Fatty acyl-CoA/aldehyde reductase" is an enzyme that catalyzes the reduction of an acyl-CoA molecule to a primary alcohol.

"Fatty acyl-CoA reductase" is an enzyme that catalyzes the reduction of an acyl-CoA molecule to an aldehyde.

"Fatty aldehyde decarbonylase" is an enzyme that catalyzes the conversion of a fatty aldehyde to an alkane.

"Fatty aldehyde reductase" is an enzyme that catalyzes the reduction of an aldehyde to a primary alcohol.

"Fixed carbon source" is a molecule(s) containing carbon, typically an organic molecule, that is present at ambient temperature and pressure in solid or liquid form in a culture media that can be utilized by a microorganism cultured therein.

"Homogenate" is biomass that has been physically disrupted.

"Hydrocarbon" is (a) a molecule containing only hydrogen and carbon atoms wherein the carbon atoms are covalently linked to form a linear, branched, cyclic, or partially cyclic backbone to which the hydrogen atoms are attached. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, and squalene.

"Hydrogen:carbon ratio" is the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

"Hydrophobic fraction" is the portion, or fraction, of a material that is more soluble in a hydrophobic phase in comparison to an aqueous phase. A hydrophobic fraction is substantially insoluble in water and usually non-polar.

"Increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

"Inducible promoter" is a promoter that mediates transcription of an operably linked gene in response to a particular stimulus.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"In situ" means "in place" or "in its original position".

"Limiting concentration of a nutrient" is a concentration of a compound in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

"Lipase" is a water-soluble enzyme that catalyzes the hydrolysis of ester bonds in water-insoluble, lipid substrates. Lipases catalyze the hydrolysis of lipids into glycerols and fatty acids.

"Lipid modification enzyme" refers to an enzyme that alters the covalent structure of a lipid. Examples of lipid modification enzymes include a lipase, a fatty acyl-ACP thioesterase, a fatty acyl-CoA/aldehyde reductase, a fatty acyl-CoA reductase, a fatty aldehyde reductase, and a fatty aldehyde decarbonylase.

"Lipid pathway enzyme" is any enzyme that plays a role in lipid metabolism, i.e., either lipid synthesis, modification, or degradation, and any proteins that chemically modify lipids, as well as carrier proteins.

"Lipids" are a class of molecules that are soluble in nonpolar solvents (such as ether and chloroform) and are relatively or completely insoluble in water. Lipid molecules have these properties, because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). "Fats" are a subgroup of lipids called "triacylglycerides."

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Microalgae" is a eukaryotic microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella*, *Dunaliella*, and *Prototheca*. Microalgae also include other microbial photosynthetic organisms that exhibit cell-cell adhesion, such as *Agmenellum*, *Anabaena*, and *Pyrobotrys*. Microalgae also include obligate heterotrophic microorganisms that have lost the ability to perform photosynthesis, such as certain dinoflagellate algae species and species of the genus *Prototheca*.

"Microorganism" and "microbe" are microscopic unicellular organisms.

"Naturally co-expressed" with reference to two proteins or genes means that the proteins or their genes are co-expressed naturally in a tissue or organism from which they are derived, e.g., because the genes encoding the two proteins are under the control of a common regulatory sequence or because they are expressed in response to the same stimulus.

"Osmotic shock" is the rupture of cells in a solution following a sudden reduction in osmotic pressure. Osmotic shock is sometimes induced to release cellular components of such cells into a solution.

"Polysaccharide-degrading enzyme" is any enzyme capable of catalyzing the hydrolysis, or saccharification, of any polysaccharide. For example, cellulases catalyze the hydrolysis of cellulose.

"Polysaccharides" or "glycans" are carbohydrates made up of monosaccharides joined together by glycosidic linkages. Cellulose is a polysaccharide that makes up certain plant cell walls. Cellulose can be depolymerized by enzymes to yield monosaccharides such as xylose and glucose, as well as larger disaccharides and oligosaccharides.

"Promoter" is a nucleic acid control sequence that directs transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Recombinant" is a cell, nucleic acid, protein or vector, that has been modified due to the introduction of an exogenous nucleic acid or the alteration of a native nucleic acid. Thus, e.g., recombinant cells express genes that are not found within the native (non-recombinant) form of the cell or express native genes differently than those genes are expressed by a non-recombinant cell. A "recombinant nucleic acid" is a nucleic acid originally formed in vitro, in general, by the manipulation of nucleic acid, e.g., using polymerases and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Renewable diesel" is a mixture of alkanes (such as C10:0, C12:0, C14:0, C16:0 and C18:0) produced through hydrogenation and deoxygenation of lipids.

"Saccharification" is a process of converting biomass, usually cellulosic or lignocellulosic biomass, into monomeric sugars, such as glucose and xylose. "Saccharified" or "depolymerized" cellulosic material or biomass refers to cellulosic material or biomass that has been converted into monomeric sugars through saccharification.

"Sonication" is a process of disrupting biological materials, such as a cell, by use of sound wave energy.

"Species of furfural" is 2-furancarboxaldehyde or a derivative that retains the same basic structural characteristics.

"Stover" is the dried stalks and leaves of a crop remaining after a grain has been harvested.

"Sucrose utilization gene" is a gene that, when expressed, aids the ability of a cell to utilize sucrose as an energy source. Proteins encoded by a sucrose utilization gene are referred to herein as "sucrose utilization enzymes" and include sucrose transporters, sucrose invertases, and hexokinases such as glucokinases and fructokinases.

II. CULTIVATION

The present invention generally relates to cultivation of *Prototheca* strains, particularly recombinant *Prototheca* strains, for the production of lipid. For the convenience of the reader, this section is subdivided into subsections. Subsection 1 describes *Prototheca* species and strains and how to identify new *Prototheca* species and strains and related microalgae by genomic DNA comparison. Subsection 2 describes bioreactors useful for cultivation. Subsection 3 describes media for cultivation. Subsection 4 describes oil production in accordance with illustrative cultivation methods of the invention.

1. *Prototheca* Species and Strains

*Prototheca* is a remarkable microorganism for use in the production of lipid, because it can produce high levels of lipid, particularly lipid suitable for fuel production. The lipid produced by *Prototheca* has hydrocarbon chains of shorter chain length and a higher degree of saturation than that produced by other microalgae. Moreover, *Prototheca* lipid is generally free of pigment (low to undetectable levels of chlorophyll and certain carotenoids) and in any event contains much less pigment than lipid from other microalgae. Moreover, recombinant *Prototheca* cells provided by the invention can be used to produce lipid in greater yield and efficiency, and with reduced cost, relative to the production of lipid from other microorganisms. Illustrative *Prototheca* strains for use in the methods of the invention include In addition, this microalgae grows heterotrophically and can be genetically engineered as *Prototheca wickerhamii, Prototheca stagnora* (including UTEX 327), *Prototheca portoricensis, Prototheca moriformis* (including UTEX strains 1441, 1435), and *Prototheca zopfii*. Species of the genus *Prototheca* are obligate heterotrophs.

Species of *Prototheca* for use in the invention can be identified by amplification of certain target regions of the genome. For example, identification of a specific *Prototheca* species or strain can be achieved through amplification and sequencing of nuclear and/or chloroplast DNA using primers and methodology using any region of the genome, for example using the methods described in Wu et al., *Bot. Bull. Acad. Sin.* (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Prototheca*, but other hydrocarbon and lipid producing organisms with similar lipid profiles and production capability. For examples of methods of identification and classification of algae also see for example *Genetics*, 2005 August; 170(4):1601-10 and *RNA*, 2005 April; 11(4): 361-4.

Thus, genomic DNA comparison can be used to identify suitable species of microalgae to be used in the present invention. Regions of conserved genomic DNA, such as but not limited to DNA encoding for 23S rRNA, can be amplified from microalgal species and compared to consensus sequences in order to screen for microalgal species that are taxonomically related to the preferred microalgae used in the present invention. Examples of such DNA sequence comparison for species within the *Prototheca* genus are shown below. Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship.

Microalgae for use in the present invention typically have genomic DNA sequences encoding for 23S rRNA that have at least 99%, least 95%, at least 90%, or at least 85% nucleotide identity to at least one of the sequences listed in SEQ ID NOs: 11-19.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Other considerations affecting the selection of microorganisms for use in the invention include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light).

2. Bioreactor

Microrganisms are cultured both for purposes of conducting genetic manipulations and for production of hydrocarbons (e.g., lipids, fatty acids, aldehydes, alcohols, and alkanes). The former type of culture is conducted on a small scale and initially, at least, under conditions in which the starting microorganism can grow. Culture for purposes of hydrocarbon production is usually conducted on a large scale (e.g., 10,000 L, 40,000 L, 100,000 L or larger bioreactors) in a bioreactor. *Prototheca* are typically cultured in the methods of the invention in liquid media within a bioreactor. Typically, the bioreactor does not allow light to enter.

The bioreactor or fermentor is used to culture microalgal cells through the various phases of their physiological cycle. Bioreactors offer many advantages for use in heterotrophic growth and propagation methods. To produce biomass for use in food, microalgae are preferably fermented in large quantities in liquid, such as in suspension cultures as an example. Bioreactors such as steel fermentors can accommodate very large culture volumes (40,000 liter and greater capacity bioreactors are used in various embodiments of the invention). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor.

Bioreactors can be configured to flow culture media though the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgal cultures to mixing. Mixing may be continuous or intermittent. For example, in some embodiments, a turbulent flow regime of gas entry and media entry is not maintained for reproduction of microalgae until a desired increase in number of said microalgae has been achieved.

Bioreactor ports can be used to introduce, or extract, gases, solids, semisolids, and liquids, into the bioreactor chamber containing the microalgae. While many bioreactors have more than one port (for example, one for media entry, and another for sampling), it is not necessary that only one substance enter or leave a port. For example, a port can be used to flow culture media into the bioreactor and later used for sampling, gas entry, gas exit, or other purposes. Preferably, a sampling port can be used repeatedly without altering compromising the axenic nature of the culture. A sampling port can be configured with a valve or other device that allows the flow of sample to be stopped and started or to provide a means of continuous sampling. Bioreactors typically have at least one port that allows inoculation of a culture, and such a port can also be used for other purposes such as media or gas entry.

Bioreactors ports allow the gas content of the culture of microalgae to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

3. Media

Microalgal culture media typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, without limitation, molecular nitrogen, nitrate, nitrate salts, ammonia (pure or in salt form, such as, $(NH_4)_2SO_4$ and $NH_4OH$), protein, soybean meal, cornsteep liquor, and yeast extract. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$.

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at http://www.utex.org/, a site maintained by the University of Texas at Austin, 1 University Station A6700, Austin, Tex., 78712-

0183, for its culture collection of algae (UTEX). For example, various fresh water and salt water media include those described in PCT. Pub. No. 2008/151149, incorporated herein by reference.

In a particular example, Proteose Medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2.2H_2O$, 0.3 mM $MgSO_4.7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use. Another example is the *Prototheca* isolation medium (PIM), which comprises 10 g/L postassium hydrogen phthalate (KHP), 0.9 g/L sodium hydroxide, 0.1 g/L magnesium sulfate, 0.2 g/L potassium hydrogen phosphate, 0.3 g/L ammonium chloride, 10 g/L glucose 0.001 g/L thiamine hydrochloride, 20 g/L agar, 0.25 g/L 5-fluorocytosine, at a pH in the range of 5.0 to 5.2 (see Pore, 1973, App. Microbiology, 26: 648-649). Other suitable media for use with the methods of the invention can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic). Additionally, U.S. Pat. No. 5,900,370 describes media formulations and conditions suitable for heterotrophic fermentation of *Prototheca* species.

For oil production, selection of a fixed carbon source is important, as the cost of the fixed carbon source must be sufficiently low to make oil production economical. Thus, while suitable carbon sources include, for example, acetate, floridoside, fructose, galactose, glucuronic acid, glucose, glycerol, lactose, mannose, N-acetylglucosamine, rhamnose, sucrose, and/or xylose, selection of feedstocks containing those compounds is an important aspect of the methods of the invention. Suitable feedstocks useful in accordance with the methods of the invention include, for example, black liquor, corn starch, depolymerized cellulosic material, milk whey, molasses, potato, sorghum, sucrose, sugar beet, sugar cane, rice, and wheat. Carbon sources can also be provided as a mixture, such as a mixture of sucrose and depolymerized sugar beet pulp. The one or more carbon source(s) can be supplied at a concentration of at least about 50 μM, at least about 100 μM, at least about 500 μM, at least about 5 mM, at least about 50 mM, and at least about 500 mM, of one or more exogenously provided fixed carbon source(s). Carbon sources of particular interest for purposes of the present invention include cellulose (in a depolymerized form), glycerol, sucrose, and sorghum, each of which is discussed in more detail below.

In accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstocks have been found to be inhibitory to yeast growth, and yeast cannot use the 5-carbon sugars produced from cellulosic materials (e.g., xylose from hemi-cellulose). By contrast, microalgae can grow on processed cellulosic material. Cellulosic materials generally include about 40-60% cellulose; about 20-40% hemicellulose; and 10-30% lignin.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

Cellulosic materials are treated to increase the efficiency with which the microbe can utilize the sugar(s) contained within the materials. The invention provides novel methods for the treatment of cellulosic materials after acid explosion so that the materials are suitable for use in a heterotrophic culture of microbes (e.g., microalgae and oleaginous yeast). As discussed above, lignocellulosic biomass is comprised of various fractions, including cellulose, a crystalline polymer of beta 1,4 linked glucose (a six-carbon sugar), hemicellulose, a more loosely associated polymer predominantly comprised of xylose (a five-carbon sugar) and to a lesser extent mannose, galactose, arabinose, lignin, a complex aromatic polymer comprised of sinapyl alcohol and its derivatives, and pectins, which are linear chains of an alpha 1,4 linked polygalacturonic acid. Because of the polymeric structure of cellulose and hemicellulose, the sugars (e.g., monomeric glucose and xylose) in them are not in a form that can be efficiently used (metabolized) by many microbes. For such microbes, further processing of the cellulosic biomass to generate the monomeric sugars that make up the polymers can be very helpful to ensuring that the cellulosic materials are efficiently utilized as a feedstock (carbon source).

Celluose or cellulosic biomass is subjected to a process, termed "explosion", in which the biomass is treated with dilute sulfuric (or other) acid at elevated temperature and pressure. This process conditions the biomass such that it can be efficiently subjected to enzymatic hydrolysis of the cellulosic and hemicellulosic fractions into glucose and xylose monomers. The resulting monomeric sugars are termed cellulosic sugars. Cellulosic sugars can subsequently be utilized by microorganisms to produce a variety of metabolites (e.g., lipid). The acid explosion step results in a partial hydrolysis of the hemicellulose fraction to constitutent monosaccharides. These sugars can be completely liberated from the biomass with further treatment. In some embodiments, the further treatment is a hydrothermal treatment that includes washing the exploded material with hot water, which removes contaminants such as salts. This step is not necessary for cellulosic ethanol fermentations due to the more dilute sugar concentrations used in such processes. In other embodiments, the further treatment is additional acid treatment. In still other embodiments, the further treatment is enzymatic hydrolysis of the exploded material. These treatments can also be used in any combination. The type of treatment can affect the type of sugars liberated (e.g., five carbon sugars versus six carbon sugars) and the stage at which they are liberated in the process. As a consequence, different streams of sugars, whether they are predominantly five-carbon or six-carbon, can be created. These enriched five-carbon or six-carbon streams can thus be directed to specific microorganisms with different carbon utilization cabilities.

The methods of the present invention typically involve fermentation to higher cell densities than what is achieved in ethanol fermentation. Because of the higher densities of the cultures for heterotrophic cellulosic oil production, the fixed carbon source (e.g., the cellulosic derived sugar stream(s)) is preferably in a concentrated form. The glucose level of the depolymerized cellulosic material is preferably at least 300 g/liter, at least 400 g/liter, at least 500 g/liter or at least 600 g/liter prior to the cultivation step, which is optionally a fed batch cultivation in which the material is fed to the cells over time as the cells grow and accumulate lipid. Cellulosic sugar streams are not used at or near this concentration range in the production of cellulosic ethanol. Thus, in order to generate and sustain the very high cell densities during the production of lignocellulosic oil, the carbon feedstock(s) must be delivered into the heterotrophic cultures in a highly concentrated form. However, any component in the feedstream that is not a substrate for, and is not metabolized by, the oleaginous microorganism will accumulate in the bioreactor, which can lead to problems if the component is toxic or inhibitory to production of the desired end product. While ligin and lignin-derived by-products, carbohydrate-derived byproducts such as furfurals and hydroxymethyl furfurals and salts derived from the generation of the cellulosic materials (both in the explosion process and the subsequent neutralization process), and even non-metabolized pentose/hexose sugars can present problems in ethanolic fermentations, these effects are amplified significantly in a process in which their concentration in the initial feedstock is high. To achieve sugar concentrations in the 300 g/L range (or higher) for six-carbon sugars that may be used in large scale production of lignocellulosic oil described in the present invention, the concentration of these toxic materials can be 20 times higher than the concentrations typically present in ethanolic fermentations of cellulosic biomass.

The explosion process treatment of the cellulosic material utilizes significant amounts of sulfuric acid, heat and pressure, thereby liberating by-products of carbohydrates, namely furfurals and hydroxymethyl furfurals. Furfurals and hydroxymethyl furfurals are produced during hydrolysis of hemicellulose through dehydration of xylose into furfural and water. In some embodiments of the present invention, these by-products (e.g., furfurals and hydroxymethyl furfurals) are removed from the saccharified lignocellulosic material prior to introduction into the bioreactor. In certain embodiments of the present invention, the process for removal of the by-products of carbohydrates is hydrothermal treatment of the exploded cellulosic materials. In addition, the present invention provides methods in which strains capable of tolerating compounds such as furfurals or hydroxymethyl furfurals are used for lignocellulosic oil production. In another embodiment, the present invention also provides methods and microorganisms that are not only capable of tolerating furfurals in the fermentation media, but are actually able to metabolize these by-products during the production of lignocellulosic oil.

The explosion process also generates significant levels of salts. For example, typical conditions for explosion can result in conductivites in excess of 5 mS/cm when the exploded cellulosic biomass is resuspended at a ratio of 10:1 water: solids (dry weight). In certain embodiments of the present invention, the diluted exploded biomass is subjected to enzymatic saccharification, and the resulting supernatant is concentrated up to 25 fold for use in the bioreactor. The salt level (as measured by conductivity) in the concentrated sugar stream(s) can be unacceptably high (up to 1.5 M $Na^+$ equivalents). Additional salts are generated upon neutralization of the exploded materials for the subsequent enzymatic saccharification process as well. The present invention provides methods for removing these salts so that the resulting concentrated cellulosic sugar stream(s) can be used in heterotrophic processes for producing lignocellulosic oil. In some embodiments, the method of removing these salts is deionization with resins, such as, but not limited to, DOWEX. Marathon MR3. In certain embodiments, the deionization with resin step occurs before sugar concentration or pH adjustment and hydrothermal treatment of biomass prior to saccharification, or any combination of the preceding; in other embodiments, the step is conducted after one or more of these processes. In other embodiments, the explosion process itself is changed so as to avoid the generation of salts at unacceptably high levels. For example, a suitable alternative to sulfuric acid (or other acid) explosion of the cellulosic biomass is mechanical pulping to render the cellulosic biomass receptive to enzymatic hydrolysis (saccharification). In still other embodiments, native strains of microorganisms resistant to high levels of salts or genetically engineered strains with resistance to high levels of salts are used.

Figure 10:
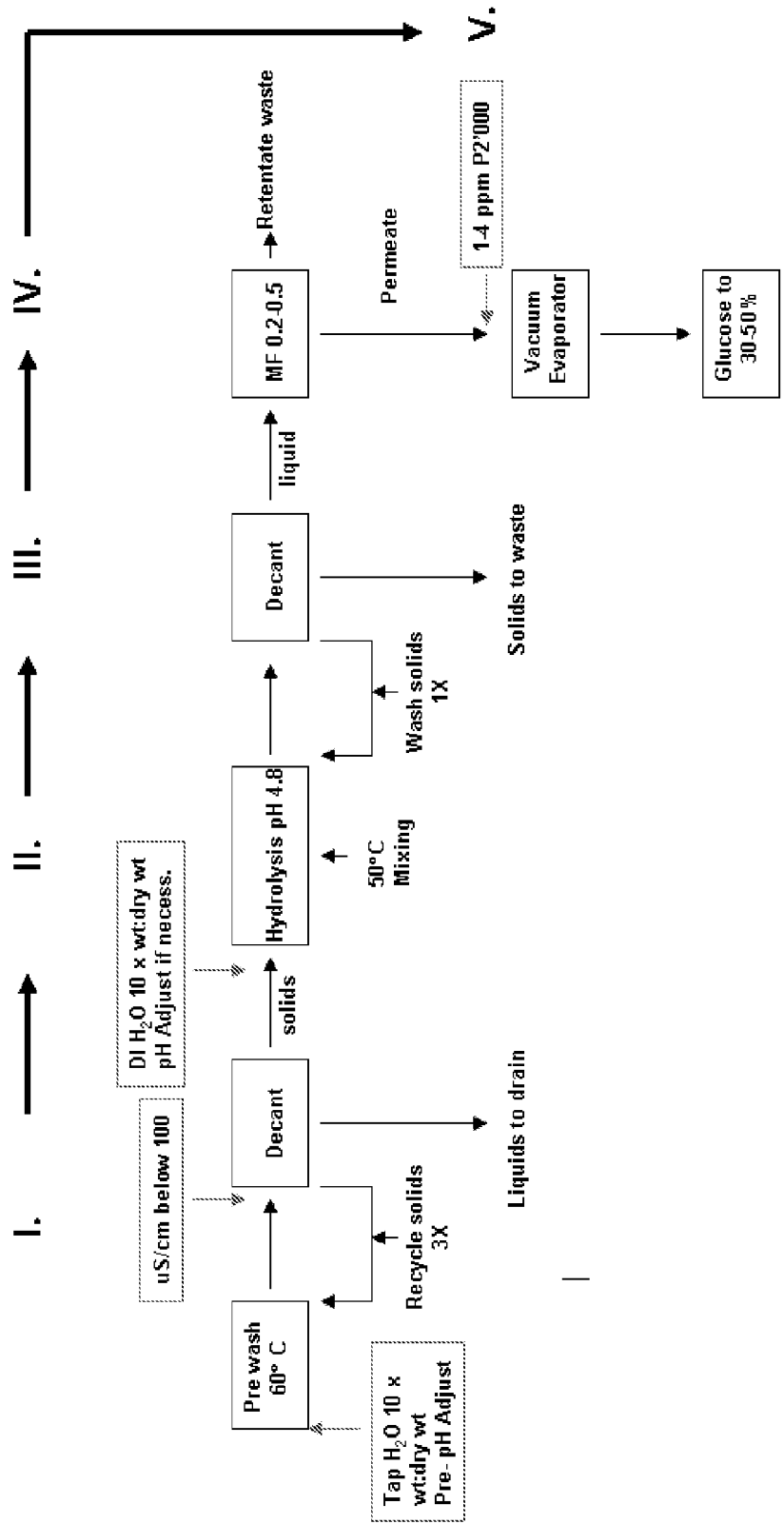
FIG. 10 shows a schematic of a saccharification process of cellulosic materials to generate sugar streams suitable for use in heterotrophic oil production in a fermentor.
Figure 11:
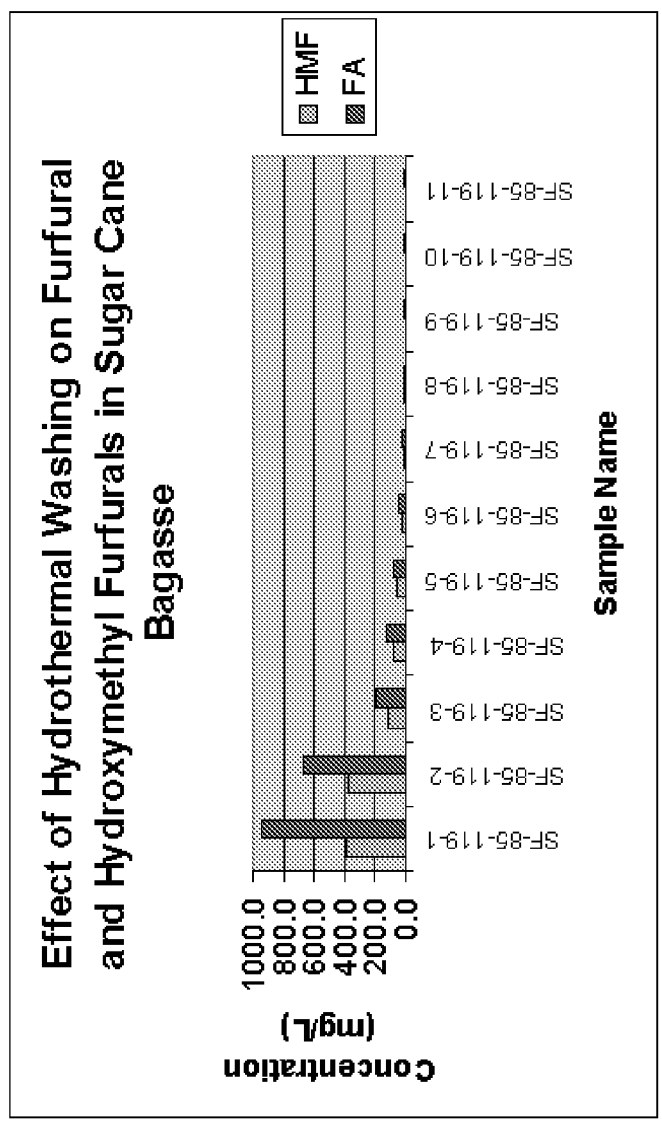
FIG. 11 shows decreasing levels of HMF and furfurals in exploded sugar cane bagasse after repeated cycles of hydrothermal treatment.
Figure 12:
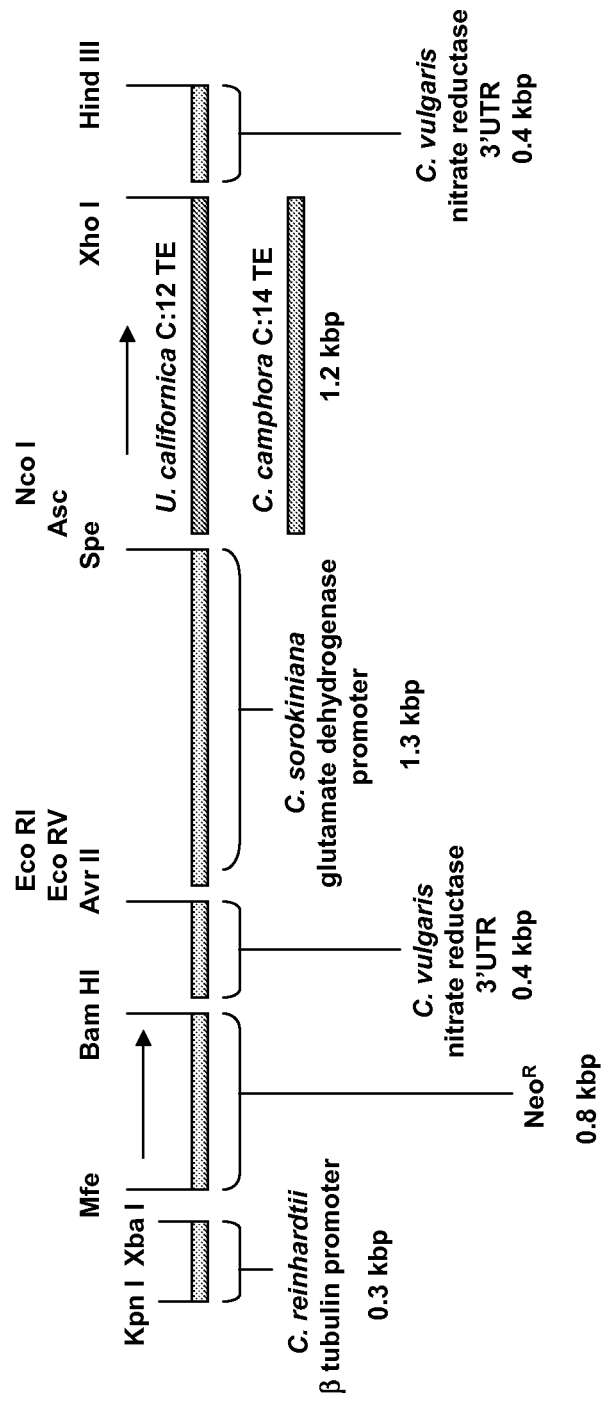
FIG. 12 shows a schematic of thioesterase constructs used in *Prototheca* transformations. The heterologous beta-tubulin (driving Neo®) and glutamate dehydrogenase promoters are derived from *Chlamydomonas reinhardtii* and *Chlorella sorokiniana*, respectively. The nitrate reductase 3'UTR was derived from *Chlorella vulgaris*. The relevant restriction cloning sites are indicated and arrows indicate the direction of transcription.

A preferred embodiment for the process of preparing of exploded cellulosic biomass for use in heterotrophic lignocellulosic oil production using oleaginous microbes is diagramed in FIG. 10. Step I. comprises adjusting the pH of the resuspended exploded cellulosic biomass to the range of 5.0-5.3 followed by washing the cellulosic biomass three times. This washing step can be accomplished by a variety of means including the use of desalting and ion exchange resins, reverse osmosis, hydrothermal treatment (as described above), or just repeated re-suspension and centrifugation in deionized water. This wash step results in a cellulosic stream whose conductivity is between 100-300 µS/cm and the removal of significant amounts of furfurals and hydroxymethyl furfurals. Decants from this wash step can be saved to concentrate five-carbon sugars liberated from the hemicellulose fraction. Step II comprises enzymatic saccharification of the washed cellulosic biomass. In a preferred embodiment, Accellerase (Genencor) is used. Step III comprises the recovery of sugars via centrifugation or decanting and rinsing of the saccharified biomass. The resulting biomass (solids) is an energy dense, lignin rich component that can be used as fuel or sent to waste. The recovered sugar stream in the centrifugation/decanting and rinse process is collected. Step IV comprises microfiltration to remove contaminating solids with recovery of the permeate. Step V comprises a concentration step which can be accomplished using a vacuum evaporator. This step can optionally include the addition of antifoam agents such as P'2000 (Sigma/Fluka), which is sometimes necessary due to the protein content of the resulting sugar feedstock.

In another embodiment of the methods of the invention, the carbon source is glycerol, including acidulated and non-acidulated glycerol byproduct from biodiesel transesterification. In one embodiment, the carbon source includes glycerol and at least one other carbone source. In some cases, all of the glycerol and the at least one other fixed carbon source are provided to the microorganism at the beginning of the fermentation. In some cases, the glycerol and the at least one other fixed carbon source are provided to the microorganism simultaneously at a predetermined ratio. In some cases, the glycerol and the at least one other fixed carbon source are fed to the microbes at a predetermined rate over the course of fermentation.

Some microalgae undergo cell division faster in the presence of glycerol than in the presence of glucose (see PCT Pub. No. 2008/151149). In these instances, two-stage growth processes in which cells are first fed glycerol to rapidly increase cell density, and are then fed glucose to accumulate lipids can improve the efficiency with which lipids are produced. The use of the glycerol byproduct of the transesterification process provides significant economic advantages when put back into the production process. Other feeding methods are provided as well, such as mixtures of glycerol and glucose. Feeding such mixtures also captures the same economic benefits. In addition, the invention provides methods of feeding alternative sugars to microalgae such as sucrose in various combinations with glycerol.

In another embodiment of the methods of the invention, the carbon source is sucrose, including a complex feedstock containing sucrose, such as thick cane juice from sugar cane processing. In one embodiment, the culture medium further includes at least one sucrose utilization enzyme. In some cases, the culture medium includes a sucrose invertase. In one embodiment, the sucrose invertase enzyme is a secretable sucrose invertase enzyme encoded by an exogenous sucrose invertase gene expressed by the population of microorganisms. Thus, in some cases, as described in more detail in Section IV, below, the microalgae has been genetically engineered to express a sucrose utilization enzyme, such as a sucrose transporter, a sucrose invertase, a hexokinase, a glucokinase, or a fructokinase.

Complex feedstocks containing sucrose include waste molasses from sugar cane processing; the use of this low-value waste product of sugar cane processing can provide significant cost savings in the production of hydrocarbons and other oils. Another complex feedstock containing sucrose that is useful in the methods of the invention is sorghum, including sorghum syrup and pure sorghum. Sorghum syrup is produced from the juice of sweet sorghum cane. Its sugar profile consists of mainly glucose (dextrose), fructose and sucrose.

4. Oil Production

For the production of oil in accordance with the methods of the invention, it is preferable to culture cells in the dark, as is the case, for example, when using extremely large (40,000 liter and higher) fermentors that do not allow light to strike the culture. *Prototheca* species are grown and propagated for the production of oil in a medium containing a fixed carbon source and in the absence of light; such growth is known as heterotrophic growth.

As an example, an inoculum of lipid-producing microalgal cells are introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining lipid rich biomass, the culture is typically harvested well after then end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of lipid species produced, and/or production of a specific oil.

As discussed above, a bioreactor or fermentor is used to allow cells to undergo the various phases of their growth cycle. As an example, an inoculum of lipid-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells. Lipid production by cells disclosed herein can occur during the log phase or thereafter, including the stationary phase wherein nutrients are supplied, or still available, to allow the continuation of lipid production in the absence of cell division.

Preferably, microorganisms grown using conditions described herein and known in the art comprise at least about 20% by weight of lipid, preferably at least about 40% by weight, more preferably at least about 50% by weight, and most preferably at least about 60% by weight. Process conditions can be adjusted to increase the yield of lipids suitable for a particular use and/or to reduce production cost. For example, in certain embodiments, a microalgae is cultured in the presence of a limiting concentration of one or more nutrients, such as, for example, nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 50%, 100%, 200%, or 500%. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period. Lipid content of cells can be increased by continuing the culture for increased periods of time while providing an excess of carbon, but limiting or no nitrogen.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into microbes (e.g., microalgae), using constructs and techniques such as those described above.

The specific examples of bioreactors, culture conditions, and heterotrophic growth and propagation methods described herein can be combined in any suitable manner to improve efficiencies of microbial growth and lipid and/or protein production.

Microalgal biomass with a high percentage of oil/lipid accumulation by dry weight has been generated using different methods of culture, which are known in the art (see PCT Pub. No. 2008/151149). Microalgal biomass generated by the culture methods described herein and useful in accordance with the present invention comprises at least 10% microalgal oil by dry weight. In some embodiments, the microalgal biomass comprises at least 25%, at least 50%, at least 55%, or at least 60% microalgal oil by dry weight. In some embodiments, the microalgal biomass contains from 10-90% microalgal oil, from 25-75% microalgal oil, from 40-75% microalgal oil, or from 50-70% microalgal oil by dry weight.

The microalgal oil of the biomass described herein, or extracted from the biomass for use in the methods and compositions of the present invention can comprise glycerolipids with one or more distinct fatty acid ester side chains. Glycerolipids are comprised of a glycerol molecule esterified to one, two or three fatty acid molecules, which can be of varying lengths and have varying degrees of saturation. The length and saturation characteristics of the fatty acid molecules (and the microalgal oils) can be manipulated to modify the properties or proportions of the fatty acid molecules in the microalgal oils of the present invention via culture conditions or via lipid pathway engineering, as described in more detail in Section IV, below. Thus, specific blends of algal oil can be prepared either within a single species of algae by mixing together the biomass or algal oil from two or more species of microalgae, or by blending algal oil of the invention with oils from other sources such as soy, rapeseed, canola, palm, palm kernel, coconut, corn, waste vegetable, Chinese tallow, olive, sunflower, cottonseed, chicken fat, beef tallow, porcine tallow, microalgae, macroalgae, microbes, *Cuphea*, flax, peanut, choice white grease, lard, *Camelina sativa*, mustard seed, cashew nut, oats, lupine, kenaf, calendula, help, coffee, linseed (flax), hazelnut, euphorbia, pumpkin seed, coriander, camellia, sesame, safflower, rice, tung tree, cocoa, copra, pium poppy, castor beans, pecan, jojoba, macadamia, Brazil nuts, avocado, petroleum, or a distillate fraction of any of the preceding oils.

The oil composition, i.e., the properties and proportions of the fatty acid consitutents of the glycerolipids, can also be manipulated by combining biomass or oil from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid consituents in the cell's glycerolipids.

Generally, *Prototheca* strains have very little or no fatty acids with the chain length C8-C14. For example, *Prototheca moriformis* (UTEX 1435), *Prototheca krugani* (UTEX 329), *Prototheca stagnora* (UTEX 1442) and *Prototheca zopfii* (UTEX 1438) contains no (or undectable amounts) C8 fatty acids, between 0-0.01% C10 fatty acids, between 0.03-2.1% C12 fatty acids and between 1.0-1.7% C14 fatty acids.

In some cases, the *Protheca* strains containing a transgene encoding a fatty acyl-ACP thioesterase that has activity towards fatty acyl-ACP substrate of chain lengths C8-10 has at least 0.3%, at least 0.8%, at least 1.5% or more fatty acids of chain length C8 and at least 0.3%, at least 1.0%, at least 3.0%, at least 5% or more fatty acids of chain length C10. In other instances, the *Prototheca* strains containing a transgene encoding a fatty acyl-ACP thioesterase that has activity towards fatty acyl-ACP substrate of chain length C12 has at least 3.0%, at least 5%, at least 7%, at least 10%, at least 13% or more fatty acids of the chain length C12 and at least 1.5%, at least 2%, or at least 3% or more fatty acids of the chain length C14. In other cases, the *Prototheca* strains containing a transgene encoding a fatty acyl-ACP thioesterase that has activity towards fatty acyl-ACP substrate of chain length C14 has at least 4.0%, at least 7%, at least 10%, at least 15%, at least 20%, at least 25% or more fatty acids of the chain length C14, and at least 0.4%, at least 1%, at least 1.5%, or more fatty acids of the chain length C12.

In non-limiting examples, the *Prototheca* strains containing a transgene encoding a fatty acyl-ACP thioesterase that has activity towards fatty acyl-ACP substrate of chain length C8 and C10 has between 0.3-1.58% fatty acids of chain length C8 and between 0.35-6.76% fatty acids of the chain length C10. In other non-limiting examples, *Prototheca* strains containing a transgene encoding a fatty acyl-ACP thioesterase that has activity towards fatty acyl-ACP substrate of chain length C12 has between 3.9-14.11% fatty acids of the chain length C12 and between 1.95-3.05% fatty acids of the chain length C14. In other non-limiting examples, *Prototheca* strains containing a transgene encoding a fatty acyl-ACP thioesterase that has activity towards fatty acyl-ACP substrate of chain length C14 has between 4.40-17.35% fatty acids of the chain length C14 and between 0.4-1.83 Area % fatty acids of the chain length C12. In some cases, the *Prototheca* strains containing a transgene encoding a fatty acyl-ACP thioesterase that has activity towards fatty acyl-ACP substrate of chain lengths between C8 and C14 have between 3.5-20% medium chain (C8-C14) fatty acids. In some instances, keeping the transgenic *Prototheca* strains under constant and high selective pressure to retain exogenous genes is advantageous due to the increase in the desired fatty acid of a specific chain length. In a non-limiting example, Example 5 demonstrates a two fold increase in C14 chain length fatty acids (more than 30% C8-C14 chain length fatty acids) when the culture of *Prototheca moriformis* containing a C14 preferring thioesterase exogenous gene is retained. High levels of exogenous gene retention can also be achieved by inserting exogenous genes into the nuclear chromosomes of the cells using homologous recombination vectors and methods disclosed herein. Recombinant cells containing exogenous genes integrated into nuclear chromosomes are an object of the invention.

Microalgal oil can also include other constituents produced by the microalgae, or incorporated into the microalgal oil from the culture medium. These other constituents can be present in varying amount depending on the culture conditions used to culture the microalgae, the species of microalgae, the extraction method used to recover microalgal oil from the biomass and other factors that may affect microalgal oil composition. Non-limiting examples of such constituents include carotenoids, present from 0.1-0.4 micrograms/ml, chlorophyll present from 0-0.02 milligrams/kilogram of oil, gamma tocopherol present from 0.4-0.6 milligrams/100 grams of oil, and total tocotrienols present from 0.2-0.5 milligrams/gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), and various organic or inorganic compounds.

In some cases, the oil extracted from *Prototheca* species comprises no more than 0.02 mg/kg chlorophyll. In some cases, the oil extracted from *Prototheca* species comprises no more than 0.4 mcg/ml total carotenoids. In some cases the *Prototheca* oil comprises between 0.40-0.60 milligrams of gamma tocopherol per 100 grams of oil. In other cases, the *Prototheca* oil comprises between 0.2-0.5 milligrams of total tocotrienols per gram of oil.

III. GENETIC ENGINEERING METHODS AND MATERIALS

The present invention provides methods and materials for genentically modifying *Prototheca* cells and recombinant host cells useful in the methods of the present invention, including but not limited to recombinant *Prototheca moriformis, Prototheca zopfii, Prototheca krugani*, and *Prototheca stagnora* host cells. The description of these methods and materials is divided into subsections for the convenience of the reader. In subsection 1, transformation methods are described. In subsection 2, genetic engineering methods using homologous recombination are described. In subsection 3, expression vectors and components are described.

1. Engineering Methods—Transformation

Cells can be transformed by any suitable technique including, e.g., biolistics, electroporation (see Maruyama et al. (2004), Biotechnology Techniques 8:821-826), glass bead transformation and silicon carbide whisker transformation. Another method that can be used involves forming protoplasts and using $CaCl_2$ and polyethylene glycol (PEG) to introduce recombinant DNA into microalgal cells (see Kim et al. (2002), *Mar. Biotechnol.* 4:63-73, which reports the use of this method for the transformation of *Chorella ellipsoidea*). Co-transformation of microalgae can be used to introduce two distinct vector molecules into a cell simultaneously (see for example Protist 2004 December; 155(4):381-93).

Biolistic methods (see, for example, Sanford, Trends In Biotech. (1988) 6:299 302, U.S. Pat. No. 4,945,050; electroporation (Fromm et al., Proc. Nat'l. Acad. Sci. (USA) (1985) 82:5824 5828); use of a laser beam, microinjection or any other method capable of introducing DNA into a microalgae can also be used for transformation of a *Prototheca* cell.

2. Engineering Methods—Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences. The mechanistic steps of this process, in most cases, include: (1) pairing of homologous DNA segments; (2) introduction of double-stranded breaks into the donor DNA molecule; (3) invasion of the template DNA molecule by the free donor DNA ends followed by DNA synthesis; and (4) resolution of double-strand break repair events that result in final recombination products.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

Particularly useful genetic engineering applications using homologous recombination is to co-opt specific host regulatory elements such as promoters/UTRs to drive heterologous gene expression in a highly specific fashion. For example, precise ablation of the endogenous stearoyl ACP desaturase gene with a heterologous C12:0 specific FATB (thioesterase) gene cassette and suitable selective marker, might be expected to dramatically decrease endogenous levels of C18:1 fatty acids concomitant with increased levels of the C12:0 fatty acids. Example 13 describes the homologous recombination targeting construct that is suitable for the eblation of an endogenous *Prototheca moriformis* stearoyl ACP destaurase gene.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the gost genome resulting in gene targeting, gene conversion, gene deletion, gene duplication, gene inversion and exchanging gene expression regulatory elements such as promoters, enhancers and 3'UTRs.

Homologous recombination can be achieve by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

3. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell. To aid the reader, this subsection is divided into subsections. Subsection A describes control sequences typically contained on vectors as well as novel control sequences provided by the present invention. Subsection B describes genes typically contained in vectors as well as novel codon optimization methods and genes prepared using them provided by the invention.

A. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microalgae contains a coding sequence for a desired gene product (for example, a selectable marker, a lipid pathway modification enzyme, or a sucrose utilization enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration. The promoterless method of transformation has been proven to work in microalgae (see for example Plant Journal 14:4, (1998), pp. 441-447).

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Illustrative exogenous and/or endogenous promoters that are active in microalgae (as well as antibiotic resistance genes functional in microalgae) are described in PCT Pub. No. 2008/151149 and references cited therein).

The promoter used to express an exogenous gene can be the promoter naturally linked to that gene or can be a heterologous gene. Some promoters are active in more than one species of microalgae. Other promoters are species-specific. Illustrative promoters include promoters such as β-tubulin from *Chlamydomonas reinhardtii*, used in the Examples below, and viral promoters, such as cauliflower mosaic virus (CMV) and chlorella virus, which have been shown to be active in multiple species of microalgae (see for example Plant Cell Rep. 2005 March; 23(10-11):727-35; J Microbiol. 2005 August; 43(4):361-5; Mar Biotechnol (NY). 2002 January; 4(1):63-73). Another promoter that is suitable for use for expression of exogenous genes in *Prototheca* is the *Chlorella sorokiniana* glutamate dehydrogenase promoter/5'UTR (SEQ ID NO: 69). Optionally, at least 10, 20, 30, 40, 50, or 60 nucleotides or more of these sequences containing a promoter are used. Illustrative promoters useful for expression of exogenous genes in *Prototheca* are listed in the sequence listing of this application, such as the promoter of the *Chlorella* HUP1 gene (SEQ ID NO:1) and the *Chlorella ellipsoidea* nitrate reductase promoter (SEQ ID NO:2). *Chlorella* virus promoters can also be used to express genes in *Prototheca*, such as SEQ ID NOs: 1-7 of U.S. Pat. No. 6,395,965. Additional promoters active in *Prototheca* can be found, for example, in Biochem Biophys Res Commun. 1994 Oct. 14; 204(1):187-94; Plant Mol Biol. 1994 October; 26(1):85-93; Virology. 2004 Aug. 15; 326(1):150-9; and Virology. 2004 Jan. 5; 318 (1):214-23.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule (e.g, glucose, as in SEQ ID NO:1), temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

The present invention also provides control sequences and recombinant genes and vectors containing them that provide for the compartmentalized expression of a gene of interest. Organelles for targeting are chloroplasts, plastids, mitochondria, and endoplasmic reticulum. In addition, the present invention provides control sequences and recombinant genes and vectors containing them that provide for the secretion of a protein outside the cell.

Proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors of the present invention to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella protothecodies* cells and are described in Examples 12 and Example 11 below. Sequences were BLASTed and analyzed for homology to known proteins that traffic to the plastid/chloroplast. The cDNAs encoding these proteins were cloned and plastid targeting sequences were isolated from these cDNAs. The amino acid sequences of the algal plastid targeting sequences identified from the cDNA libraries and the amino acid sequences of plant fatty acyl-ACP thioesterases that are used in the heterologous expression Examples below are listed in SEQ ID NOs: 127-133.

In another embodiment of the present invention, the expression of a polypeptide in *Prototheca* is targeted to the endoplasmic reticulum. The inclusion of an appropriate retention or sorting signal in an expression vector ensure that proteins are retained in the endoplasmic reticulum (ER) and do not go downstream into Golgi. For example, the IMPACTVECTOR1.3 vector, from Wageningen UR—Plant Research International, includes the well known KDEL retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci USA. 2005 Apr. 26; 102(17):6225-30.

In another embodiment of the present invention, a polypeptide is targeted for secretion outside the cell into the culture media. See Hawkins et al., Current Microbiology Vol. 38 (1999), pp. 335-341 for examples of secretion signals active in *Chlorella* that can be used, in accordance with the methods of the invention, in *Prototheca*.

B. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated, in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker. Any of a wide variety of selectable markers can be employed in a transgene construct useful for transforming *Prototheca*. Examples of suitable selectable markers include the G418 resistance gene, the nitrate reductase gene (see Dawson et al. (1997), Current Microbiology 35:356-362), the hygromycin phosphotransferase gene (HPT; see Kim et al. (2002), Mar. Biotechnol. 4:63-73), the neomycin phosphotransferase gene, and the ble gene, which confers resistance to phleomycin (Huang et al. (2007), Appl. Microbiol. Biotechnol. 72:197-205). Methods of determining sensitivity of microalgae to antibiotics are well known. For example, Mol Gen Genet. 1996 October 16; 252(5):572-9.

For purposes of the present invention, the expression vector used to prepare a recombinant host cell of the invention will include at least two, and often three, genes, if one of the genes is a selectable marker. For example, a genetically engineered *Prototheca* of the invention can be made by transformation with vectors of the invention that comprise, in addition to a selectable marker, one or more exogenous genes, such as, for example, sucrose invertase gene or acyl ACP-thioesterase gene. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of different inducible (or constitutive) promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced).

In other embodiments, the two or more exogenous genes (in addition to any selectable marker) are: a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In one embodiment, the vector provides for the combination of a fatty acyl-ACP thioesterase, a fatty acyl-CoA reductase, and a fatty aldehyde decarbonylase to generate alkanes. In each of these embodiments, one or more of the exogenous genes can be expressed using an inducible promoter.

Other illustrative vectors of the invention that express two or more exogenous genes include those encoding both a sucrose transporter and a sucrose invertase enzyme and those encoding both a selectable marker and a secreted sucrose invertase. The recombinant *Prototheca* transformed with either type of vector produce lipids at lower manufacturing cost due to the engineered ability to use sugar cane (and sugar cane-derived sugars) as a carbon source. Insertion of the two exogenous genes described above can be combined with the disruption of polysaccharide biosynthesis through directed and/or random mutagenesis, which steers ever greater carbon flux into lipid production. Individually and in combination, trophic conversion, engineering to alter lipid production and treatment with exogenous enzymes alter the lipid composition produced by a microorganism. The alteration can be a change in the amount of lipids produced, the amount of one or more hydrocarbon species produced relative to other lipids, and/or the types of lipid species produced in the microorganism. For example, microalgae can be engineered to produce a higher amount and/or percentage of TAGs.

For optimal expression of a recombinant protein, it is beneficial to employ coding sequences that produce mRNA with codons preferentially used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

The present invention provides codon-optimized nucleic acids useful for the successful expression of recombinant proteins in *Prototheca*. Codon usage in *Prototheca* species was analyzed by studying cDNA sequences isolated from *Prototheca moriformis*. This analysis represents the interrogation over 24,000 codons and resulted in Table 1 below.

TABLE 1

Preferred codon usage in *Prototheca* strains.

| | | | | | |
|---|---|---|---|---|---|
| Ala | GCG | 345 (0.36) | Asn | AAT | 8 (0.04) |
| | GCA | 66 (0.07) | | AAC | 201 (0.96) |
| | GCT | 101 (0.11) | | | |
| | GCC | 442 (0.46) | Pro | CCG | 161 (0.29) |
| | | | | CCA | 49 (0.09) |
| Cys | TGT | 12 (0.10) | | CCT | 71 (0.13) |
| | TGC | 105 (0.90) | | CCC | 267 (0.49) |
| Asp | GAT | 43 (0.12) | Gln | CAG | 226 (0.82) |
| | GAC | 316 (0.88) | | CAA | 48 (0.18) |
| Glu | GAG | 377 (0.96) | Arg | AGG | 33 (0.06) |
| | GAA | 14 (0.04) | | AGA | 14 (0.02) |
| | | | | CGG | 102 (0.18) |
| Phe | TTT | 89 (0.29) | | CGA | 49 (0.08) |
| | TTC | 216 (0.71) | | CGT | 51 (0.09) |
| | | | | CGC | 331 (0.57) |
| Gly | GGG | 92 (0.12) | | | |
| | GGA | 56 (0.07) | Ser | AGT | 16 (0.03) |
| | GGT | 76 (0.10) | | AGC | 123 (0.22) |
| | GGC | 559 (0.71) | | TCG | 152 (0.28) |
| | | | | TCA | 31 (0.06) |
| His | CAT | 42 (0.21) | | TCT | 55 (0.10) |
| | CAC | 154 (0.79) | | TCC | 173 (0.31) |

TABLE 1-continued

Preferred codon usage in Prototheca strains.

| | | | | | |
|---|---|---|---|---|---|
| Ile | ATA | 4 (0.01) | Thr | ACG | 184 (0.38) |
| | ATT | 30 (0.08) | | ACA | 24 (0.05) |
| | ATC | 338 (0.91) | | ACT | 21 (0.05) |
| | | | | ACC | 249 (0.52) |
| Lys | AAG | 284 (0.98) | | | |
| | AAA | 7 (0.02) | Val | GTG | 308 (0.50) |
| | | | | GTA | 9 (0.01) |
| Leu | TTG | 26 (0.04) | | GTT | 35 (0.06) |
| | TTA | 3 (0.00) | | GTC | 262 (0.43) |
| | CTG | 447 (0.61) | | | |
| | CTA | 20 (0.03) | Trp | TGG | 107 (1.00) |
| | CTT | 45 (0.06) | | | |
| | CTC | 190 (0.26) | Tyr | TAT | 10 (0.05) |
| | | | | TAC | 180 (0.95) |
| Met | ATG | 191 (1.00) | | | |
| | | | Stop | TGA/TAG/TAA | |

In other embodiments, the gene in the recombinant vector has been codon-optimized with reference to a microalgal strain other than a *Prototheca* strain. For example, methods of recoding genes for expression in microalgae are described in U.S. Pat. No. 7,135,290. Additional information for codon optimization is available, e.g., at the codon usage database of GenBank.

While the methods and materials of the invention allow for the introduction of any exogenous gene into *Prototheca*, genes relating to sucrose utilization and lipid pathway modification are of particular interest, as discussed in the following sections.

IV. SUCROSE UTILIZATION

In embodiment, the recombinant *Prototheca* cell of the invention further contains one or more exogenous sucrose utilization genes. In various embodiments, the one or more genes encode one or more proteins selected from the group consisting of a fructokinase, a glucokinase, a hexokinase, a sucrose invertase, a sucrose transporter. For example, expression of a sucrose transporter and a sucrose invertase allows *Prototheca* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable fructokinases are Genbank accession numbers P26984, P26420 and CAA43322.

In one embodiment, the present invention provides a *Prototheca* host cell that secretes a sucrose invertase. Secretion of a sucrose invertase obviates the need for expression of a transporter that can transport sucrose into the cell. This is because a secreted invertase catalyzes the conversion of a molecule of sucrose into a molecule of glucose and a molecule of fructose, both of which can be transported and utilized by microbes provided by the invention. For example, expression of a sucrose invertase (such as SEQ ID NO:3) with a secretion signal (such as that of SEQ ID NO: 4 (from yeast), SEQ ID NO: 5 (from higher plants), SEQ ID NO: 6 (eukaryotic consensus secretion signal), and SEQ ID NO: 7 (combination of signal sequence from higher plants and eukaryotic consensus) generates invertase activity outside the cell. Expression of such a protein, as enabled by the genetic engineering methodology disclosed herein, allows cells already capable of utilizing extracellular glucose as an energy source to utilize sucrose as an extracellular energy source.

*Prototheca* species expressing an invertase in media containing sucrose are a preferred microalgal species for the production of oil. Example 3 illustrates how the methods and reagents of the invention can be used to express a recombinant yeast invertase and secrete it from a recombinant *Prototheca* cell. The expression and extracellular targeting of this fully active protein allows the resulting host cells to grow on sucrose, whereas their non-transformed counterparts cannot. Thus, the present invention provides *Prototheca* recombinant cells with a codon-optimized invertase gene, including but not limited to the yeast invertase gene, integrated into their genome such that the invertase gene is expressed as assessed by invertase activity and sucrose hydrolysis. The present invention also provides invertase genes useful as selectable markers in *Prototheca* recombinant cells, as such cells are able to grow on sucrose, while their non-transformed counterparts cannot; and methods for selecting recombinant host cells using an invertase as a powerful, selectable marker for algal molecular genetics.

The successful expression of a sucrose invertase in *Prototheca* also illustrates another aspect of the present invention in that it demonstrates that heterologous (recombinant) proteins can be expressed in the algal cell and successfully transit outside of the cell and into the culture medium in a fully active and functional form. Thus, the present invention provides methods and reagents for expressing a wide and diverse array of heterologous proteins in microalgae and secreting them outside of the host cell. Such proteins include, for example, industrial enzymes such as, for example, lipases, proteases, cellulases, pectinases, amylases, esterases, oxidoreductases, transferases, lactases, isomerases, and invertases, as well as therapeutic proteins such as, for example, growth factors, cytokines, full length antibodies comprising two light and two heavy chains, Fabs, scFvs (single chain variable fragment), camellid-type antibodies, antibody fragments, antibody fragment-fusions, antibody-receptor fusions, insulin, interferons, and insulin-like growth factors.

The successful expression of a sucrose invertase in *Prototheca* also illustrates another aspect of the present invention in that it provides methods and reagents for the use of fungal transit peptides in algae to direct secretion of proteins in *Prototheca*; and methods and reagents for determining if a peptide can function, and the ability of it to function, as a transit peptide in *Prototheca* cells. The methods and reagents of the invention can be used as a tool and platform to identify other transit peptides that can successfully traffic proteins outside of a cell, and that the yeast invertase has great utility in these methods. As demonstrated in this example, removal of the endogenous yeast invertase transit peptide and its replacement by other transit peptides, either endogenous to the host algae or from other sources (eukaryotic, prokaryotic and viral), can identify whether any peptide of interest can function as a transit peptide in guiding protein egress from the cell.

Examples of suitable sucrose invertases include those identified by Genbank accession numbers CAB95010, NP_012104 and CAA06839. Non-limiting examples of suitable invertases are listed below in Table 2 Amino acid sequences for each listed invertase are included in the Sequence Listing below. In some cases, the exogenous sucrose utilization gene suitable for use in the methods and vectors of the invention encodes a sucrose invertase that has at least 40, 50, 60, 75, or 90% or higher amino acid identity with a sucrose invertase selected from Table 2.

TABLE 2

Sucrose invertases.

| Description | Organism | GenBank Accession No. | SEQ ID NO: |
|---|---|---|---|
| Invertase | *Chicorium intybus* | Y11124 | SEQ ID NO: 20 |
| Invertase | *Schizosaccharomyces pombe* | AB011433 | SEQ ID NO: 21 |
| beta-fructofuranosidase (invertase) | *Pichia anomala* | X80640 | SEQ ID NO: 22 |
| Invertase | *Debaryomyces occidentalis* | X17604 | SEQ ID NO: 23 |
| Invertase | *Oryza sativa* | AF019113 | SEQ ID NO: 24 |
| Invertase | *Allium cepa* | AJ006067 | SEQ ID NO: 25 |
| Invertase | *Beta vulgaris* subsp. *Vulgaris* | AJ278531 | SEQ ID NO: 26 |
| beta-fructofuranosidase (invertase) | *Bifidobacterium breve* UCC2003 | AAT28190 | SEQ ID NO: 27 |
| Invertase | *Saccharomyces cerevisiae* | NP_012104 | SEQ ID NO: 8 (nucleotide) SEQ ID NO: 28 (amino acid) |
| Invertase A | *Zymomonas mobilis* | AAO38865 | SEQ ID NO: 29 |

The secretion of an invertase to the culture medium by *Prototheca* enable the cells to grow as well on waste molasses from sugar cane processing as they do on pure reagent-grade glucose; the use of this low-value waste product of sugar cane processing can provide significant cost savings in the production of lipids and other oils. Thus, the present invention provides a microbial culture containing a population of *Prototheca* microorganisms, and a culture medium comprising (i) sucrose and (ii) a sucrose invertase enzyme. In various embodiments the sucrose in the culture comes from sorghum, sugar beet, sugar cane, molasses, or depolymerized cellulosic material (which may optionally contain lignin). In another aspect, the methods and reagents of the invention significantly increase the number and type of feedstocks that can be utilized by recombinant *Prototheca*. While the microbes exemplified here are altered such that they can utilize sucrose, the methods and reagents of the invention can be applied so that feedstocks such as cellulosics are utilizable by an engineered host microbe of the invention with the ability to secrete cellulases, pectinases, isomerases, or the like, such that the breakdown products of the enzymatic reactions are no longer just simply tolerated but rather utilized as a carbon source by the host.

V. LIPID PATHWAY ENGINEERING

In addition to altering the ability of *Prototheca* to utilize feedstocks such as sucrose-containing feedstocks, the present invention also provides recombinant *Prototheca* that have been modified to alter the properties and/or proportions of lipids produced. The pathway can further, or alternatively, be modified to alter the properties and/or proportions of various lipid molecules produced through enzymatic processing of lipids and intermediates in the fatty acid pathway. In various embodiments, the recombinant *Prototheca* cells of the invention have, relative to their untransformed counterparts, optimized lipid yield per unit volume and/or per unit time, carbon chain length (e.g., for renewable diesel production or for industrial chemicals applications requiring lipid feedstock), reduced number of double or triple bonds, optionally to zero, and increasing the hydrogen:carbon ratio of a particular species of lipid or of a population of distinct lipid.

In particular embodiments, one or more key enzymes that control branch points in metabolism to fatty acid synthesis have been up-regulated or down-regulated to improve lipid production. Up-regulation can be achieved, for example, by transforming cells with expression constructs in which a gene encoding the enzyme of interest is expressed, e.g., using a strong promoter and/or enhancer elements that increase transcription. Such constructs can include a selectable marker such that the transformants can be subjected to selection, which can result in amplification of the construct and an increase in the expression level of the encoded enzyme. Examples of enzymes suitable for up-regulation according to the methods of the invention include pyruvate dehydrogenase, which plays a role in converting pyruvate to acetyl-CoA (examples, some from microalgae, include Genbank accession numbers NP_415392; AAA53047; Q1XDM1; and CAF05587). Up-regulation of pyruvate dehydrogenase can increase production of acetyl-CoA, and thereby increase fatty acid synthesis. Acetyl-CoA carboxylase catalyzes the initial step in fatty acid synthesis. Accordingly, this enzyme can be up-regulated to increase production of fatty acids (examples, some from microalgae, include Genbank accession numbers BAA94752; AAA75528; AAA81471; YP_537052; YP_536879; NP_045833; and BAA57908). Fatty acid production can also be increased by up-regulation of acyl carrier protein (ACP), which carries the growing acyl chains during fatty acid synthesis (examples, some from microalgae, include Genbank accession numbers A0T0F8; P51280; NP_849041; YP_874433). Glycerol-3-phosphate acyltransferase catalyzes the rate-limiting step of fatty acid synthesis. Up-regulation of this enzyme can increase fatty acid production (examples, some from microalgae, include Genbank accession numbers AAA74319; AAA33122; AAA37647; P44857; and ABO94442).

Up- and/or down-regulation of genes can be applied to global regulators controlling the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples see Genbank accession numbers NP_035610 and Q9WTN3).

The present invention also provides recombinant *Prototheca* cells that have been modified to contain one or more exogenous genes encoding lipid modification enzymes such as, for example, fatty acyl-ACP thioesterases (see Table 3), fatty acyl-CoA/aldehyde reductases (see Table 4), fatty acyl-CoA reductases (see Table 5), fatty aldehyde decarbonylase (see Table 6), fatty aldehyde reductases, and squalene synthases (see GenBank Accession number AF205791). In some embodiments, genes encoding a fatty acyl-ACP thioesterase and a naturally co-expressed acyl carrier protein are transformed into a *Prototheca* cell, optionally with one or more genes encoding other lipid modification enzymes. In other embodiments, the ACP and the fatty acyl-ACP thioesterase may have an affinity for one another that imparts an advantage when the two are used together in the microbes and methods of the present invention, irrespective of whether they are or are not naturally co-expressed in a particular tissue or organism. Thus, the present invention contemplates both naturally co-expressed pairs of these enzymes as well as those that share an affinity for interacting with one another to facilitate cleavage of a length-specific carbon chain from the ACP.

In still other embodiments, an exogenous gene encoding a desaturase is transformed into the *Prototheca* cell in conjunction with one or more genes encoding other lipid modification enzymes to provide modifications with respect to lipid saturation. Stearoyl-ACP desaturase (see, e.g., GenBank Accession numbers AAF15308; ABM45911; and AAY86086), for example, catalyzes the conversion of stearoyl-ACP to oleoyl-ACP. Up-regulation of this gene can increase the proportion of monounsaturated fatty acids produced by a cell; whereas down-regulation can reduce the proportion of monounsaturates. Similarly, the expression of one or more glycerolipid desaturases can be controlled to alter the ratio of unsaturated to saturated fatty acids such as ω-6 fatty acid desaturase, ω-3 fatty acid desaturase, or ω-6-oleate desaturase. In some embodiments, the desaturase can be selected with reference to a desired carbon chain length, such that the desaturase is capable of making location specific modifications within a specified carbon-length substrate, or substrates having a carbon-length within a specified range.

Thus, in particular embodiments, microbes of the present invention are genetically engineered to express one or more exogenous genes selected from an acyl-ACP thioesterase, an acyl-CoA/aldehyde reductase, a fatty acyl-CoA reductase, a fatty aldehyde reductase, a fatty aldehyde decarbonylase, or a naturally co-expressed acyl carrier protein. Suitable expression methods are described above with respect to the expression of a lipase gene, including, among other methods, inducible expression and compartmentalized expression. A fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane or alkene.

In some embodiments, fatty acids, glycerolipids, or the corresponding primary alcohols, aldehydes, alkanes or alkenes, generated by the methods described herein, contain 8, 10, 12, or 14 carbon atoms. Preferred fatty acids for the production of diesel, biodiesel, renewable diesel, or jet fuel, or the corresponding primary alcohols, aldehydes, alkanes and alkenes, for industrial applications contain 8 to 14 carbon atoms. In certain embodiments, the above fatty acids, as well as the other corresponding hydrocarbon molecules, are saturated (with no carbon-carbon double or triple bonds); mono unsaturated (single double bond); poly unsaturated (two or more double bonds); are linear (not cyclic) or branched. For fuel production, greater saturation is preferred.

The enzymes described directly above have a preferential specificity for hydrolysis of a substrate containing a specific number of carbon atoms. For example, a fatty acyl-ACP thioesterase may have a preference for cleaving a fatty acid having 12 carbon atoms from the ACP. In some embodiments, the ACP and the length-specific thioesterase may have an affinity for one another that makes them particularly useful as a combination (e.g., the exogenous ACP and thioesterase genes may be naturally co-expressed in a particular tissue or organism from which they are derived). Therefore, in various embodiments, the recombinant *Prototheca* cell of the invention can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane) with regard to the number of carbon atoms contained in the substrate. The enzymatic specificity can, in various embodiments, be for a substrate having from 8 to 34 carbon atoms, preferably from 8 to 18 carbon atoms, and more preferably from 8 to 14 carbon atoms. A preferred specificity is for a substrate having fewer, i.e., 12, rather than more, i.e., 18, carbon atoms.

In non-limiting but illustrative examples, the present invention provides vectors and *Prototheca* host cells that express an exogenous thioesterase and accordingly produce lipid enriched, relative to the lipid profile of untransformed *Prototheca* cells, in the chain length for which the thioesterase is specific. The thioesterases illustrated are (i) *Cinnamomum camphorum* FatB1 (GenBank Accession No. Q39473, amino acid sequence is in SEQ ID NO: 59, amino acid sequence without plastid targeting sequence (PTS) is in SEQ ID NO: 139, and codon optimized cDNA sequence based on Table 1 is in SEQ ID NO: 60), which has a preference for fatty acyl-ACP substrate with a carbon chain length of 14; (ii) *Cuphea hookeriana* FatB2 (GenBank Accession No. AAC49269, amino acid sequence is in SEQ ID NO: 61, amino acid sequence without PTS is in SEQ ID NO: 138, and codon optimized cDNA sequence based on Table 1 is in SEQ ID NO: 62), which has a preference for a fatty acyl-ACP substrate with a carbon chain length of 8-10; and (iii) *Umbellularia* Fat B1 (GenBank Accession No. Q41635, amino acid sequence is included in SEQ ID NO: 63, amino acid sequence without PTS is in SEQ ID NO: 139, and codon optimized cDNA sequence based on Table 1 is included in SEQ ID NO: 64), which has a preference for a fatty acyl-ACP substrate with a carbon chain length of 12.

Other fatty acyl-ACP thioesterases suitable for use with the microbes and methods of the invention include, without limitation, those listed in Table 3.

TABLE 3

Fatty acyl-ACP thioesterases and GenBank accession numbers.

*Umbellularia californica* fatty acyl-ACP thioesterase (GenBank #AAC49001)
*Cinnamomum camphora* fatty acyl-ACP thioesterase (GenBank #Q39473)
*Umbellularia californica* fatty acyl-ACP thioesterase (GenBank #Q41635)
*Myristica fragrans* fatty acyl-ACP thioesterase (GenBank #AAB71729)
*Myristica fragrans* fatty acyl-ACP thioesterase (GenBank #AAB71730)
*Elaeis guineensis* fatty acyl-ACP thioesterase (GenBank #ABD83939)
*Elaeis guineensis* fatty acyl-ACP thioesterase (GenBank #AAD42220)
*Populus tomentosa* fatty acyl-ACP thioesterase (GenBank #ABC47311)
*Arabidopsis thaliana* fatty acyl-ACP thioesterase (GenBank #NP_172327)
*Arabidopsis thaliana* fatty acyl-ACP thioesterase (GenBank #CAA85387)
*Arabidopsis thaliana* fatty acyl-ACP thioesterase (GenBank #CAA85388)
*Gossypium hirsutum* fatty acyl-ACP thioesterase (GenBank #Q9SQI3)
*Cuphea lanceolata* fatty acyl-ACP thioesterase (GenBank #CAA54060)
*Cuphea hookeriana* fatty acyl-ACP thioesterase (GenBank #AAC72882)
*Cuphea calophylla* subsp. *mesostemon* fatty acyl-ACP thioesterase (GenBank #ABB71581)
*Cuphea lanceolata* fatty acyl-ACP thioesterase (GenBank #CAC19933)
*Elaeis guineensis* fatty acyl-ACP thioesterase (GenBank #AAL15645)
*Cuphea hookeriana* fatty acyl-ACP thioesterase (GenBank #Q39513)
*Gossypium hirsutum* fatty acyl-ACP thioesterase (GenBank #AAD01982)
*Vitis vinifera* fatty acyl-ACP thioesterase (GenBank #CAN81819)
*Garcinia mangostana* fatty acyl-ACP thioesterase (GenBank #AAB51525)
*Brassica juncea* fatty acyl-ACP thioesterase (GenBank #ABI18986)
*Madhuca longifolia* fatty acyl-ACP thioesterase (GenBank #AAX51637)
*Brassica napus* fatty acyl-ACP thioesterase (GenBank #ABH11710)
*Oryza sativa* (*indica* cultivar-group) fatty acyl-ACP thioesterase (GenBank #EAY86877)
*Oryza sativa* (*japonica* cultivar-group) fatty acyl-ACP thioesterase (GenBank #NP_001068400)
*Oryza sativa* (*indica* cultivar-group) fatty acyl-ACP thioesterase (GenBank #EAY99617)
*Cuphea hookeriana* fatty acyl-ACP thioesterase (GenBank #AAC49269)
*Ulmus Americana* fatty acyl-ACP thioesterase (GenBank #AAB71731)
*Cuphea lanceolata* fatty acyl-ACP thioesterase (GenBank #CAB60830)
*Cuphea palustris* fatty acyl-ACP thioesterase (GenBank #AAC49180)
*Iris germanica* fatty acyl-ACP thioesterase (GenBank #AAG43858)

TABLE 3-continued

Fatty acyl-ACP thioesterases and GenBank accession numbers.

*Cuphea palustris* fatty acyl-ACP thioesterase (GenBank #AAC49179)
*Myristica fragrans* fatty acyl-ACP thioesterase (GenBank# AAB71729)
*Cuphea hookeriana fatty acyl-ACP thioesterase (GenBank #U39834)*
*Umbelluaria californica* fatty acyl-ACP thioesterase (GenBank # M94159)
*Cinnamomum camphora* fatty acyl-ACP thioesterase (GenBank #U31813)

The Examples below describe the successful targeting and expression of heterologous fatty acyl-ACP thioesterases from *Cuphea hookeriana, Umbellularia californica, Cinnamomun camphora* in *Prototheca* species. Additionally, alterations in fatty acid profiles were confirmed in the host cells expression these heterologous fatty acyl-ACP thioesterases. These results were quite unexpected given the lack of sequence identity between algal and higher plant thioesterases in general, and between *Prototheca moriformis* fatty acyl-ACP thioesterase and the above listed heterologous fatty acyl-ACP thioesterases. Two *Prototheca moriformis* acyl-ACP thioesterases were isolated and sequenced. The sequences of the two cDNAs showed a high degree of identity between each other, differing in only 12 positions at the nucleotide level and five positions at the amino acid level, four of these in the plastid transit peptide. Further analysis of genomic sequence from *Prototheca moriformis* confirmed that these two cDNAs were indeed encoded on separate contigs, and although highly homolous, are encoded by two distinct genes. The cDNA and amino acid sequence of the two *Prototheca moriformis* fatty acyl-ACP thioesterase, *P. moriformis* fatty acyl-ACP thioesterase-1 and *P. moriformis* fatty acyl-ACP thioesterase-2, are listed as SEQ ID NOs: 134-137.

When the amino acid sequences of these two cDNAs were BLASTed against the NCBI database, the two most homologous sequences were fatty acyl-ACP thioesterases from *Chlamydomonas reinhardtii* and *Arabidopsis thaliana*. Surprisingly, the level of amino acid identity between the *Prototheca moriformis* fatty acyl-ACP thioesterases and higher plant thioesterases was fairly low, at only 49 and 37% identity. In addition, there also is a subtle difference in the sequences surrounding the amino terminal portion of the catalytic triad ($NXHX_{36}C$) among these fatty acyl-ACP thioesterases. Thirty nine of forty higher plant fatty acyl-ACP thioesterases surveyed showed the sequence LDMNQH surrounding the N and H residues at the amino terminus of the triad, while all of the algal sequences identified had the sequence MDMNGH. Given the low amino acid sequence identity and the differences surrounding the catalytic triad of the thioesterases, the successful results of expression of exogenous fatty acyl-ACP thioesterases obtained and described in the Examples were unexpected, particularly given the fact that activity of the exogenous fatty acyl-ACP thioesterases was dependent on a functional protein-protein interaction with the endogenous *Prototheca* acyl carrier protein.

Fatty acyl-CoA/aldehyde reductases suitable for use with the microbes and methods of the invention include, without limitation, those listed in Table 4.

TABLE 4

Fatty acyl-CoA/aldehyde reductases listed by GenBank accession numbers.

AAC45217, YP_047869, BAB85476, YP_001086217, YP_580344,
YP_001280274, YP_264583, YP_436109, YP_959769,
ZP_01736962, ZP_01900335, ZP_01892096, ZP_01103974,
ZP_01915077, YP_924106, YP_130411, ZP_01222731,

TABLE 4-continued

Fatty acyl-CoA/aldehyde reductases listed by GenBank accession numbers.

YP_550815, YP_983712, YP_001019688, YP_524762,
YP_856798, ZP_01115500, YP_001141848, NP_336047,
NP_216059, YP_882409, YP_706156, YP_001136150,
YP_952365, ZP_01221833, YP_130076, NP_567936,
AAR88762, ABK28586, NP_197634, CAD30694, NP_001063962,
BAD46254, NP_001030809, EAZ10132, EAZ43639, EAZ07989,
NP_001062488, CAB88537, NP_001052541, CAH66597, CAE02214,
CAH66590, CAB88538, EAZ39844, AAZ06658, CAA68190,
CAA52019, and BAC84377

Fatty acyl-CoA reductases suitable for use with the microbes and methods of the invention include, without limitation, those listed in Table 5.

TABLE 5

Fatty acyl-CoA reductases listed by GenBank accession numbers.

NP_187805, ABO14927, NP_001049083, CAN83375, NP_191229,
EAZ42242, EAZ06453, CAD30696, BAD31814, NP_190040,
AAD38039, CAD30692, CAN81280, NP_197642, NP_190041,
AAL15288, and NP_190042

Fatty aldehyde decarbonylases suitable for use with the microbes and methods of the invention include, without limitation, those listed in Table 6.

TABLE 6

Fatty aldehyde decarbonylases listed by GenBank accession numbers.

NP_850932, ABN07985, CAN60676, AAC23640, CAA65199,
AAC24373, CAE03390, ABD28319, NP_181306, EAZ31322,
CAN63491, EAY94825, EAY86731, CAL55686, XP_001420263,
EAZ23849, NP_200588, NP_001063227, CAN83072,
AAR90847, and AAR97643

Combinations of naturally co-expressed fatty acyl-ACP thioesterases and acyl carrier proteins are suitable for use with the microbes and methods of the invention.

Additional examples of hydrocarbon or lipid modification enzymes include amino acid sequences contained in, referenced in, or encoded by nucleic acid sequences contained or referenced in, any of the following U.S. Pat. Nos. 6,610,527; 6,451,576; 6,429,014; 6,342,380; 6,265,639; 6,194,185; 6,114,160; 6,083,731; 6,043,072; 5,994,114; 5,891,697; 5,871,988; 6,265,639, and further described in GenBank Accession numbers: AAO18435; ZP_00513891; Q38710; AAK60613; AAK60610; AAK60611; NP_113747; CAB75874; AAK60612; AAF20201; BAA11024; AF205791; and CAA03710.

Other suitable enzymes for use with the microbes and the methods of the invention include those that have at least 70% amino acid identity with one of the proteins listed in Tables 3-6, and that exhibit the corresponding desired enzymatic activity (e.g., cleavage of a fatty acid from an acyl carrier protein, reduction of an acyl-CoA to an aldehyde or an alcohol, or conversion of an aldehyde to an alkane). In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth.

By selecting the desired combination of exogenous genes to be expressed, one can tailor the product generated by the microbe, which may then be extracted from the aqueous biomass. For example, the microbe can contain: (i) an exogenous gene encoding a fatty acyl-ACP thioesterase; and, optionally, (ii) a naturally co-expressed acyl carrier protein or an acyl carrier protein otherwise having affinity for the fatty acyl-ACP thioesterase (or conversely); and, optionally, (iii) an exogenous gene encoding a fatty acyl-CoA/aldehyde reductase or a fatty acyl-CoA reductase; and, optionally, (iv) an exogenous gene encoding a fatty aldehyde reductase or a fatty aldehyde decarbonylase. The microbe, under culture conditions described herein, synthesizes a fatty acid linked to an ACP and the fatty acyl-ACP thioesterase catalyzes the cleavage of the fatty acid from the ACP to yield, through further enzymatic processing, a fatty acyl-CoA molecule. When present, the fatty acyl-CoA/aldehyde reducatase catalyzes the reduction of the acyl-CoA to an alcohol. Similarly, the fatty acyl-CoA reductase, when present, catalyzes the reduction of the acyl-CoA to an aldehyde. In those embodiments in which an exogenous gene encoding a fatty acyl-CoA reductase is present and expressed to yield an aldehyde product, a fatty aldehyde reductase, encoded by the third exogenous gene, catalyzes the reduction of the aldehyde to an alcohol. Similarly, a fatty aldehyde decarbonylase catalyzes the conversion of the aldehyde to an alkane or an alkene, when present.

Genes encoding such enzymes can be obtained from cells already known to exhibit significant lipid production such as *Chlorella protothecoides*. Genes already known to have a role in lipid production, e.g., a gene encoding an enzyme that saturates double bonds, can be transformed individually into recipient cells. However, to practice the invention it is not necessary to make a priori assumptions as to which genes are required. Methods for identifying genes that can alter (improve) lipid production in microalgae are described in PCT Pub. No. 2008/151149.

Thus, the present invention provides a *Prototheca* cell that has been genetically engineered to express a lipid pathway enzyme at an altered level compared to a wild-type cell of the same species. In some cases, the cell produces more lipid compared to the wild-type cell when both cells are grown under the same conditions. In some cases, the cell has been genetically engineered and/or selected to express a lipid pathway enzyme at a higher level than the wild-type cell. In some cases, the lipid pathway enzyme is selected from the group consisting of pyruvate dehydrogenase, acetyl-CoA carboxylase, acyl carrier protein, and glycerol-3 phosphate acyltransferase. In some cases, the cell has been genetically engineered and/or selected to express a lipid pathway enzyme at a lower level than the wild-type cell. In at least one embodiment in which the cell expresses the lipid pathway enzyme at a lower level, the lipid pathway enzyme comprises citrate synthase.

In some embodiments, the cell has been genetically engineered and/or selected to express a global regulator of fatty acid synthesis at an altered level compared to the wild-type cell, whereby the expression levels of a plurality of fatty acid synthetic genes are altered compared to the wild-type cell. In some cases, the lipid pathway enzyme comprises an enzyme that modifies a fatty acid. In some cases, the lipid pathway enzyme is selected from a stearoyl-ACP desaturase and a glycerolipid desaturase.

In other embodiments, the present invention is directed to an oil-producing microbe containing one or more exogenous genes, wherein the exogenous genes encode protein(s) selected from the group consisting of a fatty acyl-ACP thioesterase, a fatty acyl-CoA reductase, a fatty aldehyde reductase, a fatty acyl-CoA/aldehyde reductase, a fatty aldehyde decarbonylase, and an acyl carrier protein. In one embodiment, the exogenous gene is in operable linkage with a promoter, which is inducible or repressible in response to a stimulus. In some cases, the stimulus is selected from the group consisting of an exogenously provided small molecule, heat, cold, and limited or no nitrogen in the culture media. In some cases, the exogenous gene is expressed in a cellular compartment. In some embodiments, the cellular compartment is selected from the group consisting of a chloroplast, a plastid and a mitochondrion. In some embodiments the microbe is *Prototheca moriformis, Prototheca krugani, Prototheca stagnora* or *Prototheca zopfii*.

In one embodiment, the exogenous gene encodes a fatty acid acyl-ACP thioesterase. In some cases, the thioesterase encoded by the exogenous gene catalyzes the cleavage of an 8 to 18-carbon fatty acid from an acyl carrier protein (ACP). In some cases, the thioesterase encoded by the exogenous gene catalyzes the cleavage of a 10 to 14-carbon fatty acid from an ACP. In one embodiment, the thioesterase encoded by the exogenous gene catalyzes the cleavage of a 12-carbon fatty acid from an ACP.

In one embodiment, the exogenous gene encodes a fatty acyl-CoA/aldehyde reductase. In some cases, the reductase encoded by the exogenous gene catalyzes the reduction of an 8 to 18-carbon fatty acyl-CoA to a corresponding primary alcohol. In some cases, the reductase encoded by the exogenous gene catalyzes the reduction of a 10 to 14-carbon fatty acyl-CoA to a corresponding primary alcohol. In one embodiment, the reductase encoded by the exogenous gene catalyzes the reduction of a 12-carbon fatty acyl-CoA to dodecanol.

The present invention also provides a recombinant *Prototheca* cell containing two exogenous genes, wherein a first exogenous gene encodes a fatty acyl-ACP thioesterase and a second exogenous gene encodes a protein selected from the group consisting of a fatty acyl-CoA reductase, a fatty acyl-CoA/aldehyde reductase, and an acyl carrier protein. In some cases, the two exogenous genes are each in operable linkage with a promoter, which is inducible in response to a stimulus. In some cases, each promoter is inducible in response to an identical stimulus, such as limited or no nitrogen in the culture media. Limitation or complete lack of nitrogen in the culture media stimulates oil production in some microorganisms such as *Prototheca* species, and can be used as a trigger to inducec oil production to high levels. When used in combination with the genetic engineering methods disclosed herein, the lipid as a percentage of dry cell weight can be pushed to high levels such as at least 30%, at least 40%, at least 50%, at least 60%, at least 70% and at least 75%; methods disclosed herein provide for cells with these levels of lipid, wherein the lipid is at least 4% C8-C14, at least 0.3% C8, at least 2% C10, at least 2% C12, and at least 2% C14. In some embodiments the cells are over 25% lipid by dry cell weight and contain lipid that is at least 10% C8-C14, at least 20% C8-C14, at least 30% C8-C14, 10-30% C8-C14 and 20-30% C8-C14.

The novel oils disclosed herein are distinct from other naturally occurring oils that are high in mic-chain fatty acids, such as palm oil, palm kernel oil, and coconut oil. For example, levels of contaminants such as carotenoids are far higher in palm oil and palm kernel oil than in the oils of the invention. Palm and palm kernel oils in particular contain alpha and beta carotenes and lycopene in much higher amounts than is in the oils of the invention. In addition, over 20 different carotenoids are found in palm and palm kernel oil, whereas the Examples demonstrate that the oils of the invention contain very few carotenoids species and very low levels. In addition, the levels of vitamin E compounds such as tocotrienols are far higher in palm, palm kernel, and coconut oil than in the oils of the invention.

In one embodiment, the thioesterase encoded by the first exogenous gene catalyzes the cleavage of an 8 to 18-carbon fatty acid from an ACP. In some embodiments, the second exogenous gene encodes a fatty acyl-CoA/aldehyde reductase which catalyzes the reduction of an 8 to 18-carbon fatty acyl-CoA to a corresponding primary alcohol. In some cases, the thioesterase encoded by the first exogenous gene catalyzes the cleavage of a 10 to 14-carbon fatty acid from an ACP, and the reductase encoded by the second exogenous gene catalyzes the reduction of a 10 to 14-carbon fatty acyl-CoA to the corresponding primary alcohol, wherein the thioesterase and the reductase act on the same carbon chain length. In one embodiment, the thioesterase encoded by the first exogenous gene catalyzes the cleavage of a 12-carbon fatty acid from an ACP, and the reductase encoded by the second exogenous gene catalyzes the reduction of a 12-carbon fatty acyl-CoA to dodecanol. In some embodiments, the second exogenous gene encodes a fatty acyl-CoA reductase which catalyzes the reduction of an 8 to 18-carbon fatty acyl-CoA to a corresponding aldehyde. In some embodiments, the second exogenous gene encodes an acyl carrier protein that is naturally co-expressed with the fatty acyl-ACP thioesterase.

In some embodiments, the second exogenous gene encodes a fatty acyl-CoA reductase, and the microbe further contains a third exogenous gene encoding a fatty aldehyde decarbonylase. In some cases, the thioesterase encoded by the first exogenous gene catalyzes the cleavage of an 8 to 18-carbon fatty acid from an ACP, the reductase encoded by the second exogenous gene catalyzes the reduction of an 8 to 18-carbon fatty acyl-CoA to a corresponding fatty aldehyde, and the decarbonylase encoded by the third exogenous gene catalyzes the conversion of an 8 to 18-carbon fatty aldehyde to a corresponding alkane, wherein the thioesterase, the reductase, and the decarbonylase act on the same carbon chain length.

In some embodiments, the second exogenous gene encodes an acyl carrier protein, and the microbe further contains a third exogenous gene encoding a protein selected from the group consisting of a fatty acyl-CoA reductase and a fatty acyl-CoA/aldehyde reductase. In some cases, the third exogenous gene encodes a fatty acyl-CoA reductase, and the microbe further contains a fourth exogenous gene encoding a fatty aldehyde decarbonylase.

The present invention also provides methods for producing an alcohol comprising culturing a population of recombinant Prototheca cells in a culture medium, wherein the cells contain (i) a first exogenous gene encoding a fatty acyl-ACP thioesterase, and (ii) a second exogenous gene encoding a fatty acyl-CoA/aldehyde reductase, and the cells synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA/aldehyde reductase catalyzes the reduction of the acyl-CoA to an alcohol.

The present invention also provides methods of producing a lipid molecule in a Prototheca cell. In one embodiment, the method comprises culturing a population of Prototheca cells in a culture medium, wherein the cells contain (i) a first exogenous gene encoding a fatty acyl-ACP thioesterase, and (ii) a second exogenous gene encoding a fatty acyl-CoA reductase, and wherein the microbes synthesize a fatty acid linked to an acyl carrier protein (ACP), the fatty acyl-ACP thioesterase catalyzes the cleavage of the fatty acid from the ACP to yield, through further processing, a fatty acyl-CoA, and the fatty acyl-CoA reductase catalyzes the reduction of the acyl-CoA to an aldehyde.

The present invention also provides methods of producing a fatty acid molecule having a specified carbon chain length in a Prototheca cell. In one embodiment, the method comprises culturing a population of lipid-producing Prototheca cells in a culture medium, wherein the microbes contain an exogenous gene encoding a fatty acyl-ACP thioesterase having an activity specific or preferential to a certain carbon chain length, such as 8, 10, 12 or 14 carbon atoms, and wherein the microbes synthesize a fatty acid linked to an acyl carrier protein (ACP) and the thioesterase catalyzes the cleavage of the fatty acid from the ACP when the fatty acid has been synthesized to the specific carbon chain length.

In the various embodiments described above, the Prototheca cell can contain at least one exogenous gene encoding a lipid pathway enzyme. In some cases, the lipid pathway enzyme is selected from the group consisting of a stearoyl-ACP desaturase, a glycerolipid desaturase, a pyruvate dehydrogenase, an acetyl-CoA carboxylase, an acyl carrier protein, and a glycerol-3 phosphate acyltransferase. In other cases, the Prototheca cell contains a lipid modification enzyme selected from the group consisting of a fatty acyl-ACP thioesterase, a fatty acyl-CoA/aldehyde reductase, a fatty acyl-CoA reductase, a fatty aldehyde reductase, a fatty aldehyde decarbonylase, and/or an acyl carrier protein.

VI. FUELS AND CHEMICALS PRODUCTION

For the production of fuel in accordance with the methods of the invention lipids produced by cells of the invention are harvested, or otherwise collected, by any convenient means. Lipids can be isolated by whole cell extraction. The cells are first disrupted, and then intracellular and cell membrane/cell wall-associated lipids as well as extracellular hydrocarbons can be separated from the cell mass, such as by use of centrifugation as described above. Intracellular lipids produced in microorganisms are, in some embodiments, extracted after lysing the cells of the microorganism. Once extracted, the lipids are further refined to produce oils, fuels, or oleochemicals.

After completion of culturing, the microorganisms can be separated from the fermentation broth. Optionally, the separation is effected by centrifugation to generate a concentrated paste. Centrifugation does not remove significant amounts of intracellular water from the microorganisms and is not a drying step. The biomass can then optionally be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially. The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of cellular lipid and/or hydrocarbon for extraction or further processing. The timing of lipase expression (e.g., via an inducible promoter) or cell lysis can be adjusted to optimize the yield of lipids and/or hydrocarbons. Below are described a number of lysis techniques. These techniques can be used individually or in combination.

In one embodiment of the present invention, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50° C. Higher temperatures, such as, at least 30° C. at least 60° C., at least 70° C., at least 80° C., at least 90° C., at least 100° C., at least 110° C., at least 120° C., at least 130° C. or higher are used for more efficient cell lysis. Lysing cells by heat treatment can be performed by boiling the microorganism. Alternatively, heat treatment (without boiling) can be performed in an autoclave. The heat treated lysate may be cooled for further treatment. Cell disruption can also be performed by steam treatment, i.e., through addition of pressurized steam. Steam treatment of microalgae for cell disruption is described, for example, in U.S. Pat. No. 6,750,048. In some embodiments, steam treatment may be achieved by sparging steam into the fermentor and maintaining the broth at a desired temperature for less than about 90 minutes, preferably less than about 60 minutes, and more preferably less than about 30 minutes.

In another embodiment of the present invention, the step of lysing a microorganism comprises adding a base to a cellular suspension containing the microorganism. The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

In another embodiment of the present invention, the step of lysing a microorganism comprises adding an acid to a cellular suspension containing the microorganism. Acid lysis can be effected using an acid at a concentration of 10-500 mN or preferably 40-160 nM. Acid lysis is preferably performed at above room temperature (e.g., at 40-160°, and preferably a temperature of 50-130°. For moderate temperatures (e.g., room temperature to 100° C. and particularly room temperature to 65°, acid treatment can usefully be combined with sonication or other cell disruption methods.

In another embodiment of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515.

In other embodiments of the present invention, lysis is accomplished using an enzyme such as, for example, a cellulase such as a polysaccharide-degrading enzyme, optionally from *Chlorella* or a Chlorella virus, or a proteases, such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32 (4), Alcalase 2.4 FG (Novozymes), and Flavourzyme 100 L (Novozymes). Any combination of a protease and a polysaccharide-degrading enzyme can also be used, including any combination of the preceding proteases and polysaccharide-degrading enzymes.

In another embodiment, lysis can be performed using an expeller press. In this process, biomass is forced through a screw-type device at high pressure, lysing the cells and causing the intracellular lipid to be released and separated from the protein and fiber (and other components) in the cell.

In another embodiment of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

In another embodiment of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

In another embodiment of the present invention, the step of lysing a microorganism is performed by applying an osmotic shock.

In another embodiment of the present invention, the step of lysing a microorganism comprises infection of the microorganism with a lytic virus. A wide variety of viruses are known to lyse microorganisms suitable for use in the present invention, and the selection and use of a particular lytic virus for a particular microorganism is within the level of skill in the art. For example, paramecium bursaria chlorella virus (PBCV-1) is the prototype of a group (family Phycodnaviridae, genus Chlorovirus) of large, icosahedral, plaque-forming, double-stranded DNA viruses that replicate in, and lyse, certain unicellular, eukaryotic *chlorella*-like green algae. Accordingly, any susceptible microalgae can be lysed by infecting the culture with a suitable chlorella virus. Methods of infecting species of *Chlorella* with a chlorella virus are known. See for example *Adv. Virus Res.* 2006; 66:293-336; *Virology*, 1999 Apr. 25; 257(1):15-23; *Virology*, 2004 Jan. 5; 318(1):214-23; *Nucleic Acids Symp. Ser.* 2000; (44):161-2; *J. Virol.* 2006 March; 80(5):2437-44; and *Annu. Rev. Microbiol.* 1999; 53:447-94.

In another embodiment of the present invention, the step of lysing a microorganism comprises autolysis. In this embodiment, a microorganism according to the invention is genetically engineered to produce a lytic protein that will lyse the microorganism. This lytic gene can be expressed using an inducible promoter so that the cells can first be grown to a desirable density in a fermentor, followed by induction of the promoter to express the lytic gene to lyse the cells. In one embodiment, the lytic gene encodes a polysaccharide-degrading enzyme. In certain other embodiments, the lytic gene is a gene from a lytic virus. Thus, for example, a lytic gene from a Chlorella virus can be expressed in an algal cell; see *Virology* 260, 308-315 (1999); *FEMS Microbiology Letters* 180 (1999) 45-53; *Virology* 263, 376-387 (1999); and *Virology* 230, 361-368 (1997). Expression of lytic genes is preferably done using an inducible promoter, such as a promoter active in microalgae that is induced by a stimulus such as the presence of a small molecule, light, heat, and other stimuli.

Various methods are available for separating lipids from cellular lysates produced by the above methods. For example, lipids and lipid derivatives such as fatty aldehydes, fatty alcohols, and hydrocarbons such as alkanes can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12): 1735-1738); and supercritical $CO_2$ extraction (see for example Mendes et al. 2003, Inorganica Chimica Acta 356: 328-334). Miao and Wu describe a protocol of the recovery of microalgal lipid from a culture of *Chlorella prototheocoides* in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Thus, lipids, lipid derivatives and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Lipids and lipid derivatives such as fatty aldehydes, fatty alcohols, and hydrocarbons such as alkanes produced by cells as described herein can be modified by the use of one or more enzymes, including a lipase, as described above. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

Thus, lipids and hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process is used as described in Section IV herein.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

Increasing interest is directed to the use of hydrocarbon components of biological origin in fuels, such as biodiesel, renewable diesel, and jet fuel, since renewable biological starting materials that may replace starting materials derived from fossil fuels are available, and the use thereof is desirable. There is an urgent need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel if it is a fatty acid methyl ester (ASTM D6751).

After extraction, lipid and/or hydrocarbon components recovered from the microbial biomass described herein can be subjected to chemical treatment to manufacture a fuel for use in diesel vehicles and jet engines.

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers. Biodiesel can be used as an additive in formulations of diesel to increase the lubricity of pure Ultra-Low Sulfur Diesel (ULSD) fuel, which is advantageous because it has virtually no sulfur content. Biodiesel is a better solvent than petrodiesel and can be used to break down deposits of residues in the fuel lines of vehicles that have previously been run on petrodiesel.

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced. Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel.

The lipid profile of the biodiesel is usually highly similar to the lipid profile of the feedstock oil. Other oils provided by the methods and compositions of the invention can be subjected to transesterification to yield biodiesel with lipid profiles including (a) at least 4% C8-C14; (b) at least 0.3% C8; (c) at least 2% C10; (d) at least 2% C12; and (3) at least 30% C8-C14.

Lipid compositions can be subjected to transesterification to yield long-chain fatty acid esters useful as biodiesel. Preferred transesterification reactions are outlined below and include base catalyzed transesterification and transesterification using recombinant lipases. In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol. A typical reaction scheme is as follows:

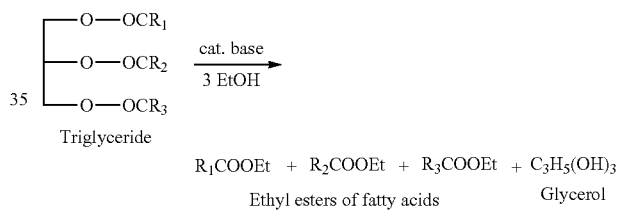

In this reaction, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base can be used to help the reaction proceed more quickly. The acid or base are not consumed by the transesterification reaction, thus they are not reactants but catalysts. Almost all biodiesel has been produced using the base-catalyzed technique as it requires only low temperatures and pressures and produces over 98% conversion yield (provided the starting oil is low in moisture and free fatty acids).

Transesterification has also been carried out, as discussed above, using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1. Lipases suitable for use in transesterification include, but are not limited to, those listed in Table 7. Other examples of lipases useful for transesterification are found in, e.g. U.S. Pat. Nos. 4,798,793; 4,940,845 5,156,963; 5,342,768; 5,776,741 and WO89/01032. Such lipases include, but are not limited to, lipases produced by microorganisms of *Rhizopus, Aspergillus, Candida, Mucor, Pseudomonas, Rhizomucor, Candida*, and *Humicola* and pancreas lipase.

TABLE 7

Lipases suitable for use in transesterification.

*Aspergillus niger* lipase ABG73614, *Candida antarctica* lipase B (novozym-435) CAA83122, *Candida cylindracea* lipase AAR24090, *Candida lipolytica* lipase (Lipase L; Amano Pharmaceutical Co., Ltd.), *Candida rugosa* lipase (e.g., Lipase-OF; Meito Sangyo Co., Ltd.), *Mucor miehei* lipase (Lipozyme IM 20), *Pseudomonas fluorescens* lipase AAA25882, *Rhizopus japonicas* lipase (Lilipase A-10FG) Q7M4U7_1, *Rhizomucor miehei* lipase B34959, *Rhizopus oryzae* lipase (Lipase F) AAF32408, *Serratia marcescens* lipase (SM Enzyme) ABI13521, *Thermomyces lanuginosa* lipase CAB58509, Lipase P (Nagase ChemteX Corporation), and Lipase QLM (Meito Sangyo Co., Ltd., Nagoya, Japan)

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity. Some suitable methods include immersing an immobilized lipase in an alcohol having a carbon atom number not less than 3 for a period of time, preferably from 0.5-48 hours, and more preferably from 0.5-1.5 hours. Some suitable methods also include washing a deactivated immobilized lipase with an alcohol having a carbon atom number not less than 3 and then immersing the deactivated immobilized lipase in a vegetable oil for 0.5-48 hours.

In particular embodiments, a recombinant lipase is expressed in the same microorganisms that produce the lipid on which the lipase acts. Suitable recombinant lipases include those listed above in Table 7 and/or having GenBank Accession numbers listed above in Table 7, or a polypeptide that has at least 70% amino acid identity with one of the lipases listed above in Table 7 and that exhibits lipase activity. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth. DNA encoding the lipase and selectable marker is preferably codon-optimized cDNA. Methods of recoding genes for expression in microalgae are described in U.S. Pat. No. 7,135,290.

The common international standard for biodiesel is EN 14214. ASTM D6751 is the most common biodiesel standard referenced in the United States and Canada. Germany uses DIN EN 14214 and the UK requires compliance with BS EN 14214. Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

Although biodiesel that meets the ASTM standards has to be non-toxic, there can be contaminants which tend to crystallize and/or precipitate and fall out of solution as sediment. Sediment formation is particularly a problem when biodiesel is used at lower temperatures. The sediment or precipitates may cause problems such as decreasing fuel flow, clogging fuel lines, clogging filters, etc. Processes are well-known in the art that specifically deal with the removal of these contaminants and sediments in biodiesel in order to produce a higher quality product. Examples for such processes include, but are not limited to, pretreatment of the oil to remove contaiminants such as phospholipids and free fatty acids (e.g., degumming, caustic refining and silica adsorbant filtration) and cold filtration. Cold filtration is a process that was developed specifically to remove any particulates and sediments that are present in the biodiesel after production. This process cools the biodiesel and filters out any sediments or precipitates that might form when the fuel is used at a lower temperature. Such a process is well known in the art and is described in US Patent Application Publication No. 2007-0175091. Suitable methods may include cooling the biodiesel to a temperature of less than about 38° C. so that the impurities and contaminants precipitate out as particulates in the biodiesel liquid. Diatomaceous earth or other filtering material may then added to the cooled biodiesel to form a slurry, which may then filtered through a pressure leaf or other type of filter to remove the particulates. The filtered biodiesel may then be run through a polish filter to remove any remaining sediments and diatomaceous earth, so as to produce the final biodiesel product.

Example 14 described the production of biodiesel using triglyceride oil from *Prototheca moriformis*. The Cold Soak Filterability by the ASTM D6751 A1 method of the biodiesel produced in Example 14 was 120 seconds for a volume of 300 ml. This test involves filtration of 300 ml of B100, chilled to 40° F. for 16 hours, allowed to warm to room temp, and filtered under vacuum using 0.7 micron glass fiber filter with stainless steel support. Oils of the invention can be transesterified to generate biodiesel with a cold soak time of less than 120 seconds, less than 100 seconds, and less than 90 seconds.

Subsequent processes may also be used if the biodiesel will be used in particularly cold temperatures. Such processes include winterization and fractionation. Both processes are designed to improve the cold flow and winter performance of the fuel by lowering the cloud point (the temperature at which the biodiesel starts to crystallize). There are several approaches to winterizing biodiesel. One approach is to blend the biodiesel with petroleum diesel. Another approach is to use additives that can lower the cloud point of biodiesel. Another approach is to remove saturated methyl esters indiscriminately by mixing in additives and allowing for the crystallization of saturates and then filtering out the crystals. Fractionation selectively separates methyl esters into individual components or fractions, allowing for the removal or inclusion of specific methyl esters. Fractionation methods include urea fractionation, solvent fractionation and thermal distillation.

Another valuable fuel provided by the methods of the present invention is renewable diesel, which comprises alkanes, such as C10:0, C12:0, C14:0, C16:0 and C18:0 and thus, are distinguishable from biodiesel. High quality renewable diesel conforms to the ASTM D975 standard. The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In one embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696. Some suitable methods may include mechanical pressing and centrifuging.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet an ASTM D975 standard while leaving components that are heavier than desired for meeting the D975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

In one embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

One suitable method for the hydrogenation of triglycerides includes preparing an aqueous solution of copper, zinc, magnesium and lanthanum salts and another solution of alkali metal or preferably, ammonium carbonate. The two solutions may be heated to a temperature of about 20° C. to about 85° C. and metered together into a precipitation container at rates such that the pH in the precipitation container is maintained between 5.5 and 7.5 in order to form a catalyst. Additional water may be used either initially in the precipitation container or added concurrently with the salt solution and precipitation solution. The resulting precipitate may then be thoroughly washed, dried, calcined at about 300° C. and activated in hydrogen at temperatures ranging from about 100° C. to about 400° C. One or more triglycerides may then be contacted and reacted with hydrogen in the presence of the above-described catalyst in a reactor. The reactor may be a trickle bed reactor, fixed bed gas-solid reactor, packed bubble column reactor, continuously stirred tank reactor, a slurry phase reactor, or any other suitable reactor type known in the art. The process may be carried out either batchwise or in continuous fashion. Reaction temperatures are typically in the range of from about 170° C. to about 250° C. while reaction pressures are typically in the range of from about 300 psig to about 2000 psig. Moreover, the molar ratio of hydrogen to triglyceride in the process of the present invention is typically in the range of from about 20:1 to about 700:1. The process is typically carried out at a weight hourly space velocity (WHSV) in the range of from about 0.1 $hr^{-1}$ to about 5 $hr^{-1}$. One skilled in the art will recognize that the time period required for reaction will vary according to the temperature used, the molar ratio of hydrogen to triglyceride, and the partial pressure of hydrogen. The products produced by the such hydrogenation processes include fatty alcohols, glycerol, traces of paraffins and unreacted triglycerides. These products are typically separated by conventional means such as, for example, distillation, extraction, filtration, crystallization, and the like.

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes. Solid catalysts are employed to increase certain reaction rates, improve selectivity for certain products, and optimize hydrogen consumption.

Suitable methods for the deoxygenation of an oil includes heating an oil to a temperature in the range of from about 350° F. to about 550° F. and continuously contacting the heated oil with nitrogen under at least pressure ranging from about atmospheric to above for at least about 5 minutes.

Suitable methods for isomerization includes using alkali isomerization and other oil isomerization known in the art.

Hydrotreating and hydroprocessing ultimately lead to a reduction in the molecular weight of the triglyceride feed. The triglyceride molecule is reduced to four hydrocarbon molecules under hydroprocessing conditions: a propane molecule and three heavier hydrocarbon molecules, typically in the C8 to C18 range.

Thus, in one embodiment, the product of one or more chemical reaction(s) performed on lipid compositions of the invention is an alkane mixture that comprises ASTM D975 renewable diesel. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

The distillation properties of a diesel fuel is described in terms of T10-T90 (temperature at 10% and 90%, respectively, volume distilled). Renewable diesel was produced from *Prototheca moriformis* triglyceride oil and is described in Example 14. The T10-T90 of the material produced in Example 14 was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

The T10 of the material produced in Example 14 was 242.1° C. Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

The T90 of the material produced in Example 14 was 300° C. Methods of hydrotreating, isomerization, and other covalent modification of oils disclosed herein, as well as methods of distillation and fractionation (such as cold filtration) disclosed herein can be employed to generate renewable diesel compositions with other T90 values, such as T90 between 280 and 380, between 290 and 360, between 300 and 350, between 310 and 340, and at least 290.

The FBP of the material produced in Example 14 was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 4% C8-C14; (b) at least 0.3% C8; (c) at least 2% C10; (d) at least 2% C12; and (3) at least 30% C8-C14.

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosone-type Aeroplane fuel (including Jet A and Jet A-1) has a carbon number distribution between about 8 and 16 carbon numbers. Wide-cut or naphta-type Aeroplane fuel (including Jet B) typically has a carbon number distribution between about 5 and 15 carbons.

Both Aeroplanes (Jet A and Jet B) may contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A is used for civilian and military fuels and DCI-6A is used for military fuels. FSII agents, include, e.g., Di-EGME.

In one embodiment of the invention, a jet fuel is produced by blending algal fuels with existing jet fuel. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking (FCC) is one method which is used to produce olefins, especially propylene from heavy crude fractions. The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In one embodiment, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced. In one embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method, it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

Suitable FCC catalysts generally comprise at least two components that may or may not be on the same matrix. In some embodiments, both two components may be circulated throughout the entire reaction vessel. The first component generally includes any of the well-known catalysts that are used in the art of fluidized catalytic cracking, such as an active amorphous clay-type catalyst and/or a high activity, crystalline molecular sieve. Molecular sieve catalysts may be preferred over amorphous catalysts because of their much-improved selectivity to desired products. IN some preferred embodiments, zeolites may be used as the molecular sieve in the FCC processes. Preferably, the first catalyst component comprises a large pore zeolite, such as an Y-type zeolite, an active alumina material, a binder material, comprising either silica or alumina and an inert filler such as kaolin.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

In another embodiment of the method for producing a jet fuel using the lipid composition or the lipids produced as described herein, the structure of the lipid composition or the lipids is broken by a process referred to as hydrodeoxygenation (HDO). HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step, i.e. HDO step, of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle. In the HDO step, the pressure varies between 20 and 150 bar, preferably between 50 and 100 bar, and the temperature varies between 200 and 500° C., preferably in the range of 300-400° C. In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, NiMo/ $Al_2O_3$ and CoMo/$Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50 400° C. and at hydrogen pressures of 1 200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner. In the isomerzation step, the pressure varies in the range of 20 150 bar, preferably in the range of 20 100 bar, the temperature being between 200 and 500° C., preferably between 300 and 400° C. In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. The isomerization step and the HDO step may be carried out in the same pressure vessel or in separate pressure vessels. Optional prehydrogenation may be carried out in a separate pressure vessel or in the same pressure vessel as the HDO and isomerization steps.

Thus, in one embodiment, the product of the one or more chemical reactions is an alkane mixture that comprises ASTM D1655 jet fuel. In some embodiments, the composition comforming to the specification of ASTM 1655 jet fuel has a sulfur content that is less than 10 ppm. In other embodiments, the composition conforming to the specification of ASTM 1655 jet fuel has a T10 value of the distillation curve of less than 205° C. In another embodiment, the composition conforming to the specification of ASTM 1655 jet fuel has a final boiling point (FBP) of less than 300° C. In another embodiment, the composition conforming to the specification of ASTM 1655 jet fuel has a flash point of at least 38° C. In another embodiment, the composition conforming to the specification of ASTM 1655 jet fuel has a density between 775K/$M^3$ and 840K/$M^3$. In yet another embodiment, the composition conforming to the specification of ASTM 1655 jet fuel has a freezing point that is below −47° C. In another embodiment, the composition conforming to the specification of ASTM 1655 jet fuel has a net Heat of Combustion that is at least 42.8 MJ/K. In another embodiment, the composition conforming to the specification of ASTM 1655 jet fuel has a hydrogen content that is at least 13.4 mass %. In another embodiment, the composition conforming to the specification of ASTM 1655 jet fuel has a thermal stability, as tested by quantitative gravimetric JFTOT at 260° C., that is below 3 mm of Hg. In another embodiment, the composition conforming to the specification of ASTM 1655 jet fuel has an existent gum that is below 7 mg/dl.

Thus, the present invention discloses a variety of methods in which chemical modification of microalgal lipid is undertaken to yield products useful in a variety of industrial and other applications. Examples of processes for modifying oil produced by the methods disclosed herein include, but are not limited to, hydrolysis of the oil, hydroprocessing of the oil, and esterification of the oil. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein. Examples of basic oleochemicals include, but are not limited to, soaps, fatty acids, fatty acid methyl esters, and glycerol. Examples of derivative oleochemicals include, but are not limited to, fatty nitriles, esters, dimer acids, quats, surfactants, fatty alkanolamides, fatty alcohol sulfates, resins, emulsifiers, fatty alcohols, olefins, and higher alkanes.

Hydrolysis of the fatty acid constituents from the glycerolipids produced by the methods of the invention yields free fatty acids that can be derivatized to produce other useful chemicals. Hydrolysis occurs in the presence of water and a catalyst which may be either an acid or a base. The liberated free fatty acids can be derivatized to yield a variety of products, as reported in the following: U.S. Pat. No. 5,304,664 (Highly sulfated fatty acids); U.S. Pat. No. 7,262,158 (Cleansing compositions); U.S. Pat. No. 7,115,173 (Fabric softener compositions); U.S. Pat. No. 6,342,208 (Emulsions for treating skin); U.S. Pat. No. 7,264,886 (Water repellant compositions); U.S. Pat. No. 6,924,333 (Paint additives); U.S. Pat. No. 6,596,768 (Lipid-enriched ruminant feedstock); and U.S. Pat. No. 6,380,410 (Surfactants for detergents and cleaners).

With regard to hydrolysis, in one embodiment of the invention, a triglyceride oil is optionally first hydrolyzed in a liquid medium such as water or sodium hydroxide so as to obtain glycerol and soaps. There are various suitable triglyceride hydrolysis methods, including, but not limited to, saponification, acid hydrolysis, alkaline hydrolysis, enzymatic hydrolysis (referred herein as splitting), and hydrolysis using hot-compressed water. One skilled in the art will recognize that a triglyceride oil need not be hydrolyzed in order to produce an oleochemical; rather, the oil may be converted directly to the desired oleochemical by other known process. For example, the triglyceride oil may be directly converted to a methyl ester fatty acid through esterification.

In some embodiments, catalytic hydrolysis of the oil produced by methods disclosed herein occurs by splitting the oil into glycerol and fatty acids. As discussed above, the fatty acids may then be further processed through several other modifications to obtained derivative oleochemicals. For example, in one embodiment the fatty acids may undergo an amination reaction to produce fatty nitrogen compounds. In another embodiment, the fatty acids may undergo ozonolysis to produce mono- and dibasic-acids.

In other embodiments hydrolysis may occur via the, splitting of oils produced herein to create oleochemicals. In some preferred embodiments of the invention, a triglyceride oil may be split before other processes is performed. One skilled in the art will recognize that there are many suitable triglyceride splitting methods, including, but not limited to, enzymatic splitting and pressure splitting.

Generally, enzymatic oil splitting methods use enzymes, lipases, as biocatalysts acting on a water/oil mixture. Enzymatic splitting then splits the oil or fat, respectively, is into glycerol and free fatty acids. The glycerol may then migrates into the water phase whereas the organic phase enriches with free fatty acids.

The enzymatic splitting reactions generally take place at the phase boundary between organic and aqueous phase, where the enzyme is present only at the phase boundary. Triglycerides that meet the phase boundary then contribute to or participate in the splitting reaction. As the reaction proceeds, the occupation density or concentration of fatty acids still chemically bonded as glycerides, in comparison to free fatty acids, decreases at the phase boundary so that the reaction is slowed down. In certain embodiments, enzymatic splitting may occur at room temperature. One of ordinary skill in the art would know the suitable conditions for splitting oil into the desired fatty acids.

By way of example, the reaction speed can be accelerated by increasing the interface boundary surface. Once the reaction is complete, free fatty acids are then separated from the organic phase freed from enzyme, and the residue which still contains fatty acids chemically bonded as glycerides is fed back or recycled and mixed with fresh oil or fat to be subjected to splitting. In this manner, recycled glycerides are then subjected to a further enzymatic splitting process. In some embodiments, the free fatty acids are extracted from an oil or fat partially split in such a manner. In that way, if the chemically bound fatty acids (triglycerides) are returned or fed back into the splitting process, the enzyme consumption can be drastically reduced.

The splitting degree is determined as the ratio of the measured acid value divided by the theoretically possible acid value which can be computed for a given oil or fat. Preferably, the acid value is measured by means of titration according to standard common methods. Alternatively, the density of the aqueous glycerol phase can be taken as a measure for the splitting degree.

In one embodiment, the slitting process as described herein is also suitable for splitting the mono-, di- and triglyceride that are contained in the so-called soap-stock from the alkali refining processes of the produced oils. In this manner, the soap-stock can be quantitatively converted without prior saponification of the neutral oils into the fatty acids. For this purpose, the fatty acids being chemically bonded in the soaps are released, preferably before splitting, through an addition of acid. In certain embodiments, a buffer solution is used in addition to water and enzyme for the splitting process.

In one embodiment, oils produced in accordance with the methods of the invention can also be subjected to saponification as a method of hydrolysis Animal and plant oils are typically made of triacylglycerols (TAGs), which are esters of fatty acids with the trihydric alcohol, glycerol. In an alkaline hydrolysis reaction, the glycerol in a TAG is removed, leaving three carboxylic acid anions that can associate with alkali metal cations such as sodium or potassium to produce fatty acid salts. In this scheme, the carboxylic acid constituents are cleaved from the glycerol moiety and replaced with hydroxyl groups. The quantity of base (e.g., KOH) that is used in the reaction is determined by the desired degree of saponification. If the objective is, for example, to produce a soap product that comprises some of the oils originally present in the TAG composition, an amount of base insufficient to convert all of the TAGs to fatty acid salts is introduced into the reaction mixture. Normally, this reaction is performed in an aqueous solution and proceeds slowly, but may be expedited by the addition of heat. Precipitation of the fatty acid salts can be facilitated by addition of salts, such as water-soluble alkali metal halides (e.g., NaCl or KCl), to the reaction mixture. Preferably, the base is an alkali metal hydroxide, such as NaOH or KOH. Alternatively, other bases, such as alkanolamines, including for example triethanolamine and aminomethylpropanol, can be used in the reaction scheme. In some cases, these alternatives may be preferred to produce a clear soap product.

In some methods, the first step of chemical modification may be hydroprocessing to saturate double bonds, followed by deoxygenation at elevated temperature in the presence of hydrogen and a catalyst. In other methods, hydrogenation and deoxygenation may occur in the same reaction. In still other methods deoxygenation occurs before hydrogenation. Isomerization may then be optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

In some embodiments of the invention, the triglyceride oils are partially or completely deoxygenated. The deoxygenation reactions form desired products, including, but not limited to, fatty acids, fatty alcohols, polyols, ketones, and aldehydes. In general, without being limited by any particular theory, the deoxygenation reactions involve a combination of various different reaction pathways, including without limitation: hydrogenolysis, hydrogenation, consecutive hydrogenation-hydrogenolysis, consecutive hydrogenolysis-hydrogenation, and combined hydrogenation-hydrogenolysis reactions, resulting in at least the partial removal of oxygen from the fatty acid or fatty acid ester to produce reaction products, such as fatty alcohols, that can be easily converted to the desired chemicals by further processing. For example, in one embodiment, a fatty alcohol may be converted to olefins through FCC reaction or to higher alkanes through a condensation reaction.

One such chemical modification is hydrogenation, which is the addition of hydrogen to double bonds in the fatty acid constituents of glycerolipids or of free fatty acids. The hydrogenation process permits the transformation of liquid oils into semi-solid or solid fats, which may be more suitable for specific applications.

Hydrogenation of oil produced by the methods described herein can be performed in conjunction with one or more of the methods and/or materials provided herein, as reported in the following: U.S. Pat. No. 7,288,278 (Food additives or medicaments); U.S. Pat. No. 5,346,724 (Lubrication products); U.S. Pat. No. 5,475,160 (Fatty alcohols); U.S. Pat. No. 5,091,116 (Edible oils); U.S. Pat. No. 6,808,737 (Structural fats for margarine and spreads); U.S. Pat. No. 5,298,637 (Reduced-calorie fat substitutes); U.S. Pat. No. 6,391,815 (Hydrogenation catalyst and sulfur adsorbent); U.S. Pat. Nos. 5,233,099 and 5,233,100 (Fatty alcohols); U.S. Pat. No. 4,584,139 (Hydrogenation catalysts); U.S. Pat. No. 6,057,375 (Foam suppressing agents); and U.S. Pat. No. 7,118,773 (Edible emulsion spreads).

One skilled in the art will recognize that various processes may be used to hydrogenate carbohydrates. One suitable method includes contacting the carbohydrate with hydrogen or hydrogen mixed with a suitable gas and a catalyst under conditions sufficient in a hydrogenation reactor to form a hydrogenated product. The hydrogenation catalyst generally can include Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports, depending on the desired functionality of the catalyst. The hydrogenation catalysts may be prepared by methods known to those of ordinary skill in the art.

In some embodiments the hydrogenation catalyst includes a supported Group VIII metal catalyst and a metal sponge material (e.g., a sponge nickel catalyst). Raney nickel provides an example of an activated sponge nickel catalyst suitable for use in this invention. In other embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (i.e., molybdenum or chromium) in the amount such that about 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than about 1% by weight. The solid may then be reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 80° C. to 250° C., and preferably at 90° C. to 200° C., and most preferably at 100° C. to 150° C. In some embodiments, the hydrogenation reaction is conducted at pressures from 500 KPa to 14000 KPa.

The hydrogen used in the hydrogenolysis reaction of the current invention may include external hydrogen, recycled hydrogen, in situ generated hydrogen, and any combination thereof. As used herein, the term "external hydrogen" refers to hydrogen that does not originate from the biomass reaction itself, but rather is added to the system from another source.

In some embodiments of the invention, it is desirable to convert the starting carbohydrate to a smaller molecule that will be more readily converted to desired higher hydrocarbons. One suitable method for this conversion is through a hydrogenolysis reaction. Various processes are known for performing hydrogenolysis of carbohydrates. One suitable method includes contacting a carbohydrate with hydrogen or hydrogen mixed with a suitable gas and a hydrogenolysis catalyst in a hydrogenolysis reactor under conditions sufficient to form a reaction product comprising smaller molecules or polyols. As used herein, the term "smaller molecules or polyols" includes any molecule that has a smaller molecular weight, which can include a smaller number of carbon atoms or oxygen atoms than the starting carbohydrate. In an embodiment, the reaction products include smaller molecules that include polyols and alcohols. Someone of ordinary skill in the art would be able to choose the appropriate method by which to carry out the hydrogenolysis reaction.

In some embodiments, a 5 and/or 6 carbon sugar or sugar alcohol may be converted to propylene glycol, ethylene glycol, and glycerol using a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The hydrogenolysis catalyst may also include a carbonaceous pyropolymer catalyst containing transition metals (e.g., chromium, molybdemum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst may include any of the above metals combined with an alkaline earth metal oxide or adhered to a catalytically active support. In certain embodiments, the catalyst described in the hydrogenolysis reaction may include a catalyst support as described above for the hydrogenation reaction.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, they hydrogenolysis reaction is conducted at temperatures of 110° C. to 300° C., and preferably at 170° C. to 220° C., and most preferably at 200° C. to 225° C. In some embodiments, the hydrogenolysis reaction is conducted under basic conditions, preferably at a pH of 8 to 13, and even more preferably at a pH of 10 to 12. In some embodiments, the hydrogenolysis reaction is conducted at pressures in a range between 60 KPa and 16500 KPa, and preferably in a range between 1700 KPa and 14000 KPa, and even more preferably between 4800 KPa and 11000 KPa.

The hydrogen used in the hydrogenolysis reaction of the current invention can include external hydrogen, recycled hydrogen, in situ generated hydrogen, and any combination thereof.

In some embodiments, the reaction products discussed above may be converted into higher hydrocarbons through a condensation reaction in a condensation reactor (shown schematically as condensation reactor 110 in FIG. 1). In such embodiments, condensation of the reaction products occurs in the presence of a catalyst capable of forming higher hydrocarbons. While not intending to be limited by theory, it is believed that the production of higher hydrocarbons proceeds through a stepwise addition reaction including the formation of carbon-carbon, or carbon-oxygen bond. The resulting reaction products include any number of compounds containing these moieties, as described in more detail below.

In certain embodiments, suitable condensation catalysts include an acid catalyst, a base catalyst, or an acid/base catalyst. As used herein, the term "acid/base catalyst" refers to a catalyst that has both an acid and a base functionality. In some embodiments the condensation catalyst can include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the condensation catalyst can also include a modifier. Suitable modifiers include La, Y, Sc, P, B, Bi, Li, Na, K, Rb, Cs, Mg, Ca, Sr, Ba, and any combination thereof. In some embodiments, the condensation catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof.

In certain embodiments, the catalyst described in the condensation reaction may include a catalyst support as described above for the hydrogenation reaction. In certain embodiments, the condensation catalyst is self-supporting. As used herein, the term "self-supporting" means that the catalyst does not need another material to serve as support. In other embodiments, the condensation catalyst in used in conjunction with a separate support suitable for suspending the catalyst. In an embodiment, the condensation catalyst support is silica.

The conditions under which the condensation reaction occurs will vary based on the type of starting material and the desired products. One of ordinary skill in the art, with the benefit of this disclosure, will recognize the appropriate conditions to use to carry out the reaction. In some embodiments, the condensation reaction is carried out at a temperature at which the thermodynamics for the proposed reaction are favorable. The temperature for the condensation reaction will vary depending on the specific starting polyol or alcohol. In some embodiments, the temperature for the condensation reaction is in a range from 80° C. to 500° C., and preferably from 125° C. to 450° C., and most preferably from 125° C. to 250° C. In some embodiments, the condensation reaction is conducted at pressures in a range between 0 Kpa to 9000 KPa, and preferably in a range between 0 KPa and 7000 KPa, and even more preferably between 0 KPa and 5000 KPa.

The higher alkanes formed by the invention include, but are not limited to, branched or straight chain alkanes that have from 4 to 30 carbon atoms, branched or straight chain alkenes that have from 4 to 30 carbon atoms, cycloalkanes that have from 5 to 30 carbon atoms, cycloalkenes that have from 5 to 30 carbon atoms, aryls, fused aryls, alcohols, and ketones. Suitable alkanes include, but are not limited to, butane, pentane, pentene, 2-methylbutane, hexane, hexene, 2-methylpentane, 3-methylpentane, 2,2,-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, nonyldecane, nonyldecene, eicosane, eicosene, uneicosane, uneicosene, doeicosane, doeicosene, trieicosane, trieicosene, tetraeicosane, tetraeicosene, and isomers thereof. Some of these products may be suitable for use as fuels.

In some embodiments, the cycloalkanes and the cycloalkenes are unsubstituted. In other embodiments, the cycloalkanes and cycloalkenes are mono-substituted. In still other embodiments, the cycloalkanes and cycloalkenes are multi-substituted. In the embodiments comprising the substituted cycloalkanes and cycloalkenes, the substituted group includes, without limitation, a branched or straight chain alkyl having 1 to 12 carbon atoms, a branched or straight chain alkylene having 1 to 12 carbon atoms, a phenyl, and any combination thereof. Suitable cycloalkanes and cycloalkenes include, but are not limited to, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, isomers and any combination thereof.

In some embodiments, the aryls formed are unsubstituted. In another embodiment, the aryls formed are mono-substituted. In the embodiments comprising the substituted aryls, the substituted group includes, without limitation, a branched or straight chain alkyl having 1 to 12 carbon atoms, a branched or straight chain alkylene having 1 to 12 carbon atoms, a phenyl, and any combination thereof. Suitable aryls for the invention include, but are not limited to, benzene, toluene, xylene, ethyl benzene, para xylene, meta xylene, and any combination thereof.

The alcohols produced in the invention have from 4 to 30 carbon atoms. In some embodiments, the alcohols are cyclic. In other embodiments, the alcohols are branched. In another embodiment, the alcohols are straight chained. Suitable alcohols for the invention include, but are not limited to, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The ketones produced in the invention have from 4 to 30 carbon atoms. In an embodiment, the ketones are cyclic. In another embodiment, the ketones are branched. In another embodiment, the ketones are straight chained. Suitable ketones for the invention include, but are not limited to, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Another such chemical modification is interesterification. Naturally produced glycerolipids do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g, 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a percentage of dry cell weight as lipid at least 20%.

Directed interesterification, in which a specific distribution pattern of fatty acids is sought, can be performed by maintaining the oil mixture at a temperature below the melting point of some TAGs which might occur. This results in selective crystallization of these TAGs, which effectively removes them from the reaction mixture as they crystallize. The process can be continued until most of the fatty acids in the oil have precipitated, for example. A directed interesterification process can be used, for example, to produce a product with a lower calorie content via the substitution of longer-chain fatty acids with shorter-chain counterparts. Directed interesterification can also be used to produce a product with a mixture of fats that can provide desired melting characteristics and structural features sought in food additives or products (e.g., margarine) without resorting to hydrogenation, which can produce unwanted trans isomers.

Interesterification of oils produced by the methods described herein can be performed in conjunction with one or more of the methods and/or materials, or to produce products, as reported in the following: U.S. Pat. No. 6,080,853 (Non-digestible fat substitutes); U.S. Pat. No. 4,288,378 (Peanut butter stabilizer); U.S. Pat. No. 5,391,383 (Edible spray oil); U.S. Pat. No. 6,022,577 (Edible fats for food products); U.S. Pat. No. 5,434,278 (Edible fats for food products); U.S. Pat. No. 5,268,192 (Low calorie nut products); U.S. Pat. No. 5,258,197 (Reduce calorie edible compositions); U.S. Pat. No. 4,335,156 (Edible fat product); U.S. Pat. No. 7,288,278 (Food additives or medicaments); U.S. Pat. No. 7,115,760 (Fractionation process); U.S. Pat. No. 6,808,737 (Structural fats); U.S. Pat. No. 5,888,947 (Engine lubricants); U.S. Pat. No. 5,686,131 (Edible oil mixtures); and U.S. Pat. No. 4,603,188 (Curable urethane compositions).

In one embodiment in accordance with the invention, transesterification of the oil, as described above, is followed by reaction of the transesterified product with polyol, as reported in U.S. Pat. No. 6,465,642, to produce polyol fatty acid polyesters. Such an esterification and separation process may comprise the steps as follows: reacting a lower alkyl ester with polyol in the presence of soap; removing residual soap from the product mixture; water-washing and drying the product mixture to remove impurities; bleaching the product mixture for refinement; separating at least a portion of the unreacted lower alkyl ester from the polyol fatty acid polyester in the product mixture; and recycling the separated unreacted lower alkyl ester.

Transesterification can also be performed on microbial biomass with short chain fatty acid esters, as reported in U.S. Pat. No. 6,278,006. In general, transesterification may be performed by adding a short chain fatty acid ester to an oil in the presence of a suitable catalyst and heating the mixture. In some embodiments, the oil comprises about 5% to about 90% of the reaction mixture by weight. In some embodiments, the short chain fatty acid esters can be about 10% to about 50% of the reaction mixture by weight. Non-limiting examples of catalysts include base catalysts, sodium methoxide, acid catalysts including inorganic acids such as sulfuric acid and acidified clays, organic acids such as methane sulfonic acid, benzenesulfonic acid, and toluenesulfonic acid, and acidic resins such as Amberlyst 15. Metals such as sodium and magnesium, and metal hydrides also are useful catalysts.

Another such chemical modification is hydroxylation, which involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027. Hydroxylated fatty acids, including castor oil and its derivatives, are useful as components in several industrial applications, including food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants. One example of how the hydroxylation of a glyceride may be performed is as follows: fat may be heated, preferably to about 30-50° C. combined with heptane and maintained at temperature for thirty minutes or more; acetic acid may then be added to the mixture followed by an aqueous solution of sulfuric acid followed by an aqueous hydrogen peroxide solution which is added in small increments to the mixture over one hour; after the aqueous hydrogen peroxide, the temperature may then be increased to at least about 60° C. and stirred for at least six hours; after the stirring, the mixture is allowed to settle and a lower aqueous layer formed by the reaction may be removed while the upper heptane layer formed by the reaction may be washed with hot water having a temperature of about 60° C.; the washed heptane layer may then be neutralized with an aqueous potassium hydroxide solution to a pH of about 5 to 7 and then removed by distillation under vacuum; the reaction product may then be dried under vacuum at 100° C. and the dried product steam-deodorized under vacuum conditions and filtered at about 50° to 60° C. using diatomaceous earth.

Hydroxylation of microbial oils produced by the methods described herein can be performed in conjunction with one or more of the methods and/or materials, or to produce products, as reported in the following: U.S. Pat. No. 6,590,113 (Oil-based coatings and ink); U.S. Pat. No. 4,049,724 (Hydroxylation process); U.S. Pat. No. 6,113,971 (Olive oil butter); U.S. Pat. No. 4,992,189 (Lubricants and lube additives); U.S. Pat. No. 5,576,027 (Hydroxylated milk); and U.S. Pat. No. 6,869,597 (Cosmetics).

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., *JAOCS* 71(2):169-174 (1994). Estolides are useful in a variety of applications, including without limitation those reported in the following: U.S. Pat. No. 7,196,124 (Elastomeric materials and floor coverings); U.S. Pat. No. 5,458,795 (Thickened oils for high-temperature applications); U.S. Pat. No. 5,451,332 (Fluids for industrial applications); U.S. Pat. No. 5,427,704 (Fuel additives); and U.S. Pat. No. 5,380,894 (Lubricants, greases, plasticizers, and printing inks).

Other chemical reactions that can be performed on microbial oils include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No.

6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004).

The generation of oil-bearing microbial biomass for fuel and chemical products as described above results in the production of delipidated biomass meal. Delipidated meal is a byproduct of preparing algal oil and is useful as animal feed for farm animals, e.g., ruminants, poultry, swine and aquaculture. The resulting meal, although of reduced oil content, still contains high quality proteins, carbohydrates, fiber, ash, residual oil and other nutrients appropriate for an animal feed. Because the cells are predominantly lysed by the oil separation process, the delipidated meal is easily digestible by such animals. Delipidated meal can optionally be combined with other ingredients, such as grain, in an animal feed. Because delipidated meal has a powdery consistency, it can be pressed into pellets using an extruder or expander or another type of machine, which are commercially available.

The invention, having been described in detail above, is exemplified in the following examples, which are offered to illustrate, but not to limit, the claimed invention.

VII. EXAMPLES

Example 1

Methods for Culturing Prototheca

*Prototheca* strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4.7H_2O$, 0.25 g/L Citric Acid monohydrate, 0.025 g/L $CaCl_22H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and dry cell weights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 8.

TABLE 8

| Percent oil by dry cell weight | | |
|---|---|---|
| Species | Strain | % Oil |
| Prototheca stagnora | UTEX 327 | 13.14 |
| Prototheca moriformis | UTEX 1441 | 18.02 |
| Prototheca moriformis | UTEX 1435 | 27.17 |

Microalgae samples from the strains listed in Table 22 above were genotyped. Genomic DNA was isolated from algal biomass as follows. Cells (approximately 200 mg) were centifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2× iProof HF master mix (BIO-RAD) was added to 0.4 µl primer SZ02613 (5'-TGTTGAAGAATGAGCCGGCGAC-3' (SEQ ID NO:9) at 10 mM stock concentration). This primer sequence runs from position 567-588 in Gen Bank accession no. L43357 and is highly conserved in higher plants and algal plastid genomes. This was followed by the addition of 0.4 µl primer SZ02615 (5'-CAGTGAGCTATTACGCACTC-3' (SEQ ID NO:10) at 10 mM stock concentration). This primer sequence is complementary to position 1112-1093 in Gen Bank accession no. L43357 and is highly conserved in higher plants and algal plastid genomes. Next, 5 µl of diluted total DNA and 3.2 µl $dH_2O$ were added. PCR reactions were run as follows: 98° C., 45"; 98° C., 8"; 53° C., 12"; 72° C., 20" for 35 cycles followed by 72° C. for 1 mM and holding at 25° C. For purification of PCR products, 20 µl of 10 mM Tris, pH 8.0, was added to each reaction, followed by extraction with 40 µl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. In total, twelve *Prototheca* strains were selected to have their 23S rRNA DNA sequenced and the sequences are listed in the Sequence Listing. A summary of the strains and Sequence Listing Numbers is included below. The sequences were analyzed for overall divergence from the UTEX 1435 (SEQ ID NO: 15) sequence. Two pairs emerged (UTEX 329/UTEX 1533 and UTEX 329/UTEX 1440) as the most divergent. In both cases, pairwise alignment resulted in 75.0% pairwise sequence identity. The percent sequence identity to UTEX 1435 is also included below.

| Species | Strain | % nt identity | SEQ ID NO. |
|---|---|---|---|
| Prototheca kruegani | UTEX 329 | 75.2 | SEQ ID NO: 11 |
| Prototheca wickerhamii | UTEX 1440 | 99 | SEQ ID NO: 12 |
| Prototheca stagnora | UTEX 1442 | 75.7 | SEQ ID NO: 13 |

-continued

| Species | Strain | % nt identity | SEQ ID NO. |
|---|---|---|---|
| Prototheca moriformis | UTEX 288 | 75.4 | SEQ ID NO: 14 |
| Prototheca moriformis | UTEX 1439; 1441; 1435; 1437 | 100 | SEQ ID NO: 15 |
| Prototheca wikerhamii | UTEX 1533 | 99.8 | SEQ ID NO: 16 |
| Prototheca moriformis | UTEX 1434 | 75.9 | SEQ ID NO: 17 |
| Prototheca zopfii | UTEX 1438 | 75.7 | SEQ ID NO: 18 |
| Prototheca moriformis | UTEX 1436 | 88.9 | SEQ ID NO: 19 |

Lipid samples from a subset of the above-listed strains were analyzed for lipid profile using HPLC. Results are shown below in Table 9.

TABLE 9

Diversity of lipid chains in microalgal species

| Strain | C14:0 | C16:0 | C16:1 | C18:0 | C18:1 | C18:2 | C18:3 | C20:0 | C20:1 |
|---|---|---|---|---|---|---|---|---|---|
| UTEX 327 | 0 | 12.01 | 0 | 0 | 50.33 | 17.14 | 0 | 0 | 0 |
| UTEX 1441 | 1.41 | 29.44 | 0.70 | 3.05 | 57.72 | 12.37 | 0.97 | 0.33 | 0 |
| UTEX 1435 | 1.09 | 25.77 | 0 | 2.75 | 54.01 | 11.90 | 2.44 | 0 | 0 |

Algal plastid transit peptides were identified through the analysis of UTEX 1435 (Prototheca moriformis) or UTEX 250 (Chlorella protothecoides) cDNA libraries as described in Examples 12 and Example 11 below. cDNAs encoding potentially plastid targeted proteins based upon BLAST hit homology to other known plastid targeted proteins were subjected to further analysis by the sowftawre programs PSORT (http://psort.ims.u-tokyo.ac.jp/form.html), ChloroP (http://www.cbs.dtu.dk/services/ChloroP/) are TargetP (http://www.cbs.dtu.dk/services/TargetP/). Candidate plastid transit peptides identified through at least one of these three programs were then PCR amplified from the appropriate genomic DNA. Below is a summary of the amino acid sequences algal plastid targeting sequences (PTS) that were identified from this screen. Also included are the amino acid sequences of plant fatty acyl-ACP thioesterases that are used in the heterologous expression Examples below.

| cDNA | SEQ ID NO. |
|---|---|
| P. moriformis isopentenyl diphosphate synthase PTS | SEQ ID NO: 127 |
| P. moriformis delta 12 fatty acid desaturase PTS | SEQ ID NO: 128 |
| P. moriformis stearoyl ACP desaturase PTS | SEQ ID NO: 129 |
| C. protothecoides stearoyl ACP desaturase PTS | SEQ ID NO: 130 |
| Cuphea hookeriana fatty acyl-ACP thioesterase (C8-10) | SEQ ID NO: 131 |
| Umbellularia californica fatty acyl-ACP thioesterase (C12) | SEQ ID NO: 132 |
| Cinnamomum camphora fatty acyl-ACP thioesterase (C14) | SEQ ID NO: 133 |

Example 2

Culturing Prototheca on Various Feedstocks

A. Sorghum

The following strains were shown to be capable of utilizing sorghum as a sole carbon source: Prototheca moriformis strains UTEX 1435, UTEX 1437, UTEX 288, UTEX 1439, UTEX 1441 and UTEX 1434, and Prototheca stagnora strain UTEX 1442. The "UTEX" designation indicates the strain number from the algal culture collection of the University of Texas, 1 University State A6700, Austin, Tex. 78712-0183.

Figure 2:
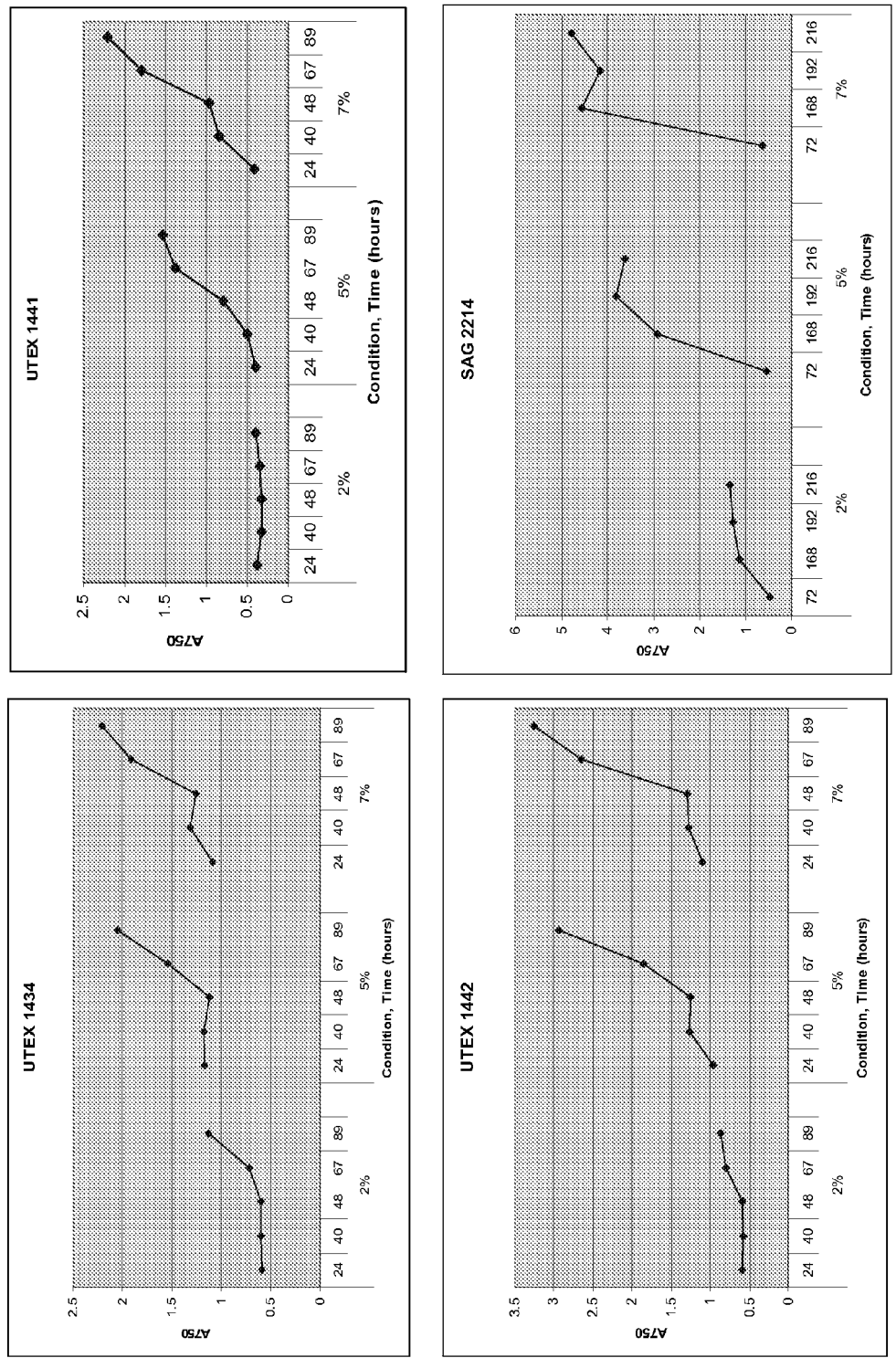

Pure sorghum was purchased from Maasdam Sorghum Mills (Lynnville, Iowa) with a sugar profile of fructose 21.0% w/w, dextrose 28.0% w/w, sucrose 16.0% w/w and maltose <0.5% w/w. The cultures were grown in liquid medium containing 2%, 5%, or 7% (v/v) pure sorghum (diluted from the pure stock) as the sole carbon source and the cultures were grown heterotrophically in the dark, agitating at ~350 rpm. Samples from the cultures were pulled at 24, 40, 48, 67 and 89 hours and growth was measured using A750 readings on a spectrophotometer. Growth was observed for each of the strains tested as shown in FIGS. 1-2.

B. Cellulose

Wet, exploded corn stover, Miscanthus, forage sorghum, beet pulp and sugar cane bagasse were prepared by The National Renewable Energy Laboratory (Golden, Colo.) by cooking in a 1.4% sulfuric acid solution and dewatering the resultant slurry. Percent solids were determined gravimetrically by drying and were as follows: corn stover, 25% solids; Miscanthus, 28.7% solids; forage sorghum, 26.7% solids; and sugar cane bagasse, 26% solids.

100 gram wet samples of exploded cellulosic materials (corn stover or switch grass) were resuspended in deionized water to a final volume of 420 mL and the pH was adjusted to 4.8 using 10N NaOH. For beet pulp, 9.8 grams dry solids were brought to 350 mL with deionized water and pH was adjusted to 4.8 with 10 N NaOH. For all of the above feedstocks, Accellerase 1000 (Genencor, N.Y.) was used at a ratio of 0.25 ml enzyme per gram of dry biomass for saccharification of the cellulosic materials. Samples were incubated with agitation (110 rpm) at 50° C. for 72 hours. The pH of each of the samples was adjusted to 7.0 with NaOH (with negligible volume change), filter sterilized through a 0.22 μm filter and used in the processes detailed below. For larger scale processes, the same procedure for saccharification was followed except an additional step of tangential flow filtration (TFF) or microfiltration step was performed to aid in filter sterilization of feedstocks. A sample from each of the feedstocks prepared was reserved for determination of glucose and xylose concentration using an HPLC/ELSD-based system or a hexokinase-based kit (Sigma). Additionally, for beet pulp, the material was initially brought to volume as with the other feedstocks, the pH was then adjusted to 4.0 and a pectinase treatment was carried out at 50° C. for 24 hours. The pH was then adjusted to 4.8 if no washing steps were conducted or 5.3 if washing steps were conducted. Enzymatic saccharification was then performed with the same procedure used for the other feedstocks as described above.

Microalgae Prototheca moriformis strain UTEX 1435 was assessed for its ability to grow on a series of cellulosic feedstocks prepared as described above (corn stover, beet pulp, sorghum cane, Miscanthus and glucose control). The microalgae culture was grown in conditions described in Example 1 above with the exception of the carbon source. The carbon source was either 4% glucose (for control conditions) or 4% glucose as measured by available glucose in the cellulosic materials. Growth was assessed by A750 readings and the culturing time was 168 hours, with A750 readings at 48, 72, 96, 120, 144 and 168 hours after initiation of the culture. As can be seen in FIG. 7a, the *Prototheca moriformis* culture grew best in corn stover. The other cellulosic feedstocks used, *Miscanthus*, sorghum cane and beet pulp, all exhibited inhibition of growth.

Based on the above results with corn stover derived cellulosic sugars, lipid accumulation was also assessed in *Prototheca moriformis* using different levels of corn stover derived cellulosic sugars and reagent glucose as a control. Cultures were grown in 18 g/L glucose that was completely from corn stover derived cellulosic sugars (100% corn stover condition in FIG. 7b), 9 g/L glucose from corn stover derived cellulosic sugars supplemented with 9 g/L reagent glucose (50% corn stover supplemented with glucose to 18 g/L condition in FIG. 7b), 9 g/L glucose from corn stover derived cellulosic sugars (50% corn stover, not supplemented; glucose at 9 g/L condition in FIG. 7b) and a control culture of 42 g/L reagent glucose and 13 g/L reagent xylose for osmolarity control. All cultures were fed with cellulosic sugars to maintain the glucose concentration at 20 g/L, except for the control culture, which was fed with reagent glucose to maintain the glucose concentration at 20 g/L. Growth was measured based on the dry cell weight of the culture and lipid productivity was determined as a percent dry cell weight. Total lipids were determined gravimetrically using an Ankom acid hydrolysis/solvent extraction system as described in Example 1 above.

Figure 7B:
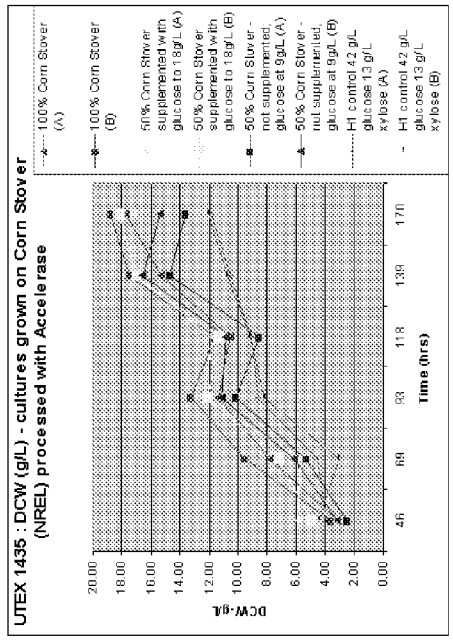
FIG. 7b shows the results of growth experiments using *Prototheca moriformis* using different levels of corn stover-derived cellulosic sugar as compared to glucose/xylose control.

As can be seen in FIG. 7b, based on biomass accumulation (as measured by DCW), all concentrations of the corn stover derived cellulosics out-performed (higher DCW) the control media that was fed glucose alone. Lipid production as a percentage of DCW was also calculated for all of the conditions. In addition to the higher biomass accumulation seen for growth on corn stover, lipid accumulation was also higher in the corn stover derived cellulosics conditions as compared to the glucose control condition. These data demonstrate that, in addition to providing cellulosic derived sugars, corn stover provides additional nutrients/components that contribute to an increased biomass accumulation (growth) and increased product yield.

Figure 7D:
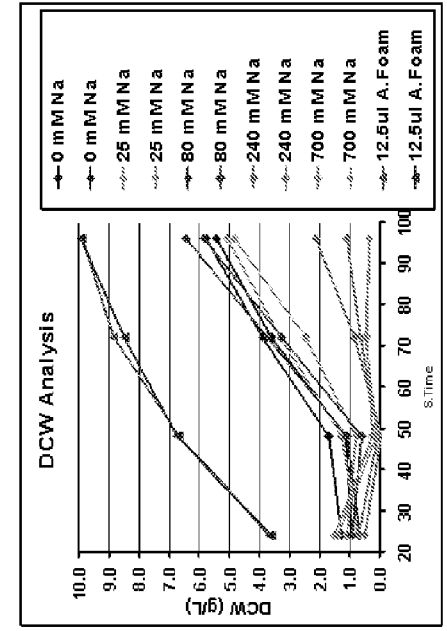
FIG. 7d shows the impact of salt concentration ($Na_2SO_4$) and antifoam on the growth (in dry cell weight (DCW)) of *Prototheca*.
Figure 7A:
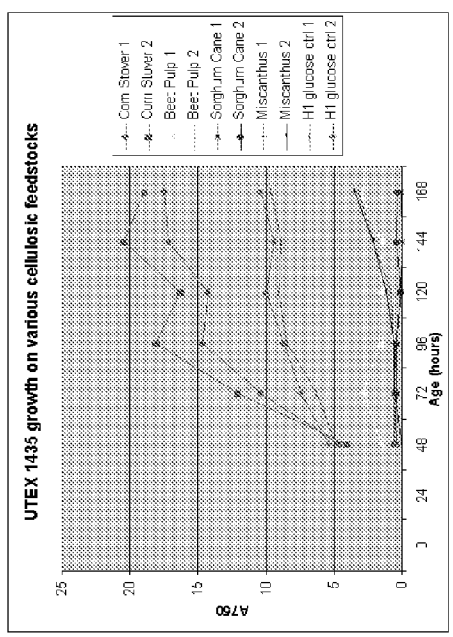
FIG. 7a shows the results of *Prototheca moriformis* grown on cellulosic-derived sugars (corn stover, beet pulp, sorghum cane, *Miscanthus* and glucose control). Growth is expressed in optical density measurements (A750 readings).
Figure 7C:
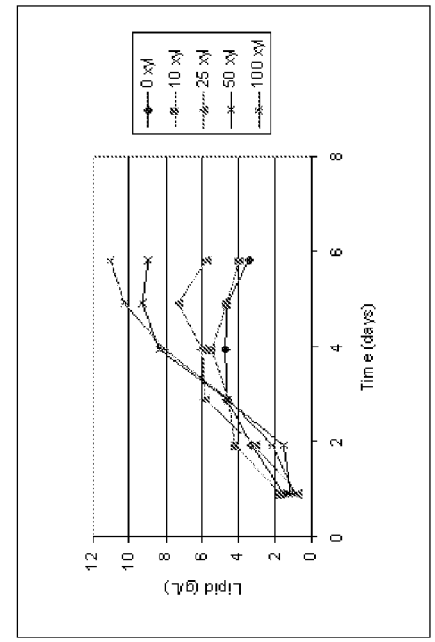
FIG. 7c shows the impact that xylose has on the lipid production in *Prototheca* cultures.

Because the cellulosic feedstocks contain components in addition to glucose, some of these additional components can accumulate to undesirable levels during culture as more cellulosic derived sugars are fed into the culture as the main carbon source (usually, but not limited to, glucose) is consumed. For example, the xylose present in the cellulosic derived sugar feedstock may build up during the high density cultivation of microalgae to levels inhibitory to growth and end product production. To test the effects of xylose build up during *Prototheca* cultivation, cultures were grown with 4% glucose in the media and supplemented with 0, 10 g/L, 25 g/L, 50 g/L and 100 g/L xylose. After 6 days of culture, growth and lipid accumulation were assessed using the methods described above. As seen in FIG. 7c, surprisingly, the highest concentrations of xylose tested were not inhibitory to *Prototheca moriformis*' ability to grow and accumulate lipid, and the culture actually grew better and accumulated more lipids at the highest xylose concentrations. To explore this phenomenon, a similar experiment was carried out with sucrose, a carbon source which wild type *Prototheca moriformis* is unable to metabolize. No positive impact was observed with sucrose, suggesting that the increased growth and lipid accumulation seen with xylose is attributable to a mechanism other than the osmotic stress from high concentrations of unmetabolized components in the media and is xylose-specific.

In addition to non-metabolized sugars, salts may accumulate to inhibitory levels as a result of concentrating lignocellulosic derived sugars. Due to the acid hydrolysis step with $H_2SO_4$ during the typical preparation of cellulosic materials followed by neutralization of the acid with NaOH, $Na_2SO_4$ is formed during the generation of lignocellulosic sugars. To assess the impact of salt concentration on growth and lipid production, *Prototheca moriformis* cultures were grown at $Na_2SO_4$ concentrations ranging from 0-700 mM in media supplemented with 4% glucose. As shown in FIG. 7d, a significant inhibition of growth was observed, as measured by DCW accumulation, where $Na_2SO_4$ concentrations exceeded 25 mM, specifically at the 80 mM, 240 mM and 700 mM concentrations. In addition, the impact of antifoam P2000 was assessed in the same test. The antifoam compound had a significant, positive impact on biomass productivity. Lipid productivity was also assessed for each condition, and Na2SO4 concentrations above 80 mM, specifically 240 mM and 700 mM, were inhibitory while the addition of antifoam P2000 significantly increased lipid productivity. Thus, in one embodiment, the culturing steps of the methods of the present invention include culturing in media containing an antifoaming agent.

Figure 8:
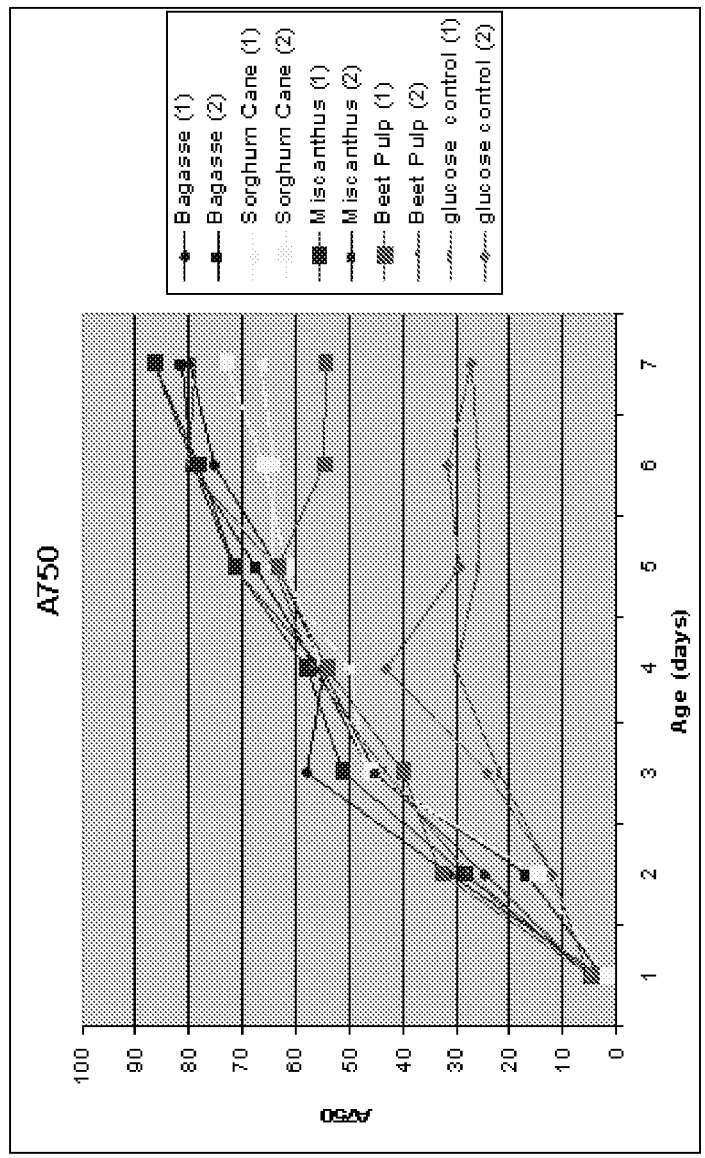
FIG. 8 shows the impact of hydrothermal treatment of various cellulosic materials (sugar cane bagasse, sorghum cane, *Miscanthus* and beet pulp) and the resulting sugar stream on the growth of *Prototheca*.

Based on the results discussed above and summarized in FIG. 7a, inhibitors were likely present in the cellulosic feedstocks exhibiting poor growth. The present invention provides means of removing such compounds by washing the materials with hot water (hydrothermal treatment). FIG. 8 summarizes the growth results, as measured by A750, using sugar derived from cellulosic feedstock with a single hot water wash. The culture conditions were identical to those used in the processes summarized in FIG. 7a. Compared to the results shown in FIG. 7a, after just one hot water wash, *Prototheca moriformis* cultures grew better in all cellulosic feedstocks tested, specifically sugar cane bagasse, sorghum cane, *Miscanthus* and beet pulp, as compared to glucose control. Lipid productivity was also assessed in each of the conditions. Except for the beet pulp condition, which was comparable to the glucose control, cultures grown in sugars derived from cellulosic materials subjected to one hot water wash exhibited better lipid productivity than the glucose control.

One potential impact of hydrothermal treatment (hot water washing) of cellulosic biomass is the removal of furfurals and hydroxymethyl furfurals released by acid explosion of the material. The presence of furfurals and hydroxymethyl furfurals may have contributed to limited growth observed in some of the processes summarized in FIG. 7a. To assess how hydrothermal treatment affected the levels of furfurals (FA) and hydroxymethyl furfurals (HMF), supernatants resulting from one to three washes of cellulosic biomass derived from sugarcane bagasse (B), sorghum cane (S), *Miscanthus* (M) or beet pulp (BP) were assayed for FA and HMF by HPLC. As shown in FIG. 8, FA and HMF levels decrease significantly with each washing step. This result is consistent with the observation that FA and HMF can be inhibitory to microalgal growth (as seen in FIG. 7a) and that hydrothermal treatment removes these compounds and results in improved microalgal growth, even better than the growth in the control glucose conditions (as seen in FIG. 8).

The impact on the lipid profile of *Prototheca moriformis* cultures grown on the various hydrothermally treated lignocellulosic derived sugars was assessed. *Prototheca moriformis* cultures were grown on the following 4×-washed cellulosic feedstocks: *Miscanthus*, sugar cane bagasse and sorghum cane, with glucose levels maintained at 20 g/L through feeding of the cellulosic sugars. At the conclusion of the culturing, microalgae biomass from each condition was analyzed for lipid profile using the methods described in Example 1. The results of the lipid profile analysis (expressed in Area %) are summarized in Table 10 below. Each condition was tested in duplicates, and the results from each of the duplicate test conditions are included. Growth on cellulosic feedstocks resulted in a significant re-distribution in the lipid profile as compared to the glucose control. For example, there was a significant increase in C18:0 Area % in all of the cellulosic feedstock conditions as compared to the glucose control condition.

(DOWEX Marathon MR3) were used (1:2, 1:4 and 1:10). Table 11 summarize results demonstrating the ability of a mixed bed ion exchange (IEX) resin to reduce salts (as measured by conductivity) significantly in a previously concentrated corn stover derived cellulosic sugar stream in diluted feedstocks.

TABLE 10

Lipid profile of *Prototheca moriformis* grown on glucose and cellulosics derived sugars.

|  | glucose 1 (ctrl) | glucose 2 (ctrl) | bagasse 1 | bagasse 2 | sorgh 1 | sorgh 2 | Miscan 1 | Miscan 2 |
|---|---|---|---|---|---|---|---|---|
| C10:0 | n.d. | n.d. | 0.03 | 0.02 | n.d. | n.d. | n.d. | n.d. |
| C12:0 | 0.04 | 0.05 | 0.04 | 0.04 | 0.05 | 0.04 | 0.04 | 0.04 |
| C14:0 | 1.64 | 1.64 | 1.07 | 1.10 | 1.17 | 1.14 | 1.08 | 1.12 |
| C14:1 | 0.03 | 0.04 | 0.04 | 0.04 | 0.06 | 0.06 | 0.03 | 0.03 |
| C15:0 | 0.04 | 0.05 | 0.07 | 0.05 | 0.08 | 0.08 | 0.06 | 0.06 |
| C16:0 | 26.80 | 26.81 | 22.32 | 22.81 | 22.09 | 22.19 | 23.45 | 23.62 |
| C16:1 | 0.75 | 0.82 | 1.68 | 1.70 | 1.92 | 2.12 | 1.38 | 1.23 |
| C17:0 | 0.14 | 0.16 | 0.28 | 0.17 | 0.29 | 0.27 | 0.21 | 0.19 |
| C17:1 | 0.07 | 0.06 | 0.10 | 0.10 | 0.13 | 0.12 | 0.10 | 0.09 |
| C18:0 | 3.56 | 3.64 | 15.88 | 10.40 | 15.30 | 12.37 | 10.15 | 8.69 |
| C18:1 | 54.22 | 54.01 | 49.87 | 53.87 | 49.35 | 50.80 | 54.05 | 55.26 |
| C18:2 | 11.23 | 11.11 | 6.54 | 7.91 | 7.47 | 8.80 | 7.71 | 7.88 |
| C18:3 alpha | 0.84 | 0.85 | 0.39 | 0.56 | 0.47 | 0.53 | 0.56 | 0.60 |
| C20:0 | 0.31 | 0.30 | 0.85 | 0.63 | 0.76 | 0.69 | 0.63 | 0.56 |
| C20:1 | 0.15 | 0.15 | 0.33 | 0.28 | 0.32 | 0.32 | 0.27 | 0.25 |
| C20:3 | 0.06 | 0.06 | 0.13 | 0.12 | 0.14 | 0.12 | 0.11 | 0.11 |
| C24:0 | 0.12 | 0.12 | 0.22 | 0.19 | 0.22 | 0.20 | 0.18 | 0.15 | n.d. denotes none detected

Cellulosic sugar stream was generated from exploded corn stover, saccharified using Accellerase enzyme and concentrated using vacuum evaportation. This sugar stream was tested in *Prototheca moriformis* growth assays at a 4% glucose concentration. The results of the growth assays showed very poor growth and the cellulosic sugar stream was tested for conductivity (salt content). The conductivity was very high, far greater than 700 mM sodium equivalents, a level that was shown to be inhibitory to growth as described above and shown in FIG. 7d. Methods of the invention include methods in which salt is reduced or removed from lignocellulosic derived sugars prior to utilizing these feedstocks in the production of lignocellulosic derived microalgal oil. Surprisingly, however, one cannot use resins to desalt concentrated sugar streams, one must first dilute the concentrated sugar stream. To demonstrate this embodiment of the invention, cellulosic sugars derived from corn stover material were diluted eight-fold prior to removing contaminating salts with the resin. The initial conductivity of the concentrated starting material was 87 mS/cm while that of the eight-fold diluted stream was 10990 µS/cm at a pH of 5.61. Previous studies had indicated that failure to dilute the concentrated sugar stream prior to de-ionization resulted in an inability to remove salts quantitatively as well as a significant loss of glucose from the sugar stream. Three different bed volumes of IEX resin

TABLE 11

Ability of IEX resin to reduce salts.

| Bed volume resin:cellulosics | pH post-deionization | Conductivity post-deionization (µS/cm) | Calculated conductivity post deionization and 8x re-concentration (µS/cm) | Na⁺ equivalents (based on std curve) in mM |
|---|---|---|---|---|
| 1:2 | 3.1 | 74 | 592 | 7.42 |
| 1:4 | 3.1 | 97 | 776 | 9.7 |
| 1:10 | 5.25 | 6320 | 50560 | 634 |

A process employing a 1:4 bed volume:cellulosic feedstock and re-concentration of the material eight-fold would result in a sodium concentration is well within the range for normal biomass and lipid accumulation. Alternatively, deionization or salt removal can be performed prior to saccharification or after saccharification, but before concentration of the sugar stream. If salt removal is performed before the concentration of the sugar stream, a dilution step of the sugar stream before salt removal would likely not be necessary.

This example demonstrates the efficacy of washing of exploded cellulosic material for the use in cellulosic oil production. As described above, concentration of cellulosically derived sugars without the removal of salts (inherent to the production of exploded cellulosic material and subsequent treatment) results in less than optimal fermentations. The materials treated in the process described below were of the appropriate pH for subsequent saccharifaication. In addition, the conductivity of this material was significantly reduced (over 100 fold) from the starting feedstock. Therefore, the subsequent concentrated sugars to be used in fermentations were not inhibitory due to the presence of excessive salts. An additional advantage is seen by the removal of furfurals from the cellulosic material. Any xylose or glucose removed in the hemicellulosic fraction can either be discarded or preferably re-concentrated to be used in fermentations.

Wet, exploded sugar cane bagasse (NREL, Colorado) with an initial starting mass of 65 kg wet weight and conductivity of 15,000 µS/cm, pH 2.4 was brought to 128 kg with deionized water and the pH adjusted to 4.6 with 10 N NaOH, making the resulting conductivity 6,800 µS/cm). The percent solids were assessed by removal of an aliquot of the suspended materials to a tared (weight=t) aluminum pan, recording the wet weight (weight=w) followed by drying for three hours at 110° C. After drying samples were removed to a desiccator and allowed to come to room temperature (25° C.) at which point, they were weighed again (weight=d). Percent solids were calculated as: % solids=[(d-t/w-t)]×100. Conductivities were measured on a Thermo Electron Orion 3 Star Conductivity meter.

The sugar cane bagasse was washed in a semi-continuous fashion by continuously mixing the cellulosic slurry (initial percent solids of 8.2%) at a temperature of 50° C. in a stainless steel reactor (150 L capacity). Cellulosics were discharged from the reactor vessel via a rotary load pump at a flow rate of 1.9-3.8 kg/min to a Sharples Model 660 decanter centrifuge. Liquid permeate was retained batch wise (ca. 35-175 kg aliquots, see Table 12 below) and homogenous aliquots removed for assessment of total sugars (glucose and xylose) and percent solids as described in Table 12. Conductivity and pH of the cellulosic material were controlled via the addition of de-ionized water and 10 N NaOH, respectively. Samples 1-10 in Table 12 represent decanted centrifuge permeate, and as such, solids and sugars present in these fractions are removed from the final, washed cellulosic materials. A mass balance calculation of total solids compared to solids removed minus solids lost plus final solids for saccharification, resulted in a 99% recovery in the above process. FIG. 8 summarizes the furfural and hydroxymethyl furfurals concentration (mg/L) in each of the 11 centrifuge permeates collected and described in Table 12. These data demonstrate a clear removal of furfurals and hydroxymethyl furfurals from the sugar cane bagasse.

In another demonstration of the ability of *Prototheca* to utilize cellulosic-derived feedstock, *Prototheca moriformis* (UTEX 1435) was cultivated in three-liter bioreactors using cellulosic derived sugar as a fixed carbon feedstock. The inoculum was prepared from cryopreserved cells, which were thawed at room temperature and 1 mL of cells were added to 300 mL of inoculum medium based on the basal microalgae medium described in Example 1 with 1 g/L $(NH_4)_2SO_4$, 4 g/L yeast extract and a trace element solution, plus 4% glucose and grown for 1 day at 28° C. with agitation (200 rpm). This culture was used to inoculate a three-liter bioreactor containing 1 L medium plus 0.26 mL of Antifoam 204 (Sigma, USA). The fermentor was controlled at 28° C. and pH was maintained at 6.8 by addition of KOH. Dissolved oxygen was maintained at 30% saturation by cascading agitation and airflow. Cellulosic sugar feedstock from corn stover was fed to the culture to maintain 0-10 g/L glucose. Desalination of cellulosic sugar feedstocks to less than 300 mM salt was essential to assure similar dry cell weight and lipid accumulation performance as compared to purified sugar feedstock controls. Desalination of the cellulosic sugar feedstock was performed using the methods described above. Fermentor samples were removed to monitor fermentation performance. Cell mass accumulation was monitored by optical density and dry cell weight. Glucose, xylose, ammonia, potassium, sodium and furfural concentrations were also determined and monitored throughout the fermentation time course. Lipid concentration was determined by gravimetric methods discussed above.

Example 3

Methods for Transforming *Prototheca*

A. General Method for Biolistic Transformation of *Prototheca*

S550d gold carriers from Seashell Technology were prepared according to the protocol from manufacturer. Linearized plasmid (20 µg) was mixed with 50 µl of binding buffer and 60 µl (30 mg) of S550d gold carriers and incubated in ice

TABLE 12

Mass balance for semi-continuous hydrothermal treatment of sugar cane bagasse.

| Sample | kg (wet) | kg (dry) | pH | Conductivity µS/cm | total xylose removed (g) | total glucose removed (g) |
|---|---|---|---|---|---|---|
| 1 (initial material) | 128 | 10.50 | 4.60 | 6,880 | 0 | 0 |
| 2 | 81.8 | 2.03 | | 3,280 | 1030.68 | 286.3 |
| 3 | 76.5 | 0.49 | | 2,500 | 298.35 | 76.50 |
| 4 | 106 | 0.41 | | | 254.40 | 63.60 |
| 5 | 173.9 | 0.30 | 3.74 | 1,260 | 226.07 | 69.56 |
| 6 | 101.8 | 0.08 | 4.40 | 791 | 71.26 | 20.36 |
| 7 | 110.6 | 0.04 | 4.86 | 327 | 44.24 | 0 |
| 8 | 77.2 | 0 | | | 0 | 0 |
| 9 | 108.6 | 0.02 | 4.7 | 221 | 0 | 0 |
| 10 | 101.5 | 0 | | | 0 | 0 |
| 11 | 34.8 | 0 | 4.7 | 146 | 0 | 0 |
| Solids removed (samples 1-10) | | 3.37 | | | | |
| lost in process | | | | | | |
| Total xylose removed | | | | | 1925.00 | |
| Total glucose removed | | | | | | 516.32 |
| Final solids for saccharification | | 7.03 | | | | | for 1 min. Precipitation buffer (100 µl) was added, and the mixture was incubated in ice for another 1 min. After vortexing, DNA-coated particles were pelleted by spinning at 10,000 rpm in an Eppendorf 5415C microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane.

*Prototheca* strains were grown in proteose medium (2 g/L yeast extract, 2.94 mM NaNO3, 0.17 mM CaCl2.2H2O, 0.3 mM MgSO4.7H2O, 0.4 mM K2HPO4, 1.28 mM KH2PO4, 0.43 mM NaCl) on a gyratory shaker until it reaches a cell density of $2 \times 10^6$ cells/ml. The cells were harvested, washed once with sterile distilled water, and resuspended in 50 µl of medium. $1 \times 10^7$ cells were spread in the center third of a non-selective proteose media plate. The cells were bombarded with the PDS-1000/He Biolistic Particle Delivery system (Bio-Rad). Rupture disks (1100 and 1350 psi) were used, and the plates are placed 9 and 12 cm below the screen/macrocarrier assembly. The cells were allowed to recover at 25° C. for 12-24 h. Upon recovery, the cells were scraped from the plates with a rubber spatula, mixed with 100 µl of medium and spread on plates containing the appropriate antibiotic selection. After 7-10 days of incubation at 25° C., colonies representing transformed cells were visible on the plates from 1100 and 1350 psi rupture discs and from 9 and 12 cm distances. Colonies were picked and spotted on selective agar plates for a second round of selection.

B. Transformation of *Prototheca* with G418 Resistance Gene *Prototheca moriformis* and other *Prototheca* strains sensitive to G418 can be transformed using the methods described below. G418 is an aminoglycoside antibiotic that inhibits the function of 80S ribosomes and thereby inhibits protein synthesis. The corresponding resistance gene functions through phosphorylation, resulting in inactivation of G418. *Prototheca* strains UTEX 1435, UTEX 1439 and UTEX 1437 were selected for transformation. All three *Prototheca* strains were genotyped using the methods described above. All three *Prototheca* strains had identical 23s rRNA genomic sequences (SEQ ID NO:15).

All transformation cassettes were cloned as EcoRI-SacI fragments into pUC19. Standard molecular biology techniques were used in the construction of all vectors according to Sambrook and Russell, 2001. The *C. reinhardtii* beta-tubulin promoter/5'UTR was obtained from plasmid pHyg3 (Berthold et al., (2002) Protist: 153(4), pp 401-412) by PCR as an EcoRI-AscI fragment. The *Chlorella vulgaris* nitrate reductase 3'UTR was obtained from genomic DNA isolated from UTEX strain 1803 via PCR using the following primer pairs:

Forward:
(SEQ ID NO: 35)
5' TGACCTAGGTGATTAATTAACTCGAGGCAGCAGCAGCTCGGA

TAGTATCG 3'

Reverse:
(SEQ ID NO: 36)
5' CTACGAGCTCAAGCTTTCCATTTGTGTTC CCATCCACTAC

TTCC 3'

The *Chlorella sorokiniana* glutamate dehydrogenase promoter/UTR was obtained via PCR of genomic DNA isolated from UTEX strain 1230 via PCR using the following primer pairs:

Forward:
(SEQ ID NO: 37)
5' GATCAGAATTCCGCCTGCAACGCAAGG GCAGC 3'

Reverse:
(SEQ ID NO: 38)
5' GCATACTAGTGGCGGGACGGAGAGA GGGCG 3'

Codon optimization was based on the codons in Table 1 for *Prototheca moriformis*. The sequence of the non-codon optimized neomycin phosphotransferase (nptII) cassette was synthesized as an AscI-XhoI fragment and was based on upon the sequence of Genbank Accession No. YP_788126. The codon optimized nptII cassette was also based on this Genbank Accession number.

The three *Prototheca* strains were transformed using biolistic methods described above. Briefly, the *Prototheca* strains were grown heterophically in liquid medium containing 2% glucose until they reached the desired cell density ($1 \times 10^7$ cells/mL to $5 \times 10^7$ cells/mL). The cells were harvested, washed once with sterile distilled water and resuspended at $1 \times 10^8$ cells/mL. 0.5 mL of cells were then spread out on a non-selective solid media plate and allowed to dry in a sterile hood. The cells were bombarded with the PDS-1000/He Biolistic Particle Delivery System (BioRad). The cells were allowed to recover at 25° C. for 24 hours. Upon recovery, the cells were removed by washing plates with 1 mL of sterile media and transferring to fresh plates containing 100 µg/mL G418. Cells were allowed to dry in a sterile hood and colonies were allowed to form on the plate at room temperature for up to three weeks. Colonies of UTEX 1435, UTEX 1439 and UTEX 1437 were picked and spotted on selective agar plates for a second round of selection.

Figure 4:
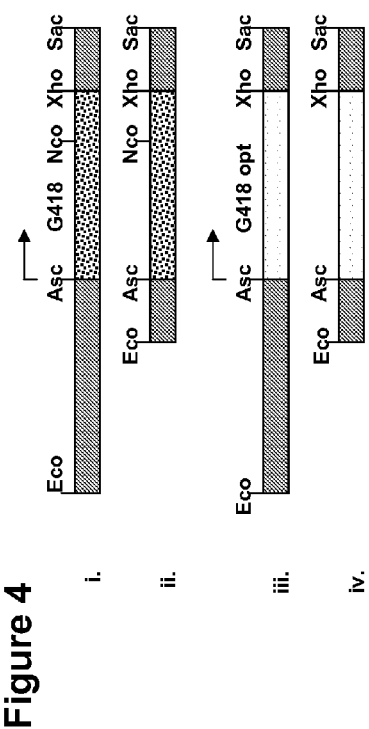
FIG. 4 shows maps of the cassettes used in *Prototheca* transformations, as described in Example 3.
Figure 5:
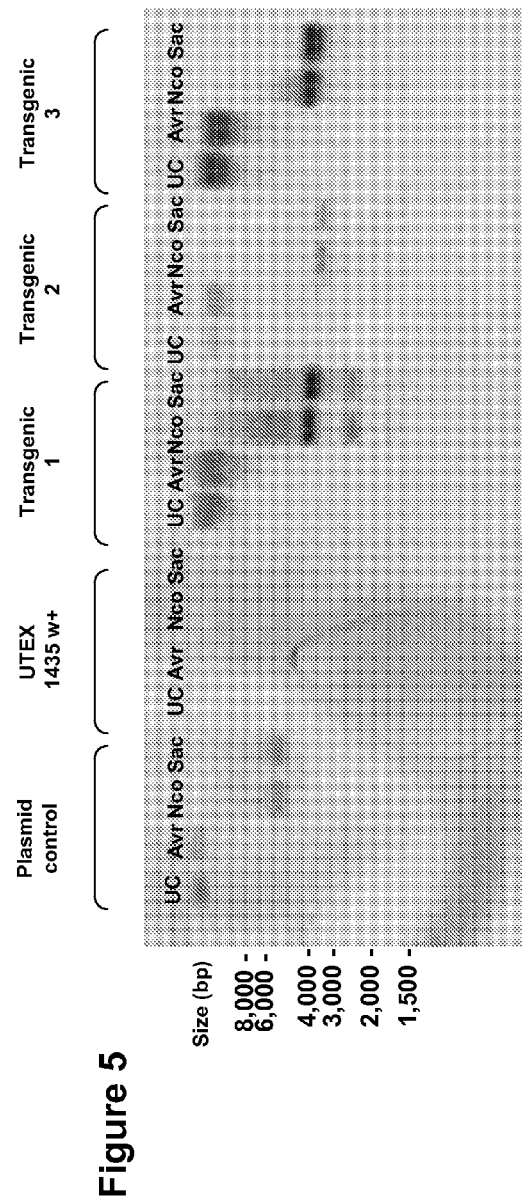
FIG. 5 shows the results of Southern blot analysis on three transformants of UTEX strain 1435, as described in Example 3.

A subset of colonies that survived a second round of selection described above, were cultured in small volume and genomic DNA and RNA were extracted using standard molecular biology methods. Southern blots were done on genomic DNA extracted from untransformed (WT), the transformants and plasmid DNA. DNA from each sample was run on 0.8% agarose gels after the following treatments: undigested (U), digested with AvrII (A), digested with NcoI (N), digested with SacI (S). DNA from these gels was blotted on Nylon+ membranes (Amersham). These membranes were probed with a fragment corresponding to the entire coding region of the nptII gene (NeoR probe). FIG. 4 shows maps of the cassettes used in the transformations. FIG. 5 shows the results of Southern blot analysis on three transformants (all generated in UTEX strain 1435) (1, 2, and 3) transformed with either the beta-tubulin::neo::nit (SEQ ID NO: 39) (transformants 1 and 2) or glutamate dehydrogenase:neo:nit (SEQ ID NO: 40) (transformant 3). The glutamate dehydrogenase: neo:nit transforming plasmid was run as a control and cut with both NcoI and SacI. AvrII does not cut in this plasmid. Genomic DNA isolated from untransformed UTEX strain 1435 shows no hybridization to the NeoR probe.

Additional transformants containing the codon-optimized glutamate dehydrogenase:neo:nit (SEQ ID NO: 41) and codon-optimized β-tubulin::neo::nit (SEQ ID NO:42) constructs were picked and analyzed by Southern blot analysis. As expected, only digests with SacI show linearization of the transforming DNA. These transformation events are consistent with integration events that occur in the form of oligomers of the transforming plasmid. Only upon digestion with restriction enzymes that cut within the transforming plasmid DNA do these molecules collapse down the size of the transforming plasmid.

Southern blot analysis was also performed on transformants generated upon transformation of *Protheca* strains UTEX 1437 and UTEX 1439 with the glutamate dehydrogenase::neo::nit cassette. The blot was probed with the NeoR probe probe and the results are similar to the UTEX 1435 transformants. The results are indicative of integration events characterized by oligomerization and integration of the transforming plasmid. This type of integration event is known to occur quite commonly in *Dictyostelium discoideum* (see, for example, Kuspa, A. and Loomis, W. (1992) PNAS, 89:8803-8807 and Morio et al., (1995) *J. Plant Res.* 108:111-114).

To further confirm expression of the transforming plasmid, Northern blot analysis and RT-PCR analysis were performed on selected transformants. RNA extraction was performed using Trizol Reagent according to manufacturer's instructions. Northern blot analysis were run according to methods published in Sambrook and Russel, 2001. Total RNA (15 µg) isolated from five UTEX 1435 transformants and untransformed UTEX 1435 (control lanes) was separated on 1% agarose-formaldehyde gel and blotted on nylon membrane. The blot was hybridized to the neo-non-optimized probe specific for transgene sequences in transformants 1 and 3. The two other transformants RNAs express the codon-optimized version of the neo-transgene and, as expected, based on the sequence homology between the optimized and non-optimized neo genes, showed significantly lower hybridization signal.

RNA (1 µg) was extracted from untransformed *Prototheca* strain UTEX 1435 and two representative UTEX 1435 transformants and reverse transcribed using an oligio dT primer or a gene specific primer. Subsequently these cDNAs (in duplicate) were subjected to qPCR analysis on ABI Veriti Thermocycler using SYBR-Green qPCR chemistry using the following primers (nptII):

```
Forward:
                                      (SEQ ID NO: 43)
5' GCCGCGACTGGCTGCTGCTGG 3'

Reverse:
                                      (SEQ ID NO: 44)
5' AGGTCCTCGCCGTCGGGCATG 3'
```

Possible genomic DNA contamination was ruled out by a no reverse transcriptase negative control sample. The results indicated that the NeoR genes used to transform these strains is actively transcribed in the transformants.

C. Transformation of *Prototheca* with Secreted Heterologous Sucrose Invertase

All of the following experiments were performed using liquid medium/agar plates based on the basal medium described in Ueno et al., (2002) *J Bioscience and Bioengineering* 94(2):160-65, with the addition of trace minerals described in U.S. Pat. No. 5,900,370, and 1×DAS Vitamin Cocktail (1000× solution): tricine: 9 g, thiamine HCL: 0.67 g, biotin: 0.01 g, cyannocobalamin (vitamin B12): 0.008 g, calcium pantothenate: 0.02 g and p-aminobenzoic acid: 0.04 g).

Figure 6:
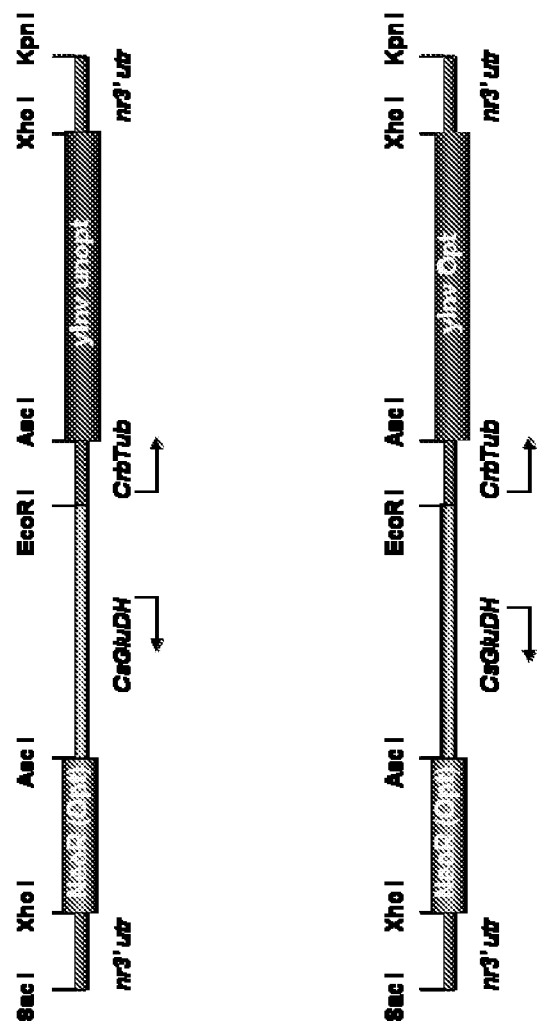
FIG. 6 shows a schematic of the codon optimized and non-codon optimized suc2 (yeast sucrose invertase (yInv)) transgene construct. The relevant restriction cloning sites are indicated and arrows indicate the direction of transcription.

Two plasmid constructs were assembled using standard recombinant DNA techniques. The yeast sucrose invertase genes (one codon optimized and one non-codon optimized), suc2, were under the control of the *Chlorella reinhardtii* beta-tubulin promoter/5'UTR and had the *Chlorella vulgaris* nitrate reductase 3'UTR. The sequences (including the 5'UTR and 3'UTR sequences) for the non-codon optimized (Crβ-tub::NCO-suc2::CvNitRed) construct, SEQ ID NO: 57, and codon optimized (Crβ-tub::CO-suc2::CvNitRed) construct, SEQ ID NO: 58, are listed in the Sequence Listing. Codon optimization was based on Table 1 for *Prototheca* sp. FIG. 6 shows a schematic of the two constructs with the relevant restriction cloning sites and arrows indicating the direction of transcription. Selection was provided by Neo R (codon optimized using Table 1).

Preparation of the DNA/gold microcarrier: DNA/gold microcarriers were prepared immediately before use and stored on ice until applied to macrocarriers. The plasmid DNA (in TE buffer) was added to 50 µl of binding buffer. Saturation of the gold beads was achieved at 15 µg plasmid DNA for 3 mg gold carrier. The binding buffer and DNA were mixed well via vortexing. The DNA and binding buffer should be pre-mix prior to gold addition to ensure uniformed plasmid binding to gold carrier particles. 60 µl of S550d (Seashell Technologies, San Diego, Calif.) gold carrier was added to the DNA/binding buffer mixture. For a gold stock at 50 mg/ml, addition of 60 µl results in an optimal ratio of 15 µg DNA/3 mg gold carrier. The gold carrier/DNA mixture was allowed to incubate on ice for 1 minute and then 100 µl of precipitation buffer was added. The mixture was allowed to incubate again on ice for 1 minute and then briefly vortexed and centrifuged at 10,000 rpm at room temperature for 10 seconds to pellet the gold carrier. The supernatant was carefully removed with a pipette and the pellet was washed with 500 µl of ice cold 100% ethanol. The gold particles were re-pelleted by centrifuging again at 10,000 rpm for 10 seconds. The ethanol was removed and 50 µl of ice cold ethanol was added to the gold mixture. Immediately prior to applying the gold to macrocarriers, the gold/ethanol was resuspended with a brief 1-2 second pulse at level 2 on a MISONIX sonicator using the micro tip. Immediately after resuspension, 10 µl of the dispersed gold particles was transferred to the macrocarrier and allowed to dry in a sterile hood.

The two *Prototheca moriformis* strains (UTEX 1435 and 1441) were grown heterotrophically in liquid medium containing 2% glucose from cryopreserved vials. Each strain was grown to a density of $10^7$ cells/ml. This seed culture was then diluted with fresh media to a density of $10^5$ cells/ml and allowed to grow for 12-15 hours to achieve a final cell density of approximately $10^6$ cells/ml. The microalgae were aliquoted into 50 ml conical tubes and centrifuged for 10 minutes at 3500 rpm. The cells were washed with fresh medium and centrifuged again for 10 minutes at 3500 rpm. The cells were then resuspended at a density of $1.25 \times 10^8$ cells/ml in fresh medium.

In a sterile hood, 0.4 ml of the above-prepared cells were removed and placed directly in the center of an agar plate (without selection agent). The plate was gently swirled with a level circular motion to evenly distribute the cells to a diameter of no more than 3 cm. The cells were allowed to dry onto the plates in the sterile hood for approximately 30-40 minutes and then were bombarded at a rupture disk pressure of 1350 psi and a plate to macrocarrier distance of 6 cm. The plates were then covered and wrapped with parafilm and allowed to incubate under low light for 24 hours.

After the 24 hour recovery, 1 ml of sterile medium (with no glucose) was added to the lawn of cells. The cells were resuspended using a sterile loop, applied in a circular motion to the lawn of cells and the resuspended cells were collected using a sterile pipette. The cells were then plated onto a fresh agar plate with 2% glucose and 100 µg/ml G418. The appearance of colonies occurred 7-12 days after plating. Individual colonies were picked and grown in selective medium with 2% glucose and 100 µg/ml G418. The wildtype (untransformed) and transgenic cells were then analyzed for successful introduction, integration and expression of the transgene.

Genomic DNA from transformed *Prototheca moriformis* UTEX 1435 and 1441 and their wildtype (untransformed) counterparts were isolated using standard methods. Briefly, the cells were centrifuged for 5 minutes at 14,000 rpm in a standard table top Eppendorf centrifuge (model 5418) and flash frozen prior to DNA extraction. Cell pellets were lysed by adding 200 uL of Lysis buffer (100 mM Tris HCl, pH 8.0, 1% Lauryl Sarcosine, 50 mM NaCl, 20 mM EDTA, 0.25 M sucrose, 0.5 mg/ml RNase A) for every 100-200 mg of cells (wet weight) and vortexing for 30-60 seconds. Cetyl trimethyammonium bromide (CTAB) and NaCl were brought to 1% and 1 M, respectively, and cell extracts were incubated at 60-65° C. for 10 minutes. Subsequently, extracts were clarified via centrifugation at 14,000 rpm for 10 minutes and the resulting supernatant was extracted with an equal volume of phenol/chloroform/isoamyl alcohol (25:24:1). Samples were then centrifuged for 5 minutes at 14,000 rpm and the aqueous phase removed. DNA was precipitated with 0.7 volumes of isopropanol. DNA was pelleted via centrifugation at 14,000 rpm for 10 minutes and washed twice with 80% ethanol, and once with ethanol. After drying, DNA was resuspended in 10 mM Tris HCl, pH 8.0 and DNA concentrations were determined by using PicoGreen fluorescence quantification assay (Molecular Probes).

RNA from transformed *Prototheca moriformis* UTEX 1435 and 1441 and their wildtype (untransformed) counterparts were isolated using standard methods. Briefly, the cells were centrifuged for 5 minutes at 14,000 rpm in a standard table top Eppendorf centrifuge (model 5418) and flash frozen before RNA extraction. Cell pellets were lysed by addition of 1 mL of Trizol reagent (Sigma) for every 100 mg of cells (wet weight) and by vortexing for 1-2 minutes. Samples were incubated at room temperature for 5 minutes and subsequently adjusted with 200 uL of chloroform per 1 mL of Trizol reagent. After extensive shaking, cells were incubated at room temperature for 15 minutes and then subjected to centrifugation at 14000 rpm for 15 minutes in a refrigerated table top microcentrifuge. RNA partitioning to the upper aqueous phase was removed and precipitated by addition of isopropanol (500 uL per 1 ml of Trizol reagent). RNA was collected by centrifugation for 10 minutes and the resulting pellet washed twice with 1 mL of 80% ethanol, dried, and resuspended in RNAse free water. RNA concentration was estimated by RiboGreen fluorescence quantification assay (Molecular Probes).

Expression of neomycin phophotransferase gene conferring G418 antibotic resistance and yeast invertase was assayed in non-transformed *Prototheca moriformis* UTEX 1435 and 1441 and transformants T98 (UTEX 1435 transformant) and T97 (UTEX 1441 transformant) using reverse transcription quantitative PCR analysis (RT-qPCR). 20 ng total RNA (isolated as described above) was subjected to one step RT-qPCR analysis using iScript SYBR Green RT-PCR kit (BioRad Laboratories) and primer pairs targeting the neomycin resistance gene (forward primer 5' CCGCCGTGCTG-GACGTGGTG 3' and reverse primer 5' GGTG-GCGGGGTCCAGGGTGT 3'; SEQ ID NOs: 65 and 66, respectively) and suc2 invertase transcripts (forward primer 5' CGGCCGGCGGCTCCTTCAAC 3' and reverse primer 5' GGCGCTCCCGTAGGTCGGGT 3'; SEQ ID NO: 67 and 68, respectively). Endogenous beta-tubulin transcripts served as an internal positive control for PCR amplification and as a normalization reference to estimate relative transcript levels.

Both codon optimized and non-codon optimized constructs were transformed into UTEX 1435 and 1441 *Prototheca moriformis* cells as described above. Initially, transformants were obtained with both constructs and the presence of the transgene was verified by Southern blot analysis followed by RTPCR to confirm the presence of the DNA and mRNA from the transgene. For the Southern blot analysis, genomic DNA isolated as described above was electrophoresed on 0.7% agarose gels in 1×TAE buffer. Gels were processed as described in Sambrook et al. (Molecular Cloning; A Laboratory Manual, $2^{nd}$ Edition. Cold Spring Harbor Laboratory Press, 1989). Probes were prepared by random priming and hybridizations carried out as described in Sambrook et al. Transformants from both the codon optimized and the non-codon optimized constructs showed the presence of the invertase cassette, while the non-transformed control was negative. Invertase mRNA was also detected in transformants with both the codon optimized and non-codon optimized constructs.

To confirm that the transformants were expressing an active invertase protein, the transformants were plated on sucrose plates. The transformants containing the non-codon optimized cassette failed to grow on the sucrose containing plates, indicating that, while the gene and the mRNA encoding the SUC2 protein were present, the protein was either (1) not being translated, or (2) being translated, but not accumulating to levels sufficient to allow for growth on sucrose as the sole carbon source. The transformants with the codon optimized cassette grew on the sucrose containing plates. To assess the levels of invertase being expressed by these transformants, two clones (T98 and T97) were subjected to an invertase assay of whole cells scraped from solid medium and direct sampling and quantitation of sugars in the culture supernatants after 48 hours of growth in liquid medium containing 2% sucrose as the sole carbon source.

For the invertase assay, the cells (T98 and T97) were grown on plates containing 2% sucrose, scraped off and assayed for invertase activity. 10 µl of the scraped cells was mixed with 40 µl of 50 mM NaOAc pH 5.1. 12.5 µl of 0.5M sucrose was added to the cell mixture and incubated at 37° C. for 10-30 minutes. To stop the reaction, 75 µl of 0.2M $K_2HPO_4$ was added. To assay for glucose liberated, 500 µl of reconstituted reagent (glucose oxidase/peroxidase+o-Dianisidine) from Sigma (GAGO-20 assay kit) was added to each tube and incubated at 37° C. for 30 minutes. A glucose standard curve was also created at this time (range: 25 µg to 0.3 µg glucose). After incubation, 500 µl of 6N HCl was added to stop the reaction and to develop the color. The samples were read at 540 nm. The amount of glucose liberated was calculated from the glucose standard curve using the formula y=mx+c, where y is the 540 nm reading, and x is µg of glucose. Weight of glucose was converted to moles of glucose, and given the equimolar relationship between moles of sucrose hydrolyzed to moles of glucose generated, the data was expressed as nmoles of sucrose hydrolyzed per unit time. The assay showed that both T98 and T97 clones were able to hydrolyze sucrose, indicating that a functional sucrose invertase was being produced and secreted by the cells.

For the sugar analysis on liquid culture media after 48 hours of algal growth, T97 and T98 cells were grown in 2% sucrose containing medium for 48 hours and the culture media were processed for sugar analysis. Culture broths from each transformant (and negative non-transformed cell control) were centrifuged at 14,000 rpm for 5 minutes. The resulting supernatant was removed and subjected to HPLC/ELSD (evaporative light scattering detection). The amount of sugar in each sample was determined using external standards and liner regression analysis. The sucrose levels in the culture media of the transformants were very low (less than 1.2 g/L, and in most cases 0 g/L). In the negative controls, the sucrose levels remained high, at approximately 19 g/L after 48 hours of growth.

These results were consistant with the invertase activity results, and taken together, indicated that the codon optimized transformants, T97 and T98, secreted an active sucrose invertase that allowed the microalgae to utilize sucrose as the sole carbon source in contrast to (1) the non-codon optimized transformants and (2) the non-transformed wildtype microalgae, both of which could not utilize sucrose as the sole carbon source in the culture medium.

*Prototheca moriformis* strains, T98 and T97, expressing a functional, secreted sucrose invertase (SUC2) transgene were assayed for growth and lipid production using sucrose as the sole carbon source.

Wild type (untransformed), T98 and T97 strains were grown in growth media (as described above) containing either 4% glucose or 4% sucrose as the sole carbon source under heterotrophic conditions for approximately 6 days. Growth, as determined by A750 optical density readings were taken of all four samples every 24 hours and the dry cell weight of the cultures and lipid profiles were determined after the 6 days of growth. The optical density readings of the transgenic strains grown in both the glucose and sucrose conditions were comparable to the wildtype strains grown in the glucose conditions. These results indicate that the transgenic strains were able to grow on either glucose or sucrose as the sole carbon source at a rate equal to wildtype strains in glucose conditions. The non-transformed, wildtype strains did not grow in the sucrose-only condition.

The biomass for the wildtype strain grown on glucose and T98 strain grown on sucrose was analyzed for lipid profile. Lipid samples were prepared from dried biomass (lyophilized) using an Acid Hydrolysis System (Ankom Technology, NY) according to manufacturer's instructions. Lipid profile determinations were carried as described in Example 4. The lipid profile for the non-transformed *Prototheca moriformis* UTEX 1435 strain, grown on glucose as the sole carbon source and two colonal T98 strains (UTEX 1435 transformed with a sucrose invertase transgene), grown on sucrose as the sole carbon source, are disclosed in Table 13 (wildtype UTEX 1435 and T98 clone 8 and clone 11 below. C:19:0 lipid was used as an internal calibration control.

TABLE 13

Lipid profile of wildtype UTEX 1435 and UTEX 1435 clones with suc2 transgene.

| Name | wildtype (Area % - ISTD) | T98 clone 11 (Area % - ISTD) | T98 clone 8 (Area % - ISTD) |
|---|---|---|---|
| C 12:0 | 0.05 | 0.05 | 0.05 |
| C 14:0 | 1.66 | 1.51 | 1.48 |
| C 14:1 | 0.04 | nd | nd |
| C 15:0 | 0.05 | 0.05 | 0.04 |
| C 16:0 | 27.27 | 26.39 | 26.50 |
| C 16:1 | 0.86 | 0.80 | 0.84 |
| C 17:0 | 0.15 | 0.18 | 0.14 |
| C 17:1 | 0.05 | 0.07 | 0.05 |
| C 18:0 | 3.35 | 4.37 | 4.50 |
| C 18:1 | 53.05 | 54.48 | 54.50 |
| C 18:2 | 11.79 | 10.33 | 10.24 |
| C 19:0 (ISTD) | — | — | — |
| C 18:3 alpha | 0.90 | 0.84 | 0.81 |
| C 20:0 | 0.32 | 0.40 | 0.38 |
| C 20:1 | 0.10 | 0.13 | 0.12 |
| C 20:1 | 0.04 | 0.05 | 0.04 |
| C 22:0 | 0.12 | 0.16 | 0.12 |
| C 20:3 | 0.07 | 0.08 | 0.07 |
| C 24:0 | 0.12 | 0.11 | 0.10 | nd—denotes none detected

Oil extracted from wildtype *Prototheca moriformis* UTEX 1435 (via solvent extraction or using an expeller press (see methods in Example 44 above) was analyzed for carotenoids, chlorophyll, tocopherols, other sterols and tocotrienols. The results are summarized below in Table 14.

TABLE 14

Carotenoid, chlorophyll, tocopherol/sterols and tocotrienol analysis in oil extracted from *Prototheca moriformis* (UTEX 1435).

| | Pressed oil (mcg/ml) | Solvent extracted oil (mcg/ml) |
|---|---|---|
| cis-Lutein | 0.041 | 0.042 |
| trans-Lutein | 0.140 | 0.112 |
| trans-Zeaxanthin | 0.045 | 0.039 |
| cis-Zeaxanthin | 0.007 | 0.013 |
| t-alpha-Crytoxanthin | 0.007 | 0.010 |
| t-beta-Crytoxanthin | 0.009 | 0.010 |
| t-alpha-Carotene | 0.003 | 0.001 |
| c-alpha-Carotene | none detected | none detected |
| t-beta-Carotene | 0.010 | 0.009 |
| 9-cis-beta-Carotene | 0.004 | 0.002 |
| Lycopene | none detected | none detected |
| Total Carotenoids | 0.267 | 0.238 |
| Chlorophyll | <0.01 mg/kg | <0.01 mg/kg |
| Tocopherols and Sterols | | |
| gamma Tocopherol | 0.49 | 0.49 |
| Campesterol | 6.09 | 6.05 |
| Stigmasterol | 47.6 | 47.8 |
| Beta-sitosterol | 11.6 | 11.5 |
| Other sterols | 445 | 446 |
| Tocotrienols | | |
| alpha Tocotrienol | 0.26 | 0.26 |
| beta Tocotrienol | <0.01 | <0.01 |
| gamma Tocotrienol | 0.10 | 0.10 |
| detal Tocotrienol | <0.01 | <0.01 |
| Total Tocotrienols | 0.36 | 0.36 |

The ability of using sucrose as the sole carbon source as the selection factor for clones containing the suc2 transgene construct instead of G418 (or another antibiotic) was assessed using the positive suc2 gene transformants. A subset of the positive transformants was grown on plates containing sucrose as the sole carbon source and without antibiotic selection for 24 doublings. The clones were then challenged with plates containing glucose as the sole carbon source and G418. There was a subset of clones that did not grow on the glucose+G418 condition, indicating a loss of expression of the transgene. An additional experiment was performed using a plate containing sucrose as the sole carbon source and no G418 and streaking out a suc2 transgene expressing clone on one half of the plate and wild-type *Prototheca moriformis* on the other half of the plate. Growth was seen with both the wild-type and transgene-containing *Prototheca moriformis* cells. Wild-type *Prototheca moriformis* has not demonstrated the ability to grow on sucrose, therefore, this result shows that unlike antibiotic resistance, the use of sucrose/invertase selection is not cell-autonomous. It is very likely that the transformants were secreting enough sucrose invertase into the plate/media to support wildtype growth as the sucrose was hydrolyzed into fructose and glucose.

Example 4

Recombinant *Prototheca* with Exogenous TE Gene

Figure 9:
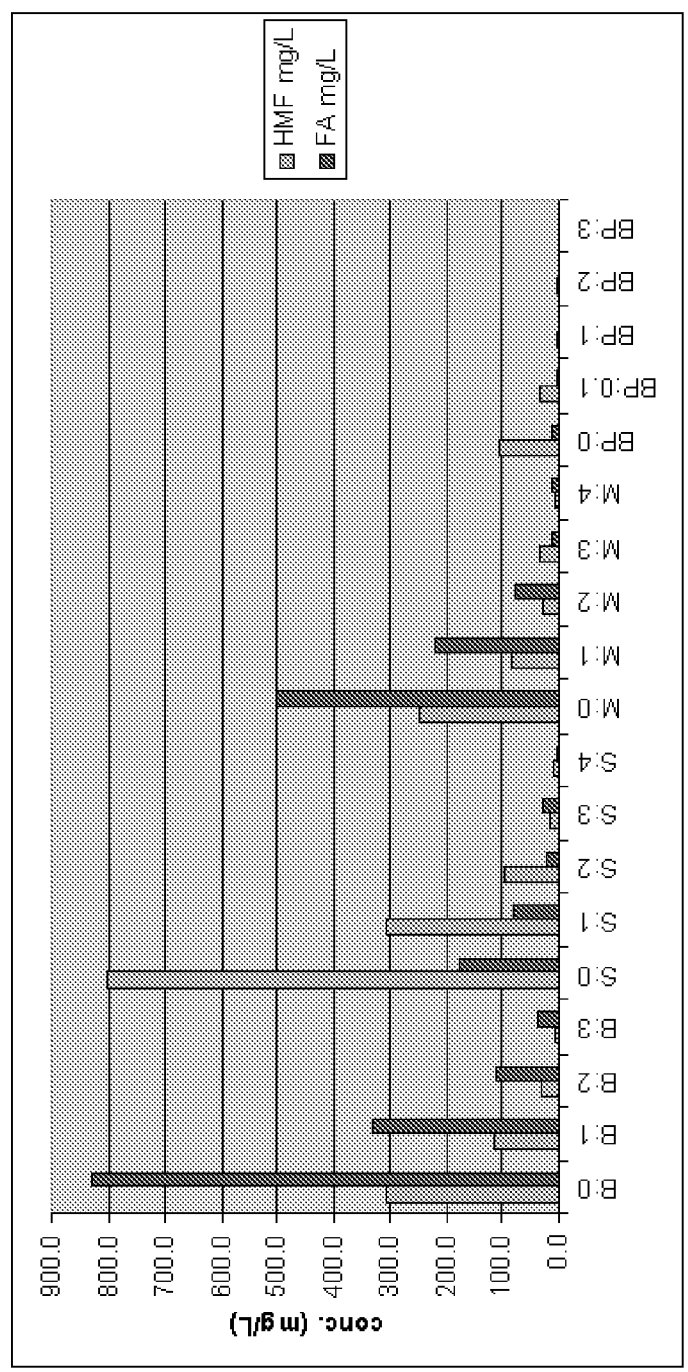
FIG. 9 shows decreasing levels of hydroxymethyl furfurals (HMF) and furfurals in cellulosic biomass (sugar cane bagasse, sorghum cane, *Miscanthus* and beet pulp) after repeated cycles of hydrothermal treatment.

As described above, *Prototheca* strains can be transformed with exogenous genes. *Prototheca moriformis* (UTEX 1435)

was transformed, using methods described above, with either *Umbellularia californica* C12 thioesterase gene or *Cinnamomum camphora* C14 thiotesterase gene (both codon optimized according to Table 1). Each of the transformation constructs contained a *Chlorella sorokiniana* glutamate dehydrogenase promoter/5'UTR region (SEQ ID NO: 69) to drive expression of the thioesterase transgene. The thioesterase transgenes coding regions of *Umbellularia californica* C12 thioesterase (SEQ ID NO: 70) or *Cinnamomum camphora* C14 thioesterase (SEQ ID NO: 71), each with the native putative plastid targeting sequence Immediately following the thioesterase coding sequence is the coding sequence for a c-terminal 3×-FLAG tag (SEQ ID NO: 72), followed by the *Chlorella vulgaris* nitrate reductase 3'UTR (SEQ ID NO: 73). A diagram of the thioesterase constructs that were used in the *Prototheca moriformis* transformations is shown in FIG. 9.

Preparation of the DNA, gold microcarrier and *Prototheca moriformis* (UTEX 1435) cells were performed using the methods described above in Example 3. The microalgae were bombarded using the gold microcarrier—DNA mixture and plated on selection plates containing 2% glucose and 100 µg/ml G418. The colonies were allowed to develop for 7 to 12 days and colonies were picked from each transformation plate and screened for DNA construct incorporation using Southern blots assays and expression of the thioesterase constructs were screened using RT-PCR.

Positive clones were picked from both the C12 and C14 thioesterase transformation plates and screened for construct incorporation using Southern blot assays. Southern blot assays were carried out using standard methods (and described above in Example 3) using an optimized c probes, based on the sequence in SEQ ID NO: 70 and SEQ ID NO: 71. Transforming plasmid DNA was run as a positive control. Out of the clones that were positive for construct incorporation, a subset was selected for reverse transcription quantitative PCR (RT-qPCR) analysis for C12 thioesterase and C14 thioesterase expression.

RNA isolation was performed using methods described in Example 3 above and RT-qPCR of the positive clones were performed using 20 ng of total RNA from each clone using the below-described primer pair and iScript SYBR Green RT-PCR kit (Bio-Rad Laboratories) according to manufacturer's protocol. Wildtype (non-transformed) *Prototheca moriformis* total RNA was included as a negative control. mRNA expression was expressed as relative fold expression (RFE) as compared to negative control. The primers that were used in the C12 thioesterase transformation RT-qPCR screening were:

*U. californica* C12 thioesterase PCR primers:

```
Forward:
                                    (SEQ ID NO: 74)
5' CTGGGCGACGGCTTCGGCAC 3'

Reverse:
                                    (SEQ ID NO: 75)
5' AAGTCGCGGCGCATGCCGTT 3'
```

The primers that were used in the C14 thioesterase transformation RT-qPCR screening were:

*Cinnamomum camphora* C14 thioesterase PCR primers:

```
Forward:
                                    (SEQ ID NO: 76)
5' TACCCCGCCTGGGGCGACAC 3'

Reverse:
                                    (SEQ ID NO: 77)
5' CTTGCTCAGGCGGCGGGTGC 3'
```

RT-qPCR results for C12 thioesterase expression in the positive clones showed an increased RFE of about 40 fold to over 2000 fold increased expression as compared to negative control. Similar results were seen with C14 thioesterase expression in the positive clones with an increase RFE of about 60-fold to over 1200 fold increased expression as compared to negative control.

A subset of the positive clones from each transformation (as screened by Southern blotting and RT-qPCR assays) were selected and grown under nitrogen-replete conditions and analyzed for total lipid production and profile. Lipid samples were prepared from dried biomass from each clone. 20-40 mg of dried biomass from each transgenic clone was resuspended in 2 mL of 3% $H_2SO_4$ in MeOH, and 200 ul of toluene containing an appropriate amount of a suitable internal standard (C19:0) was added. The mixture was sonicated briefly to disperse the biomass, then heated at 65-70° C. for two hours. 2 mL of heptane was added to extract the fatty acid methyl esters, followed by addition of 2 mL of 6% $K_2CO_3$ (aq) to neutralize the acid. The mixture was agitated vigorously, and a portion of the upper layer was transferred to a vial containing $Na_2SO_4$ (anhydrous) for gas chromatography analysis using standard FAME GC/FID (fatty acid methyl ester gas chromatography flame ionization detection) methods. Lipid profile (expressed as Area %) of the positive clones as compared to wildtype negative control are summarized in Tables 15 and 16 below. As shown in Table 15, the fold increase of C12 production in the C12 transformants ranged from about a 5-fold increase (clone C12-5) to over 11-fold increase (clone C12-1). Fold increase of C14 production in the C14 transformants ranged from about a 1.5 fold increase to about a 2.5 fold increase.

TABLE 15

Summary of total lipid profile of the *Prototheca moriformis* C12 thioesterase transformants.

|       | Wildtype | C12-1 | C12-2 | C12-3 | C12-4 | C12-5 | C12-6 | C12-7 | C12-8 |
|-------|----------|-------|-------|-------|-------|-------|-------|-------|-------|
| C6:0  | 0.03     | nd    | nd    | nd    | nd    | nd    | nd    | nd    | nd    |
| C8:0  | 0.11     | 0.09  | nd    | 0.11  | nd    | nd    | nd    | nd    | nd    |
| C10:0 | nd       | nd    | nd    | 0.01  | 0.01  | nd    | 0.01  | 0.01  | nd    |
| C12:0 | 0.09     | 1.04  | 0.27  | 0.72  | 0.71  | 0.50  | 0.67  | 0.61  | 0.92  |
| C14:0 | 2.77     | 2.68  | 2.84  | 2.68  | 2.65  | 2.79  | 2.73  | 2.56  | 2.69  |
| C14:1 | 0.01     | nd    | nd    | 0.02  | nd    | nd    | nd    | 0.01  | nd    |
| C15:0 | 0.30     | 0.09  | 0.10  | 0.54  | 0.19  | 0.09  | 0.13  | 0.97  | 0.09  |
| C15:1 | 0.05     | nd    | nd    | 0.02  | nd    | nd    | nd    | nd    | nd    |
| C16:0 | 24.13    | 23.12 | 24.06 | 22.91 | 22.85 | 23.61 | 23.14 | 21.90 | 23.18 |
| C16:1 | 0.57     | 0.62  | 0.10  | 0.52  | 0.69  | 0.63  | 0.69  | 0.49  | 0.63  |
| C17:0 | 0.47     | 0.24  | 0.27  | 1.02  | 0.36  | 0.17  | 0.26  | 2.21  | 0.19  |
| C17:1 | 0.08     | nd    | 0.09  | 0.27  | 0.10  | 0.05  | 0.09  | 0.80  | 0.05  |

TABLE 15-continued

Summary of total lipid profile of the *Prototheca moriformis* C12 thioesterase transformants.

| | Wildtype | C12-1 | C12-2 | C12-3 | C12-4 | C12-5 | C12-6 | C12-7 | C12-8 |
|---|---|---|---|---|---|---|---|---|---|
| C18:0 | nd | nd | 2.14 | 1.75 | 2.23 | 2.16 | 2.38 | 1.62 | 2.47 |
| C18:1 | 22.10 | 23.15 | 24.61 | 21.90 | 23.52 | 19.30 | 22.95 | 20.22 | 22.85 |
| C18:1 | nd | 0.33 | 0.24 | nd | nd | 0.09 | 0.09 | nd | 0.11 |
| C18:2 | 37.16 | 34.71 | 35.29 | 35.44 | 35.24 | 36.29 | 35.54 | 36.01 | 35.31 |
| C18:3 alpha | 11.68 | 11.29 | 9.26 | 11.62 | 10.76 | 13.61 | 10.64 | 11.97 | 10.81 |
| C20:0 | 0.15 | 0.16 | 0.19 | 0.16 | 0.16 | 0.14 | 0.18 | 0.14 | 0.18 |
| C20:1 | 0.22 | 0.17 | 0.19 | 0.20 | 0.21 | 0.19 | 0.21 | 0.20 | 0.21 |
| C20:2 | 0.05 | nd | 0.04 | 0.05 | 0.05 | 0.05 | 0.04 | 0.05 | 0.04 |
| C22:0 | nd | nd | nd | 0.01 | nd | nd | nd | 0.02 | nd |
| C22:1 | nd | nd | nd | nd | nd | 0.01 | nd | 0.01 | nd |
| C20:3 | 0.05 | nd | 0.07 | 0.06 | 0.06 | 0.10 | 0.07 | 0.05 | 0.06 |
| C20:4 | nd | nd | nd | nd | nd | 0.02 | nd | nd | nd |
| C24:0 | nd | nd | 0.24 | 0.01 | 0.20 | 0.19 | 0.19 | 0.14 | 0.20 |

TABLE 16

Summary of total lipid profile of the *Prototheca moriformis* C14 thioesterase transformants.

| | Wildtype | C14-1 | C14-2 | C14-3 | C14-4 | C14-5 | C14-6 | C14-7 |
|---|---|---|---|---|---|---|---|---|
| C6:0 | 0.03 | nd | nd | nd | nd | nd | nd | nd |
| C8:0 | 0.11 | nd | nd | nd | nd | nd | nd | nd |
| C10:0 | nd | 0.01 | nd | 0.01 | nd | 0.01 | nd | nd |
| C12:0 | 0.09 | 0.20 | 0.16 | 0.25 | 0.21 | 0.19 | 0.40 | 0.17 |
| C14:0 | 2.77 | 4.31 | 4.76 | 4.94 | 4.66 | 4.30 | 6.75 | 4.02 |
| C14:1 | 0.01 | nd | 0.01 | nd | nd | 0.01 | nd | nd |
| C15:0 | 0.30 | 0.43 | 0.45 | 0.12 | 0.09 | 0.67 | 0.10 | 0.33 |
| C15:1 | 0.05 | nd | nd | nd | nd | nd | nd | nd |
| C16:0 | 24.13 | 22.85 | 23.20 | 23.83 | 23.84 | 23.48 | 24.04 | 23.34 |
| C16:1 | 0.57 | 0.65 | 0.61 | 0.60 | 0.60 | 0.47 | 0.56 | 0.67 |
| C17:0 | 0.47 | 0.77 | 0.76 | 0.21 | 0.19 | 1.11 | 0.18 | 0.54 |
| C17:1 | 0.08 | 0.23 | 0.15 | 0.06 | 0.05 | 0.24 | 0.05 | 0.12 |
| C18:0 | nd | 1.96 | 1.46 | 2.48 | 2.34 | 1.84 | 2.50 | 2.06 |
| C18:1 | 22.10 | 22.25 | 19.92 | 22.36 | 20.57 | 19.50 | 20.63 | 22.03 |
| C18:1 | nd | nd | nd | nd | nd | nd | 0.10 | nd |
| C18:2 | 37.16 | 34.97 | 36.11 | 34.35 | 35.70 | 35.49 | 34.03 | 35.60 |
| C18:3 alpha | 11.68 | 10.71 | 12.00 | 10.15 | 11.03 | 12.08 | 9.98 | 10.47 |
| C20:0 | 0.15 | 0.16 | 0.19 | 0.17 | 0.17 | 0.14 | 0.18 | 0.16 |
| C20:1 | 0.22 | 0.20 | 0.12 | .019 | 0.19 | 0.19 | 0.17 | 0.20 |
| C20:2 | 0.05 | 0.04 | 0.02 | 0.03 | 0.04 | 0.05 | 0.03 | 0.04 |
| C22:0 | nd | nd | nd | nd | 0.02 | 0.01 | nd | nd |
| C22:1 | nd | 0.01 | nd | nd | nd | nd | nd | 0.01 |
| C20:3 | 0.05 | 0.08 | 0.03 | 0.06 | 0.09 | 0.05 | 0.05 | 0.07 |
| C20:4 | nd | 0.01 | nd | nd | nd | nd | 0.02 | nd |
| C24:0 | nd | 0.17 | 0.14 | 0.19 | 0.20 | 0.16 | 0.22 | 0.17 |

The above-described experiments indicate the successful transformation of *Prototheca moriformis* (UTEX 1435) with transgene constructs of two different thioesterases (C12 and C14), which involved not only the successful expression of the transgene, but also the correct targeting of the expressed protein to the plastid and a functional effect (the expected change in lipid profile) as a result of the transformation. The same transformation experiment was performed using an expression construct containing a codon-optimized (according to Table 1) *Cuphea hookeriana* C8-10 thioesterase coding region with the native plastid targeting sequence (SEQ ID NO: 78) yielded no change in lipid profile. While the introduction of the *Cuphea hookeriana* C8-10 transgene into *Prototheca moriformis* (UTEX 1435) was successful and confirmed by Southern blot analysis, no change in C8 or C10 fatty acid production was detected in the transformants compared to the wildtype strain.

Example 5

Generation of *Prototheca moriformis* Strain with Exogenous Plant TE with Algal Plastid Targeting Sequence In order to investigate whether the use of algal chloroplast/plastid targeting sequences would improve medium chain (C8-C14) thioesterase expression and subsequent medium chain lipid production in *Prototheca moriformis* (UTEX 1435), several putative algal plastid targeting sequences were cloned from *Chlorella protothecoides* and *Prototheca moriformis*. Thioesterase constructs based on *Cuphea hookeriana* C8-10 thioesterase, *Umbellularia californica* C12 thioesterase, and *Cinnamomum camphora* C14 thioesterase were made using made with a *Chlorella sorokiniana* glutamate dehydrogenase promoter/5'UTR and a *Chlorella vulgaris* nitrate reductase 3'UTR. The thioesterase coding sequences were modified by removing the native plastid targeting sequences and replacing them with plastid targeting sequences from the *Chlorella protothecoides* and the *Prototheca moriformis* genomes. The thioesterase expression constructs and their corresponding sequence identification numbers are listed below. Each transformation plasmid also contained a Neo resistance construct that was identical to the ones described in Example 3 above. Additionally, another algal-derived promoter, the *Chlamydomonas reinhardtii* β-tubulin promoter, was also tested in conjunction with the thioesterase constructs. "Native" plastid targeting sequence refers to the higher plant thioesterase plastid targeting sequence. A summary of the constructs used in these experiments is provided below:

| Construct Name | Promoter/ 5'UTR | Plastid targeting seq | Gene | 3'UTR | SEQ ID NO. |
|---|---|---|---|---|---|
| Construct 1 | *C. sorokiniana* glutamate dehydrogenase | *C. protothecoides* stearoyl ACP desaturase | *Cuphea hookeriana* C8-10 TE | *C. vulgaris* nitrate reductase | SEQ ID NO: 79 |
| Construct 2 | *C. sorokiniana* glutamate dehydrogenase | *P. moriformis* delta 12 fatty acid desaturase | *Cuphea hookeriana* C8-10 TE | *C. vulgaris* nitrate reductase | SEQ ID NO: 80 |
| Construct 3 | *C. sorokiniana* glutamate dehydrogenase | *P. moriformis* isopentenyl diphosphate synthase | *Cuphea hookeriana* C8-10 TE | *C. vulgaris* nitrate reductase | SEQ ID NO: 81 |
| Construct 4 | *C. sorokiniana* glutamate dehydrogenase | *P. moriformis* isopentenyl diphosphate synthase | *Umbellularia californica* C12 TE | *C. vulgaris* nitrate reductase | SEQ ID NO: 82 |
| Construct 5 | *C. sorokiniana* glutamate dehydrogenase | *P. moriformis* stearoyl ACP desaturase | *Umbellularia californica* C12 TE | *C. vulgaris* nitrate reductase | SEQ ID NO: 83 |
| Construct 6 | *C. sorokiniana* glutamate dehydrogenase | *C. protothecoides* stearoyl ACP desaturase | *Umbellularia californica* C12 TE | *C. vulgaris* nitrate reductase | SEQ ID NO: 84 |
| Construct 7 | *C. sorokiniana* glutamate dehydrogenase | *P. moriformis* delta 12 fatty acid desaturase | *Umbellularia californica* C12 TE | *C. vulgaris* nitrate reductase | SEQ ID NO: 85 |
| Construct 8 | *C. sorokiniana* glutamate dehydrogenase | *C. protothecoides* stearoyl ACP desaturase | *Cinnamomum camphora* C14 TE | *C. vulgaris* nitrate reductase | SEQ ID NO: 86 |
| Construct 9 | *Chlamydomonas reinhardtii* β-tubulin | Native | *Cuphea hookeriana* C8-10 TE | *C. vulgaris* nitrate reductase | SEQ ID NO: 113 |
| Construct 10 | *Chlamydomonas reinhardtii* β-tubulin | *P. moriformis* isopentenyl diphosphate synthase | *Cuphea hookeriana* C8-10 TE | *C. vulgaris* nitrate reductase | SEQ ID NO: 114 |
| Construct 11 | *Chlamydomonas reinhardtii* β-tubulin | *P. moriformis* delta 12 fatty acid desaturase | *Cuphea hookeriana* C8-10 TE | *C. vulgaris* nitrate reductase | SEQ ID NO: 115 |
| Construct 12 | *Chlamydomonas reinhardtii* β-tubulin | *C. protothecoides* stearoyl ACP desaturase | *Cuphea hookeriana* C8-10 TE | *C. vulgaris* nitrate reductase | SEQ ID NO: 116 |
| Construct 13 | *Chlamydomonas reinhardtii* β-tubulin | *P. moriformis* stearoyl ACP desaturase | *Cuphea hookeriana* C8-10 TE | *C. vulgaris* nitrate reductase | SEQ ID NO: 117 |
| Construct 14 | *Chlamydomonas reinhardtii* β-tubulin | Native | *Umbellularia californica* C12 TE | *C. vulgaris* nitrate reductase | SEQ ID NO: 118 |
| Construct 15 | *Chlamydomonas reinhardtii* β-tubulin | *P. moriformis* isopentenyl diphosphate | *Umbellularia californica* C12 TE | *C. vulgaris* nitrate reductase | SEQ ID NO: 119 |
| Construct 16 | *Chlamydomonas reinhardtii* β-tubulin | *P. moriformis* delta 12 fatty acid desaturase | *Umbellularia californica* C12 TE | *C. vulgaris* nitrate reductase | SEQ ID NO: 120 |
| Construct 17 | *Chlamydomonas reinhardtii* β-tubulin | *C. protothecoides* stearoyl ACP desaturase | *Umbellularia californica* C12 TE | *C. vulgaris* nitrate reductase | SEQ ID NO: 121 |
| Construct 18 | *Chlamydomonas reinhardtii* β-tubulin | *P. moriformis* stearoyl ACP desaturase | *Umbellularia californica* C12 TE | *C. vulgaris* nitrate reductase | SEQ ID NO: 122 |
| Construct 19 | *Chlamydomonas reinhardtii* β-tubulin | Native | *Cinnamomum camphora* C14 TE | *C. vulgaris* nitrate reductase | SEQ ID NO: 123 |
| Construct 20 | *Chlamydomonas reinhardtii* β-tubulin | *P. moriformis* isopentenyl diphosphate synthase | *Cinnamomum camphora* C14 TE | *C. vulgaris* nitrate reductase | SEQ ID NO: 124 |
| Construct 21 | *Chlamydomonas reinhardtii* β-tubulin | *P. moriformis* delta 12 fatty acid desaturase | *Cinnamomum camphora* C14 TE | *C. vulgaris* nitrate reductase | SEQ ID NO: |

| Construct Name | Promoter/ 5'UTR | Plastid targeting seq | Gene | 3'UTR | SEQ ID NO. |
|---|---|---|---|---|---|
| Construct 22 | Chlamydomonas reinhardtii β-tubulin | C. protothecoides stearoyl ACP desaturase | Cinnamomum camphora C14 TE | C. vulgaris nitrate reductase | SEQ ID NO: 87 |
| Construct 23 | Chlamydomonas reinhardtii β-tubulin | P. moriformis stearoyl ACP desaturase | Cinnamomum camphora C14 TE | C. vulgaris nitrate reductase | SEQ ID NO: 88 |

Each construct was transformed into *Prototheca moriformis* (UTEX 1435) and selection was performed using G418 using the methods described in Example 4 above. Several positive clones from each transformation were picked and screened for the presence thioesterase transgene using Southern blotting analysis. Expression of the thioesterase transgene was confirmed using RT-PCR. A subset of the positive clones (as confirmed by Southern blotting analysis and RT-PCR) from each transformation was selected and grown for lipid profile analysis. Lipid samples were prepared from dried biomass samples of each clone and lipid profile analysis was performed using acid hydrolysis methods described in Example 4. Changes in area percent of the fatty acid corresponding to the thioesterase transgene were compared to wildtype levels, and clones transformed with a thioesterase with the native plastid targeting sequence.

As mentioned in Example 4, the clones transformed with *Cuphea hookeriana* C8-10 thioesterase constructs with the native plastid targeting sequence had the same level of C8 and C10 fatty acids as wildtype. The clones transformed with *Cuphea hookeriana* C8-10 thioesterase constructs (Constructs 1-3) with algal plastid targeting sequences had over a 10-fold increase in C10 fatty acids for Construct 3 and over 40-fold increase in C10 fatty acids for Constructs 1 and 2 (as compared to wildtype). The clones transformed with *Umbellularia californica* C12 thioesterase constructs with the native plastid targeting sequence had a modest 6-8 fold increase in C12 fatty acid levels as compared to wildtype. The clones transformed with the *Umbellularia californica* C12 thioesterase constructs with the algal plasid targeting constructs (Constructs 4-7) had over an 80-fold increase in C12 fatty acid level for Construct 4, about an 20-fold increase in C12 fatty acid level for Construct 6, about a 10-fold increase in C12 fatty acid level for Construct 7 and about a 3-fold increase in C12 fatty acid level for Construct 5 (all compared to wildtype). The clones transformed with *Cinnamomum camphora* C14 thioesterase with either the native plastid targeting sequence or the construct 8 (with the *Chlorella protothecoides* stearoyl ACP desaturase plastid targeting sequence) had about a 2-3 fold increase in C14 fatty acid levels as compared to wildtype. In general clones transformed with an algal plastid targeting sequence thioesterase constructs had a higher fold increase in the corresponding chain-length fatty acid levels than when using the native higher plant targeting sequence.

A. *Clamydomonas reinhartii* β-Tubulin Promoter

Additional heterologous thioesterase expression constructs were prepared using the *Chlamydomonas reinhardtii* β-tubulin promoter instead of the *C. sorokinana* glutamate dehydrogenase promoter. The construct elements and sequence of the expression constructs are listed above. Each construct was transformed into *Prototheca moriformis* UTEX 1435 host cells using the methods described above. Lipid profiles were generated from a subset of positive clones for each construct in order to assess the success and productivity of each construct. The lipid profiles compare the fatty acid levels (expressed in area %) to wildtype host cells. The "Mean" column represents the numerical average of the subset of positive clones. The "Sample" column represents the best positive clone that was screened (best being defined as the sample that produced the greatest change in area % of the corresponding chain-length fatty acid production). The "low-high" column represents the lowest area % and the highest area % of the fatty acid from the clones that were screened. The lipid profiles results of Constructs 9-23 are summarized below.

Construct 9. *Cuphea hookeriana* C8-10 TE

| Fatty Acid | wildtype | Mean | Sample | low/high |
|---|---|---|---|---|
| C 8:0 | 0 | 0.05 | 0.30 | 0-0.29 |
| C 10:0 | 0.01 | 0.63 | 2.19 | 0-2.19 |
| C 12:0 | 0.03 | 0.06 | 0.10 | 0-0.10 |
| C 14:0 | 1.40 | 1.50 | 1.41 | 1.36-3.59 |
| C 16:0 | 24.01 | 24.96 | 24.20 | |
| C 16:1 | 0.67 | 0.80 | 0.85 | |
| C 17:0 | 0 | 0.16 | 0.16 | |
| C 17:1 | 0 | 0.91 | 0 | |
| C 18:0 | 4.15 | 17.52 | 3.19 | |
| C 18:1 | 55.83 | 44.81 | 57.54 | |
| C 18:2 | 10.14 | 7.58 | 8.83 | |
| C 18:3α | 0.93 | 0.68 | 0.76 | |
| C 20:0 | 0.33 | 0.21 | 0.29 | |
| C 24:0 | 0 | 0.05 | 0.11 | |

Construct 10. *Cuphea hookeriana* C8-10 TE

| Fatty Acid | wildtype | Mean | Sample | low/high |
|---|---|---|---|---|
| C 8:0 | 0 | 0.01 | 0.02 | 0-0.03 |
| C 10:0 | 0 | 0.16 | 0.35 | 0-0.35 |
| C 12:0 | 0.04 | 0.05 | 0.07 | 0-0.07 |
| C 14:0 | 1.13 | 1.62 | 1.81 | 0-0.05 |
| C 14:1 | 0 | 0.04 | 0.04 | |
| C 15:0 | 0.06 | 0.05 | 0.05 | |
| C 16:0 | 19.94 | 26.42 | 28.08 | |
| C 16:1 | 0.84 | 0.96 | 0.96 | |
| C 17:0 | 0.19 | 0.14 | 0.13 | |
| C 17:1 | 0.10 | 0.06 | 0.05 | |
| C 18:0 | 2.68 | 3.62 | 3.43 | |
| C 18:1 | 63.96 | 54.90 | 53.91 | |
| C 18:2 | 9.62 | 9.83 | 9.11 | |
| C18:3 γ | 0 | 0.01 | 0 | |
| C 18:3α | 0.63 | 0.79 | 0.73 | |
| C 20:0 | 0.26 | 0.35 | 0.33 | |
| C 20:1 | 0.06 | 0.08 | 0.09 | |
| C 20:1 | 0.08 | 0.06 | 0.07 | |
| C 22:0 | 0 | 0.08 | 0.09 | |
| C 24:0 | 0.13 | 0.13 | 0.11 | |

| Construct 11. *Cuphea hookeriana* C8-10 TE | | | | |
|---|---|---|---|---|
| Fatty Acid | wildtype | Mean | Sample | low/high |
| C 8:0 | 0 | 0.82 | 1.57 | 0-1.87 |
| C 10:0 | 0 | 3.86 | 6.76 | 0-6.76 |
| C 12:0 | 0.04 | 0.13 | 0.20 | 0.03-0.20 |
| C 14:0 | 1.13 | 1.80 | 1.98 | 1.64-2.05 |
| C 14:1 | 0 | 0.04 | 0.04 | |
| C 15:0 | 0.06 | 0.06 | 0.06 | |
| C 16:0 | 19.94 | 25.60 | 25.44 | |
| C 16:1 | 0.84 | 1.01 | 1.02 | |
| C 17:0 | 0.19 | 0.13 | 0.11 | |
| C 17:1 | 0.10 | 0.06 | 0.05 | |
| C 18:0 | 2.68 | 2.98 | 2.38 | |
| C 18:1 | 63.96 | 51.59 | 48.85 | |
| C 18:2 | 9.62 | 9.85 | 9.62 | |
| C18:3 γ | 0 | 0.01 | 0 | |
| C 18:3α | 0.63 | 0.91 | 0.92 | |
| C 20:0 | 0.26 | 0.29 | 0.26 | |
| C 20:1 | 0.06 | 0.06 | 0 | |
| C 20:1 | 0.08 | 0.06 | 0.03 | |
| C 22:0 | 0 | 0.08 | 0.08 | |
| C 24:0 | 0.13 | 0.06 | 0 | |

| Construct 12. *Cuphea hookeriana* C8-10 TE | | | | |
|---|---|---|---|---|
| Fatty Acid | wildtype | Mean | Sample | low/high |
| C 8:0 | 0 | 0.31 | 0.85 | 0-0.85 |
| C 10:0 | 0 | 2.16 | 4.35 | 0.20-4.35 |
| C 12:0 | 0.04 | 0.10 | 0.15 | 0-0.18 |
| C 14:0 | 1.13 | 1.96 | 1.82 | 1.66-2.97 |
| C 14:1 | 0 | 0.03 | 0.04 | |
| C 15:0 | 0.06 | 0.07 | 0.07 | |
| C 16:0 | 19.94 | 26.08 | 25.00 | |
| C 16:1 | 0.84 | 1.04 | 0.88 | |
| C 17:0 | 0.19 | 0.16 | 0.16 | |
| C 17:1 | 0.10 | 0.05 | 0.07 | |
| C 18:0 | 2.68 | 3.02 | 3.19 | |
| C 18:1 | 63.96 | 51.08 | 52.15 | |
| C 18:2 | 9.62 | 11.44 | 9.47 | |
| C18:3 γ | 0 | 0.01 | 0 | |
| C 18:3α | 0.63 | 0.98 | 0.90 | |
| C 20:0 | 0.26 | 0.30 | 0.28 | |
| C 20:1 | 0.06 | 0.06 | 0.05 | |
| C 20:1 | 0.08 | 0.04 | 0 | |
| C 22:0 | 0 | 0.07 | 0 | |
| C 24:0 | 0.13 | 0.05 | 0 | |

| Construct 14. *Umbellularia californica* C12 TE | | | | |
|---|---|---|---|---|
| Fatty Acid | wildtype | Mean | Sample | low/high |
| C 10:0 | 0.01 | 0.02 | 0.03 | 0.02-0.03 |
| C 12:0 | 0.03 | 2.62 | 3.91 | 0.04-3.91 |
| C 14:0 | 1.40 | 1.99 | 2.11 | 1.83-2.19 |
| C 16:0 | 24.01 | 27.64 | 27.01 | |
| C 16:1 | 0.67 | 0.92 | 0.92 | |
| C 18:0 | 4.15 | 2.99 | 2.87 | |
| C 18:1 | 55.83 | 53.22 | 52.89 | |
| C 18:2 | 10.14 | 8.68 | 8.41 | |
| C 18:3α | 0.93 | 0.78 | 0.74 | |
| C 20:0 | 0.33 | 0.29 | 0.27 | |

| Construct 15. *Umbellularia californica* C12 TE | | | | |
|---|---|---|---|---|
| Fatty Acid | wildtype | Mean | Sample | low/high |
| C 10:0 | 0 | 0.05 | 0.08 | 0-0.08 |
| C 12:0 | 0.04 | 8.12 | 12.80 | 4.35-12.80 |

-continued

| Construct 15. *Umbellularia californica* C12 TE | | | | |
|---|---|---|---|---|
| Fatty Acid | wildtype | Mean | Sample | low/high |
| C 13:0 | 0 | 0.02 | 0.03 | 0-0.03 |
| C 14:0 | 1.13 | 2.67 | 3.02 | 2.18-3.37 |
| C 14:1 | 0 | 0.04 | 0.03 | 0.03-0.10 |
| C 15:0 | 0.06 | 0.07 | 0.06 | |
| C 16:0 | 19.94 | 25.26 | 23.15 | |
| C 16:1 | 0.84 | 0.99 | 0.86 | |
| C 17:0 | 0.19 | 0.14 | 0.14 | |
| C 17:1 | 0.10 | 0.05 | 0.05 | |
| C 18:0 | 2.68 | 2.59 | 2.84 | |
| C 18:1 | 63.96 | 46.91 | 44.93 | |
| C 18:2 | 9.62 | 10.59 | 10.01 | |
| C 18:3α | 0.63 | 0.92 | 0.83 | |
| C 20:0 | 0.26 | 0.27 | 0.24 | |
| C 20:1 | 0.06 | 0.06 | 0.06 | |
| C 20:1 | 0.08 | 0.05 | 0.04 | |
| C 22:0 | 0 | 0.07 | 0.09 | |
| C 24:0 | 0.13 | 0.13 | 0.12 | |

| Construct 16. *Umbellularia californica* C12 TE | | | | |
|---|---|---|---|---|
| Fatty Acid | wildtype | Mean | Sample | low/high |
| C 10:0 | 0 | 0.03 | 0.04 | 0.02-0.04 |
| C 12:0 | 0.04 | 2.43 | 5.32 | 0.98-5.32 |
| C 13:0 | 0 | 0.01 | 0.02 | 0-0.02 |
| C 14:0 | 1.13 | 1.77 | 1.93 | 1.62-1.93 |
| C 14:1 | 0 | 0.03 | 0.02 | 0.02-0.04 |
| C 15:0 | 0.06 | 0.06 | 0.05 | |
| C 16:0 | 19.94 | 24.89 | 22.29 | |
| C 16:1 | 0.84 | 0.91 | 0.82 | |
| C 17:0 | 0.19 | 0.16 | 0.15 | |
| C 17:1 | 0.10 | 0.06 | 0.06 | |
| C 18:0 | 2.68 | 3.81 | 3.67 | |
| C 18:1 | 63.96 | 53.19 | 52.82 | |
| C 18:2 | 9.62 | 10.38 | 10.57 | |
| C 18:3α | 0.63 | 0.80 | 0.77 | |
| C 20:0 | 0.26 | 0.35 | 0.32 | |
| C 20:1 | 0.06 | 0.06 | 0.07 | |
| C 20:1 | 0.08 | 0.07 | 0.08 | |
| C 22:0 | 0 | 0.08 | 0.07 | |
| C 24:0 | 0.13 | 0.15 | 0.14 | |

| Construct 17. *Umbellularia californica* C12 TE | | | | |
|---|---|---|---|---|
| Fatty Acid | wildtype | Mean | Sample | low/high |
| C 10:0 | 0 | 0.04 | 0.07 | 0.03-0.08 |
| C 12:0 | 0.04 | 7.02 | 14.11 | 4.32-14.11 |
| C 13:0 | 0 | 0.03 | 0.04 | 0.01-0.04 |
| C 14:0 | 1.13 | 2.25 | 3.01 | 1.95-3.01 |
| C 14:1 | 0 | 0.03 | 0.03 | 0.02-0.03 |
| C 15:0 | 0.06 | 0.06 | 0.06 | |
| C 16:0 | 19.94 | 23.20 | 21.46 | |
| C 16:1 | 0.84 | 0.82 | 0.77 | |
| C 17:0 | 0.19 | 0.15 | 0.14 | |
| C 17:1 | 0.10 | 0.06 | 0.06 | |
| C 18:0 | 2.68 | 3.47 | 2.93 | |
| C 18:1 | 63.96 | 50.30 | 45.17 | |
| C 18:2 | 9.62 | 10.33 | 9.98 | |
| C18:3 γ | 0 | 0.01 | 0 | |
| C 18:3α | 0.63 | 0.84 | 0.86 | |
| C 20:0 | 0.26 | 0.32 | 0.27 | |
| C 20:1 | 0.06 | 0.07 | 0.06 | |
| C 20:1 | 0.08 | 0.06 | 0.06 | |
| C 22:0 | 0 | 0.08 | 0.09 | |
| C 24:0 | 0.13 | 0.14 | 0.13 | |

Construct 18. *Umbellularia californica* C12 TE

| Fatty Acid | wildtype | Mean | Sample | low/high |
|---|---|---|---|---|
| C 10:0 | 0 | 0.03 | 0.05 | 0.01-0.05 |
| C 12:0 | 0.04 | 5.06 | 7.77 | 0.37-7.77 |
| C 13:0 | 0 | 0.02 | 0 | 0-0.03 |
| C 14:0 | 1.13 | 2.11 | 2.39 | 1.82-2.39 |
| C 14:1 | 0 | 0.03 | 0.03 | 0.02-0.05 |
| C 15:0 | 0.06 | 0.06 | 0.06 | |
| C 16:0 | 19.94 | 24.60 | 23.95 | |
| C 16:1 | 0.84 | 0.86 | 0.83 | |
| C 17:0 | 0.19 | 0.15 | 0.14 | |
| C 17:1 | 0.10 | 0.06 | 0.05 | |
| C 18:0 | 2.68 | 3.31 | 2.96 | |
| C 18:1 | 63.96 | 51.26 | 49.70 | |
| C 18:2 | 9.62 | 10.18 | 10.02 | |
| C18:3 γ | 0 | 0.01 | 0.02 | |
| C 18:3α | 0.63 | 0.86 | 0.86 | |
| C 20:0 | 0.26 | 0.32 | 0.29 | |
| C 20:1 | 0.06 | 0.05 | 0.05 | |
| C 20:1 | 0.08 | 0.07 | 0.04 | |
| C 22:0 | 0 | 0.08 | 0.08 | |
| C 24:0 | 0.13 | 0.13 | 0.13 | |

Construct 19. *Cinnamomum camphora* C14 TE

| Fatty Acid | wildtype | Mean | Sample | low/high |
|---|---|---|---|---|
| C 10:0 | 0.02 | 0.01 | 0.01 | 0.01-0.02 |
| C 12:0 | 0.05 | 0.27 | 0.40 | 0.08-0.41 |
| C 14:0 | 1.52 | 4.47 | 5.81 | 2.10-5.81 |
| C 16:0 | 25.16 | 28.14 | 28.55 | |
| C 16:1 | 0.72 | 0.84 | 0.82 | |
| C 18:0 | 3.70 | 3.17 | 2.87 | |
| C 18:1 | 54.28 | 51.89 | 51.01 | |
| C 18:2 | 12.24 | 9.36 | 8.62 | |
| C 18:3α | 0.87 | 0.74 | 0.75 | |
| C 20:0 | 0.33 | 0.33 | 0.31 | |

Construct 20. *Cinnamomum camphora* C14 TE

| Fatty Acid | wildtype | Mean | Sample | low/high |
|---|---|---|---|---|
| C 10:0 | 0.01 | 0.01 | 0.02 | 0.01-0.02 |
| C 12:0 | 0.03 | 0.39 | 0.65 | 0.08-0.65 |
| C 13:0 | 0 | 0.01 | 0.01 | 0.01-0.02 |
| C 14:0 | 1.40 | 5.61 | 8.4 | 2.1-8.4 |
| C 14:1 | 0 | 0.03 | 0.03 | 0.02-0.03 |
| C 15:0 | 0 | 0.06 | 0.07 | |
| C 16:0 | 24.01 | 25.93 | 25.57 | |
| C 16:1 | 0.67 | 0.75 | 0.71 | |
| C 17:0 | 0 | 0.13 | 0.12 | |
| C 17:1 | 0 | 0.05 | 0.05 | |
| C 18:0 | 4.15 | 3.30 | 3.23 | |
| C 18:1 | 55.83 | 51.00 | 48.48 | |
| C 18:2 | 10.14 | 10.38 | 10.35 | |
| C 18:3α | 0.93 | 0.91 | 0.88 | |
| C 20:0 | 0.33 | 0.35 | 0.32 | |
| C 20:1 | 0 | 0.08 | 0.08 | |
| C 20:1 | 0 | 0.07 | 0.07 | |
| C 22:0 | 0 | 0.08 | 0.08 | |
| C 24:0 | 0 | 0.14 | 0.13 | |

Construct 21. *Cinnamomum camphora* C14 TE

| Fatty Acid | wildtype | Mean | Sample | low/high |
|---|---|---|---|---|
| C 10:0 | 0.01 | 0.01 | 0.01 | 0-0.01 |
| C 12:0 | 0.03 | 0.10 | 0.27 | 0.04-0.27 |
| C 14:0 | 1.40 | 2.28 | 4.40 | 1.47-4.40 |
| C 16:0 | 24.01 | 26.10 | 26.38 | |
| C 16:1 | 0.67 | 0.79 | 0.73 | |
| C 17:0 | 0 | 0.15 | 0.16 | |
| C 17:1 | 0 | 0.06 | 0.06 | |
| C 18:0 | 4.15 | 3.59 | 3.51 | |
| C 18:1 | 55.83 | 53.53 | 50.86 | |
| C 18:2 | 10.14 | 10.83 | 11.11 | |
| C 18:3α | 0.93 | 0.97 | 0.87 | |
| C 20:0 | 0.33 | 0.36 | 0.37 | |
| C 20:1 | 0 | 0.09 | 0.08 | |
| C 20:1 | 0 | 0.07 | 0.07 | |
| C 22:0 | 0 | 0.09 | 0.09 | |

Construct 22. *Cinnamomum camphora* C14 TE

| Fatty Acid | wildtype | Mean | Sample | low/high |
|---|---|---|---|---|
| C 10:0 | 0.01 | 0.02 | 0.02 | 0.02-0.02 |
| C 12:0 | 0.03 | 1.22 | 1.83 | 0.59-1.83 |
| C 13:0 | 0 | 0.02 | 0.03 | 0.01-0.03 |
| C 14:0 | 1.40 | 12.77 | 17.33 | 7.97-17.33 |
| C 14:1 | 0 | 0.02 | 0.02 | 0.02-0.04 |
| C 15:0 | 0 | 0.07 | 0.08 | |
| C 16:0 | 24.01 | 24.79 | 24.22 | |
| C 16:1 | 0.67 | 0.64 | 0.58 | |
| C 17:0 | 0 | 0.11 | 0.10 | |
| C 17:1 | 0 | 0.04 | 0.04 | |
| C 18:0 | 4.15 | 2.85 | 2.75 | |
| C 18:1 | 55.83 | 45.16 | 41.23 | |
| C 18:2 | 10.14 | 9.96 | 9.65 | |
| C 18:3α | 0.93 | 0.91 | 0.85 | |
| C 20:0 | 0.33 | 0.30 | 0.30 | |
| C 20:1 | 0 | 0.07 | 0.06 | |
| C 20:1 | 0 | 0.06 | 0.05 | |
| C 22:0 | 0 | 0.08 | 0.08 | |

Construct 23. *Cinnamomum camphora* C14 TE

| Fatty Acid | wildtype | Mean | Sample | low/high |
|---|---|---|---|---|
| C 10:0 | 0.01 | 0.01 | 0.02 | 0-0.02 |
| C 12:0 | 0.05 | 0.57 | 1.08 | 0.16-1.08 |
| C 13:0 | 0 | 0.02 | 0.02 | 0-0.02 |
| C 14:0 | 1.45 | 7.18 | 11.24 | 2.96-11.24 |
| C 14:1 | 0.02 | 0.03 | 0.03 | 0.02-0.03 |
| C 15:0 | 0.06 | 0.07 | 0.07 | |
| C 16:0 | 24.13 | 25.78 | 25.21 | |
| C 16:1 | 0.77 | 0.72 | 0.66 | |
| C 17:0 | 0.19 | 0.13 | 0.11 | |
| C 17:1 | 0.08 | 0.05 | 0.04 | |
| C 18:0 | 3.53 | 3.35 | 3.12 | |
| C 18:1 | 56.15 | 49.65 | 46.35 | |
| C 18:2 | 11.26 | 10.17 | 9.72 | |
| C 18:3α | 0.84 | 0.95 | 0.83 | |
| C 20:0 | 0.32 | 0.34 | 0.32 | |
| C 20:1 | 0.09 | 0.08 | 0.09 | |
| C 20:1 | 0.07 | 0.05 | 0.06 | |
| C 22:0 | 0.07 | 0.08 | 0.08 | |
| C 24:0 | 0.13 | 0.13 | 0.12 | |

Constructs 9-13 were expression vectors containing the *Cuphea hookeriana* C8-10 thioesterase construct. As can be seen in the data summaries above, the best results were seen with Construct 11, with the Sample C8 fatty acid being 1.57 Area % (as compared to 0 in wildtype) and C10 fatty acid being 6.76 Area % (as compared to 0 in wildtype). There was also a modest increase in C12 fatty acids (approximately 2-5 fold increase). While the native plastid targeting sequence produced no change when under the control of the *C. sorokinana* glutamate dehydrogenase promoter, the same expression construct driven by the *C. reinhardtii* β-tubulin promoter produced significant changes in C8-10 fatty acids in the host cell. This is further evidence of the idiosyncrasies of heterologous expression of thioesterases in *Prototheca* species. All of the clones containing the *C. reinhardtii* β-tubulin promoter C8-10 thioesterase construct had greater increases in C8-10 fatty acids than the clones containing the *C. sorokinana* glutamate dehydrogenase promoter C8-10 thioesterase construct. Lipid profile data for Construct 13 was not obtained and therefore, not included above.

Constructs 14-18 were expression vectors containing the *Umbellularia californica* C12 thioesterase construct. As can be seen in the data summaries above, the best results were seen with Constructs 15 (*P. moriformis* isopentenyl diphosphate synthase plastid targeting sequence) and 17 (*C. protothecoides* stearoyl ACP desaturase plastid targeting sequence). The greatest change in C12 fatty acid production was seen with Construct 17, with C12 fatty acids levels of up to 14.11 area %, as compared to 0.04 area % in wildtype. Modest changes (about 2-fold) were also seen with C14 fatty acid levels. When compared to the same constructs with the *C. sorokinana* glutamate dehydrogenase promoter, the same trends were true with the *C. reinhardtii* β-tubulin promoter— the *C. protothecoides* stearoyl ACP desaturase and *P. moriformis* isopentenyl diphosphate synthase plastid targeting sequences produced the greatest change in C12 fatty acid levels with both promoters.

Constructs 19-23 were expression vectors containing the *Cinnamomum camphora* C14 thioesterase construct. As can be seen in the data summaries above, the best results were seen with Constructs 22 and Construct 23. The greatest change in C14 fatty acid production was seen with Construct 22, with C14 fatty acid levels of up to 17.35 area % (when the values for C140 and C141 are combined), as compared to 1.40% in wildtype. Changes in C12 fatty acids were also seen (5-60 fold). When compared to the same constructs with the *C. sorokinana* glutamate dehydrogenase promoter, the same trends were true with the *C. reinhardtii* β-tubulin promoter—the *C. protothecoides* stearoyl ACP desaturase and *P. moriformis* stearoyl ACP desaturase plastid targeting sequences produced the greatest change in C14 fatty acid levels with both promoters. Consistently with all thioesterase expression constructs, the *C. reinhardtii* β-tubulin promoter constructs produced greater changes in C8-14 fatty acid levels than the *C. sorokiniana* glutamate dehydrogenase Two positive clones from the Construct 22 were selected and grown under high selective pressure (50 mg/L G418). After 6 days in culture, the clones were harvested and their lipid profile was determined using the methods described above. The lipid profile data is summarized below and is expressed in area %.

| | Construct 22 clones + 50 mg/L G418 | |
|---|---|---|
| Fatty Acid | Construct 22 A | Construct 22 B |
| C 12:0 | 3.21 | 3.37 |
| C 14:0 | 27.55 | 26.99 |
| C 16:0 | 25.68 | 24.37 |
| C 16:1 | 0.99 | 0.92 |
| C 18:0 | 1.37 | 1.23 |
| C 18:1 | 28.35 | 31.07 |
| C 18:2 | 11.73 | 11.05 |
| C 18:3α | 0.92 | 0.81 |
| C 20:0 | 0.16 | 0.17 |

Both clones, when grown under constant, high selective pressure, produced an increased amount of C14 and C12 fatty acids, about double the levels seen with Construct 22 above. These clones yielded over 30 area % of C12-14 fatty acids, as compared to 1.5 area % of C12-14 fatty acids seen in wildtype cells.

Example 6

Heterologous Expression of *Cuphea palustris* and *Ulmus americanca* Thioesterase in *Prototheca*

Given the success of the above-described heterologous expression thioesterases in *Prototheca* species, expression cassettes containing codon-optimized (according to Table 1) sequences encoding fatty acyl-ACP thioesterases from *Cuphea palustris* and *Ulmus americana* were constructed and described below.

| Construct Name | Promoter/ 5'UTR | Plastid targeting seq | Gene | 3'UTR | SEQ ID NO. |
|---|---|---|---|---|---|
| Construct 27 | *C. reinhardtii* β-tubulin | *C. protothecoides* stearoyl ACP desaturase | *Cuphea palustris* thioesterase | *C. vulgaris* nitrate reductase | SEQ ID NO: 107 |

The *Ulmus americana* (codon-optimized coding sequence) can be inserted into the expression cassette. The codon-optimized coding sequence without the native plastid targeting sequence for the *Ulmus americana* thioesterase is listed as SEQ ID NO: 108 and can be fused any desired plastid targeting sequence and expression element (i.e., promoter/ 5'UTR and 3'UTR).

These expression cassettes can be transformed in to *Prototheca* species using the methods described above. Positive clones can be screened with the inclusion of an antibiotic resistance gene (e.g, neoR) on the expression construct and screened on G418-containing plates/media. Positive clones can be confirmed using Southern blot assays with probes specific to the heterologous thioesterase coding region and expression of the construct can also be confirmed using RT-PCR and primers specific to the coding region of the heterologous thioesterase. Secondary confirmation of positive clones can be achieved by looking for changes in levels of fatty acids in the host cell's lipid profile. As seen in the above Examples, heterologous expression in *Prototheca* species of thioesterase can be idiosyncratic to the particular thioesterase. Promoter elements and plastid targeting sequences (and other expression regulatory elements) can be interchanged until the expression of the thioesterase (and the subsequent increase in the corresponding fatty acid) reaches a desired level.

Example 7

Dual Transformants—Simultaneous Expression of Two Heterologous Proteins

Microalgae strain *Prototheca moriformis* (UTEX 1435) was transformed using the above disclosed methods with a expression construct containing the yeast sucrose invertase suc2 gene encoding the secreted form of the *S. cerevisiae* invertase. Successful expression of this gene and targeting to the periplasm results in the host cell's ability to grow on (and utilize) sucrose as a sole carbon source in heterotrophic conditions (as demonstrated in Example 3 above). The second set of genes expressed are thioesterases which are responsible for the cleavage of the acyl moiety from the acyl carrier protein. Specifically, thioesterases from *Cuphea hookeriana* (a C8-10 preferring thioesterase), *Umbellularia californica* (a C12 preferring thioesterase), and *Cinnamomum camphora* (a C14 preferring thioesterase). These thioesterase expression cassettes were cloned as fusions with N-terminal microalgal plastid targeting sequences from either *Prototheca moriformis* or *Chlorella protothecoides*, which have been shown (in the above Examples) to be more optimal than the native higher plant plastid targeting sequences. The successful expression of the thioesterase genes and the targeting to the plastid resulted in measurable changes in the fatty acid profiles within the host cell. These changes in profiles are consistent with the enzymatic specificity or preference of each thioesterase. Below is a summary of dual expression constructs that were assembled and transformed into *Prototheca moriformis* (UTEX 1435). Each construct contained the yeast suc2 gene under the control of the *C. reinhardtii* β-tubulin 5'UTR/promoter and contained the *C. vulgaris* nitrate reductase 3'UTR and a higher plant thioesterase with a microalgal plastid targeting sequence replacing the native sequence under the control of *C. sorokinana* glutamate dehydrogenase 5'UTR and contained the *C. vulgaris* nitrate reductase 3'UTR. Below is a summary of the thioesterase portion of the constructs that were assembled and transformed into *Prototheca moriformis* (UTEX 1435). The entire dual expression cassette with the suc2 gene and the thioesterase gene and the is listed in the Sequence Identification Listing.

| Construct Name | Promoter/ 5'UTR | Plastid targeting seq | Gene | 3'UTR | SEQ ID NO. |
|---|---|---|---|---|---|
| Construct 24 | *C. sorokiniana* glutamate dehydrogenase | *C. protothecoides* stearoyl ACP desaturase | *Cuphea hookeriana* C8-10 TE | *C. vulgaris* nitrate reductase | SEQ ID NO: 109 |
| Construct 25 | *C. sorokinana* glutamate dehydrogenase | *P. moriformis* isopentenyl diphosphate synthase | *Umbellularia californica* C12 TE | *C. vulgaris* nitrate reductase | SEQ ID NO: 110 |
| Construct 26 | *C. sorokinana* glutamate dehydrogenase | *C. protothecoides* stearoyl ACP desaturase | *Cinnamomum camphora* C14 TE | *C. vulgaris* nitrate reductase | SEQ ID NO: 111 |

Similar dual expression constructs with the thioesterase cassettes described in Example 5 (e.g., under the control of a different promoter such as *C. reinhardtii*β-tubulin promoter/5'UTR) can also be generated using standard molecular biology methods and methods described herein.

Positive clones containing each of expression constructs were screened using their ability to grow on sucrose-containing plates, where sucrose is the sole-carbon source, as the selection factor. A subset of these positive clones from each construct transformation was selected and the presence of the expression construct was confirmed using Southern blot assays. The function of the yeast sucrose invertase was also confirmed using a sucrose hydrolysis assay. Positive clones were selected and grown in media containing sucrose as the sole carbon source at a starting concentration of 40 g/L. A negative control of wildtype *Prototheca moriformis* (UTEX 1435) grown in media containing glucose as the sole carbon source at the same 40 g/L starting concentration was also included. Utilization of sucrose was measured throughout the course of the experiment by measuring the level of sucrose in the media using a YSI 2700 Biochemistry Analyzer with a sucrose-specific membrane. After six days in culture, the cultures were harvested and processed for lipid profile using the same methods as described above. The lipid profile results are summarized below in Table 17 and are show in area %.

TABLE 17

Lipid profiles of dual transformants with suc2 sucrose invertase and thioesterase.

| Fatty Acid | Wt | C24 A | C24 B | C24 C | C25 A | C25 B | C25 C | C26 A | C26 B | C26 C |
|---|---|---|---|---|---|---|---|---|---|---|
| C 10:0 | 0.01 | 0.03 | 0.04 | 0.08 | 0.01 | 0.01 | 0.01 | 0.01 | 0.01 | 0.0 |
| C 12:0 | 0.04 | 0.04 | 0.04 | 0.04 | 0.28 | 0.40 | 0.10 | 0.04 | 0.04 | 0.13 |
| C 14:0 | 1.6 | 1.55 | 1.53 | 1.56 | 1.59 | 1.59 | 1.60 | 1.65 | 1.56 | 2.69 |
| C 14:1 | 0.03 | 0.03 | 0.03 | 0.02 | 0.03 | 0.03 | 0.03 | 0.03 | 0.03 | 0.03 |
| C 15:0 | 0.04 | 0.03 | 0.03 | 0.04 | 0.04 | 0.03 | 0.03 | 0.03 | 0.03 | 0.04 |
| C 16:0 | 29.2 | 29.1 | 29.0 | 28.6 | 28.9 | 28.6 | 29.0 | 28.8 | 29.5 | 27.5 |
| C 16:1 | 0.86 | 0.80 | 0.79 | 0.82 | 0.77 | 0.81 | 0.82 | 0.79 | 0.79 | 0.86 |
| C 17:0 | 0.1 | 0.08 | 0.08 | 0.09 | 0.09 | 0.08 | 0.09 | 0.08 | 0.08 | 0.09 |
| C 17:1 | 0.04 | 0.03 | 0.03 | 0.04 | 0.03 | 0.03 | 0.03 | 0.03 | 0.03 | 0.04 |
| C 18:0 | 3.26 | 3.33 | 3.37 | 3.27 | 3.36 | 3.28 | 3.18 | 3.33 | 3.36 | 3.03 |
| C 18:1 | 54.5 | 53.9 | 54.1 | 53.9 | 53.5 | 53.7 | 53.5 | 54.2 | 53.9 | 52.7 |
| C 18:2 | 8.72 | 9.35 | 9.22 | 9.45 | 9.68 | 9.65 | 9.87 | 9.31 | 9.06 | 10.8 |
| C 18:3 alpha | 0.63 | 0.71 | 0.69 | 0.73 | 0.74 | 0.73 | 0.75 | 0.71 | 0.66 | 0.83 |
| C 20:0 | 0.29 | 0.31 | 0.31 | 0.31 | 0.32 | 0.32 | 0.31 | 0.32 | 0.31 | 0.29 |

All of the positive clones selected for the sucrose utilization assay were able to hydrolyze the sucrose in the media and at the end of the 6 day culture period, there were no measurable levels of sucrose in the media. This data, in addition to the successful use of sucrose as a selection tool for positive clones, indicates that the exogenous yeast suc2 sucrose invertase gene was targeted correctly and expressed in the transformants. As show in Table 17 above, the clones expressing Construct 24 (C8-10 thioesterase) had a measurable increase in C10 fatty acids (as high as an eight-fold increase). Likewise there were measurable increases in clones expressing Construct 25 (C12 thioesterase) and Construct 26 (C14 thioesterase) in the corresponding medium chain fatty acids. Taken together, the data shows the successful simultaneous expression in *Prototheca moriformis* two recombinant proteins (e.g., sucrose invertase and a fatty acid acyl-ACP thioesterase), both of which confer useful and quantifiable phenotypic changes on the host organism.

Example 8

Effects of Glycerol on C10-C14 Fatty Acid Production in C14 Thioesterase Transformants Clones from all the thioesterase transformations were selected and further evaluated. One clone expressing Construct 8 (*Cinnamomum camphora* C14 TE) was grown heterotrophically using different carbon sources: glucose only, fructose only and glycerol only. The glucose only condition resulted in higher cell growth and total lipid production when compared to the fructose only and glycerol only conditions. However, the proportion of C12-14 fatty acids produced in the glycerol only condition was two-fold higher than that attained in the glucose only condition.

Example 9

Expression of *Arabidopsis thaliana* Invertase in *Prototheca moriformis*

Microalgae strain *Prototheca moriformis* (UTEX 1435) was transformed using methods described above, with an expression construct containing a codon-optimized (according to Table 1) cell wall associated invertase from *Arabidopsis thaliana*. The *Araboposis* invertase sequence was modified to include the N-terminal 39 amino acids from yeast invertase (SUC2 protein) to ensure efficient targeting to the ER and ultimately the periplasm. To aid detection, a Flag epitope was added to the C-terminus of the recombinant protein. The transgene was cloned into an expression vector with a *Chlorella sorokinianna* glutamate dehydrogenase promoter/ 5'UTR region and a *Chlorella vulgaris* nitrate reductase 3'UTR region. The DNA sequence of this transgene cassette is listed as SEQ ID NO: 89 and the translated amino acid sequence is listed as SEQ ID NO: 90. Positive clones were screened and selected using sucrose-containing media/plates. A subset of the positive clones were confirmed for the presence of the transgene and expression of invertase using Southern blot analysis and Western blot analysis for the Flag-tagged invertase. From these screens, 10 positive clones were chosen for lipid productivity and sucrose utilization assays. All 10 clones were grown on media containing sucrose as the sole carbon source and a positive control suc2 invertase transformant was also included. The negative control, wildtype *Prototheca moriformis*, was also grown but on glucose containing media. After six days, the cells were harvested and dried and the total percent lipid by dry cell weight was determined. The media was also analyzed for total sucrose consumption.

All ten positive clones were able to hydrolyze sucrose, however, most clones grew about half as well as either wildtype or the positive control suc2 yeast invertase transformant as determined by dry cell weight at the end of the experiment. Similarly, all ten positive clones produced about half as much total lipid when compared to wildtype or the positive control transformant. This data demonstrate the successful heterologous expression of diverse sucrose invertases in *Prototheca*.

Example 10

Heterologous Expression of Yeast Invertase (Suc2) in *Prototheca krugani*, *Prototheca stagnora* and *Prototheca zopfii*

To test the general applicability of the transformation methods for use in species of the genus *Prototheca*, three other *Prototheca* species were selected: *Prototheca krugani* (UTEX 329), *Prototheca stagnora* (UTEX 1442) and *Prototheca zopfii* (UTEX 1438). These three strains were grown in the media and conditions described in Example 1 and their lipid profiles were determined using the above described methods. A summary of the lipid profiles from the three *Prototheca* strains are summarized below in Area %.

| Fatty Acid | P. krugani (UTEX 329) | P. stagnora (UTEX 1442) | P. zopfii (UTEX 1438) |
|---|---|---|---|
| C 10:0 | 0.0 | 0.0 | 0.0 |
| C 10:1 | 0.0 | 0.0 | 0.0 |
| C 12:0 | 1.5 | 0.8 | 2.1 |
| C 14:0 | 1.2 | 0.9 | 1.7 |
| C 16 | 15.1 | 17.1 | 19.7 |
| C 18:0 | 3.3 | 4.1 | 5.4 |
| C 18:1 | 66.0 | 61.5 | 53.8 |
| C 18:2 | 12.9 | 15.6 | 17.3 |

These three strains were transformed with a yeast invertase (suc2) expression cassette (SEQ ID NO: 58) using the methods described in Example 3 above. This yeast invertase (suc2) expression cassette has been demonstrated to work in *Prototheca moriformis* (UTEX 1435) above in Example 3. The transformants were screened using sucrose containing plates/media. A subset of the positive clones for each *Prototheca* species was selected and the presence of the transgene was confirmed by Southern blot analysis. Ten of confirmed positive clones from each species were selected for sucrose hydrolysis analysis and lipid productivity. The clones were grown in media containing sucrose as the sole carbon source and compared to its wildtype counterpart grown on glucose. After 6 days, the cultures were harvested and dried and total percent lipid and dry cell weight was assessed. The media from each culture was also analyzed for sucrose hydrolysis using a YSI2700 Biochemistry Analyzer for sucrose content over the course of the experiment. Clones from all three species were able to hydrolyze sucrose, with *Prototheca stagnora* and *Prototheca zopfii* transformants being able to hydrolyze sucrose more efficiently than *Prototheca krugani*. Total lipid production and dry cell weight of the three species of transformants were comparable to their wildtype counterpart grown on glucose. This data demonstrates the successful transformation and expression exogenous genes in multiple species of the genus *Prototheca*.

Example 11

Algal-Derived Promoters and Genes for Use in Microalgae

A. 5'UTR and Promoter Sequences from *Chlorella protothecoides*

A cDNA library was generated from mixotrophically grown *Chlorella protothecoides* (UTEX 250) using standard techniques. Based upon the cDNA sequences, primers were designed in certain known housekeeping genes to "walk" upstream of the coding regions using Seegene's DNA Walking kit (Rockville, Md.). Sequences isolated include an actin (SEQ ID NO:31) and elongation factor-1a (EF1a) (SEQ ID NO:32) promoter/UTR, both of which contain introns (as shown in the lower case) and exons (upper case italicized) and the predicted start site (in bold) and two beta-tubulin promoter/UTR elements: Isoform A (SEQ ID NO:33) and Isoform B (SEQ ID NO:34).

B. Lipid Biosynthesis Enzyme and Plastid Targeting Sequences from *C. protothecoides*

From the cDNA library described above, three cDNAs encoding proteins functional in lipid metabolism in *Chlorella protothecoides* (UTEX 250) were cloned using the same methods as described above. The nucleotide and amino acid sequences for an acyl ACP desaturase (SEQ ID NOs: 45 and 46) and two geranyl geranyl diphosphate synthases (SEQ ID NOs:47-50) are included in the Sequence Listing below.

Additionally, three cDNAs with putative signal sequences targeting to the plastid were also cloned. The nucleotide and amino acid sequences for a glyceraldehyde-3-phosphate dehydrogenase (SEQ ID NOs:51 and 52), an oxygen evolving complex protein OEE33 (SEQ ID NOs:53 and 54) and a Clp protease (SEQ ID NOs:55 and 56) are included in the Sequence Listing below. The putative plastid targeting sequence has been underlined in both the nucleotide and amino acid sequence. The plastid targeting sequences can be used to target the products of transgenes to the plastid of microbes, such as lipid modification enzymes.

Example 12

5'UTR/Promoters that are Nitrogen Responsive from *Prototheca moriformis*

A cDNA library was generated from *Prototheca moriformis* (UTEX 1435) using standard techniques. The *Prototheca moriformis* cells were grown for 48 hours under nitrogen replete conditions. Then a 5% innoculum (v/v) was then transferred to low nitrogen and the cells were harvested every 24 hours for seven days. After about 24 hours in culture, the nitrogen supply in the media was completely depleted. The collected samples were immediately frozen using dry ice and isopropanol. Total RNA was subsequently isolated from the frozen cell pellet samples and a portion from each sample was held in reserve for RT-PCR studies. The rest of the total RNA harvested from the samples was subjected to polyA selection. Equimolar amounts of polyA selected RNA from each condition was then pooled and used to generate a cDNA library in vector pcDNA 3.0 (Invitrogen). Roughly 1200 clones were randomly picked from the resulting pooled cDNA library and subjected to sequencing on both strands. Approximately 68 different cDNAs were selected from among these 1200 sequences and used to design cDNA-specific primers for use in real-time RT-PCR studies.

RNA isolated from the cell pellet samples that were held in reserve was used as substrate in the real time RT-PCR studies using the cDNA-specific primer sets generated above. This reserved RNA was converted into cDNA and used as substrate for RT-PCR for each of the 68 gene specific primer sets. Threshold cycle or $C_T$ numbers were used to indicate relative transcript abundance for each of the 68 cDNAs within each RNA sample collected throughout the time course. cDNAs showing significant increase (greater than three fold) between nitrogen replete and nitrogen-depleted conditions were flagged as potential genes whose expression was up-regulated by nitrogen depletion. As discussed in the specification, nitrogen depletion/limitation is a known inducer of lipogenesis in oleaginous microorganisms.

In order to identify putative promoters/5'UTR sequences from the cDNAs whose expression was upregulated during nitrogen depletion/limitation, total DNA was isolated from *Prototheca moriformis* (UTEX 1435) grown under nitrogen replete conditions and were then subjected to sequencing using 454 sequencing technology (Roche). cDNAs flagged as being up-regulated by the RT-PCR results above were compared using BLAST against assembled contigs arising from the 454 genomic sequencing reads. The 5' ends of cDNAs were mapped to specific contigs, and where possible, greater than 500 bp of 5' flanking DNA was used to putatively identify promoters/UTRs. The presence of promoters/5'UTR were subsequently confirmed and cloned using PCR amplification of genomic DNA. Individual cDNA 5' ends were used to design 3' primers and 5' end of the 454 contig assemblies were used to design 5' gene-specific primers.

As a first screen, one of the putative promoter, the 5'UTR/ promoter isolated from Aat2 (Ammonium transporter, SEQ ID NO: 99), was cloned into the *Cinnamomum camphora* C14 thioesterase construct with the *Chlorella prototheocoides* stearoyl ACP desaturase transit peptide described in Example 5 above, replacing the *C. sorokinana* glutamate dehydrogenase promoter. This construct is listed as SEQ ID NO: 112. To test the putative promoter, the thioesterase construct is transformed into *Prototheca moriformis* cells to confirm actual promoter activity by screening for an increase in C14/C12 fatty acids under low/no nitrogen conditions, using the methods described above. Similar testing of the putative nitrogen-regulated promoters isolated from the cDNA/genomic screen can be done using the same methods.

Other putative nitrogen-regulated promoters/5'UTRs that were isolated from the cDNA/genomic screen were:

| Promoter/5'UTR | SEQ ID NO. | Fold increased |
|---|---|---|
| FatB/A promoter/5'UTR | SEQ ID NO: 91 | n/a |
| NRAMP metal transporter promoter/5'UTR | SEQ ID NO: 92 | 9.65 |
| Flap Flagellar-associated protein promoter/5'UTR | SEQ ID NO: 93 | 4.92 |
| SulfRed Sulfite reductase promoter/5'UTR | SEQ ID NO: 94 | 10.91 |
| SugT Sugar transporter promoter/5'UTR | SEQ ID NO: 95 | 17.35 |
| Amt03—Ammonium transporter 03 promoter/5'UTR | SEQ ID NO: 96 | 10.1 |
| Amt02—Ammonium transporter 02 promoter/5'UTR | SEQ ID NO: 97 | 10.76 |
| Aat01—Amino acid transporter 01 promoter/5'UTR | SEQ ID NO: 98 | 6.21 |
| Aat02—Amino acid transporter 02 promoter/5'UTR | SEQ ID NO: 99 | 6.5 |
| Aat03—Amino acid transporter 03 promoter/5'UTR | SEQ ID NO: 100 | 7.87 |
| Aat04—Amino acid transporter 04 promoter/5'UTR | SEQ ID NO: 101 | 10.95 |
| Aat05—Amino acid transporter 05 promoter/5'UTR | SEQ ID NO: 102 | 6.71 |

Fold increase refers to the fold increase in cDNA abundance after 24 hours of culture in low nitrogen medium.

Example 13

Homologous Recombination in *Prototheca* Species

Homologous recombination of transgenes has several advantages over the transformation methods described in the above Examples. First, the introduction of transgenes without homologous recombination can be unpredictable because there is no control over the number of copies of the plasmid that gets introduced into the cell. Also, the introduction of transgenes without homologous recombination can be unstable because the plasmid may remain episomal and is lost over subsequent cell divisions. Another advantage of homologous recombination is the ability to "knock-out" gene targets, introduce epitope tags, switch promoters of endogenous genes and otherwise alter gene targets (e.g., the introduction of point mutations).

Two vectors were constructed using a specific region of the *Prototheca moriformis* (UTEX 1435) genome, designated KE858. KE858 is a 1.3 kb, genomic fragment that encompasses part of the coding region for a protein that shares homology with the transfer RNA (tRNA) family of proteins. Southern blots have shown that the KE858 sequence is present in a single copy in the *Prototheca moriformis* (UTEX 1435) genome. The first type of vector that was constructed, designated SZ725 (SEQ ID NO: 103), consisted of the entire 1.3 kb KE858 fragment cloned into a pUC19 vector backbone that also contains the optimized yeast invertase (suc2) gene used in Example 3 above. The KE858 fragment contains an unique SnaB1 site that does not occur anywhere else in the targeting construct. The second type of vector that was constructed, designated SZ726 (SEQ ID NO: 126), consisted of the KE858 sequence that had been disrupted by the insertion of the yeast invertase gene (suc2) at the SnaB1 site within the KE858 genomic sequence. The entire DNA fragment containing the KE858 sequences flanking the yeast invertase gene can be excised from the vector backbone by digestion with EcoRI, which cuts at either end of the KE858 region.

Both vectors were used to direct homologous recombination of the yeast invertase gene (suc2) into the corresponding KE858 region of the *Prototheca moriformis* (UTEX 1435) genome. The linear DNA ends homologous to the genomic region that was being targeted for homologous recombination were exposed by digesting the vector construct SZ725 with SnaB1 and vector construct SZ726 with EcoRI. The digested vector constructs were then introduced into *Prototheca moriformis* cultures using methods described above in Example 3. Transformants from each vector construct were then selected using sucrose plates. Ten independent, clonally pure transformants from each vector transformation were analyzed for successful recombination of the yeast invertase gene into the desired genomic location (using Southern blots) and for transgene stability.

Southern blot analysis of the SZ725 transformants showed that 4 out of the 10 transformants picked for analysis contained the predicted recombinant bands, indicating that a single crossover event had occurred between the KE858 sequences on the vector and the KE858 sequences in the genome. In contrast, all ten of the SZ726 transformants contained the predicted recombinant bands, indicating that double crossover events had occurred between the EcoRI fragment of pSZ726 carrying KE858 sequence flanking the yeast invertase transgene and the corresponding KE858 region of the genome.

Sucrose invertase expression and transgene stability were assessed by growing the transformants for over 15 generations in the absence of selection. The four SZ725 transformants and the ten SZ276 transformants that were positive for the transgene by Southern blotting were selected and 48 single colonies from each of the transformants were grown serially: first without selection in glucose containing media and then with selection in media containing sucrose as the sole carbon source. All ten SZ276 transformants (100%) retained their ability to grow on sucrose after 15 generations, whereas about 97% of the SZ725 transformants retained their ability to grow on sucrose after 15 generations. Transgenes introduced by a double crossover event (SZ726 vector) have extremely high stability over generation doublings. In contrast, transgenes introduced by a single cross over event (SZ725 vector) can result in some instability over generation doublings because is tandem copies of the transgenes were introduced, the repeated homologous regions flanking the transgenes may recombine and excise the transgenic DNA located between them.

These experiments demonstrate the successful use of homologous recombination to generate *Prototheca* transformants containing a heterologous sucrose invertase gene that is stably integrated into the nuclear chromosomes of the organism. The success of the homologous recombination enables other genomic alterations in *Prototheca*, including gene deletions, point mutations and epitope tagging a desired gene product. These experiments also demonstrate the first documented system for homologous recombination in the nuclear genome of an eukaryotic microalgae.

A. Use of Homologous Recombination to Knock-Out an Endogenous *Prototheca moriformis* Gene In the *Prototheca moriformis* cDNA/genomic screen described in Example 11 above, an endogenous stearoyl ACP desaturase (SAPD) cDNA was identified. Stearoyl ACP desaturase enzymes are part of the lipid synthesis pathway and they function to introduce double bonds into the fatty acyl chains. In some cases, it may be advantages to knock-out or reduce the expression of lipid pathway enzymes in order to alter a fatty acid profile. A homologous recombination construct was created to assess whether the expression of an endogenous stearoyl ACP desaturase enzyme can be reduced (or knocked out) and if a corresponding reduction in unsaturated fatty acids can be observed in the lipid profile of the host cell. An approximately 1.5 kb coding sequence of a stearoyl ACP desaturase gene from *Prototheca moriformis* (UTEX 1435) was identified and cloned (SEQ ID NO: 104). The homologous recombination construct was constructed using 0.5 kb of the SAPD coding sequence at the 5'end (5' targeting site), followed by the *Chlamydomonas reinhardtii* β-tublin promoter driving a codon-optimized yeast sucrose invertase suc2 gene with the *Chlorella vulgaris* 3'UTR. The rest (~1 kb) of the *Prototheca moriformis* SAPD coding sequence was then inserted after the *C. vulgaris* 3'UTR to make up the 3' targeting site. The sequence for this homologous recombination cassette is listed in SEQ ID NO: 105. As shown above, the success-rate for integration of the homologous recombination cassette into the nuclear genome can be increased by linearizing the cassette before transforming the microalgae, leaving exposed ends. The homologous recombination cassette targeting an endogenous SAPD enzyme in *Prototheca moriformis* is linearized and then transformed into the host cell (*Prototheca moriformis*, UTEX 1435). A successful integration will eliminate the endogenous SAPD enzyme coding region from the host genome via a double reciprocal recombination event, while expression of the newly inserted suc2 gene will be regulated by the *C. reinhardtii* β-tubulin promoter. The resulting clones can be screened using plates/media containing sucrose as the sole carbon source. Clones containing a successful integration of the homologous recombination cassette will have the ability to grow on sucrose as the sole carbon source and changes in overall saturation of the fatty acids in the lipid profile will serve as a secondary confirmation factor. Additionally, Southern blotting assays using a probe specific for the yeast sucrose invertase suc2 gene and RT-PCR can also confirm the presence and expression of the invertase gene in positive clones. As an alternative, the same construct without the β-tubulin promoter can be used to excise the endogenous SAPD enzyme coding region. In this case, the newly inserted yeast sucrose invertase suc2 gene will be regulated by the endogenous SAPD promoter/5'UTR.

Example 14

Fuel Production

A. Extraction of Oil from Microalgae Using an Expeller Press and a Press Aid

Microalgal biomass containing 38% oil by DCW was dried using a drum dryer resulting in resulting moisture content of 5-5.5%. The biomass was fed into a French L250 press. 30.4 kg (67 lbs.) of biomass was fed through the press and no oil was recovered. The same dried microbial biomass combined with varying percentage of switchgrass as a press aid was fed through the press. The combination of dried microbial biomass and 20% w/w switchgrass yielded the best overall percentage oil recovery. The pressed cakes were then subjected to hexane extraction and the final yield for the 20% switchgrass condition was 61.6% of the total available oil (calculated by weight). Biomass with above 50% oil dry cell weight did not require the use of a pressing aid such as switchgrass in order to liberate oil.

B. Monosaccharide Composition of Delipidated *Prototheca moriformis* Biomass

*Prototheca moriformis* (UTEX 1435) was grown in conditions and nutrient media (with 4% glucose) as described in Example 45 above. The microalgal biomass was then harvested and dried using a drum dryer. The dried algal biomass was lysed and the oil extracted using an expeller press as described in Example 44 above. The residual oil in the pressed biomass was then solvent extracted using petroleum ether. Residual petroleum ether was evaporated from the delipidated meal using a Rotovapor (Buchi Labortechnik AG, Switzerland). Glycosyl (monosaccharide) composition analysis was then performed on the delipidated meal using combined gas chromatography/mass spectrometry (GC/MS) of the per-O-trimethylsily (TMS) derivatives of the monosaccharide methyl glycosides produced from the sample by acidic methanolysis. A sample of delipidated meal was subjected to methanolysis in 1M HCl in methanol at 80° C. for approximately 20 hours, followed by re-N-acetylation with pyridine and acetic anhydride in methanol (for detection of amino sugars). The samples were then per-O-trimethylsiylated by treatment with Tri-Sil (Pierce) at 80° C. for 30 minutes (see methods in Merkle and Poppe (1994) *Methods Enzymol.* 230: 1-15 and York et al., (1985) *Methods Enzymol.* 118:3-40). GC/MS analysis of the TMS methyl glycosides was performed on an HP 6890 GC interfaced to a 5975b MSD, using a AllTech EC-1 fused silica capillary column (30 m×0.25 mm ID). The monosaccharides were identified by their retention times in comparison to standards, and the carbohydrate character of these are authenticated by their mass spectra. 20 micrograms per sample of inositol was added to the sample before derivatization as an internal standard. The monosaccharide profile of the delipidated *Prototheca moriformis* (UTEX 1435) biomass is summarized in Table 18 below. The total percent carbohydrate from the sample was calculated to be 28.7%.

TABLE 18

Monosaccharide (glycosyl) composition analysis of *Prototheca moriformis* (UTEX 1435) delipidated biomass.

|  | Mass (µg) | Mole % (of total carbohydrate) |
| --- | --- | --- |
| Arabinose | 0.6 | 1.2 |
| Xylose | n.d. | n.d. |
| Galacturonic acid (GalUA) | n.d. | n.d. |
| Mannose | 6.9 | 11.9 |
| Galactose | 14.5 | 25.2 |
| Glucose | 35.5 | 61.7 |
| N Acetyl Galactosamine (GalNAc) | n.d. | n.d. |
| N Acetyl Glucosamine (GlcNAc) | n.d. | n.d. |
| Heptose | n.d. | n.d. |
| 3 Deoxy-2-manno-2 Octulsonic acid (KDO) | n.d. | n.d. |
| Sum | 57 | 100 | n.d. = none detected

The carbohydrate content and monosaccharide composition of the delipidated meal makes it suitable for use as an animal feed or as part of an animal feed formulation. Thus, in one aspect, the present invention provides delipidated meal having the product content set forth in the table above.

C. Production of Biodiesel from *Prototheca* Oil

Degummed oil from *Prototheca moriformis* UTEX 1435, produced according to the methods described above, was subjected to transesterification to produce fatty acid methyl esters. Results are shown below:

The lipid profile of the oil was:
C10:0 0.02
C12:0 0.06
C14:0 1.81
C14:1 0.07
C16:0 24.53
C16:1 1.22
C18:0 2.34
C18:1 59.21
C18:2 8.91
C18:3 0.28
C20:0 0.23
C20:1 0.10
C20:1 0.08
C21:0 0.02
C22:0 0.06
C24:0 0.10

TABLE 19

Biodiesel profile from *Prototheca moriformis* triglyceride oil.

| Method | Test | | Result | Units |
|---|---|---|---|---|
| ASTM D6751 A1 | Cold Soak Filterability of Biodiesel Blend Fuels | Filtration Time | 120 | sec |
| | | Volume Filtered | 300 | ml |
| ASTM D93 | Pensky-Martens Closed Cup Flash Point | Procedure Used | A | |
| | | Corrected Flash Point | 165.0 | ° C. |
| ASTM D2709 | Water and Sediment in Middle Distillate Fuels (Centrifuge Method) | Sediment and Water | 0.000 | Vol % |
| EN 14538 | Determination of Ca and Mg Content by ICP OES | Sum of (Ca and Mg) | <1 | mg/kg |
| EN 14538 | Determination of Ca and Mg Content by ICP OES | Sum of (Na and K) | <1 | mg/kg |
| ASTM D445 | Kinematic/Dynamic Viscosity | Kinematic Viscosity @ 104° F./40° C. | 4.873 | mm$^2$/s |
| ASTM D874 | Sulfated Ash from Lubricating Oils and Additives | Sulfated Ash | <0.005 | Wt % |
| ASTM D5453 | Determination of Total Sulfur in Light Hydrocarbons, Spark Ignition Engine Fuel, Diesel Engine Fuel, and Engine Oil by Ultraviolet Fluorescence. | Sulfur, mg/kg | 1.7 | mg/kg |
| ASTM D130 | Corrosion - Copper Strip | Biodiesel-Cu Corrosion 50° C. (122° F.)/3 hr | 1a | |
| ASTM D2500 | Cloud Point | Cloud Point | 6 | ° C. |
| ASTM D4530 | Micro Carbon Residue | Average Micro Method Carbon Residue | <0.10 | Wt % |
| ASTM D664 | Acid Number of Petroleum Products by Potentiometric Titration | Procedure Used | A | |
| | | Acid Number | 0.20 | mg KOH/g |
| ASTM D6584 | Determination of Free and Total Glycerin in B-100 Biodiesel Methyl Esters By Gas Chromatography | Free Glycerin | <0.005 | Wt % |
| | | Total Glycerin | 0.123 | Wt % |
| ASTM D4951 | Additive Elements in Lubricating Oils by ICP-AES | Phosphorus | 0.000200 | Wt % |
| ASTM D1160 | Distillation of Petroleum Products at Reduced Pressure | IBP | 248 | ° C. |
| | | AET @ 5% Recovery | 336 | ° C. |
| | | AET @ 10% Recovery | 338 | ° C. |
| | | AET @ 20% Recovery | 339 | ° C. |
| | | AET @ 30% Recovery | 340 | ° C. |
| | | AET @ 40% Recovery | 342 | ° C. |
| | | AET @ 50% Recovery | 344 | ° C. |
| | | AET @ 60% Recovery | 345 | ° C. |
| | | AET @ 70% Recovery | 347 | ° C. |
| | | AET @ 80% Recovery | 349 | ° C. |
| | | AET @ 90% Recovery | 351 | ° C. |

TABLE 19-continued

Biodiesel profile from *Prototheca moriformis* triglyceride oil.

| Method | Test | | Result | Units |
|---|---|---|---|---|
| | | AET @ 95% Recovery | 353 | °C. |
| | | FBP | 362 | °C. |
| | | % Recovered | 98.5 | % |
| | | % Loss | 1.5 | % |
| | | % Residue | 0.0 | % |
| | | Cold Trap Volume | 0.0 | ml |
| | | IBP | 248 | °C. |
| EN 14112 | Determination of Oxidation Stability (Accelerated Oxidation Test) | Oxidation Stability | >12 | hr |
| | | Operating Temp (usually 110 deg C.) | 110 | °C. |
| ASTM D4052 | Density of Liquids by Digital Density Meter | API Gravity @ 60° F. | 29.5 | °API |
| ASTM D6890 | Determination of Ignition Delay (ID) and Derived Cetane Number (DCN) | Derived Cetane Number (DCN) | >61.0 | |

The lipid profile of the biodiesel was highly similar to the lipid profile of the feedstock oil. Other oils provided by the methods and compositions of the invention can be subjected to transesterification to yield biodiesel with lipid profiles including (a) at least 4% C8-C14; (b) at least 0.3% C8; (c) at least 2% C10; (d) at least 2% C12; and (3) at least 30% C8-C14.

The Cold Soak Filterability by the ASTM D6751 A1 method of the biodiesel produced was 120 seconds for a volume of 300 ml. This test involves filtration of 300 ml of B100, chilled to 40° F. for 16 hours, allowed to warm to room temp, and filtered under vacuum using 0.7 micron glass fiber filter with stainless steel support. Oils of the invention can be transesterified to generate biodiesel with a cold soak time of less than 120 seconds, less than 100 seconds, and less than 90 seconds.

D. Production of Renewable Diesel

Degummed oil from *Prototheca moriformis* UTEX 1435, produced according to the methods described above and having the same lipid profile as the oil used to make biodiesel in Example X above, was subjected to transesterification to produce renewable diesel.

Figure 13:
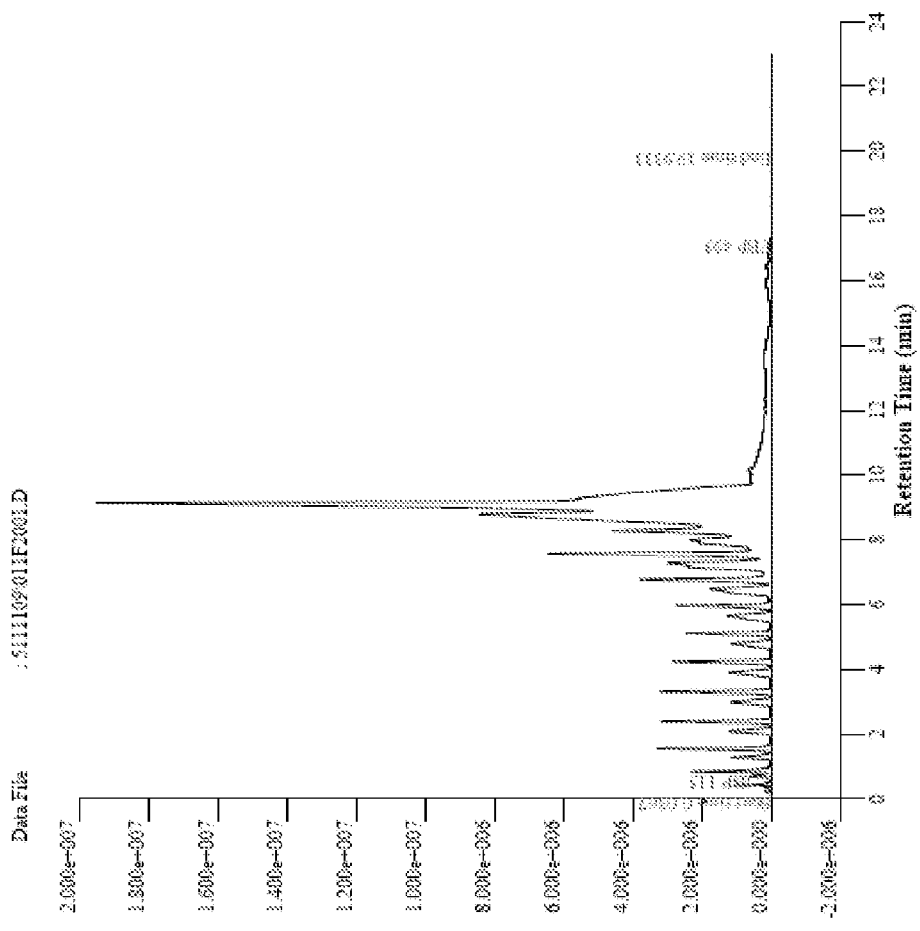
FIG. 13 shows a chromatogram of renewable diesel produced from *Prototheca* triglyceride oil.

The oil was first hydrotreated to remove oxygen and the glycerol backbone, yielding n-paraffins. The n-parrafins were then subjected to cracking and isomerization. A chromatogram of the material is shown in FIG. 13. The material was then subjected to cold filtration, which removed about 5% of the C18 material. Following the cold filtration the total volume material was cut to flash point and evaluated for flash point, ASTM D-86 distillation distribution, cloud point and viscosity. Flash point was 63° C.; viscosity was 2.86 cSt (centistokes); cloud point was 4° C. ASTM D86 distillation values are shown in Table 20:

TABLE 20

| Readings in ° C.: | |
|---|---|
| Volume | Temperature |
| IBP | 173 |
| 5 | 217.4 |
| 10 | 242.1 |
| 15 | 255.8 |
| 20 | 265.6 |
| 30 | 277.3 |
| 40 | 283.5 |
| 50 | 286.6 |

TABLE 20-continued

| Readings in ° C.: | |
|---|---|
| Volume | Temperature |
| 60 | 289.4 |
| 70 | 290.9 |
| 80 | 294.3 |
| 90 | 300 |
| 95 | 307.7 |
| FBP | 331.5 |

The T10-T90 of the material produced was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

The T10 of the material produced was 242.1° C. Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

The T90 of the material produced was 300° C. Methods of hydrotreating, isomerization, and other covalent modification of oils disclosed herein, as well as methods of distillation and fractionation (such as cold filtration) disclosed herein can be employed to generate renewable diesel compositions with other T90 values, such as T90 between 280 and 380, between 290 and 360, between 300 and 350, between 310 and 340, and at least 290.

The FBP of the material produced was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 4% C8-C14; (b) at least 0.3% C8; (c) at least 2% C10; (d) at least 2% C12; and (3) at least 30% C8-C14.

Example 15

Utilization of Sucrose by *Chlorella luteoviridis*

A. SAG 2214 Growth on Glucose and Sucrose

Figure 3:
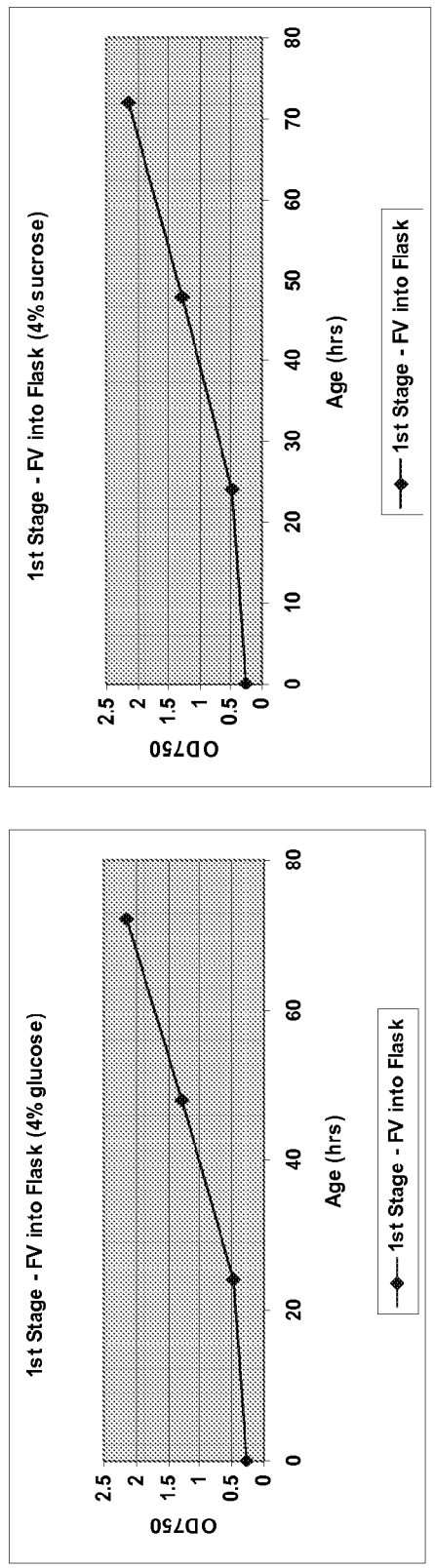
FIG. 3 shows time course growth of SAG 2214 on glucose and sucrose.

SAG 2214 (designated as *Chlorella luteoviridis*) was tested for growth in the dark on media containing either glucose or sucrose. Heterotrophic liquid cultures were initiated using inoculum from a frozen vial in either media containing 4% glucose or 4% sucrose as the sole carbon source. Cultures were grown in the dark, shaking at 200 rpm. Samples from the cultures were taken at 0, 24, 48 and 72 hour timepoints and growth was measured by relative absorbance at 750 nm (UV Mini1240, Shimadzu). SAG 2214 grew equally well on glucose as on sucrose, showing that this microalgae can utilize sucrose as effectively as glucose as a sole carbon source. The result of this experiment is represented graphically in FIG. 3.

B. Lipid Productivity and Fatty Acid Profile for SAG 2214

Microalgal strain SAG 2214 was cultivated in liquid medium containing either glucose or sucrose as the sole carbon source in similar conditions as described in Example 32 above. After 7 days, cells were harvested for dry cell weight calculation. Cells were centrifuged and lyophilized for 24 hours. The dried cell pellets were weighed and the dry cell weight per liter was calculated. Cells for lipid analysis were also harvested and centrifuged at 4000×g for 10 minutes at room temperature. The supernatant was discarded and the samples were processed for lipid analysis and fatty acid profile using standard gas chromatography (GC/FID) procedures. The results are summarized below in Tables 21 and 22.

TABLE 21

Lipid productivity and DCW for SAG 2214.

| Sample | Lipid (g/L) | DCW (g/L) | % Lipid DCW |
|---|---|---|---|
| SAG 2214 glucose | 2.43 | 5.73 | 42.44% |
| SAG 2214 sucrose | 0.91 | 2.00 | 45.56% |

TABLE 22

Fatty acid profile for SAG 2214.

| Fatty Acid | Percent (w/w) |
|---|---|
| C:16:0 | 21 |
| C:18:1 | 38 |
| C:18:2 | 41 |

C. Genomic Comparison of SAG 2214 to Other *Chlorella luteoviridis* Strains

Microalgal strain SAG 2214 proved to be of general interest due to its ability to grow on sucrose as a carbon source (illustrated above). In addition to the growth characteristics of this strain, its taxonomic relationship to other microalgal species was also of interest. Designated by the SAG collection as a *Chlorella luteoviridis* strain, the 23s rRNA gene of SAG 2214 was sequenced and compared to the 23s rRNA genomic sequence of nine other strains also identified by the SAG and UTEX collections as *Chlorella luteoviridis*. These strains were UTEX 21, 22, 28, 257 and 258, and SAG strains 2133, 2196, 2198 and 2203. The DNA genotyping methods used were the same as the methods described above in Example 1. Sequence alignments and unrooted trees were generated using Geneious DNA analysis software. Out of the nine other strains that were genotypes, UTEX 21, 22, 28 and 257 had identical 23s rRNA DNA sequence (SEQ ID NO: 106). The other five *Chlorella luteoviridis* strains had 23s rRNA sequences that were highly homologous to UTEX 21, 22, 28, and 257.

The 23s rRNA gene sequence from SAG 2214 (SEQ ID NO: 30) is decidedly different from that of the other nine *C. luteoviridis* strains, having a large insertion that was not found in the other strains. Further analysis of this 23s rRNA gene sequence using BLAST indicated that it shared the greatest homology with members of the genus *Leptosira* and *Trebouxia* (members of phycobiont portion of lichens). These results indicate that SAG 2214 may not be *Chlorella luteoviridis* strain as categorized by the strain collection, but instead shares significant 23S rRNA nucleotide identity to algal symbionts found in lichen. The genomic analysis along with the growth characteristics indicate that SAG 2214 may be a source for genes and proteins involved in the metabolism of sucrose, as well as signaling and transit peptides responsible for the correct localization of such enzymes. SAG 2214 and other strains with a high degree of genomic similarity may also be strains useful for oil production using sucrose as a source of fixed carbon.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein. In particular, the following patent applications are hereby incorporated by reference in their entireties for all purposes: U.S. Provisional Application No. 60/941,581, filed Jun. 1, 2007, entitled "Production of Hydrocarbons in Microorganisms"; U.S. Provisional Application No. 60/959,174, filed Jul. 10, 2007, entitled "Production of Hydrocarbons in Microorganisms"; U.S. Provisional Application No. 60/968,291, filed Aug. 27, 2007, entitled "Production of Hydrocarbons in Microorganisms"; U.S. Provisional Application No. 61/024,069, filed Jan. 28, 2008, entitled "Production of Hydrocarbons in Microorganims"; PCT Application No. PCT/US08/65563, filed Jun. 2, 2008, entitled "Production of Oil in Microorganisms"; U.S. patent application Ser. No. 12/131,783, filed Jun. 2, 2008, entitled "Use of Cellulosic Material for Cultivation of Microorganisms"; U.S. patent application Ser. No. 12/131,773, filed Jun. 2, 2008, entitled "Renewable Diesel and Jet Fuel from Microbial Sources"; U.S. patent application Ser. No. 12/131,793, filed Jun. 2, 2008, entitled "Sucrose Feedstock Utilization for Oil-Based Fuel Manufacturing"; U.S. patent application Ser.

No. 12/131,766, filed Jun. 2, 2008, entitled "Glycerol Feedstock Utilization for Oil-Based Fuel Manufacturing"; U.S. patent application Ser. No. 12/131,804, filed Jun. 2, 2008, entitled "Lipid Pathway Modification in Oil-Bearing Microorganisms"; U.S. Patent Application No. 61/118,590, filed Nov. 28, 2008, entitled "Production of Oil in Microorganisms"; U.S. Provisional Patent Application No. 61/118,994, filed Dec. 1, 2008, entitled "Production of Oil in Microorganisms"; U.S. Provisional Patent Application No. 61/174,357, filed Apr. 3, 2009, entitled "Production of Oil in Microorganisms"; U.S. Provisional Patent Application No. 61/219,525, filed Jun. 23, 2009, entitled "Production of Oil in Microorganisms"; U.S. patent application Ser. No. 12/628,140, filed Nov. 30, 2009, entitled "Novel Triglyceride and Fuel Compositions"; U.S. patent application Ser. No. 12/628,144, filed Nov. 30, 2009, entitled "Cellulosic Cultivation of Oleaginous Microorganisms"; U.S. patent application Ser. No. 12/628,147, filed Nov. 30, 2009, entitled "Nucleic Acids Useful in the Manufacture of Oil"; U.S. patent application Ser. No. 12/628,149, filed Nov. 30, 2009, entitled, "Renewable Chemical Production from Novel Fatty Acid Feedstocks", and U.S. patent application Ser. No. 12/628,120, filed Nov. 30, 2009, entitled "Recombinant Microalgae Cells Producing Novel Oils".

What is claimed is:

1. A fuel prepared by a process, the process comprising:
   (a) providing a triglyceride oil isolated from a cultivated oleaginous microorganism, wherein the oleaginous microorganism comprises an exogenous fatty acyl-ACP thioesterase gene that encodes a fatty acyl-ACP thioesterase having hydrolysis activity towards one or more fatty acyl-ACP substrates of chain length 8 to 18 carbon atoms, and produces triglyceride oil enriched in esterified fatty acids of chain length 8 to 18;
   (b) performing one or more chemical reactions on the triglyceride oil to produce the fuel; and
   (c) separating and recovering the fuel from the products of the chemical reaction mixture after performing step (b).

2. The fuel of claim 1, wherein the oleaginous microorganism further comprises an exogenous invertase gene and the oleaginous microorganism is cultivated in a medium comprising sucrose.

3. The fuel of claim 2, wherein the fuel is renewable diesel, jet fuel or biodiesel.

4. The fuel of claim 1, wherein the fatty acyl-ACP thioesterase gene is from Umbellularia, Cinnamomum, Myristica, Elaeis, Populus, Arabidopsis, Gossypium, Cuphea, Vitis, Garcinia, Iris, Brassica, Madhuca, Oryza, or Ulmus.

5. The fuel of claim 1, wherein the oleaginous microorganism further comprises an endogenous desaturase gene that is knocked out or down-regulated.

6. The fuel of claim 1, wherein the one or more chemical reactions comprise, transesterification, hydrogenation, hydrocracking, hydroproces sing, hydrotreating, fluid catalytic cracking, hydrodeoxygenation, hydrodesulfurization, deoxygenation, isomerization, and/or hydrolysis.

7. The fuel of claim 1, wherein the separating is performed by distillation.

8. The fuel of claim 7, wherein the fuel is renewable diesel, jet fuel or biodiesel.

9. The fuel of claim 1, wherein the triglyceride oil is blended with at least one of the following oils before performing the one or more chemical reactions: soy, rapeseed, canola, palm, palm kernel, coconut, corn, waste vegetable, Chinese tallow, olive, sunflower, cotton seed, chicken fat, beef tallow, porcine tallow, microalgae, macroalgae, Cuphea, flax, peanut, choice white grease, lard, Camelina sativa, mustard seed, cashew nut, oats, lupine kenaf, calendula, hemp, coffee, hazelnut, euphorbia, pumpkin seed, coriander, camellia, sesame, safflower, rice, tung tree, cocoa, copra, plum poppy, castor bean, pecan, jojoba, macademia, Brazil nut, avocado, petroleum, or a distillate fraction of any of the proceeding oils.

10. The fuel of claim 9, wherein the fuel is renewable diesel, jet fuel or biodiesel.

11. The fuel of claim 1, wherein the oleaginous microorganism is an obligate heterotroph.

12. The fuel of claim 1, wherein the oleaginous microorganism is a microalga.

13. The fuel of claim 12, wherein the microalga is an obligate heterotroph.

14. The fuel of claim 12, wherein the microalga is of the genus Prototheca or Chlorella.

15. The fuel of claim 14, wherein the microalga is of the species Prototheca moriformis.

16. A method of making a fuel, the method comprising the steps of :
   (a) providing a triglyceride oil isolated from a cultivated oleaginous microorganism, wherein the oleaginous microorganism comprises an exogenous fatty acyl-ACP thioesterase gene that encodes a fatty acyl-ACP thioesterase having hydrolysis activity towards one or more fatty acyl-ACP substrates of chain length 8 to 18 carbon atoms, and produces triglyceride oil enriched in esterified fatty acids of chain length 8 to 18;
   (b) performing one or more chemical reactions on the triglyceride oil to produce the fuel; and
   (c) separating and recovering the fuel from the products of the chemical reaction mixture after performing step (b).

17. The method of claim 16, wherein the oleaginous microorganism further comprises an exogenous invertase gene and the oleaginous microorganism is cultivated in a medium comprising sucrose.

18. The method of claim 17, wherein the fuel is renewable diesel, jet fuel or biodiesel.

19. The method of claim 16, wherein the fatty acyl-ACP thioesterase gene is from Umbellularia, Cinnamomum, Myristica, Elaeis, Populus, Arabidopsis, Gossypium, Cuphea, Vitis, Garcinia, Iris, Brassica, Madhuca, Oryza, or Ulmus.

20. The method of claim 16, wherein the oleaginous microorganism further comprises an endogenous desaturase gene that is knocked out or down-regulated.

21. The method of claim 16, wherein the one or more chemical reactions comprise, transesterification, hydrogenation, hydrocracking, hydroprocessing, hydrotreating, fluid catalytic cracking, hydrodeoxygenation, hydrodesulfurization, deoxygenation, isomerization, and/or hydrolysis.

22. The method of claim 16, wherein the separating is performed by distillation.

23. The method of claim 22, wherein the fuel is renewable diesel, jet fuel or biodiesel.

24. The method of claim 16, wherein the triglyceride oil is blended with at least one of the following oils before performing the one or more chemical reactions: soy, rapeseed, canola, palm, palm kernel, coconut, corn, waste vegetable, Chinese tallow, olive, sunflower, cotton seed, chicken fat, beef tallow, porcine tallow, microalgae, macroalgae, *Cuphea*, flax, peanut, choice white grease, lard, *Camelina sativa*, mustard seed, cashew nut, oats, lupine kenaf, calendula, hemp, coffee, hazelnut, euphorbia, pumpkin seed, coriander, camellia, sesame, safflower, rice, tung tree, cocoa, copra, plum poppy, castor bean, pecan, jojoba, macademia, Brazil nut, avocado, petroleum, or a distillate fraction of any of the proceeding oils.

25. The method of claim 24, wherein the fuel is renewable diesel, jet fuel or biodiesel.

26. The method of claim 16, wherein the oleaginous microorganism is an obligate heterotroph.

27. The method of claim 16, wherein the oleaginous microorganism is a microalga.

28. The method of claim 27, wherein the microalga is an obligate heterotroph.

29. The method of claim 27, wherein the microalga is of the genus *Prototheca* or *Chlorella*.

30. The method of claim 29, wherein the microalga is of the species *Prototheca moriformis*.

* * * * *